(12) United States Patent
Wu et al.

(10) Patent No.: US 12,304,898 B2
(45) Date of Patent: May 20, 2025

(54) QUINOLYL-CONTAINING COMPOUND AND PHARMACEUTICAL COMPOSITION, AND USE THEREOF

(71) Applicant: PrimeGene (Beijing) Co., Ltd., Beijing (CN)

(72) Inventors: Wei Wu, Beijing (CN); Li Zhu, Beijing (CN); Yanqing Yang, Beijing (CN); Wei Hu, Beijing (CN); Hui Zhang, Beijing (CN); Changxin Dong, Beijing (CN)

(73) Assignee: PrimeGene (Beijing) Co., Ltd., Beijing (CN)

( * ) Notice: Subject to any disclaimer, the term of this patent is extended or adjusted under 35 U.S.C. 154(b) by 828 days.

(21) Appl. No.: 17/594,039

(22) PCT Filed: Mar. 30, 2020

(86) PCT No.: PCT/CN2020/082041
§ 371 (c)(1),
(2) Date: Sep. 30, 2021

(87) PCT Pub. No.: WO2020/200160
PCT Pub. Date: Oct. 8, 2020

(65) Prior Publication Data
US 2022/0162184 A1  May 26, 2022

(30) Foreign Application Priority Data
Apr. 3, 2019 (CN) .......................... 201910266681.9

(51) Int. Cl.
C07D 409/12 (2006.01)
A61K 31/47 (2006.01)
A61K 31/4709 (2006.01)
C07D 215/22 (2006.01)
C07D 215/233 (2006.01)
C07D 401/12 (2006.01)
C07D 417/12 (2006.01)

(52) U.S. Cl.
CPC ......... C07D 401/12 (2013.01); C07D 215/22 (2013.01); C07D 409/12 (2013.01); C07D 417/12 (2013.01)

(58) Field of Classification Search
CPC .......................... C07D 401/12; C07D 215/22; C07D 215/233; C07D 409/12; C07D 417/12; A61K 31/4709; A61K 31/47; A61P 17/06; A61P 1/16; A61P 3/10; A61P 37/02; A61P 9/00; A61P 25/00; A61P 25/28; A61P 35/00; A61P 35/02
See application file for complete search history.

(56) References Cited

U.S. PATENT DOCUMENTS

| 9,186,318 B2 | 11/2015 | Yun et al. |
| 2004/0053908 A1 | 3/2004 | Funahashi et al. |
| 2007/0027184 A1 | 2/2007 | Malecha et al. |

(Continued)

FOREIGN PATENT DOCUMENTS

| AU | 2011377440 A1 | 5/2014 |
| CN | 101024627 A | 8/2007 |
| CN | 102408411 A | 4/2012 |

(Continued)

OTHER PUBLICATIONS

1st Examiner Report issued on Nov. 4, 2022 for Australian Patent Application No. 2020255702 (2 pages).

(Continued)

*Primary Examiner* — Bruck Kifle
(74) *Attorney, Agent, or Firm* — Fox Rothschild LLP

(57) ABSTRACT

Provided is a quinolyl-containing compound as shown in general formula (I) or (II) or a pharmaceutically acceptable salt, a solvate, an active metabolite, a polymorph, an isotopic label, or an isomer thereof, and further provided are a pharmaceutical composition comprising the compound and use of the compound and the pharmaceutical composition. The provided compound has a dual molecule function, can serve as multi-target inhibitors of novel tyrosine kinase/histone deacetylase, can simultaneously achieve the effect of two inhibitors, has excellent biological activity and pharmacokinetic properties, and has the application potential particularly in the field of treatment of tumors.

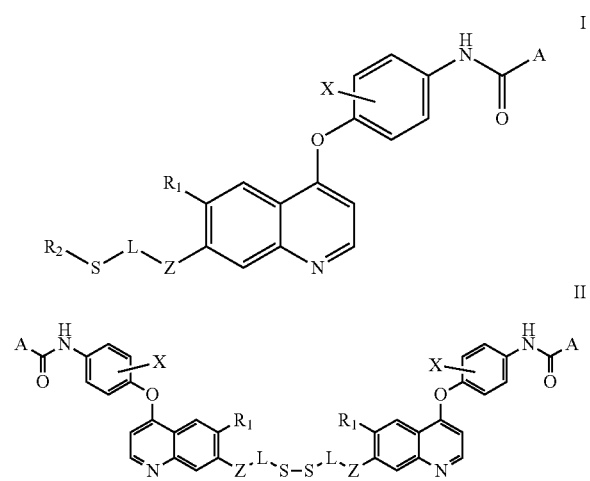

10 Claims, No Drawings

(56) References Cited

U.S. PATENT DOCUMENTS

2019/0256470 A1  8/2019  Zhang et al.

FOREIGN PATENT DOCUMENTS

| | | | | |
|---|---|---|---|---|
| CN | 105131802 | A | 12/2015 | |
| EP | 2769976 | A1 | 8/2014 | |
| JP | WO9717329 | * | 5/1997 | ........... C07D 215/20 |
| JP | 2002032872 | A | 1/2002 | |
| JP | 2014517831 | A | 7/2014 | |
| JP | 2014526522 | A | 10/2014 | |
| KR | 20140069188 | A | 6/2014 | |
| RU | 2497809 | C2 | 11/2013 | |
| RU | 2573633 | C2 | 1/2016 | |
| WO | 2007016354 | A1 | 2/2007 | |
| WO | 2010017272 | A2 | 2/2010 | |
| WO | 2018072614 | A1 | 4/2018 | |
| WO | 2018226542 | A1 | 12/2018 | |

OTHER PUBLICATIONS

Suzuki et al., "Molecularly Targeted Approach to Cancer Therapy: Design, Synthesis and Biological Activity of Non-hydroxamate Histone Deacetylase Inhibitors," Society of Synthetic Organic Chemistry, Japan (2005); 63(10): pp. 1004-1015.

Suzuki et al., "Non-hydroxamate Histone Deacetylase Inhibitors," Current Medicinal Chemistry (2005); 12(24): pp. 2867-2880.

Notice of Reasons for Refusal issued on Oct. 27, 2022 for Japanese Patent Application No. 2021-558869 (25 pages).

Segretti et al., "Thiol-Based Potent and Selective HDAC6 Inhibitors Promote Tubulin Acetylation and T-Regulatory Cell Suppressive Function," ACS Medicinal Chemistry Letters (2015); 6: pp. 1156-1161.

Kalin et al., "Chiral Mercaptoacetamides Display Enantioselective Inhibition of Histone Deacetylase 6 and Exhibit Neuroprotection in Certical Neuron Models of Oxidative Stress," ChemMedChem (2012); 7: pp. 425-439.

Gupta et al., "Inhibitors selective for HDAC6 in enzymes and cells," Bioorganic & Medicinal Chemistry Letters (2010); 20: pp. 7067-7070.

Wen et al., "Novel thiol-based histone deacetylase inhibitors bearing 3-phenyl-1H-pyrazole-5-carboxamide scaffold as surface recognition motif: Design, synthesis, and SAR study," Bioorganic & Medicinal Chemistry Letters (2015); 26: pp. 375-379.

Anandan et al., "Mercaptoamide-based non-hydroxamic acid type histone deacetylase inhibitors," Bioorganic & Medicinal Chemistry Letters (2005); 15: pp. 1969-1972.

Extended European Search Report issued on Dec. 13, 2022 for European Patent Application No. 20783185.0 (14 pages).

Dyson et al., "Chemistry of Synthetic Drugs," MIR (1964): pp. 12-19.

Byelikov, "Relationship Between the Structure of Substance Molecules and Their Action on the Organism," Pharmaceutical Chemistry (1993): pp. 43-47.

Belikov, "Pharmaceutical Chemistry," MEDpress-inform (2007): pp. 27-29.

Gusev, "Protein kinases: structure, classification, properties and biological role," Soros Educational Journal (2000); 6 (12): pp. 4-12.

Kozlov et al., "Selective Inhibitor of Histone Deacetylase 6 (Tubastatin A) Suppresses Prolifereation of Hepatitus C Virus Replicon in Culture of Human Hepatocytes," Biochemistry (Moscow) (2014); 79(7): pp. 637-642.

Zhulenko et al., "Pharmacology," KolosS (2008): pp. 34-35.

Kharkevich, "Pharmacology," GEOTAR-Media (2010): pp. 73-74.

2nd Office Action issued on Nov. 28, 2022 for Russian Patent Application No. 2021131689/04(067195) (11 pages).

Ba, "Stereostructural Selectivity Of Drug Effects And Metabolism," Basic Medicine—Molecular Pharmacology. Chapter 14 (1999); pp. 299-302, ISBN 7-5388-3483-4/R729.

Zefirova et al., "On the history of the emergence and development of the concept of bioisosterism," Bulletin of Moscow Univeresity, Series 2. Chemistry (2002); 43(4): pp. 251-256.

1st Office Action issued on Jun. 29, 2022 for Russian Patent Application No. 2021131689/04(067195) (19 pages).

Heider et al., "Histone deacetylase inhibitors reduce VEGF production and induce growth suppression and apoptosis in human mantle cell lymphoma," Eur J Haematol (2005); 76(1): 42-50.

* cited by examiner

QUINOLYL-CONTAINING COMPOUND AND PHARMACEUTICAL COMPOSITION, AND USE THEREOF

CROSS REFERENCE TO RELATED APPLICATIONS

The present application is a U.S. national phase of International Patent Application No. PCT/CN2020/082041 filed on Mar. 30, 2020, which is based upon and claims priority to Chinese Patent Application No. 201910266681.9 filed on Apr. 3, 2019.

TECHNICAL FIELD

The disclosure relates to pharmaceutical technical field, in particular to a quinolinyl-containing compound, a pharmaceutical composition and use thereof.

BACKGROUND ART

Vascular endothelial growth factor receptor (VEGFR) is a member of tyrosine kinase receptor family. It produces a series of biochemical and physiological process and ultimately promotes the formation of new blood vessels through binding to its ligand, vascular endothelial growth factor (VEGF). In normal blood vessels, angiogenesis factors and angiogenesis inhibitors maintain a balance. In the process of tumor growth, the high expression of VEGFR and VEGF disrupts this balance and promotes the formation of tumor new blood vessels. Studies have shown that the high specific expression of receptor and the formation of new blood vessels are prerequisites for tumor growth. The growth and metastasis of malignant tumors must be supported by adequate nutrition and excrete waste provided by surrounding new blood vessels. Therefore, high expression of VEGFR and VEGF is closely related to the density of microvessels and tumor proliferation and metastasis. Since VEGFR-2 is mainly distributed in vascular endothelial cells, it may directly and indirectly inhibit tumor growth and metastasis without affecting normal cells by blocking the activity of VEGFR to achieve an ideal anti-tumor effect. At present, a number of VEGFR inhibitors have been approved by FDA for the treatment of tumors. The marketed small molecule inhibitors of VEGFR include Cabozantinib (XL184, BMS-907351), sunitinib, sorafenib and vandetanib (ZD6474). There are about twenty VEGFR small molecule inhibitors that have entered clinical trial phase, of which vatalanib (PTK787/ZK222584), AMG-706, pazopanib and so on. Looking for small molecule inhibitors with high activity against VEGFR-2 has become a research hotspot in the field of tumor therapy.

Histone deacetylases (HDACs) are also closely related to the occurrence of tumors. Their inhibitors can lower the threshold of tumor cell apoptosis, have extensive anti-tumor activity, and may be used in combination with a variety of anti-tumor drugs. Human histone deacetylases are divided into four categories: the first category includes HDAC1, HDAC2, HDAC3 and HDAC8; the second category is HDAC4, HDAC5, HDAC7 and HDAC9; HDAC6 and HDAC10 contain two catalytic sites and are classified as IIa; HDAC11 belongs to Class IV, and its catalytic center contains amino acid residues common to HDACs of Class I and Class II, having zinc ions in the catalytic sites of all the eleven HDAC subtypes. HDAC inhibitors have a long history as mood stabilizers and antiepileptic drugs in psychiatry and neurology. They are used in the treatment of neurodegenerative diseases, such as Alzheimer's disease, Huntington's disease, and Parkinson's disease. Another major application of HDAC inhibitors is as anticancer drugs. At present, two HDAC inhibitors have been approved by FDA for the treatment of skin T-cell lymphoma, namely Vorinostat (SAHA) and Romidepsin (FK228). There are many other HDAC inhibitors such as PXD-101 (Phase II), LBH589 (Phase III), MS-275 (Phase II), etc., which are in the clinical trial phase.

The results of a phase I clinical trial published in *J. Clin. Oncol.* a top international clinical oncology journal, showed that HDAC inhibitors can effectively reverse the resistance of patients with advanced solid tumors to VEGFR inhibitors. Although combination drugs can effectively overcome the problems of insensitivity and drug resistance to single-target drugs caused by tumor cell heterogeneity and adaptability, there are also problems such as differences in pharmacokinetic properties between different drugs, adverse drug-drug interactions, and poor patient compliance. The development of multi-target anti-cancer drugs is expected to overcome the above-mentioned shortcomings of drug combination while solving the problem of tumor insensitivity and drug resistance to single-target drugs.

SUMMARY

In one aspect, the disclosure provides a novel quinolinyl-containing compound or a pharmaceutically acceptable salt, solvate, active metabolite, polymorph, isotopically labelled compound, isomer or prodrug thereof, may be used as a tyrosine kinase inhibitor and/or histone deacetylase inhibitor.

In another aspect, the disclosure provides a pharmaceutical composition.

In another aspect, the disclosure provides use of the above compound or a pharmaceutically acceptable salt, solvate, active metabolite, polymorph, isotopically labelled compound, isomer or prodrug thereof.

The present disclosure provides a quinolinyl-containing compound represented by general formula (I) or (II) or a pharmaceutically acceptable salt, solvate, active metabolite, polymorph, isotopically labelled compound or isomer,

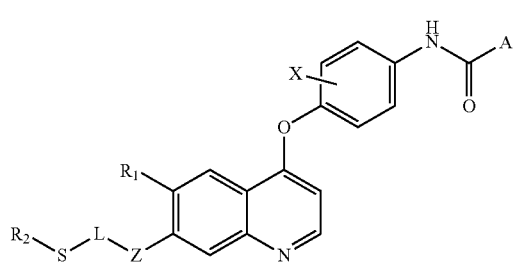

I

-continued

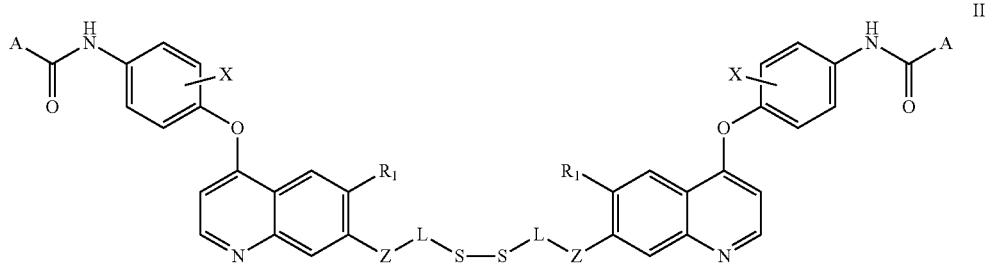

wherein,
A represents

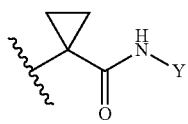

or —NR$_3$R$_4$;
X represents hydrogen, halogen or substituted or unsubstituted C$_{1-8}$ alkyl;
Y represents a substituted or unsubstituted C$_{3-8}$ cycloalkyl, C$_{3-8}$ heterocyclyl, C$_{6-20}$ aryl group or C$_{2-20}$ heteroaryl;
Z represents —O— or —S—;
L represents linear —(CH$_2$)$_n$—, n represents an integer from 3 to 10, wherein optionally one or more —CH$_2$— are replaced with one or more of —NR$_5$—, —(CO)—, —(CS)—, and —CR$_5$R$_6$—, and/or optionally one or more of —CH$_2$CH$_2$— may be replaced with —CH=CH—;
R$_1$ represents C$_{1-6}$ alkoxy, C$_{1-6}$ alkylsulfanyl or —(CO)NR$_7$R$_8$;
R$_2$ represents substituted or unsubstituted hydrogen, C$_{1-8}$ alkyl, C$_{1-8}$ alkoxy, C$_{1-8}$ alkylsulfanyl, C$_{1-8}$ haloalkyl, C$_{3-8}$ cycloalkyl, C$_{3-8}$ heterocyclyl, C$_{6-20}$ aryl, C$_{2-20}$ heteroaryl, —(CO)R$_9$, —(CS)R$_9$, or R$_2$ is connected with one of —CH$_2$— in the L groups, so that R$_2$, S and —CH$_2$— together form C$_{3-8}$ heterocyclic group or C$_{2-20}$ heteroaryl group;
R$_3$ and R$_4$ independently represent substituted or unsubstituted hydrogen, C$_{1-8}$ alkyl, C$_{1-8}$ alkoxyl, C$_{1-8}$ alkylsulfanyl, C$_{1-8}$ haloalkyl, C$_{3-8}$ cycloalkyl, C$_{3-8}$ heterocyclyl, C$_{6-20}$ aryl or C$_{2-20}$ heteroaryl;
R$_5$ and R$_6$ independently represent substituted or unsubstituted hydrogen, C$_{1-8}$ alkyl, C$_{1-8}$ alkoxyl, C$_{1-8}$ alkylsulfanyl, C$_{1-8}$ haloalkyl, hydroxyl, mercapto, carboxyl, amino or cyano;
R$_7$ and R$_8$ independently represent substituted or unsubstituted hydrogen or C$_{1-8}$ alkyl;
R$_9$ represents substituted or unsubstituted C$_{1-8}$ alkyl, C$_{1-8}$ alkoxyl, C$_{1-8}$ alkylsulfanyl, C$_{1-8}$ haloalkyl, C$_{1-6}$ alkylsulfonyl, C$_{1-6}$ alkylamino, C$_{3-8}$ cycloalkyl, C$_{3-8}$ heterocyclyl, C$_{6-20}$ aryl, C$_{2-20}$ heteroaryl, C$_{1-6}$ alkylene C$_{3-8}$ cycloalkyl, C$_{1-6}$ alkylene C$_{3-8}$ heterocyclyl, C$_{1-6}$ alkylene C$_{6-20}$ aryl, C$_{1-6}$ alkylene C$_{2-20}$ heteroaryl, hydroxyl, mercapto, nitro, amino, cyano, or R$_9$ is connected with anyone of —CH$_2$— in the L group, so that —(CO)R$_9$ or —(CS)R$_9$ together with S, —CH$_2$— forms C$_{3-8}$ heterocyclyl or C$_{2-20}$ heteroaryl;

The substituents of the above groups may be selected from halogen, C$_{1-8}$ alkyl, C$_{2-8}$ alkenyl, C$_{2-8}$ alkynyl, C$_{1-8}$ haloalkyl, C$_{1-8}$ alkoxyl, C$_{1-8}$ alkylsulfanyl, C$_{3-8}$ cycloalkyl, C$_{3-8}$ heterocyclyl, C$_{6-20}$ aryl, C$_{2-20}$ heteroaryl, C$_{1-6}$ alkyl ester group, C$_{1-6}$ alkyl acyl, C$_{1-6}$ alkylamino, C$_{1-6}$ alkylsufonyl, amino, hydroxyl, mercapto, carboxyl, nitro, amido, or cyano.

In the above general formula (I) or (II), the groups represented by X, Y, Z, L, R$_1$ to R$_9$ and their optional substituents include but are not limited to: Hydrogen may be expressed as —H, and may also be replaced with deuterium or tritium.

Halogen may include fluorine, chlorine, bromine, and iodine.

C$_{1-8}$ alkyl may include methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-Pentyl, 4-methyl-1-pentyl, 2-methyl-2-pentyl, 3-methyl-2-pentyl, 4-methyl-2-pentyl, 2,2-dimethyl Base-1-butyl, 3,3-dimethyl-1-butyl, 2-ethyl-1-butyl, n-butyl, isobutyl, sec-butyl, tert-butyl, n-pentyl, isoamyl, neopentyl, tert-amyl, hexyl, heptyl, octyl, etc.

C$_{1-8}$ alkoxy may be represented as —O—C$_{1-8}$ alkyl, wherein the C$_{1-8}$ alkyl includes the groups as defined above; for example, the C1-8 alkoxy include methoxy, ethoxy, n-propoxy, isopropoxy, n-butoxy, isobutoxy, sec-butoxy, tert-butoxy, etc.

C$_{1-8}$ alkylsulfanyl may be represented as —S—C$_{1-8}$ alkyl, wherein the C$_{1-8}$ alkyl includes the groups as defined above; for example, the C$_{1-8}$ alkylsulfanyl may include methylsulfanyl, ethylsulfanyl, etc.

C$_{1-8}$ haloalkyl may be represented as a group in which any number of hydrogen atoms in the C$_{1-8}$ alkyl is substituted by halogen, wherein the groups included in C$_{1-8}$ alkyl and in halogen are as listed above; for example, C$_{1-8}$ haloalkyl may include —CF$_3$.

C$_{1-6}$ alkylene is a divalent functional group with two substitutable bonds, which may include linear alkylene and branched alkylene, and linear alkylene may be expressed as —(CH$_2$)$_m$—, m represents 1 to 6, and may include, for example, methylene, ethylene, etc.

C$_{3-8}$ cycloalkyl may be expressed as a non-aromatic saturated carbocyclic ring, including single-carbon ring (with one ring) and bi-carbon ring (with two rings). For example, C$_{3-8}$ cycloalkyl may include

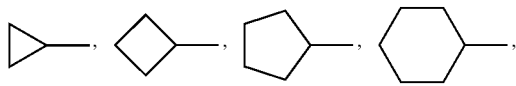

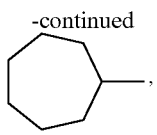

or the like.

$C_{3-8}$ heterocyclic group may be represented as a group obtained by replacing any number of ring atoms in $C_{3-8}$ cycloalkyl with heteroatoms such as O, S, N, P, Si, etc, wherein $C_{3-8}$ cycloalkyl includes those defined as above. For example, $C_{3-8}$ heterocyclic group may include oxiranyl, sulfiethanyl, azaethyl, azetidinyl, oxbutanyl, thibutyryl, tetrahydrofuranyl, pyrrolidinyl, oxazolidinyl, tetrahydropyrazolyl, pyrrolinyl, dihydrofuranyl, dihydrothienyl, piperidinyl, tetrahydropyranyl, tetrahydrothiopyranyl, morpholinyl, piperazinyl, dihydropyridinyl, tetrahydropyranyl, dihydropyranyl, tetrahydropyranyl, dihydrothiopyranyl, azacycloheptyl, oxacycloheptyl, thiacycloheptyl, oxaaza bicyclo[2.2.1]heptyl, azaspiro[3.3]heptyl, etc.

$C_{6-20}$ aryl may include a monocyclic aryl group, a bicyclic aryl group, or a multi-ring aryl group. For example, it may include phenyl, biphenyl, naphthyl, phenanthryl, anthryl, azulenyl, and the like.

$C_{2-20}$ heteroaryl may represent an unsaturated group containing any number of heteroatoms such as O, S, N, P, and Si as ring atoms. The number of carbon atoms in heteroaryl may be 2-20, for example, 2, 3, 4, 5, 6, 7, 8, 9, 10, or more than 10. For example, $C_{2-20}$ heteroaryl may include pyrrolyl, furyl, thienyl, imidazolyl, oxazolyl, pyrazolyl, pyridyl, pyrimidinyl, pyrazinyl, quinolinyl, isoquinolinyl, tetrazolyl, triazolyl, triazinyl, benzofuranyl, benzothienyl, indolyl, isoindolyl, etc.

Hydroxyl may be expressed as —OH.
Mercapto may be represented as —SH.
Nitro may be expressed as —$NO_2$.
Cyano may be represented as —CN.

The carboxyl group may be expressed as —COOH, and the H of the carboxyl group may also be substituted by a substituent to form the corresponding ester group, which may be expressed as —$COOR_a$. $R_a$ may be the substituents described in the general formula (I), for example, an ester group substituted by $C_{1-8}$ alkyl may be represented as —$COOC_{1-8}$ alkyl group, and the $C_{1-8}$ alkyl group is as defined above.

Preferably, the ester group is a $C_{1-6}$ alkyl ester group, and the $C_{1-6}$ alkyl group may include all groups with carbon atoms of 1-6 in the aforementioned definition of "$C_{1-8}$ alkyl".

The sulfonyl group may be represented as —$S(O)_2R_a$, $R_a$ may be the substituents described in the general formula (I). For example, a sulfonyl group substituted with a $C_{1-8}$ alkyl group may be represented as —$S(O)_2 C_{1-8}$ alkyl, wherein the $C_{1-8}$ alkyl is as defined above.

Preferably, the sulfonyl group is $C_{1-6}$ alkylsufonyl, and the $C_{1-6}$ alkyl group may include all groups with carbon atoms of 1 to 6 in the aforementioned definition of "$C_{1-8}$ alkyl".

The acyl group may be represented as —$COR_a$, $R_a$ may be the substituents described in the general formula (I). For example, an acyl group substituted with a $C_{1-8}$ alkyl group may be represented as —$COC_{1-8}$ alkyl, wherein the $C_{1-8}$ alkyl is as defined above.

Preferably, the acyl group is $C_{1-6}$ alkylacyl, and the $C_{1-6}$ alkyl group may include all groups with carbon atoms of 1 to 6 in the aforementioned definition of "$C_{1-8}$ alkyl".

An amino group may be represented as —$NH_2$, —$NHR_a$ or —$N(R_a)_2$, and $R_a$ may be the substituents described in the general formula (I). For example, an amino group substituted with a $C_{1-8}$ alkyl group may be represented as —$NHC_{1-8}$ alkyl or —$N(C_{1-8}$ alkyl$)_2$, wherein the $C_{1-8}$ alkyl is as defined above.

Preferably, the amino group is $C_{1-6}$ alkylamino, and the $C_{1-6}$ alkyl group may include all groups with carbon atoms of 1 to 6 in the aforementioned definition of "$C_{1-8}$ alkyl".

In the amido group, the amino group is as defined above.

In the foregoing definitions, when the number of carbon atoms changes, the above definitions only change according to the change in the number of carbon atoms, and does not affect the definition of the group type. For example, "$C_{1-6}$ alkyl" may include all groups meeting number of carbon atoms of 1 to 6 in the definition of "$C_{1-8}$ alkyl", such as methyl, ethyl, and n-propyl, isopropyl, n-butyl, isobutyl, sec-butyl, tert-butyl, n-pentyl, isopentyl, neopentyl, and n-hexyl etc. "$C_{1-4}$ alkyl" may include all groups meeting number of carbon atoms of 1 to 4 in the definition of "$C_{1-8}$ alkyl", such as methyl, ethyl, and n-propyl, isopropyl, n-butyl, isobutyl, sec-butyl, and tert-butyl.

In the foregoing definitions, the atoms in each group, such as C, H, O, N, S, etc., may be independently replaced with their isotopes. For example, hydrogen may be replaced with deuterium, tritium, etc., and $C_{1-8}$ alkyl may be replace with deuterated $C_{1-8}$ alkyl, including but not limited to deuterated methyl, deuterated ethyl, deuterated n-propyl, deuterated isopropyl, deuterated n-butyl, deuterated isobutyl, deuterated sec-butyl Base, deuterated tert-butyl, etc.

Furthermore, in the above formula (1), the substituents of the groups include but are not limited to: hydrogen, deuterium, fluorine, chlorine, bromine, methyl, ethyl, propyl, isopropyl, n-butyl, sec-butyl, tert-butyl, methoxy, ethoxy, propoxy, isopropoxy, —CN, —$CF_3$, —$NH_2$, —$NH(C_{1-4}$ alkyl), —$N(C_{1-4}$ alkyl$)_2$, —$CO_2C_{1-4}$ alkyl, —$CO_2H$, —NHC(O)$C_{1-4}$ alkyl, —$SO_2C_{1-4}$alkyl, —C(O)$NH_2$, —C(O)NH($C_{1-4}$alkyl), —C(O)N($C_{1-4}$alkyl$)_2$, cyclopropyl, cyclobutyl, cyclopentyl, cyclohexyl, pyrrolidinyl, pyrazolyl, piperidinyl, pyridyl, piperazinyl, triazinyl, furanyl, thiofuranyl, morpholinyl, thiomorpholinyl, phenyl, naphthyl, diphenyl, terphenyl, etc.

In some embodiments according to the disclosure, the general formula (I) or (II) is represented by the following formula (I-1), (I-2), (II-1) or (II-2):

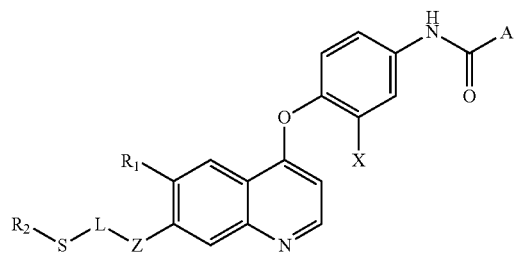

I-1

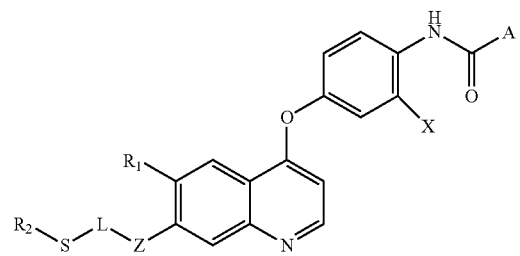

I-2

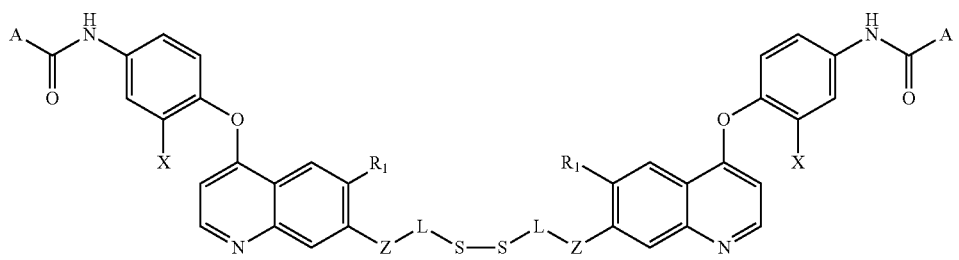

II-1

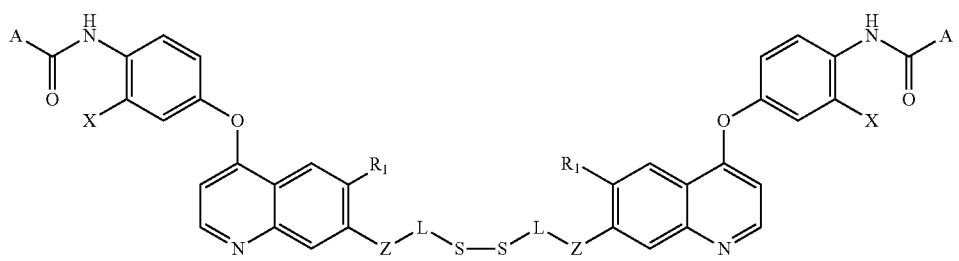

II-2 wherein, X represents hydrogen, F or Cl.

In some embodiments according to the disclosure, the symbol "A" represents one of the following groups:

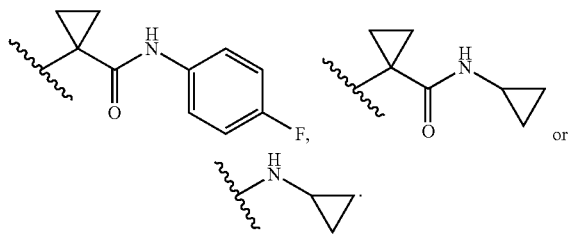

In some embodiments according to the disclosure, the symbol "L" represents one of the following groups: —CH$_2$—CO—NH—(CH$_2$)$_p$—*, p represents an integer from 3 to 6, and one or more of —CH$_2$CH$_2$— may optionally replaced with —CH=CH—, and "*" means the end connected to the group "Z"; or linear —(CH$_2$)$_o$—, "o" represents an integer from 5 to 7, and one or more of —CH$_2$CH$_2$— may optionally replaced with —CH=CH—.

In some embodiments according to the disclosure, the symbol "L" represents one of the following groups:
*—CH$_2$CH=CH(CH$_2$)$_q$—, *—(CH$_2$)$_2$CH=CH(CH$_2$)$_q$— or *—(CH$_2$)$_3$CH=CH(CH$_2$)$_q$—, q represents an integer from 1 to 4, where the "*" represents the end connected to the Z group.

In some embodiments according to the disclosure, R$_1$ represents C$_{1-4}$ alkoxyl (for example, methoxy or etheoxy) or —(CO)NH$_2$.

In some embodiments according to the disclosure, when R$_2$ is connected to a —CH$_2$— in the L group, so that R$_2$, S, —CH$_2$— together form a C$_{3-8}$ heterocyclyl or C$_{2-20}$ heteroaryl, the heterocyclyl or heteroaryl may also contain heteroatoms other than S, such as O, N, S, etc.; preferably, the structure formed is a heterocyclyl or heteroaryl containing 4 to 8 ring atoms.

In some embodiments according to the disclosure, R$_2$ represents substituted or unsubstituted hydrogen, C$_{1-4}$ alkyl, or —(CO)R$_9$. R$_9$ represents substituted or unsubstituted C$_{1-4}$ alkyl, C$_{1-4}$ alkoxyl, C$_{1-4}$ haloalkyl, C$_{3-6}$ cycloalkyl, C$_{3-6}$ heterocyclyl, C$_{6-12}$ aryl, C$_{3-12}$ heteroaryl, C$_{1-4}$ alkylene C$_{3-6}$ cycloalkyl, C$_{1-4}$ alkylene C$_{3-6}$ heterocyclyl, C$_{1-4}$ alkylene C$_{6-12}$ aryl, C$_{1-4}$ alkylene C$_{3-12}$ heteroaryl, hydroxyl, mercapto, nitro, amino or cyano; and the substituents, if any, is selected from F, Cl, Br, methyl, ethyl, n-propyl, isopropyl, —NH$_2$, hydroxyl, carboxyl, mercapto or cyano;

Preferably, R$_9$ represents substituted or unsubstituted methyl, ethyl, n-propyl, isopropyl, n-butyl, isobutyl, sec-butyl, tert-butyl, methoxy, ethoxy, methylthio, —(CH$_2$)$_m$—C$_{3-6}$ heterocyclyl, —(CH$_2$)$_m$—C$_{3-12}$ heteroaryl, phenyl, naphthyl or biphenyl, and m represents an integer of 1 to 3; more preferably, the ring atoms of heterocyclyl and heteroaryl contain at least one N atom.

In some embodiments according to the disclosure, when R$_9$ is connected to a —CH$_2$— in the L group, so that —(CO)R$_9$ or —(CS)R$_9$ and S, —CH$_2$— together form a C$_{3-8}$ heterocyclyl or C$_{2-20}$ heteroaryl, the heterocyclyl or heteroaryl may also contain heteroatoms other than S, such as O, N, S, etc.; preferably, the structure formed is a heterocyclyl or heteroaryl containing 4 to 8 ring atoms.

In some embodiments according to the disclosure, the compound of the disclosure is selected from the following:

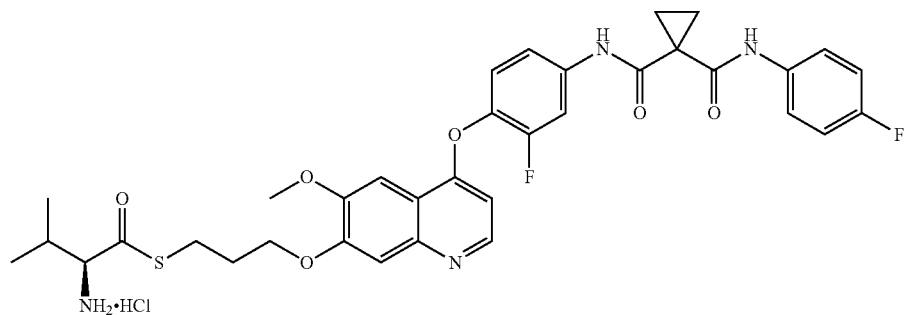
1
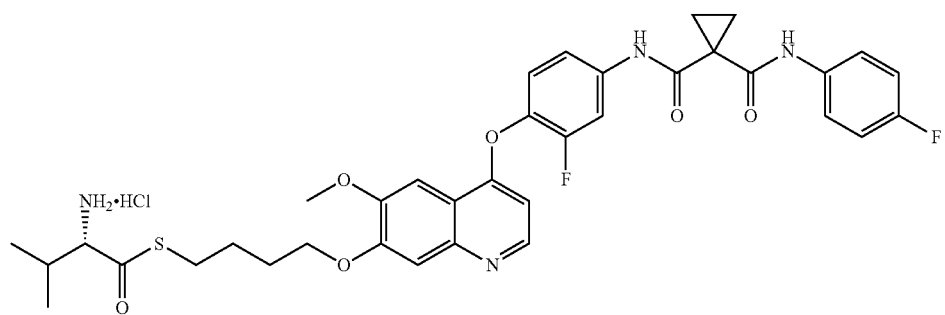
2
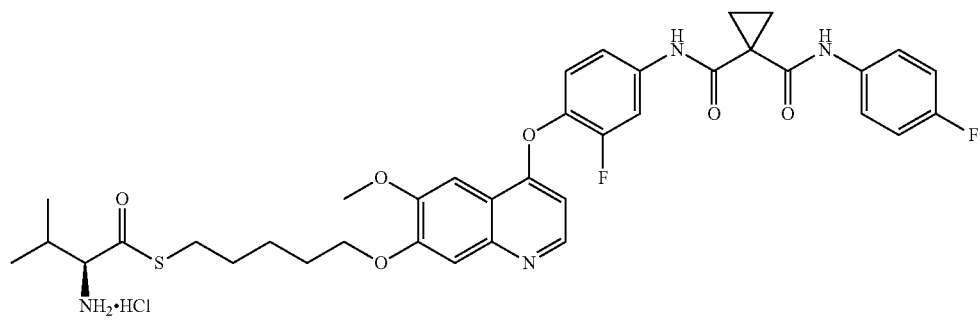
3
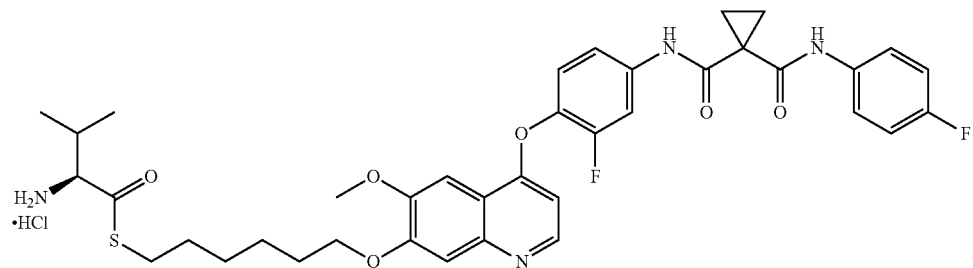
4
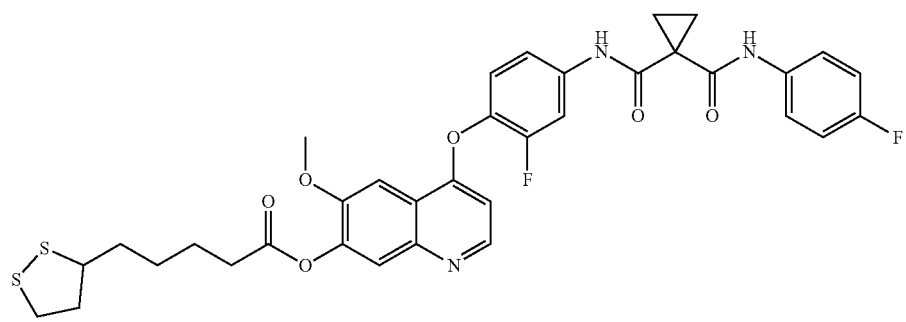
5

-continued
6
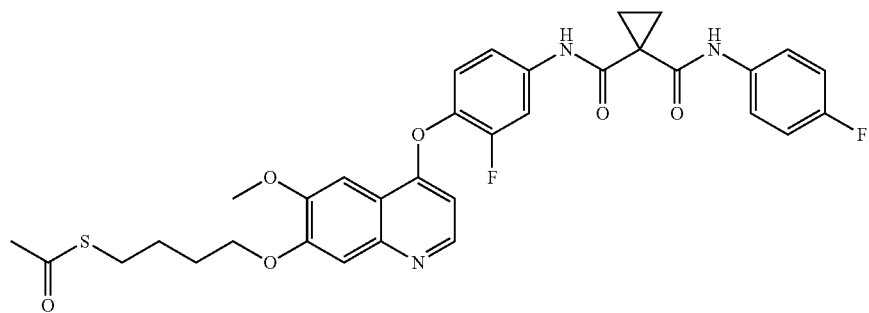
7
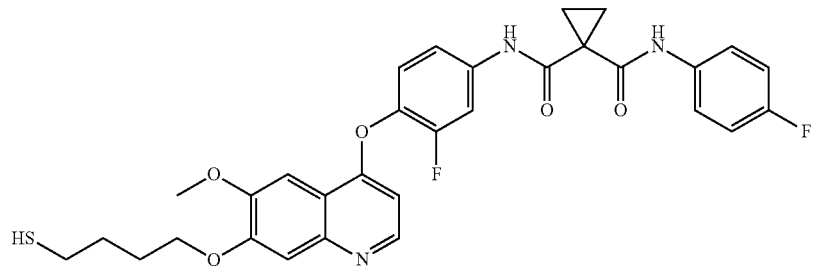
8
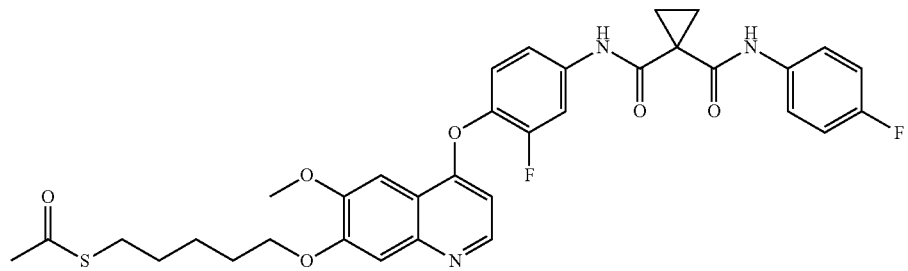
9
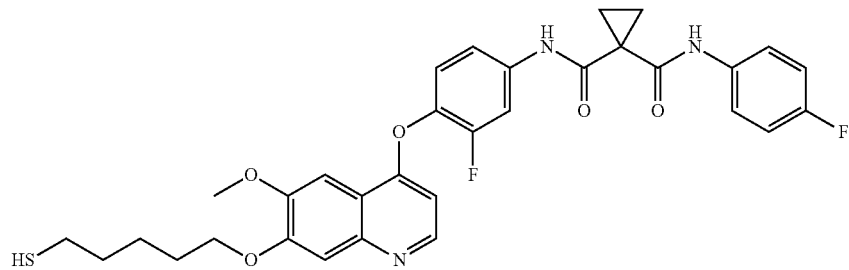
10
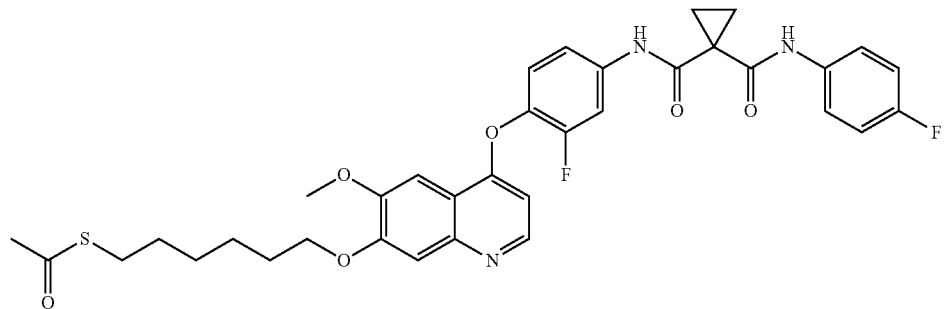

11
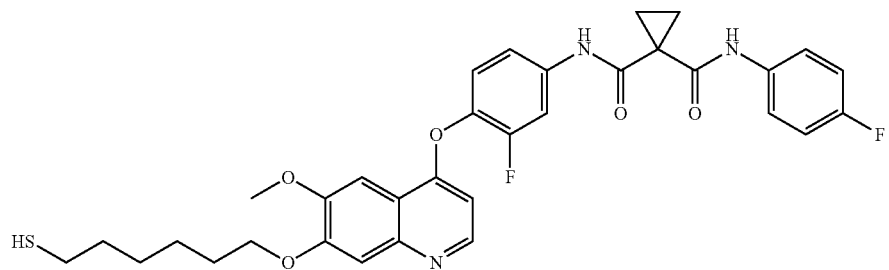
12
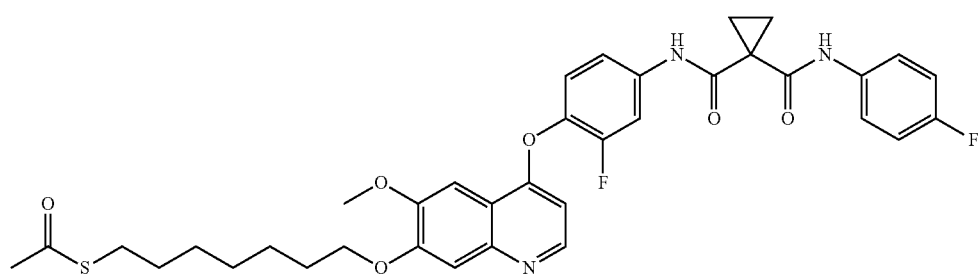
13
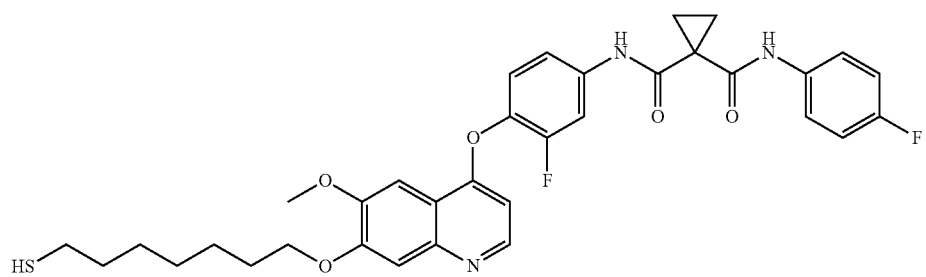
14
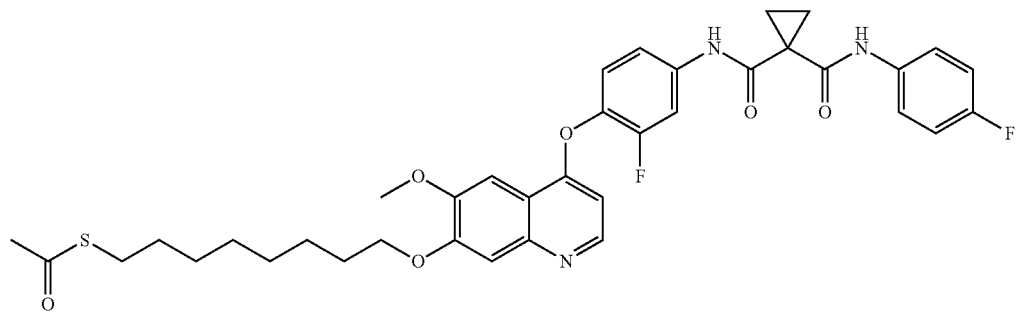
15
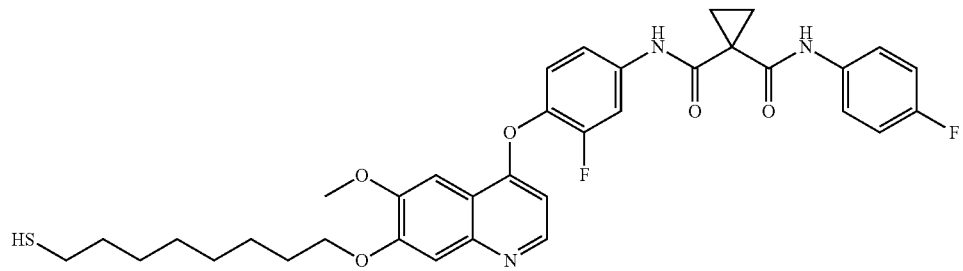

16
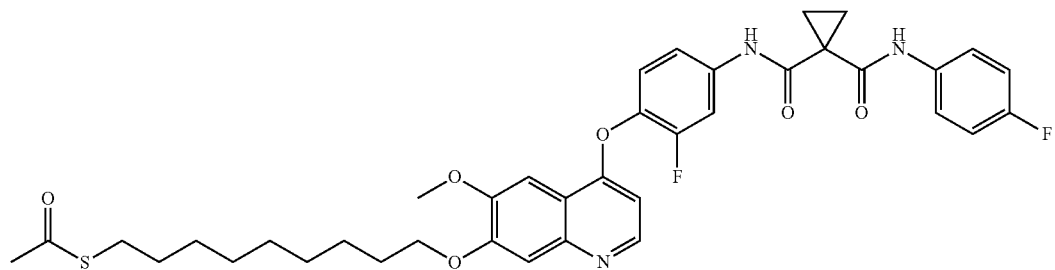
17
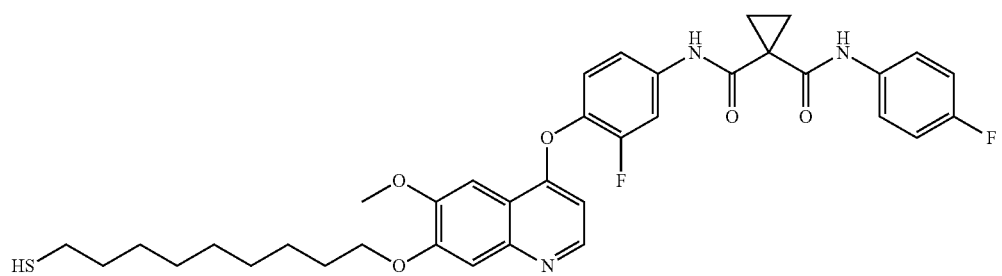
18
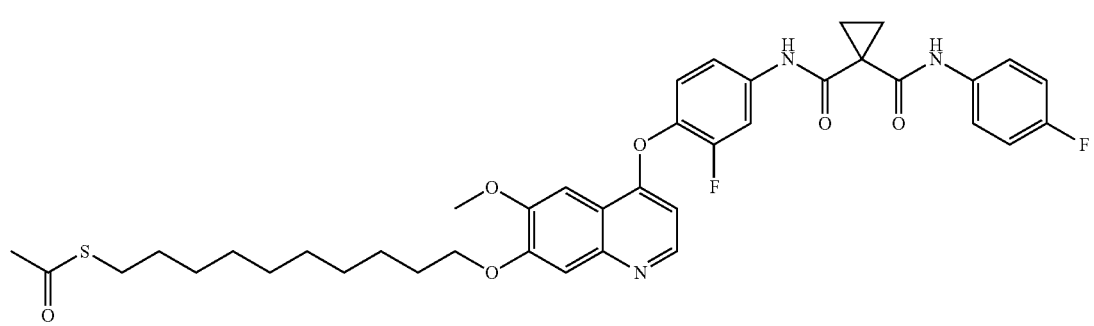
19
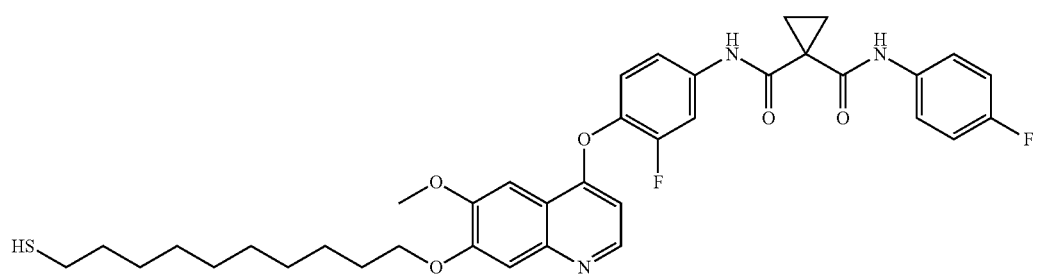
20
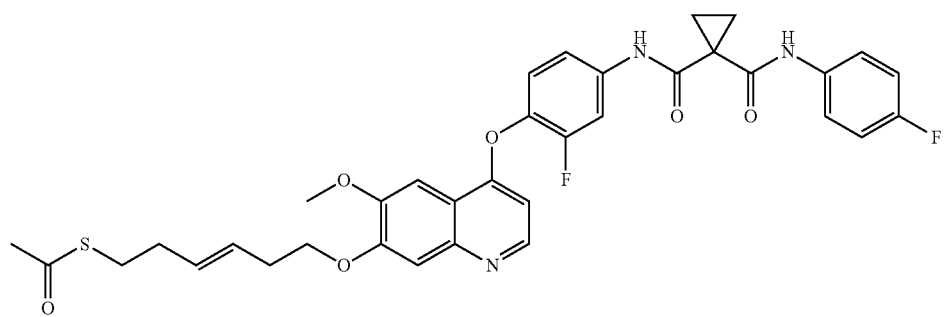

21
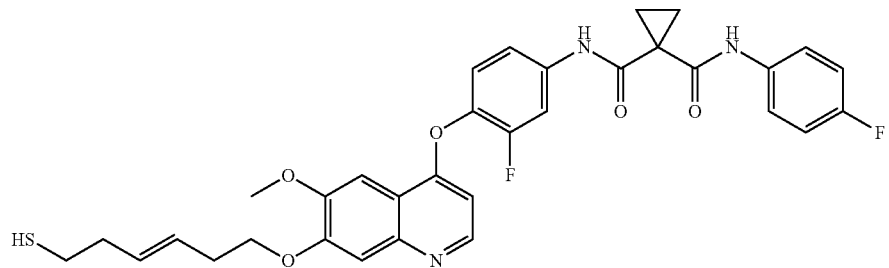
22
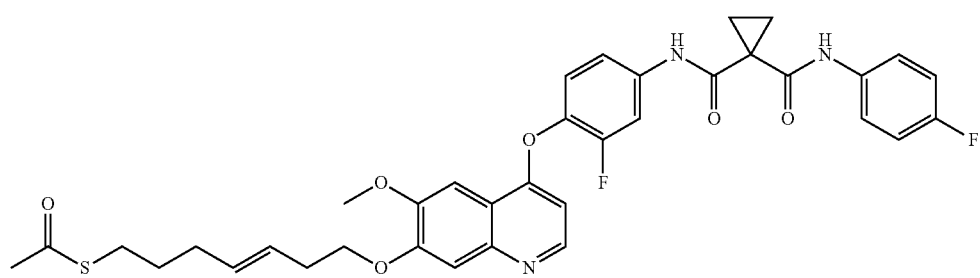
23
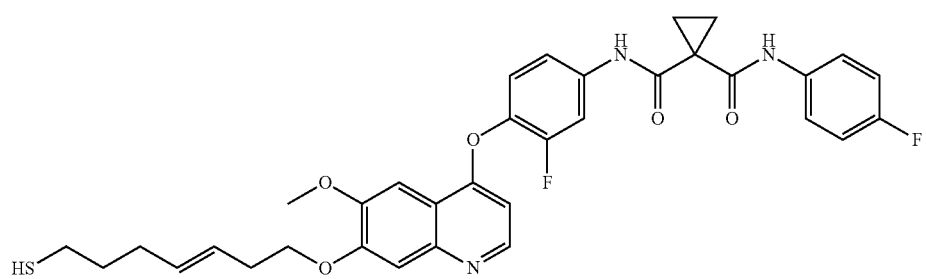
24
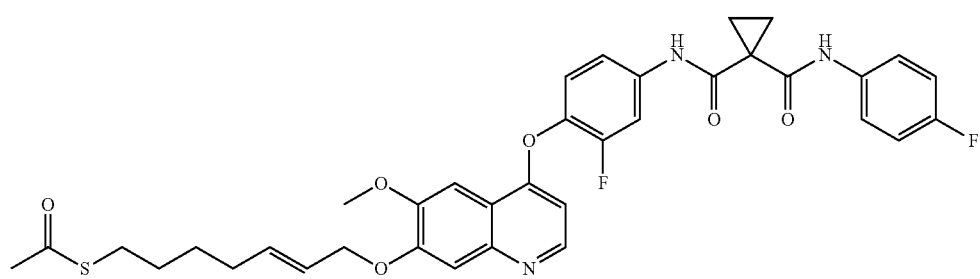
25
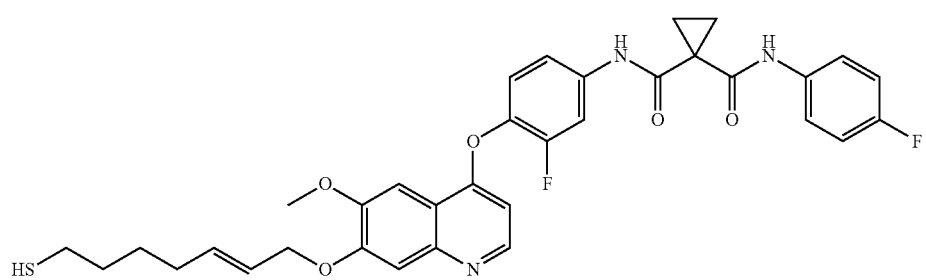

26
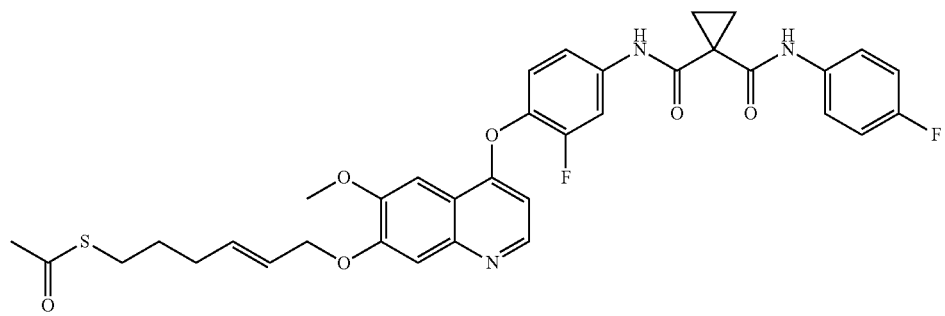
27
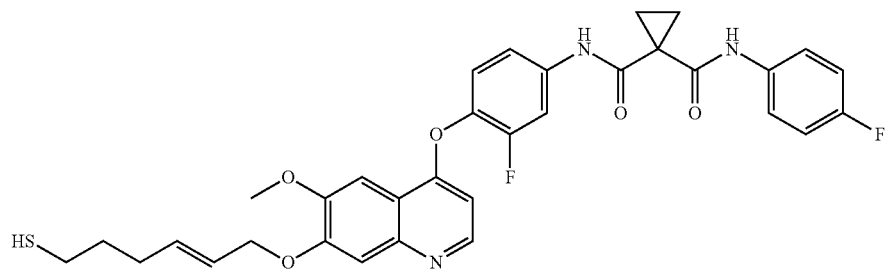
28
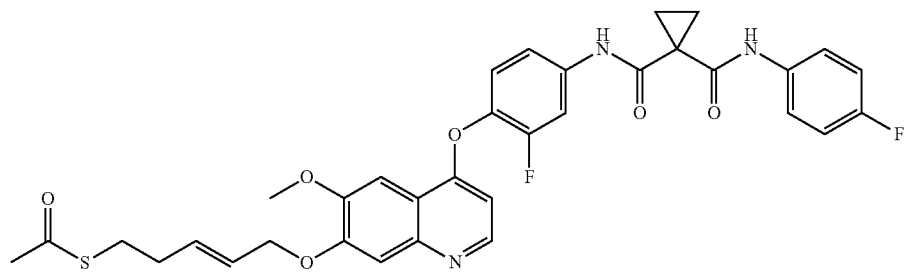
29
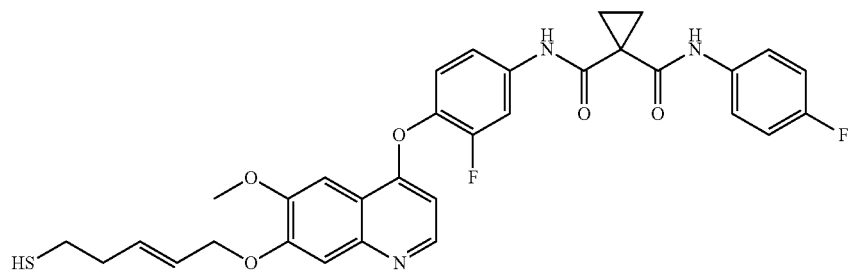
30
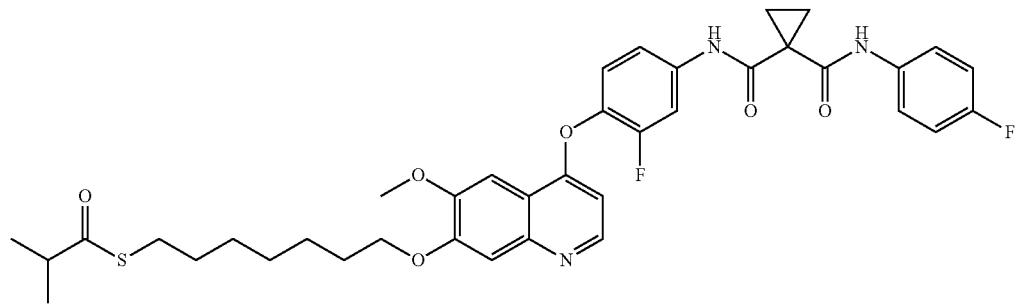

-continued
31
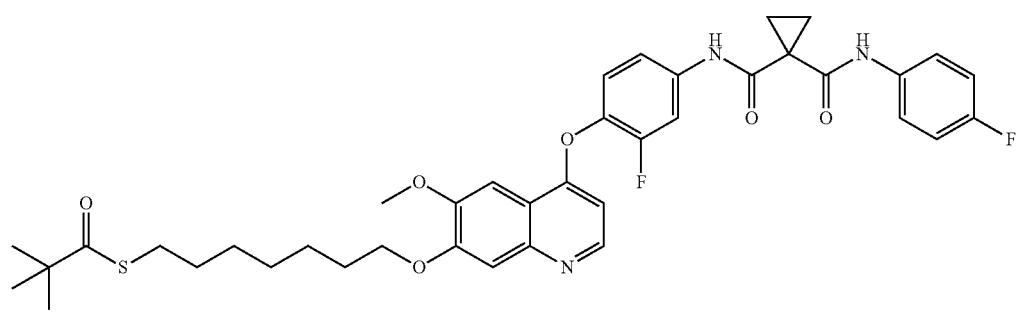
32
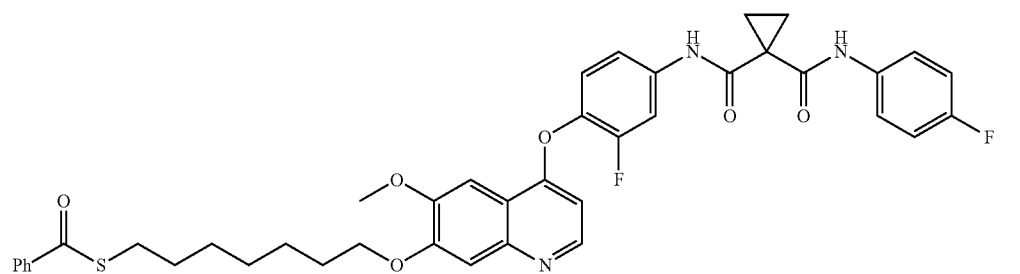
33
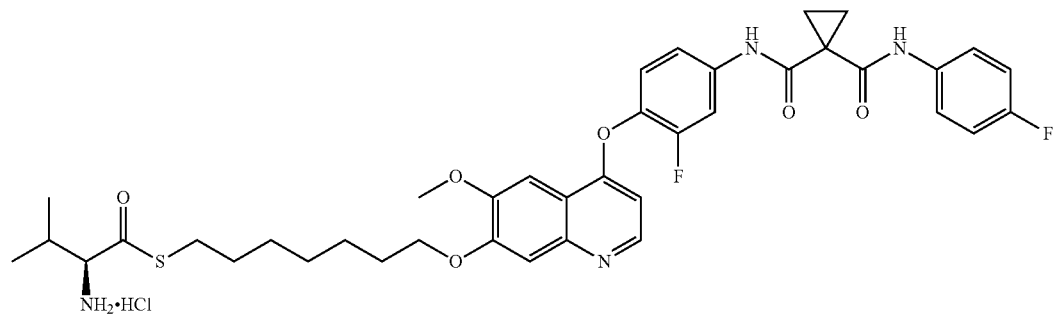
34
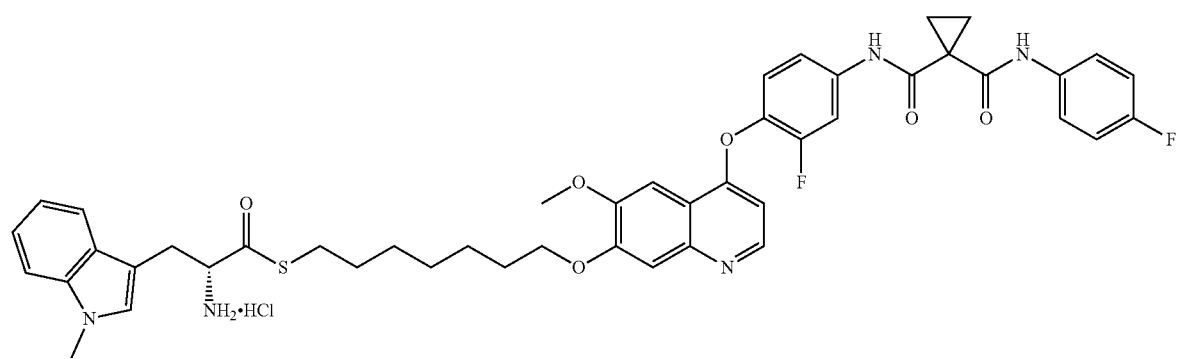
35
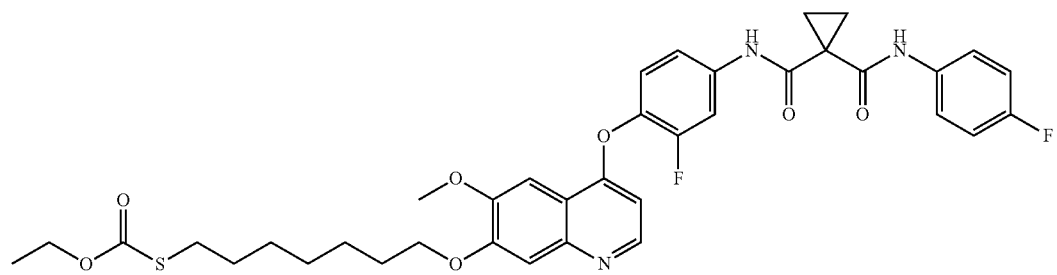

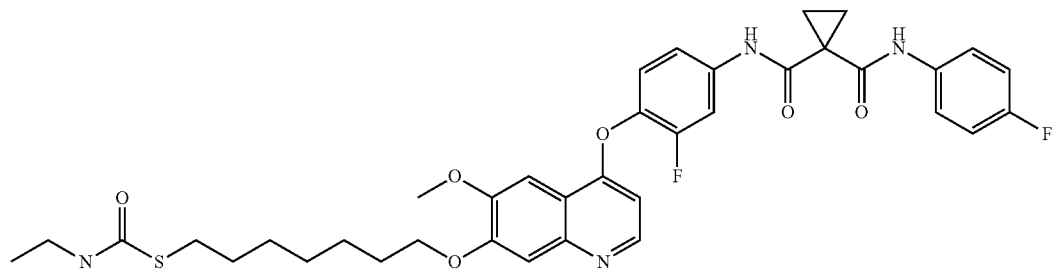
36
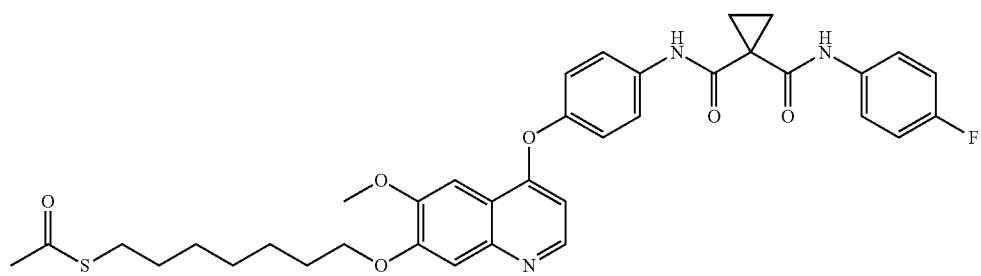
37
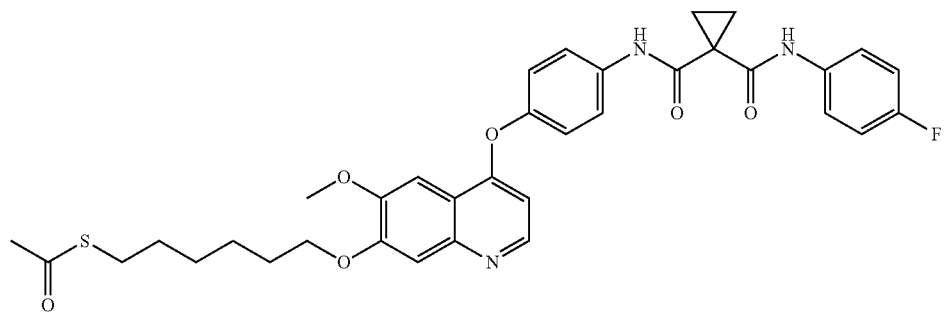
38
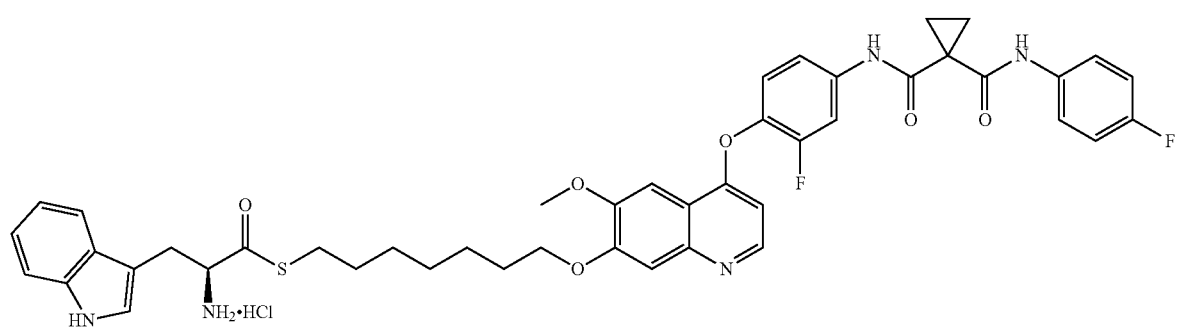
39
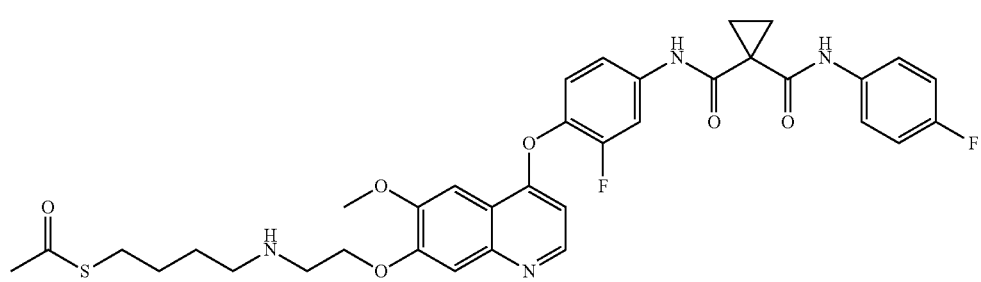
40

41
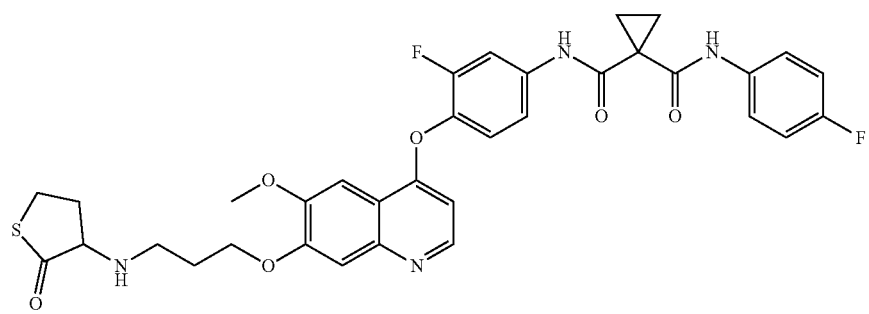
42
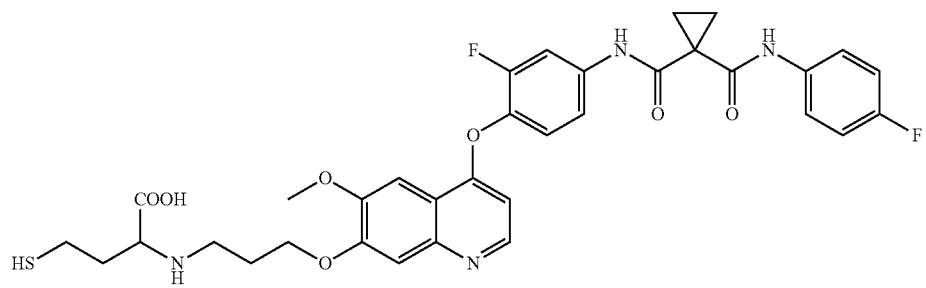
43
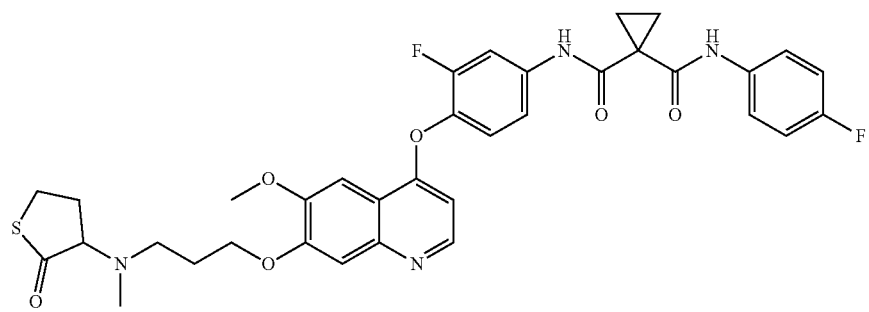
44
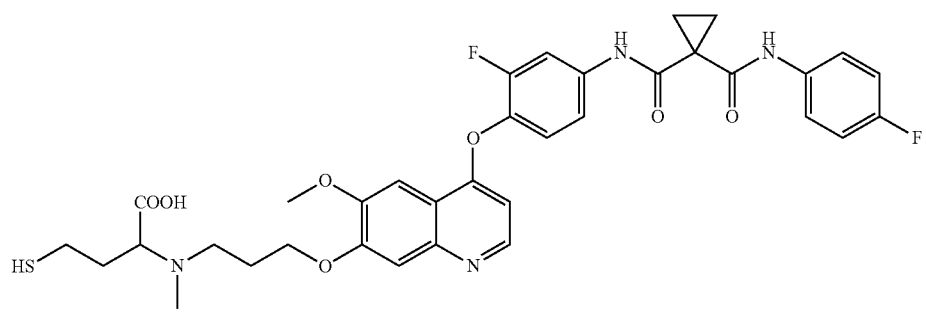
45
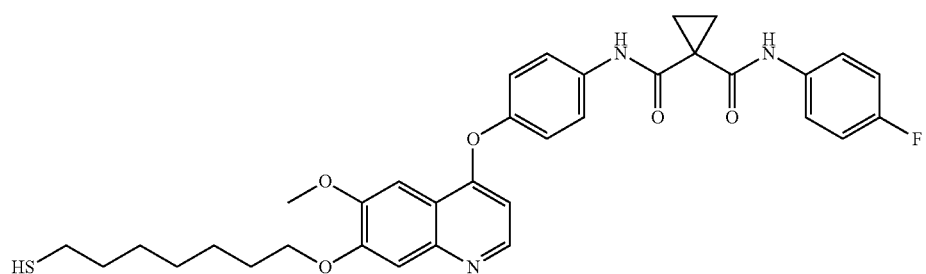

46
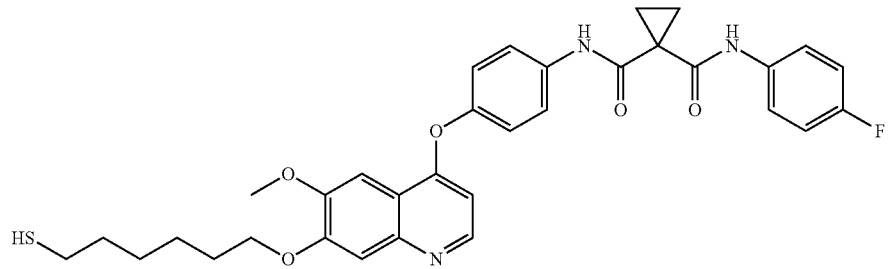
47
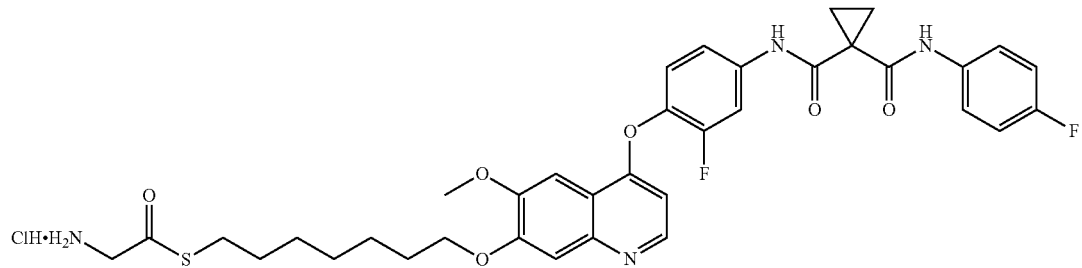
48
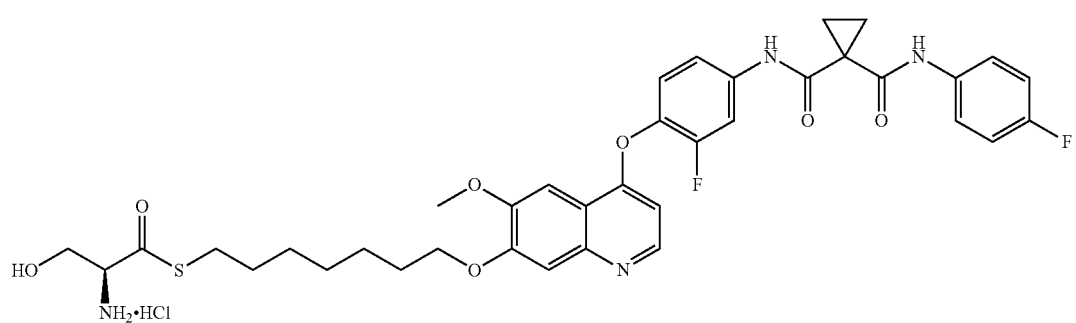
49
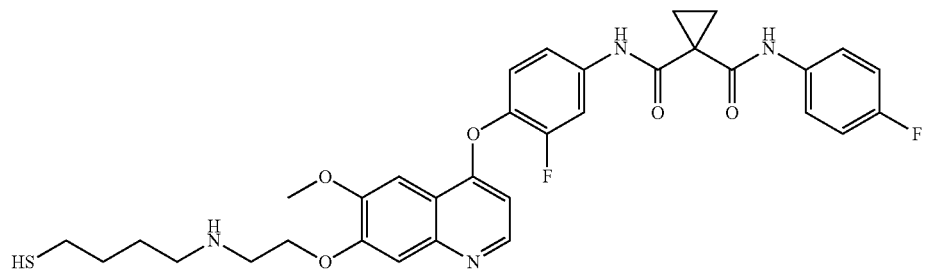
50
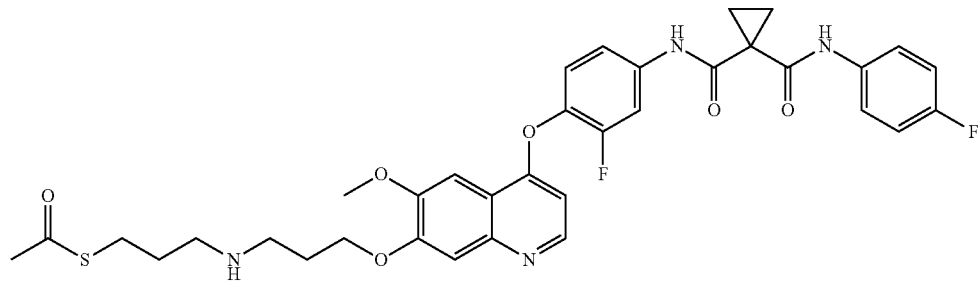

51
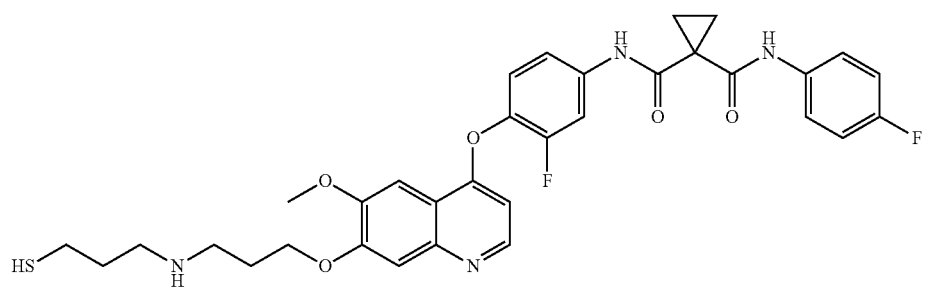
52
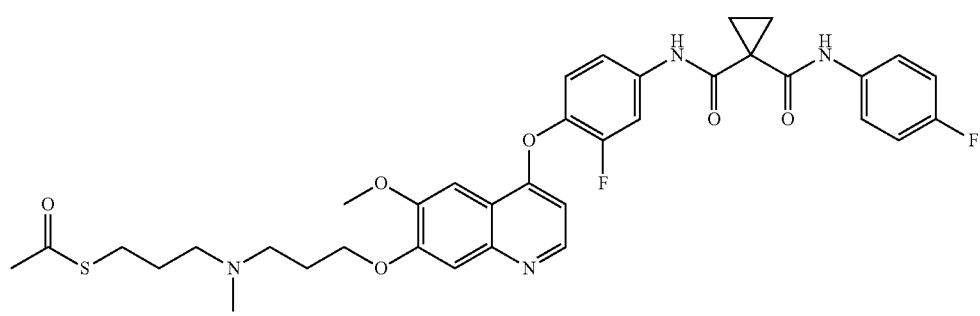
53
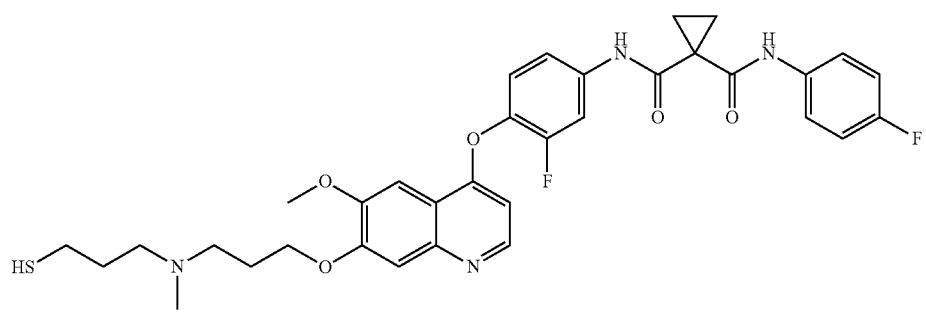
54
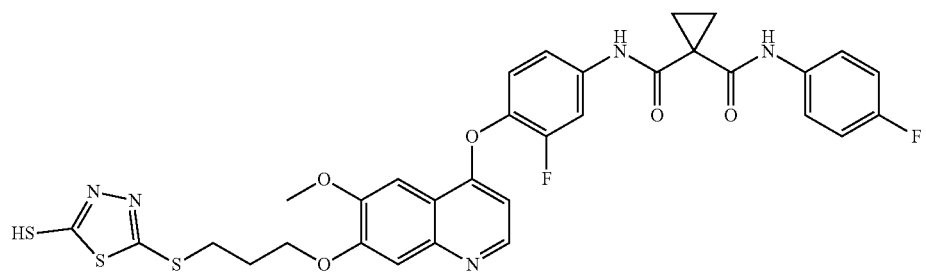
55
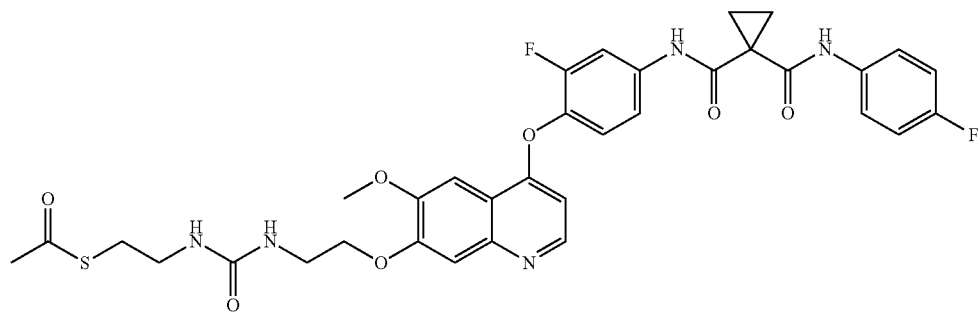

56
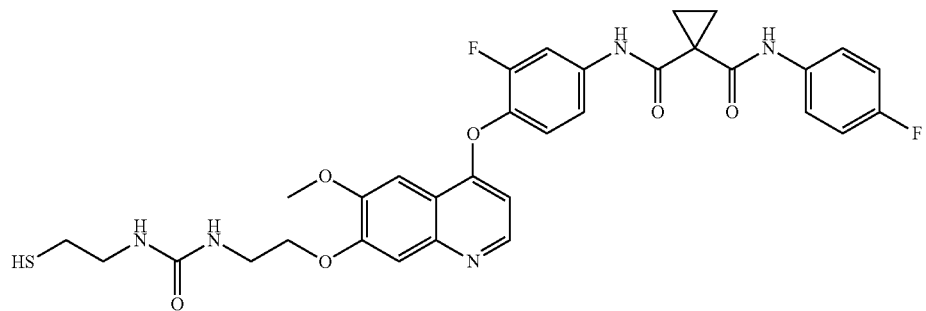
57
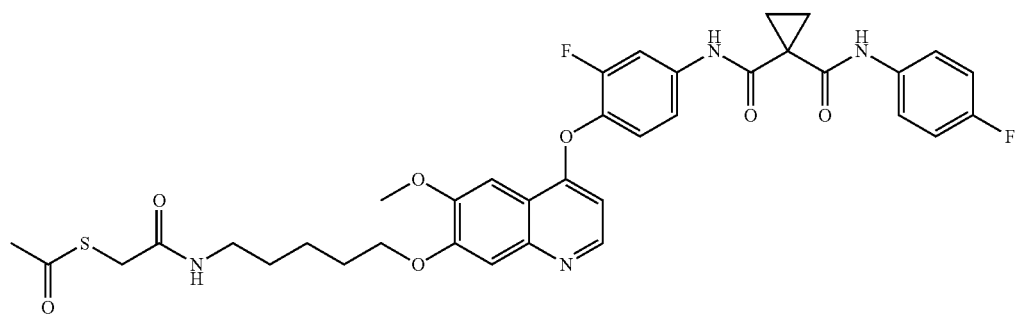
58
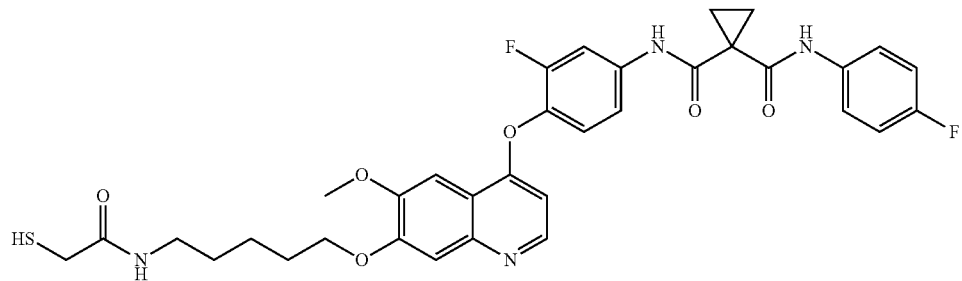
59
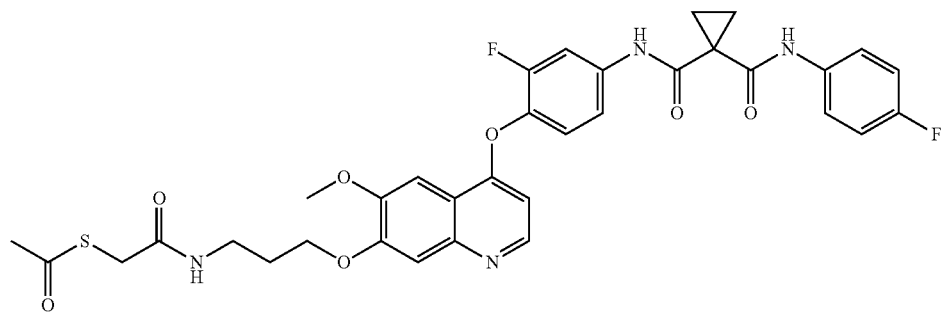
60
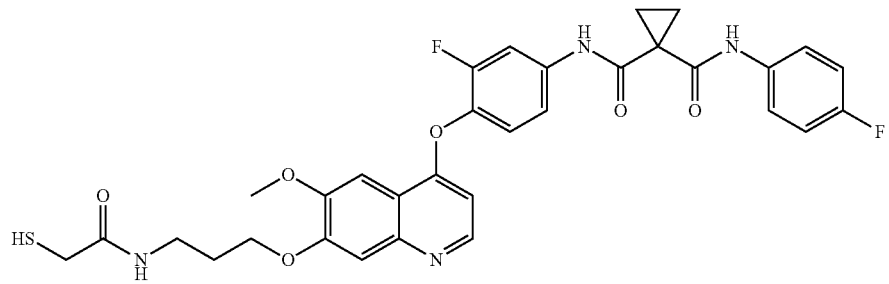

-continued
61
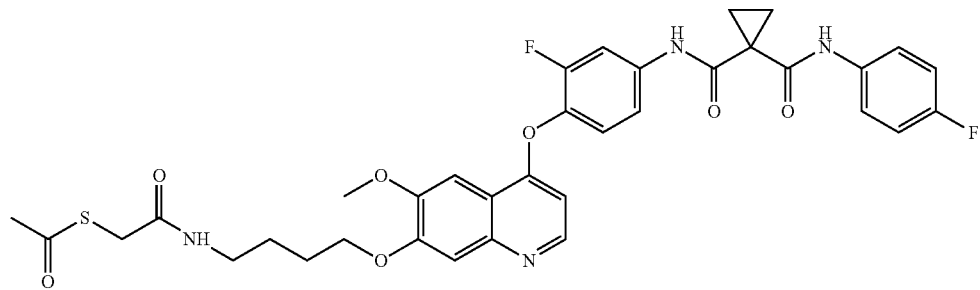
62
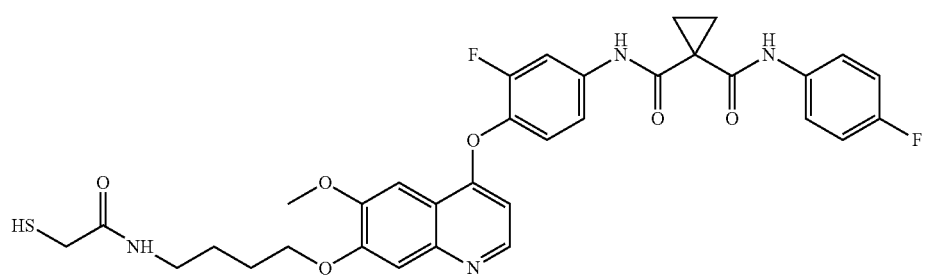
63
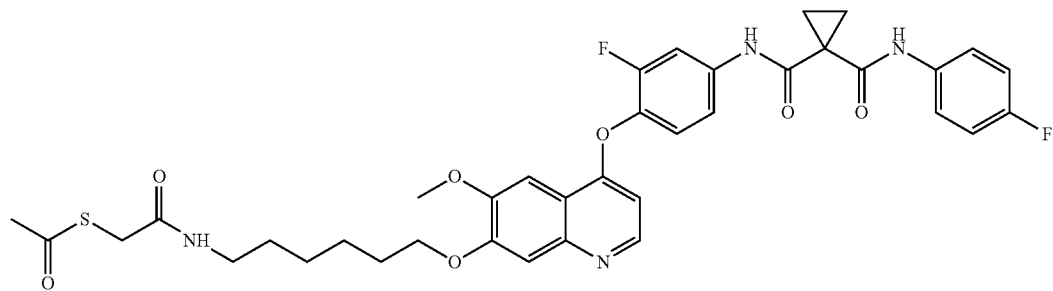
64
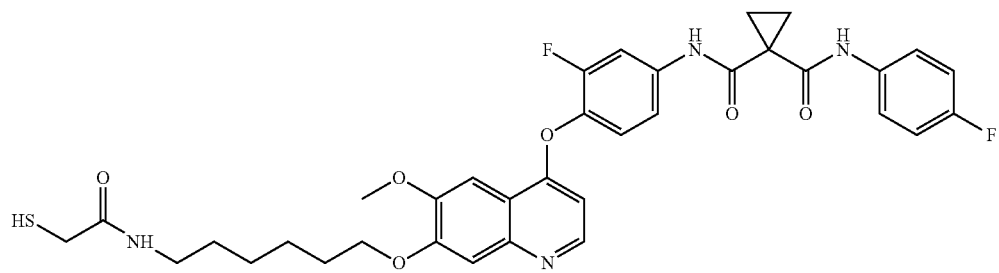
65
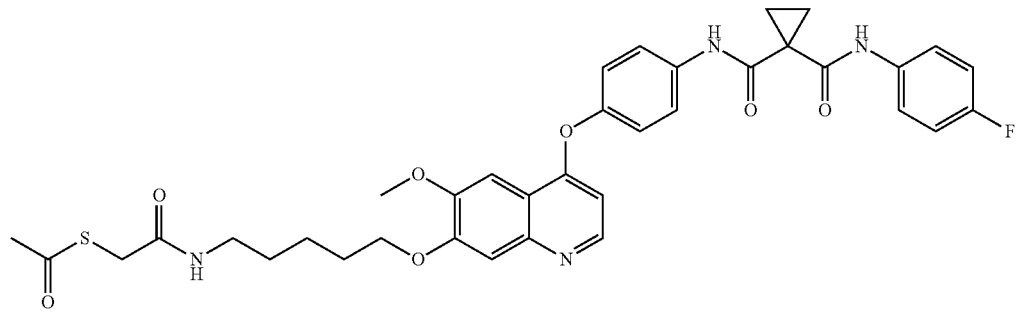

66
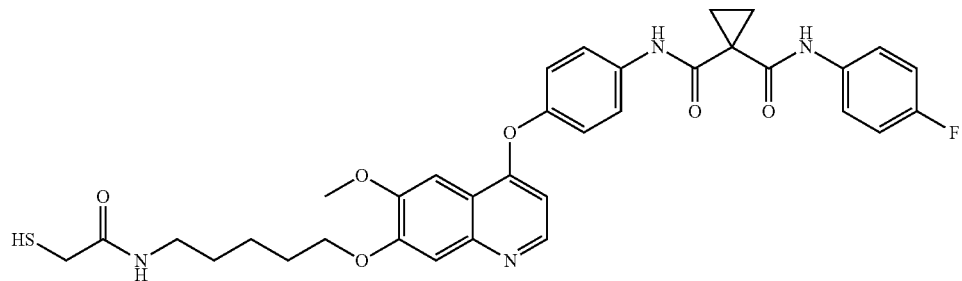
67
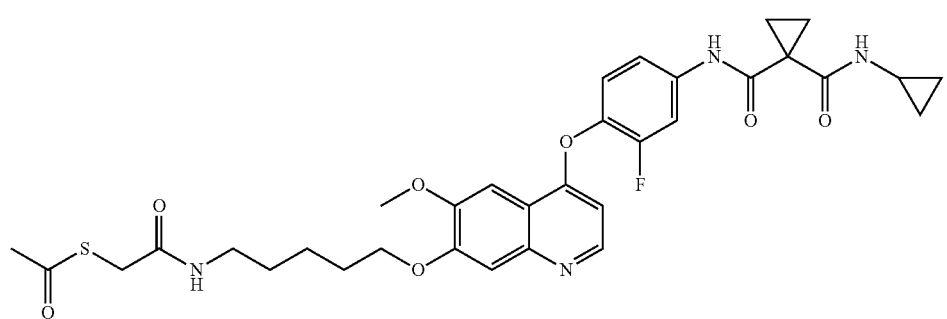
68
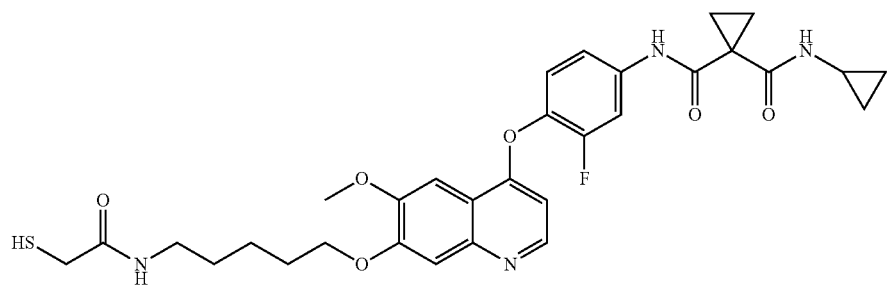
69
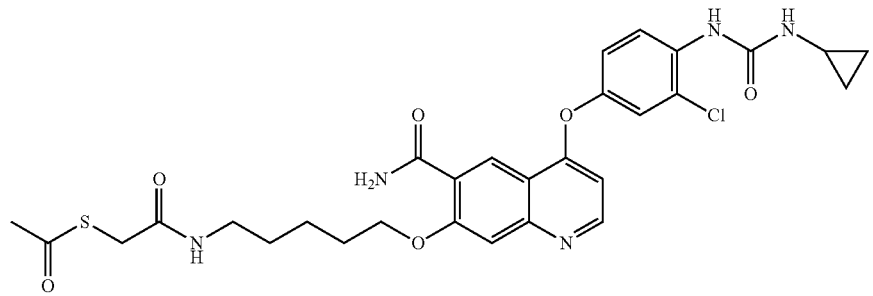
70
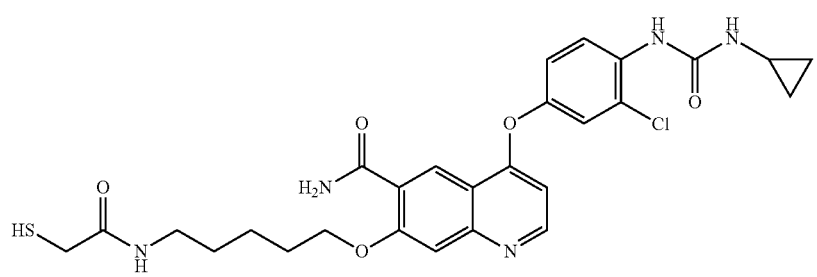

71
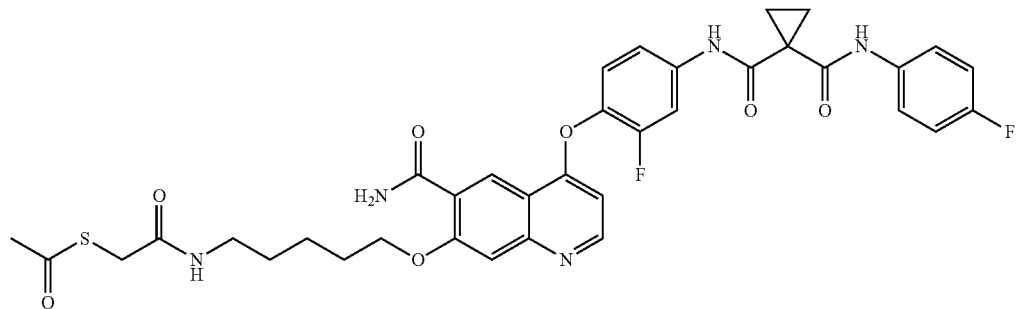
72
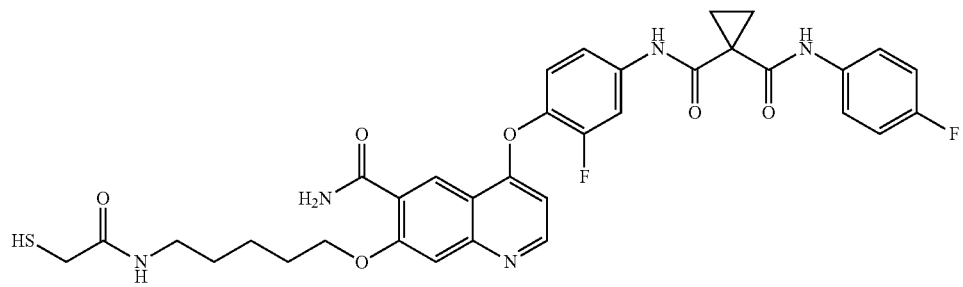
73
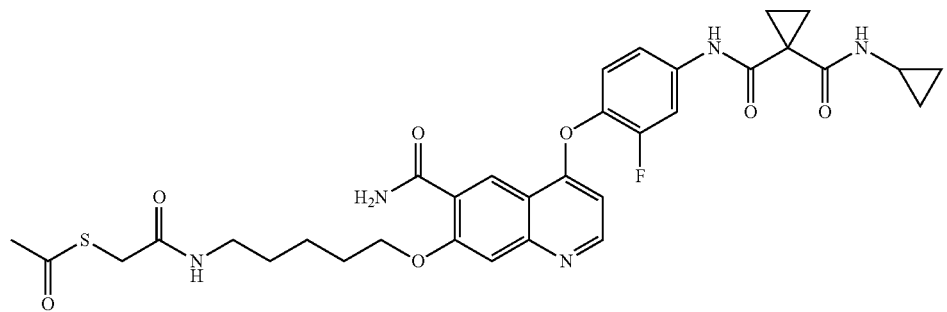
74
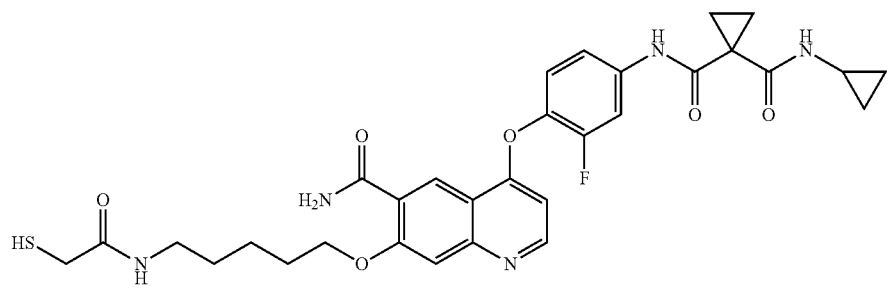
75
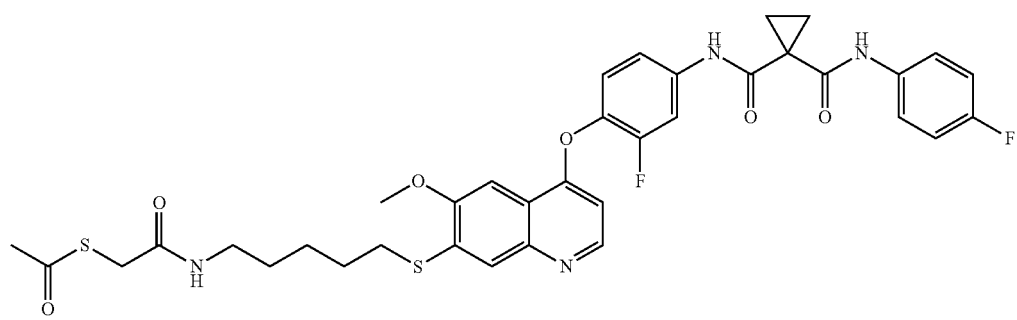

76
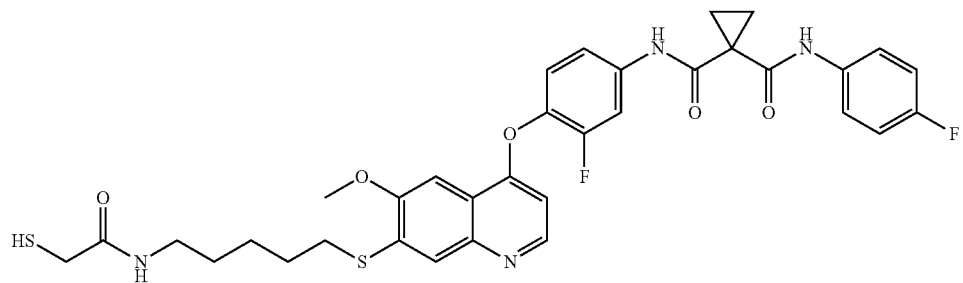
77
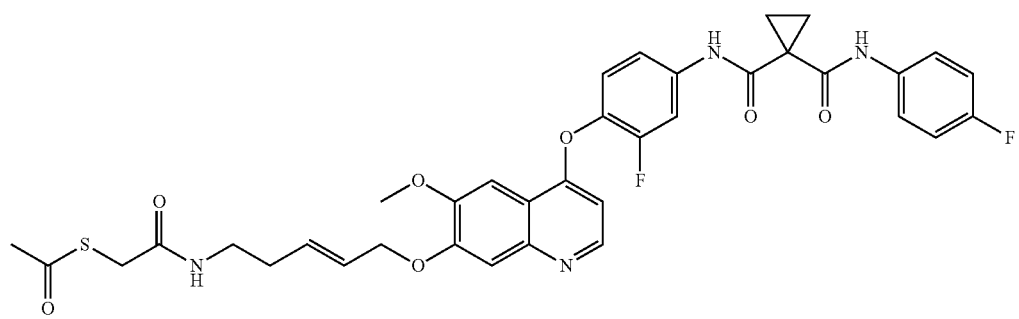
78
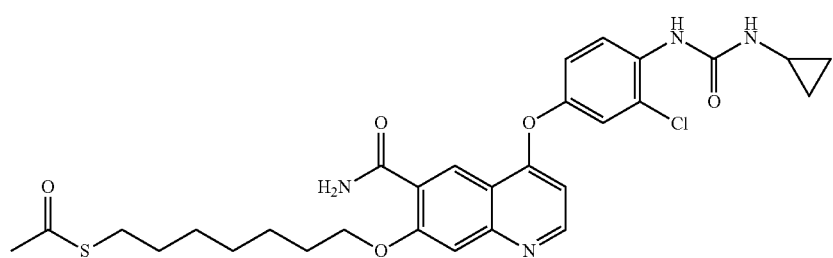
79
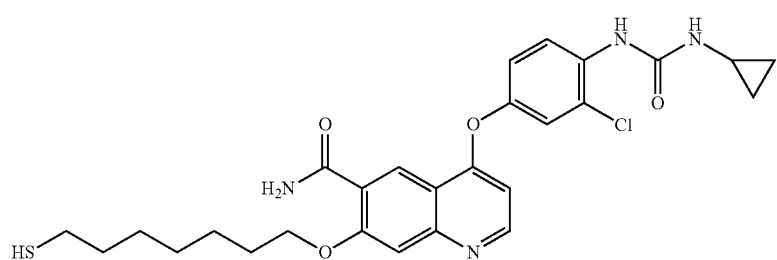
80
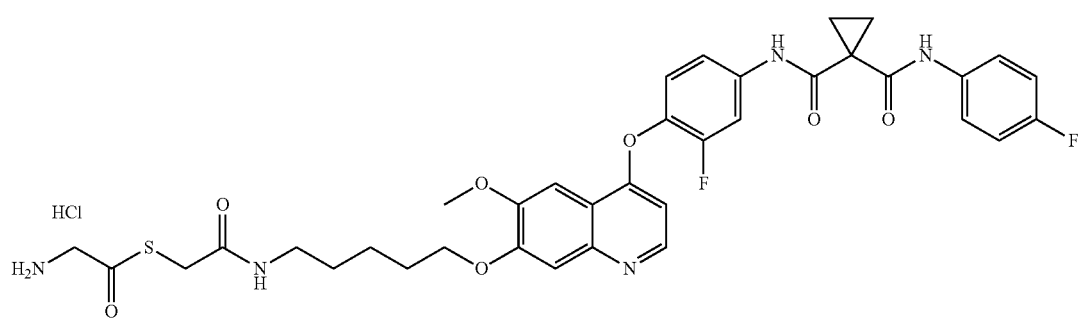

81
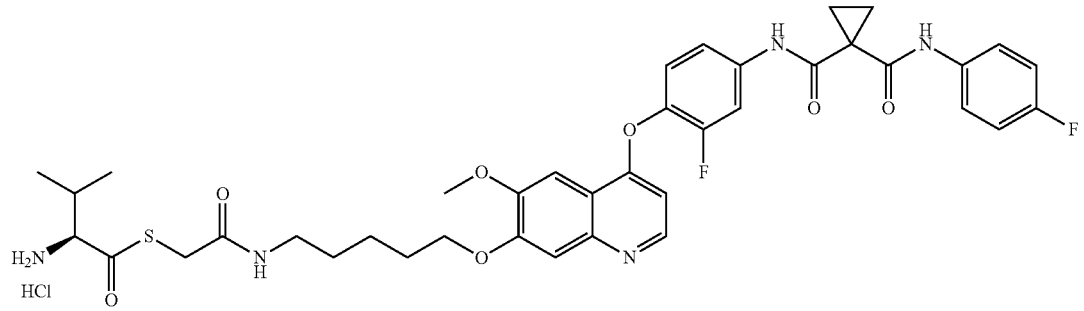
82
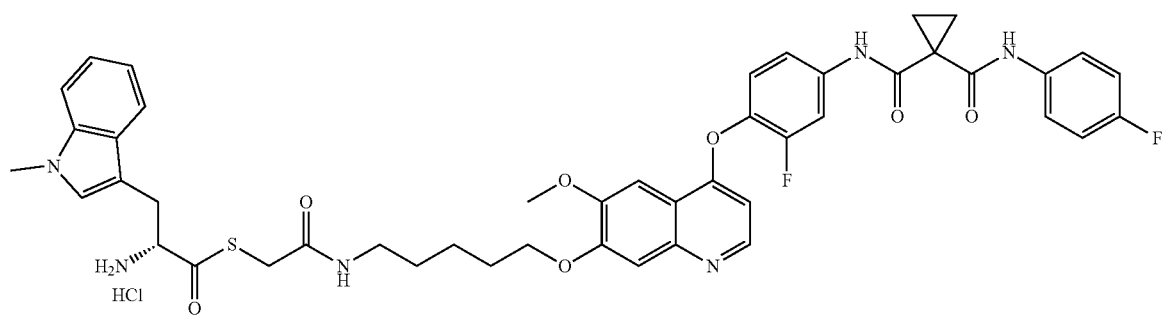
83
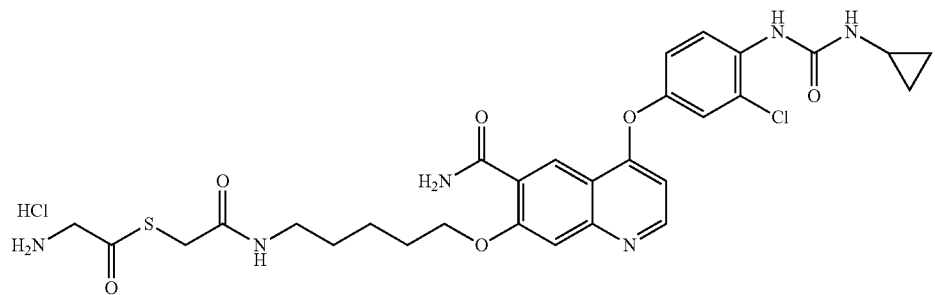
84
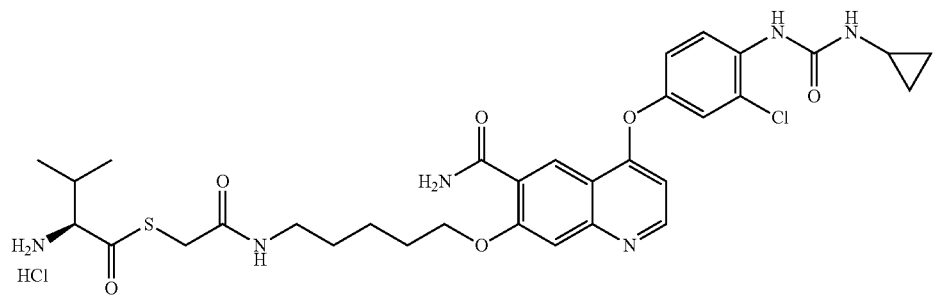
85
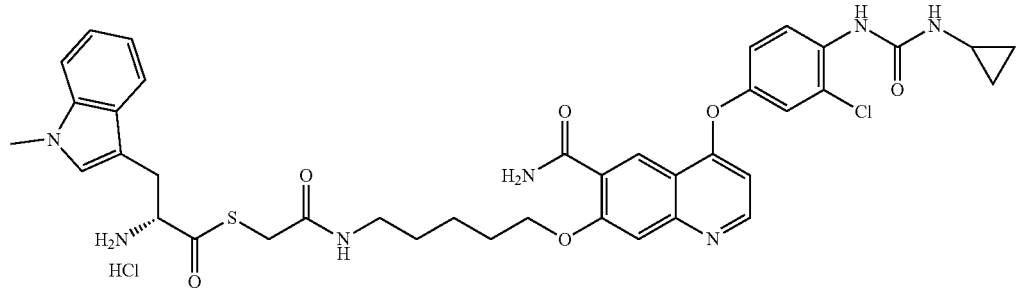

86
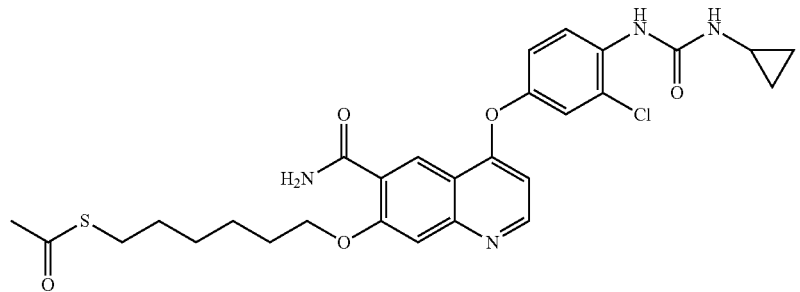
87
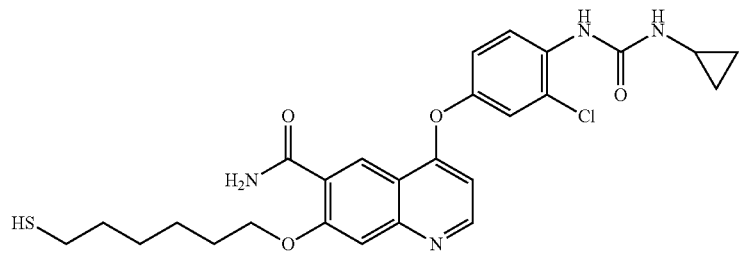
88
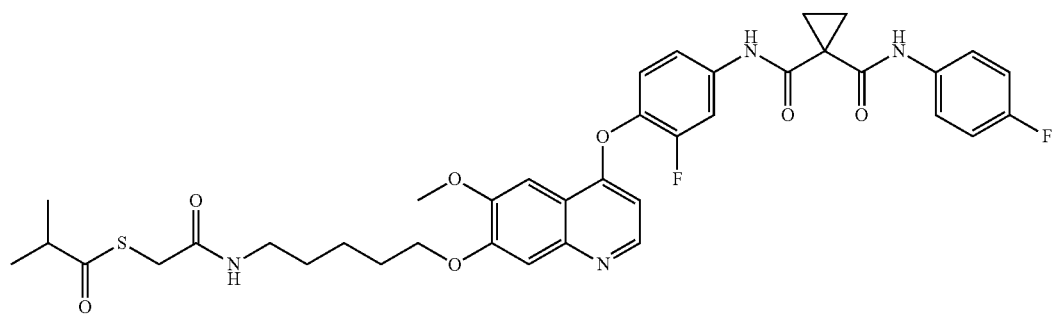
89
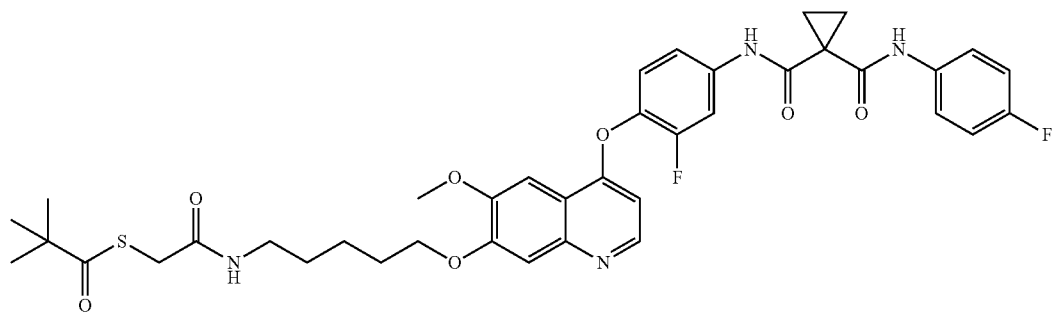
90
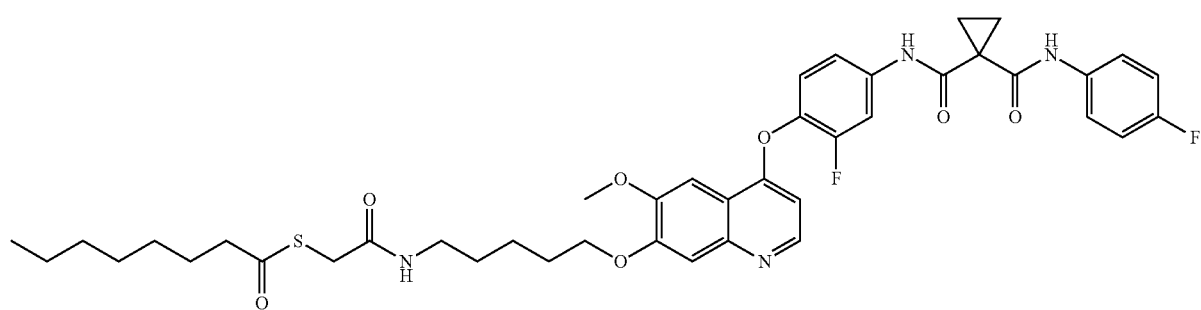

91
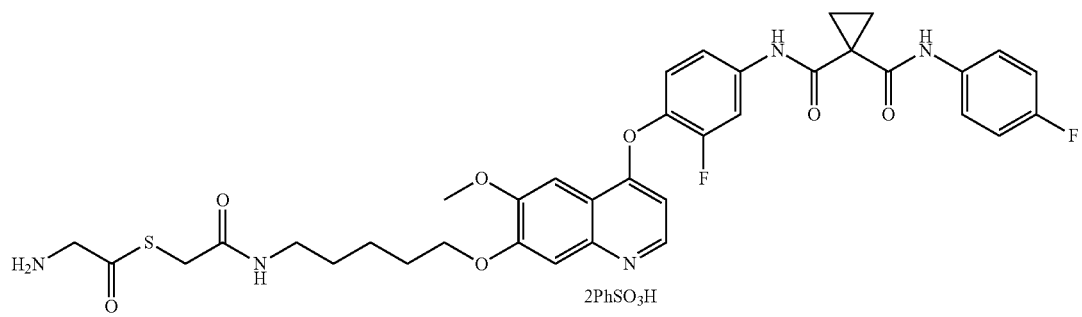
92
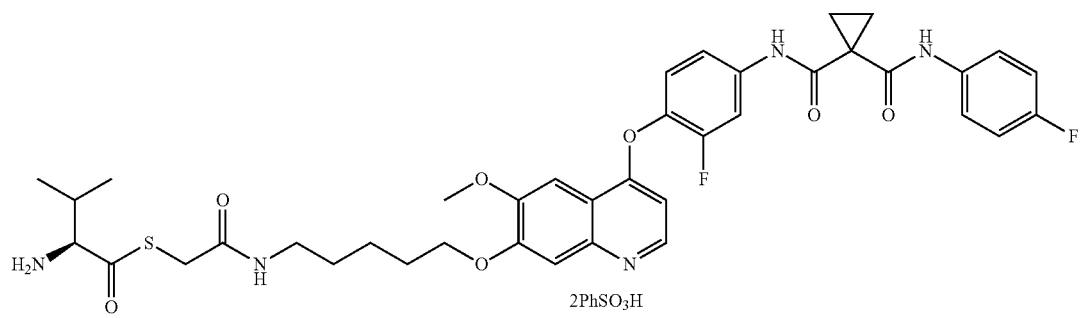
93
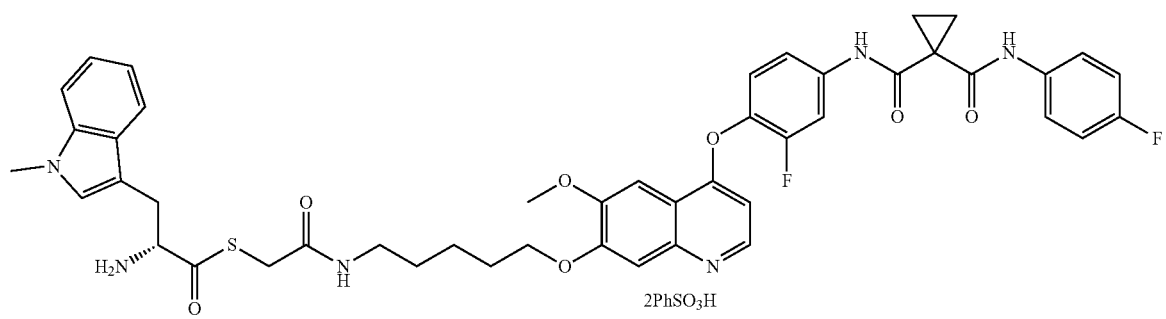
94
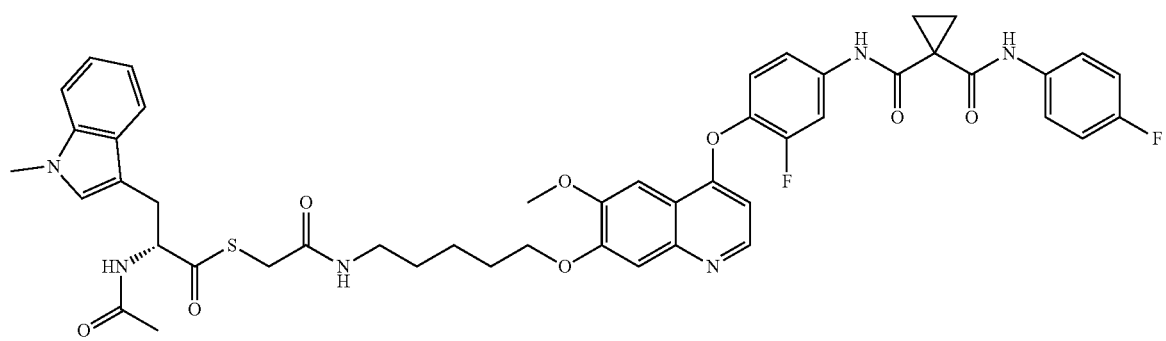
95
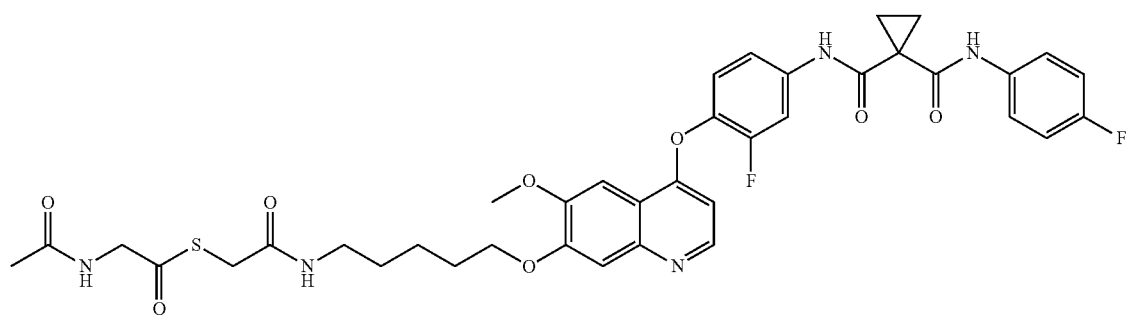

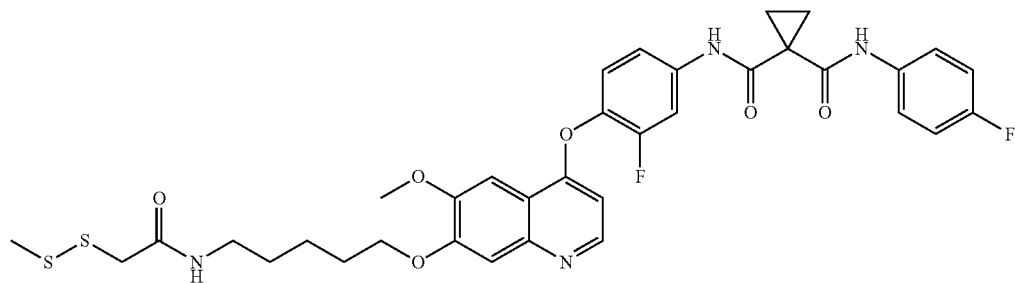

96

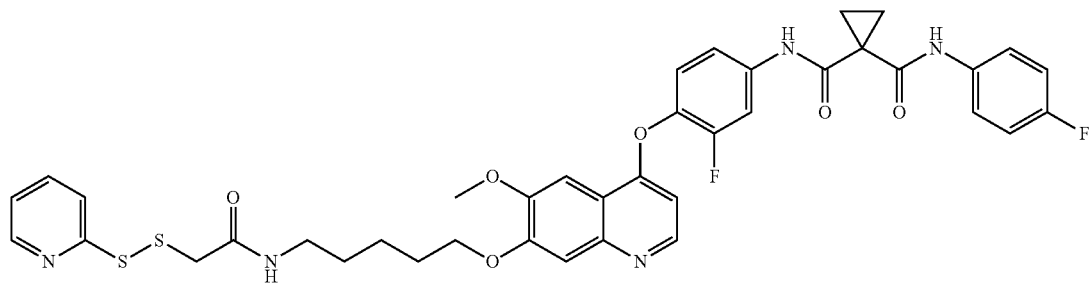

97

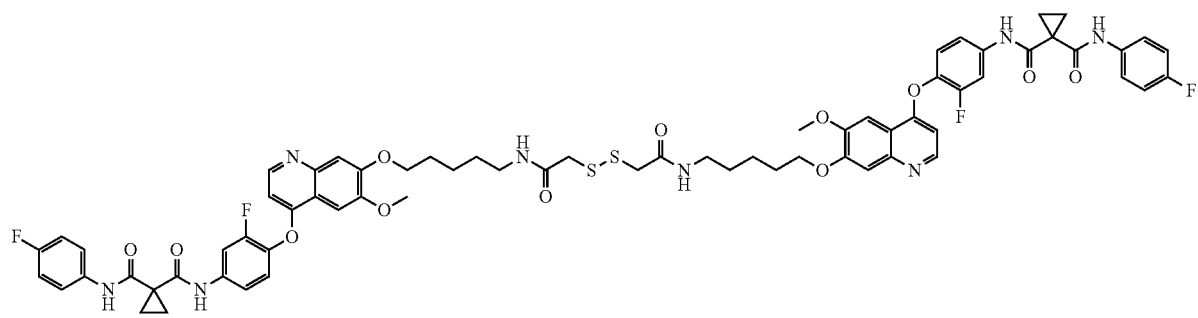

98

The present disclosure also provides a pharmaceutical composition containing the compound described in any one of the above technical solutions or a pharmaceutically acceptable salt, solvate, active metabolite, polymorph, isotopically labelled compound or isomer thereof, and a pharmaceutically acceptable carrier.

In some embodiments of the pharmaceutical composition according to the present disclosure, the pharmaceutical composition may be any common dosage form such as oral dosage form and injection dosage form, including but not limited to oral dosage forms, parenteral dosage forms, topical dosage forms, rectal dosage forms and the like. For example, the pharmaceutical composition may be tablets, capsules, pills, powders, sustained-release preparations, solutions and suspensions for oral administration; sterile solutions, suspensions or emulsions for parenteral administration; and ointments, creams, gels, etc. for topical use; or suppositories for rectal administration.

The present disclosure also provides the above-mentioned compounds or their pharmaceutically acceptable salts, solvates, active metabolites, polymorphs, isotopically labelled compound, isomers or prodrugs, and the above-mentioned pharmaceutical compositions in the preparation of a medicament for treating protein kinases and/or histone deacetylase related diseases.

The present disclosure also provides the above-mentioned compounds or their pharmaceutically acceptable salts, solvates, active metabolites, polymorphs, isotopically labelled compound, isomers or prodrugs, and the above-mentioned pharmaceutical compositions in the preparation of a medicament for treating protein tyrosine kinases and/or histone deacetylase related diseases.

In some embodiments, protein kinases may include the following categories: ALK, AXL, BTK, CDK11, c-Met, KDR, VEGFR2, RET, PDGFR-α, PDGFR-β, c-KIT, Flt3, MEK1, MEK2, CSF1R, EPHA2, MKNK2, TIE2, TRKA, SRC, PLK4, RON, EGF1R, HER2, HER3, HER4, PDGFR-α, c-fms, FLT1, Src, Frk, Btk, CsK, Abl, Fes, Fps, Fak, AcK, Yes, Fyn, Lyn, Lck, Hck, Fgr, Yrk, PDK1, TAK1, Tie-1, YSK4, TRK B, TRK C, SLK, PKN2, MST1R, MAP4K, DDR2.

In some embodiments, the histone deacetylase may include HDAC1, HDAC2, HDAC3, HDAC4, HDAC5, HDAC6, HDAC7, HDAC8, HDAC9, HDAC10, and HDAC11.

In some embodiments, histone deacetylase may include HDAC6.

In some embodiments, the protein kinases and/or histone deacetylases related diseases may include psoriasis, liver cirrhosis, diabetes, neurodegenerative diseases, tumors, immune diseases, cardiovascular diseases, etc.

The neurodegenerative diseases may include Alzheimer's disease, Parkinson's disease, Huntington's disease, etc. Tumors may include lung cancer, bone cancer, pancreatic cancer, skin cancer, head and neck cancer, skin or intraocular melanoma, uterine cancer, ovarian cancer, rectal cancer, anal cancer, stomach cancer, colon cancer, breast cancer, fallopian tube cancer, endometrial cancer, cervical cancer, vaginal cancer, cancer of vulve, Hodgkin's disease, esophageal cancer, small bowel cancer, endocrine system cancer, thyroid cancer, parathyroid cancer, soft tissue sarcoma, urethral cancer, penile cancer, prostate cancer, chronic or acute leukemia, bladder cancer, kidney cancer or ureteral cancer, liver cancer, central nervous system neoplasms, spinal axis tumors, pituitary adenomas, gastrointestinal stromal tumors, colorectal cancer, non-small cell lung cancer, small cell lung cancer, mastocytosis disease, glioma, sarcoma, lymphoma, etc.

The present disclosure also provides a method for treating tyrosine kinase and/or histone deacetylase related diseases. The method includes a step of administering an effective amount of the above-mentioned compound or a pharmaceutically acceptable salt, solvate, active metabolite, polymorph, isotopically labelled compound or isomer thereof, or the aforementioned pharmaceutical composition to a subject in need of such treatment.

The present disclosure also provides a method for inhibiting tyrosine kinase and/or histone deacetylase, including contacting tyrosine kinase and/or histone deacetylase with an effective amount of the above-mentioned compound or its pharmaceutically acceptable salt, solvate, active metabolite, polymorph, isotopically labelled compound or isomer, or with the aforementioned pharmaceutical composition.

The quinolinyl-containing compounds provided by the present disclosure has dual molecular functions, may be used as a type of multi-target inhibitor of tyrosine kinase/histone deacetylase having the effect of two types of inhibitors at the same time. It has excellent biological activity and pharmacokinetic properties, especially has great potential application in the field of tumor treatment.

DETAILED DESCRIPTION

Unless otherwise defined, all scientific and technological terms herein have the same meanings as commonly understood by those skilled in the art. Unless otherwise specified, all patents, patent applications, and publications cited in the disclosure are incorporated herein by reference in their entirety. When a trade name appears, it refers to its corresponding commodity or its active ingredient.

It should be understood that the foregoing brief description and the following detailed description are exemplary and only for explanation, and do not impose any limitation on the subject matter of the disclosure. In this application, it must be noted that, unless clearly stated otherwise in the context, the singular form used in specification and claims includes the plural form of the thing referred to. It should also be noted that the use of "or" means "and/or" unless otherwise specified. In addition, the term "including" and other forms such as "comprising", and "containing" are not limiting.

Definitions of standard chemical terms may be found in the literature, including Carey and Sundberg's "Advanced Organic Chemistry 4$^{th}$ Ed, Vol A (2000) and B (2001), Plenum Press, New York. Unless otherwise specified, conventional methods within the technical field are applied, such as mass spectrometry, NMR, HPLC, protein chemistry, biochemistry, recombinant DNA technology, and pharmacological methods. Unless specific definitions are provided, those skilled in the art know the related terms and laboratory operations and techniques in analytical chemistry, synthetic organic chemistry, and medical and pharmaceutical chemistry used in this disclosure.

Standard techniques may be used for chemical synthesis, chemical analysis, drug preparation, formulation, drug delivery and patient treatment. Standard techniques may be used for recombinant DNA, oligonucleotide synthesis, and tissue culture and transformation (such as electroporation, lipid infection). For example, a kit with instructions provided by the manufacturer may be used, or the reaction and purification techniques may be carried out according to methods known in the art, or according to the method described in the present disclosure. Generally speaking, the aforementioned techniques and process may be implemented by conventional methods well-known in the art and described in various general documents or more specific documents. These documents are described and cited in the present disclosure.

When a substituent is described by a conventional chemical formula written from left to right, the substituent also includes chemically equivalent substituents obtained when the structural formula is written from right to left. For example, $CH_2O$ is equivalent to $OCH_2$.

The term "substituted" means that any one or more hydrogen atoms on a specific atom are replaced by a substituent, as long as the valence of the specific atom is normal and the compound after substitution is stable. When the substituent is oxo (ie $=O$), it means that two hydrogen atoms are replaced, and the oxo will not occur on the aromatic group.

When any variable (such as R) occurs more than once in the composition or structure of a compound, its definition in each case is independent. Thus, for example, if a group is substituted with 0-2 Rs, the group may optionally be substituted with up to two Rs, and R has independent options in each case. In addition, combinations of substituents and/or variants thereof are only permitted if such combinations result in stable compounds.

As used herein, $C_{m\sim n}$ refers to the part having m~n carbon atoms. For example, the "$C_{1\sim6}$" group means that the part has 1-6 carbon atoms, that is, the group contains 1 carbon atom, 2 carbon atoms, 3 carbon atoms . . . 6 carbon atoms. Therefore, for example, "$C_{1\sim6}$ alkyl" refers to an alkyl containing 1-6 carbon atoms, that is, the alkyl group is selected from methyl, ethyl, propyl, isopropyl, n-butyl, isopropyl, n-butyl, sec-butyl, tert-butyl . . . , etc. Numerical ranges in this text, for example "1-6" refers to each integer in the given range. For example, "1-6 carbon atoms" means that the group may have 1 carbon atom, 2 carbon atoms, 3 carbon atoms, 4 carbon atoms, 5 carbon atoms, or 6 carbon atoms.

The term "member" refers to the number of skeletal atoms constituting the ring. For example, pyridine is a six-membered ring and pyrrole is a five-membered ring.

The term "pharmaceutically acceptable" refers to those compounds, materials, compositions and/or dosage forms that are within the scope of reliable medical judgment and are suitable for use in contact with human and animal tissues without excessive toxicity, irritation, allergic reactions or other problems or complications of the disease, and are commensurate with a reasonable benefit/risk ratio.

The term "pharmaceutical composition" refers to a biologically active compound optionally mixed with at least one pharmaceutically acceptable chemical component or agent. The pharmaceutically acceptable chemical component or agent is the "carrier", which helps for introducing the compound into cells or tissues. It includes, but is not limited to, stabilizers, diluents, suspending agents, thickeners, and/or excipients.

The term "pharmaceutically acceptable salt" refers to a salt that retains the biological efficacy of the free acid and free base of the specified compound and has no adverse effects in biology or other aspects. Unless otherwise specified, the salts in the present disclosure may include metal salts, ammonium salts, salts formed with organic bases, salts formed with inorganic acids, salts formed with organic acids, salts formed with basic or acidic amino acids, etc. Non-limiting examples of metal salts include, but are not limited to, alkali metal salts, such as sodium salt, potassium salt, etc.; alkaline earth metal salts, such as calcium salt, magnesium salt, barium salt, etc.; aluminum salt, and the like. Non-limiting examples of salts formed with organic bases include, but are not limited to, the salts formed with trimethylamine, triethylamine, pyridine, picoline, 2,6-lutidine, ethanolamine, diethanolamine, triethanolamine, cyclohexylamine, dicyclohexylamine and the like. Non-limiting examples of salts formed with inorganic acids include, but are not limited to, salts formed with hydrochloric acid, hydrobromic acid, nitric acid, sulfuric acid, phosphoric acid, and the like. Non-limiting examples of salts formed with organic acids include, but are not limited to, salts formed with formic acid, acetic acid, trifluoroacetic acid, fumaric acid, oxalic acid, malic acid, maleic acid, tartaric acid, citric acid, succinic acid, methanesulfonic acid, benzene sulfonic acid, p-toluenesulfonic acid, etc. Non-limiting examples of salts formed with basic amino acids include, but are not limited to, salts formed with arginine, lysine, ornithine, and the like. Non-limiting examples of salts formed with acidic amino acids include, but are not limited to, salts formed with aspartic acid, glutamic acid, and the like.

Pharmaceutically acceptable salts may be synthesized from parent compounds containing acid radicals or bases by conventional chemical methods. Generally, such salts are prepared by reacting these compounds in free acid or base form with a stoichiometric amount of appropriate base or acid in water or organic solvent or a mixture of both. Generally, non-aqueous media such as ether, ethyl acetate, ethanol, isopropanol or acetonitrile are preferred.

The term "solvate" refers to a physical aggregate formed by a compound of the present disclosure and one or more solvent molecules. This physical aggregate includes varying degrees of ions and covalent bonds, such as hydrogen bonds. It has been shown that this solvate may be separated, for example, when one or more solvent molecules are mixed in the crystal lattice. "solvate" includes both solvent phase and separable solvate. There are many examples of corresponding solvates, including ethanol solvates, methanol solvates and the like. "Hydrate" is a solvate that uses water ($H_2O$) molecules as a solvent. One or more compounds in the present disclosure may be prepared as solvates at will. The preparation of solvates is well known. For example, M. Caira et al, J. Pharmaceutical Sci., 93(3), 601-611 (2004) describe the preparation of a solvate of the antifungal drug fluconazole, that is, preparation with ethyl acetate and water. E. C. van Tonder et al, AAPS PharmSciTech., 5(1), article 12 (2004); and AL Bingham et al, Chem. Commun., 603-604 (2001) also describes the similar methods for preparing solvates and hydrates. A typical, non-limiting preparation process is to dissolve the compound of the present disclosure in an ideal solvent (organic solvent or water or their mixed solvent) at a temperature higher than normal temperature, to cool down, and to leave to crystallize. Then the crystals are separated by use standard methods. The I. R. spectroscopy analysis technique may confirm the existence of the solvent (water) that forms the solvate (hydrate) in the crystal.

The term "active metabolite" refers to an active derivative of the compound formed when the compound is metabolized.

The term "polymorphs" refers to compounds of the present disclosure that exist in different crystal lattice forms.

The term "isotopically labelled compound" refers to an isotopically labeled compound of the present disclosure. For example, the isotopes in the compound of the present disclosure may include various isotopes of elements such as H, C, N, O, P, F, S, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}S$.

The term "stereoisomers" refers to isomers produced by different arrangements of atoms in the molecule in space. The compounds of the present disclosure contain structures such as asymmetric or chiral centers and double bonds. Therefore, the compounds of the present disclosure may include optical isomers, geometric isomers, tautomers, atropisomers and other isomers. These isomers and their single isomers, racemates, etc. are all included in the scope of the present disclosure. For example, for optical isomers, optically active (R)- and (S)-isomers and D and L isomers may be prepared by chiral resolution, chiral synthesis or chiral reagents or other conventional techniques. For example, it may be converted into diastereomers by reacting with appropriate optically active substances (such as chiral alcohols or Mosher's Mohsyl chloride), separated and converted (such as hydrolyzed) into the corresponding single isomer. For another example, it may also be separated by a chromatographic column.

The "pharmaceutical compositions" herein may be prepared in a manner well known in the pharmaceutical field, and they may be administered or applied by various routes, depending on whether local or systemic treatment is required and the area to be treated. It may be topically administered (for example, transdermal, skin, eye and mucous membranes including intranasal, vaginal and rectal delivery), pulmonarily administered (for example, by inhalation or insufflation of powder or aerosol, including through sprayers; intratracheal, intranasal), orally or parenterally administered. Parenteral administration includes intravenous, intraarterial, subcutaneous, intraperitoneal or intramuscular injection or infusion; or intracranial, such as intrathecal or intracerebroventricular administration. It may be administered parenterally in a single bolus dose, or it may be administered by, for example, a continuous infusion vacuum. The pharmaceutical composition herein includes but is not limited to the following forms: tablets, pills, powders, lozenges, sachets, cachets, elixirs, suspensions, emulsions, solutions, syrups, aerosols (solid or dissolved in a liquid vehicle); for example, ointments, soft and hard gelatin capsules, suppositories, sterile injection solutions and sterile packaged powders.

The term "treatment" refers to therapeutic treatment and disease prevention or preventive measures, wherein the purpose is to prevent or slow down (relieve) undesirable physiological changes or diseases, such as the development or spread of cancer. For the purpose of the present disclosure, beneficial or desired clinical results include, but are not limited to, alleviation of symptoms, reduction of disease severity, stabilization (i.e., no worsening) of condition, delay or slowing down of disease progression, improvement or alleviation (either partial or all) of the condition, whether detectable or undetectable.

Compared with expected survival (if not receiving treatment), "treatment" also means prolonging survival. Patients in need of treatment include those patients who already have the condition or disease, and those who tend to have the condition or disease or those who want to prevent the condition or disease.

The term "administration" includes the route by which the compound is introduced to the subject to achieve its intended function. Examples of the route of administration that may be used include injection (subcutaneous, intravenous, parenteral, intraperitoneal, intrathecal), topical, oral, inhalation, rectal and transdermal.

The term "effective amount" includes an amount effective to achieve the desired result within the necessary dose and time period. The effective amount of the compound may be based on factors such as the subject's condition, age, and weight, and the ability of the compound to elicit the desired response in the subject. The dosage regimen may be adjusted to provide the best therapeutic response. The effective amount is also an amount in which the therapeutically beneficial effect of the compound exceeds any of its toxic or harmful effects (such as side effects).

As used herein, the phrases "systemically administered" and "peripherally administered" mean the administration of a compound, drug or other substance so that it enters the patient's system and therefore affected by metabolism and other similar processes.

The phrase "therapeutically effective amount" means the amount of the compound of the present disclosure that (i) treats or prevents a specific disease or condition, (ii) attenuates, improves or eliminates one or more symptoms of a specific disease or condition, or (iii) prevent or delay the onset of one or more symptoms of a specific disease or condition as described herein.

The term "subject" refers to animals such as mammals, including but not limited to primates (such as humans), cows, sheep, goats, horses, dogs, cats, rabbits, rats, mice, etc. In some embodiments, the subject is a human.

The pharmaceutical composition may be formulated in a unit dosage form, and each dosage may contain about 0.1 to 1000 mg, for example, about 5 to 1000 mg, or about 100 to 500 mg of active ingredient. The term "unit dosage form" refers to a physically separated single dosage unit suitable for use in human patients and other mammals, and each unit contains a predetermined amount of active substance that is calculated to produce the desired therapeutic effect mixed with a suitable pharmaceutical carrier.

EMBODIMENTS

To make the objectives, technical solutions, and advantages of the present disclosure clearer, the technical solutions of the exemplary embodiments of the present disclosure will be further described below.

In the present disclosure, the compounds described in the present disclosure may be prepared by the following methods. The following methods and examples are to illustrate these methods.

These procedures and examples should not be construed as limiting the present disclosure in any way. The compounds described herein may also be synthesized using standard synthesis techniques known to those skilled in the art, or methods known in the art and methods described herein may be used in combination.

The chemical reactions in the embodiments of the present disclosure are completed in a suitable solvent, and the solvent must be suitable for the chemical changes of the present disclosure and the reagents and materials required. In order to obtain the compounds of the present disclosure, it is sometimes necessary for those skilled in the art to modify or select the synthesis process or reaction schemes based on the existing embodiments.

An important consideration in the planning of any synthetic route in the art is to select an appropriate protecting group for the reactive functional group (such as the amino group in the present disclosure). For trained practitioners, Greene and Wuts (Protective Groups In Organic Synthesis, Wiley and Sons, 1991) is the authority in this regard. All references cited in the present disclosure are incorporated into the present disclosure in their entirety.

The reactions described herein may be monitored according to any suitable method known in the art. For example, product formation may be monitored by a broad spectrum method such as nuclear magnetic resonance spectroscopy (such as $^1$H or $^{13}$C), infrared spectroscopy, spectrophotometry (such as UV-visible light), mass spectrometry, etc., or chromatography such as high performance liquid chromatography (HPLC) or thin layer chromatography.

Preparation Example 1

N-(3-fluoro-4-((7-hydroxyl-6-methoxyquinolin-4-yl)oxy)phenyl)-N-(4-fluorophenyl)cyclopropyl-1,1-diformamide

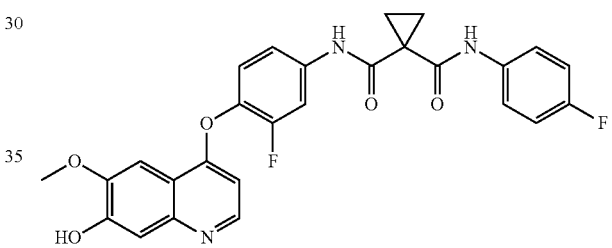

Step A: 7-(benzyloxy)-4-(2-fluoro-4-nitrophenoxy)-6-methoxyquinoline

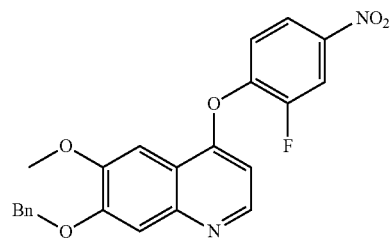 [SMILES: COc1cc2c(Oc3ccc([N+](=O)[O-])cc3F)ccnc2cc1OCc1ccccc1]

Dissolve 29.9 g (100 mmol, 1.0 eq) 7-(benzyloxy)-4-chloro-6-methoxyquinoline and 23.4 g (150 mmol, 1.5 eq) 2-fluoro-4-nitrophenol in 10 mL DMF. Then, 41.4 g (300 mmol, 3.0 eq) potassium carbonate powder was added at room temperature. After that, the reaction solution was stirred at room temperature overnight. After the reaction was complete monitored by TLC, the reaction system was poured into 550 mL water, extracted with 600 mL ethyl acetate, and the organic phase was sequentially washed twice with water and saturated brine, the organic phase was dried over anhydrous sodium sulfate, evaporated to dryness, and the residue was purified by silica gel column chromatography to afford the product (18.9 g, yield=45%).

Step B:
4-(4-amino-2-fluorophenoxy)-6-methoxyquinolin-7-ol

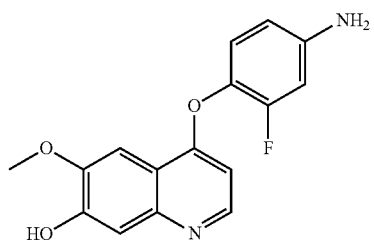 [SMILES: COc1cc2c(Oc3ccc(N)cc3F)ccnc2cc1O]

Dissolve 18.0 g (42.9 mmol, 1.0 eq) 7-(benzyloxy)-4-(2-fluoro-4-nitrophenoxy)-6-methoxyquinoline and 0.9 g Pd/C in 180 mL methanol. Under a hydrogen atmosphere of 3 atm, gas was exchanged three times. The reaction was stirred overnight at room temperature. After the reaction was complete monitored by TLC, the reaction system was vacuum filtered. The filter cake was washed with methanol, and the organic phase was evaporated to dryness under reduced pressure to afford the product (10.9 g, yield=85%).

Step C: N-(3-fluoro-4-((7-hydroxyl-6-methoxyquinolin-4-yl)oxy)phenyl)-N-(4-fluorophenyl)cyclopropane-1,1-diformamide

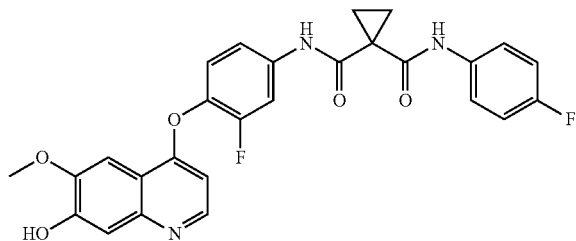 [SMILES: COc1cc2c(Oc3ccc(NC(=O)C4(C(=O)Nc5ccc(F)cc5)CC4)cc3F)ccnc2cc1O]

9.0 g (30 mmol, 1.0 eq) 4-(4-amino-2-fluorophenoxy)-6-methoxyquinoline-7-ol, 8.0 g (36 mmol, 1.2 eq) 1-((4-(fluorophenyl) formamido) cyclopropane-1-carboxylic acid and 13.8 g (36 mmol, 1.2 eq) HATU were dissolved in 200 mL of dichloromethane. Then, Add 19.5 g (150 mmol, 5.0 eq) diisopropylethylamine. After that, the reaction was stirred at room temperature overnight. After the reaction was complete monitored by TLC, the reaction system was poured into 300 mL of water, and 150 mL of DCM was added for extraction. The organic phase was washed twice with citric acid aqueous solution and saturated brine successively, and the organic phase was dried over anhydrous sodium sulfate and evaporated to dryness. The residue was purified by silica gel column chromatography to afford the product (9.5 g, yield=63%).

LC-MS: m/z=506 [M+H]$^+$.

Preparation Example 2: N-(4-fluorophenyl)-N-(4-((7-hydroxyl-6-methoxyquinolin-4-yl)oxy)phenyl) cyclopropane-1,1-diformamide

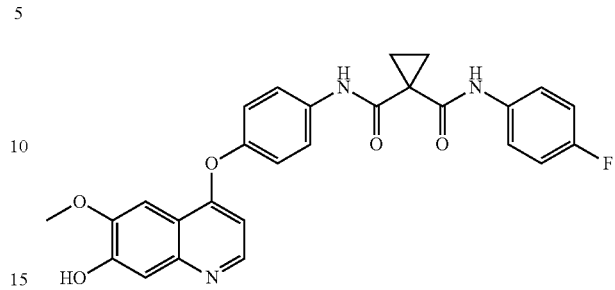

The preparation method was similar with that described in preparation example 1, except 2-fluoro-4-nitrophenol was replace with 4-nitrophenol to prepare the target compound (3.2 g, yield=65%).

LC-MS: m/z=488 [M+H]$^+$.

Preparation Example 3: N-cyclopropyl-N-(3-fluoro-4-((7-hydroxyl-6-methoxyquinolin-4-yl)oxy)phenyl) cyclopropane-1,1-diformamide

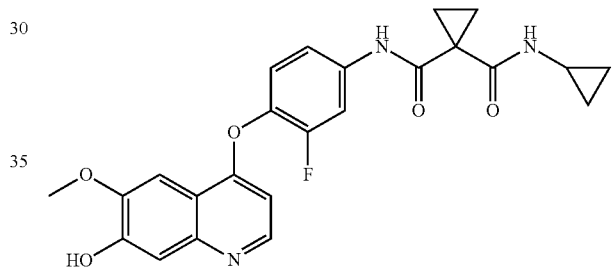

The preparation method was similar with that described in preparation example 1, except 4-fluoroaniline was replaced with cyclopropylamine to prepare the target compound (5.8 g, yield=53%).

$^1$H NMR (400 MHz, DMSO-d6) δ 10.91 (s, 1H), 10.16 (s, 1H), 8.41 (s, 1H), 7.91-7.88 (m, 2H), 7.51-7.34 (m, 3H), 7.29 (s, 1H), 6.35 (d, J=4.0 Hz, 1H), 3.96 (s, 3H), 2.71-2.66 (m, 1H), 1.36 (s, 4H), 0.65-0.64 (m, 2H), 0.63-0.62 (m, 2H).

LC-MS: m/z=452 [M+H]$^+$.

Preparation Example 4: N-(4-((6-aminoformyl-7-hydroxyquinolin-4-yl)oxy)-3-fluorophenyl)-N-(4-fluorophenyl)cyclopropane-1,1-diformamide

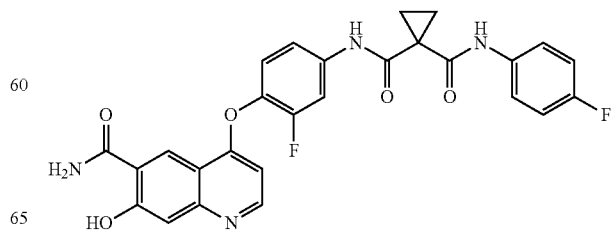

Step A: 7-(benzyloxy)-4-(2-fluoro-4-(1-((4-fluorophenyl)aminoformyl)cyclopropane-1-carboxamido)phenoxy)quinoline-6-methyl formate

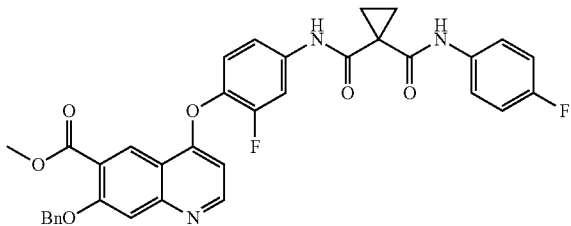 [SMILES: COC(=O)c1cc2c(Oc3ccc(NC(=O)C4(C(=O)Nc5ccc(F)cc5)CC4)cc3F)ccnc2cc1OCc1ccccc1]

The step was similar with that described in preparation example 1, except 7-(benzyloxy)-4-chloro-6-methoxyquinoline was replaced with 7-(benzyloxy)-4-chloroquinoline-6-carboxylic acid methyl ester to prepare the target compound (32.0 g, yield=65%).
LC-MS: m/z=624 [M+H]$^+$.

Step B: 7-(benzyloxy)-4-(2-fluoro-4-(1-((4-fluorophenyl)aminoformyl)cyclopropane-1-carboxamido)phenoxy)quinoline-6-carboxylic acid

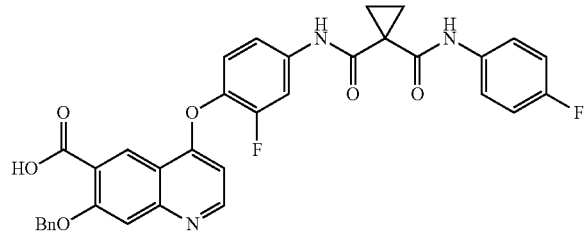 [SMILES: O=C(O)c1cc2c(Oc3ccc(NC(=O)C4(C(=O)Nc5ccc(F)cc5)CC4)cc3F)ccnc2cc1OCc1ccccc1]

15.0 g (24.0 mmol, 1.0 eq) 7-(benzyloxy)-4-(2-fluoro-4-(1-((4-fluorophenyl)aminoformyl)cyclopropane-1-carboxamido) phenoxy)quinoline-6-methyl formate was dissolved in 150 mL methanol, and 4N sodium hydroxide aqueous solution (15 ml) was slowly added to the reaction system under ice bath. After the addition, the reaction was carried out at room temperature for 1 h, and then 1N hydrochloric acid solution was added under ice bath to adjust the pH to neutral. Collect the solid by vacuum filtration and dry it naturally to afford the crude product directly for the next step (13.6 g, yield=93%). LC-MS: m/z=610 [M+H]$^+$.

Step C: N-(4-((7-(benzyloxy)-6-aminocarbamoylquinolin-4-yl)oxy)-3-fluorophenyl)-N-(4-fluorophenyl) cyclopropane-1,1-diformamide

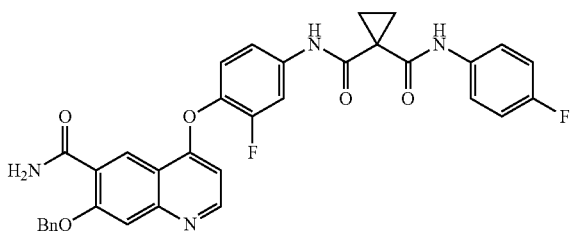

9.0 g (14.8 mmol, 1.0 eq) 7-(benzyloxy)-4-(2-fluoro-4-(1-((4-fluorophenyl)aminoformyl)cyclopropane-1-carboxamido)phenoxy)quinoline-6-carboxylic acid and 11.3 g (29.6 mmol, 2.0 eq) HATU were dissolved in 1N ammonia in dichloromethane (100 mL) solution. The tube was sealed, and reaction solution was stirred at room temperature overnight. After the completion of the reaction monitored by TLC, the reaction system was poured into 300 mL of water. The organic phase was washed successively with citric acid aqueous solution and saturated brine twice, and the organic phase was dried over anhydrous sodium sulfate, evaporated to dryness. The residue was purified by silica gel column chromatography to afford the product (5.2 g, Yield=58%).
LC-MS: m/z=609 [M+H]$^+$.

Step D: N-(4-((6-aminoformyl-7-hydroxyquinolin-4-yl)oxy)-3-fluorophenyl)-N-(4-fluorophenyl)cyclopropane-1,1-diformamide

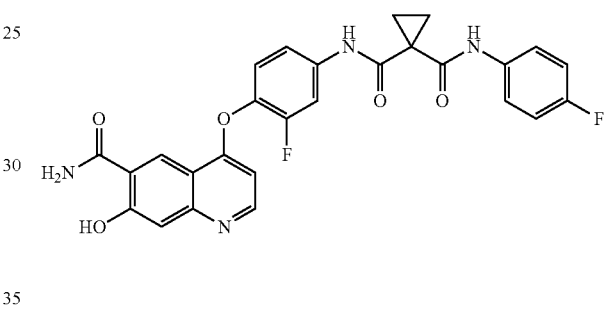

5.0 g (8.22 mmol, 1.0 eq) N-(4-((7-(benzyloxy)-6-aminoformylquinolin-4-yl)oxy)-3-fluorophenyl)-N-(4-Fluorophenyl) cyclopropane-1,1-diformamide and 0.5 g Pd/C were dissolved in 60 mL methanol, and gas exchanges three times under a hydrogen atmosphere of 3 atm. The reaction was stirred at room temperature overnight. After the completion of the reaction monitored by TLC, the reaction system was vacuum filtered. The filter cake was washed with methanol, and the organic phase was evaporated to dryness under reduced pressure to afford the product (3.6 g, yield=85%).

$^1$H NMR (400 MHz, DMSO-d6) δ 12.99 (s, 1H), 10.44 (s, 1H), 10.03 (s, 1H), 9.01 (s, 1H), 8.83 (brs, 1H), 8.63 (d, J=4.0 Hz, 1H), 8.17 (brs, 1H), 7.93 (dd, J=8.0, 4.0 Hz, 1H), 7.67-7.59 (m, 2H), 7.51-7.45 (m, 1H), 7.44-7.38 (m, 1H), 7.17 (q, J=8.0 Hz, 2H), 6.39 (d, J=4.0 Hz, 1H), 1.48 (s, 2H), 1.47 (s, 2H).
LC-MS: m/z=519 [M+H]$^+$.

Preparation Example 5: N-(4-fluorophenyl)-N-(4-((7-hydroxyl-6-methoxyquinolin-4-yl)oxy)phenyl)cyclopropane-1,1-diformamide

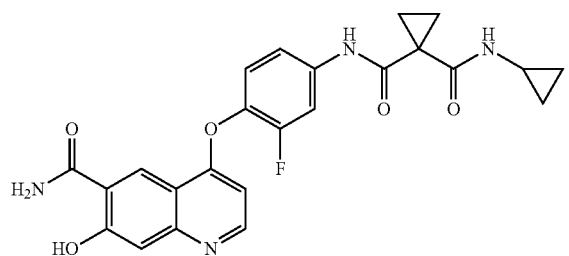 [SMILES: NC(=O)c1cc2c(Oc3ccc(NC(=O)C4(C(=O)NC5CC5)CC4)cc3F)ccnc2cc1O]

The preparation method was similar with that described in preparation example 4, except 4-fluoroaniline was replaced with cyclopropylamine to prepare the target compound (2.7 g, yield=62%).

$^1$H NMR (400 MHz, DMSO-d6) δ 12.99 (s, 1H), 10.94 (s, 1H), 9.00 (s, 1H), 8.82 (s, 1H), 8.63 (d, J=4.0 Hz, 1H), 8.15 (s, 1H), 7.94-7.91 (m, 2H), 7.52-7.44 (m, 2H), 7.34 (s, 1H), 6.39 (s, d, J=4.0 Hz, 1H), 2.71-2.51 (m, 1H), 1.36 (s, 4H), 0.66-0.56 (m, 2H), 0.52-0.39 (m, 2H).

LC-MS: m/z=465 [M+H]$^+$.

Example 1 S-(3-((4-(2-fluoro-4-(1-((4-fluorophenyl)aminoformyl)cyclopropane-1-carboxamido)phenoxy)-6-methoxyquinolin-7-yl)oxy)propyl)-(S)-2-amino-3-methylthiobutyrate hydrochloride

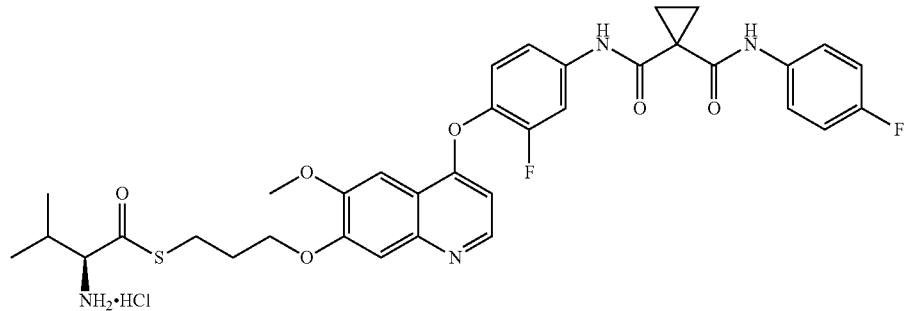

Step A:
(S)-2-(N-tert-butoxycarbonyl)-3-methylthiobutyric acid

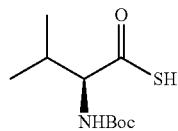

Add 1 g (4.6 mmol, 1.0 eq) N-tert-butoxycarbonyl-L-valine and 1.19 g (9.2 mmol, 2.0 eq) DIPEA to 15 mL tetrahydrofuran, dissolve it under magnetic stirring, and then cool it to 0-5° C. on ice water. Dissolve 470 mg (4.6 mmol, 1.0 eq) acetic anhydride in 5 mL THF, and then slowly add it dropwise to the reaction flask. After the addition, magnetically stir for 30 minutes and then add 389 mg (6.9 mmol, 1.5 eq) NaSH to the reaction flask. Remove the ice-water bath, and react for 10 hours at room temperature. After the reaction was complete, evaporate the THF, then add 30 mL water, and adjust the pH to 4 with 10% KHSO$_4$ solution. Extract twice with ethyl acetate (50 mL×2), collect the organic phase, wash the organic phase with saturated brine once, dry the organic phase with anhydrous sodium sulfate, and spin-evaporate the organic phase to afford the product of a dark yellow liquid (483 mg, yield=45%), which was then directly used in the next step.

Step B: N-(4-((7-(3-bromopropoxy)-6-methoxyquinolin-4-yl)oxy)-3-fluorophenyl)-N-(4-fluorophenyl)cyclopropane-1,1-diformamide

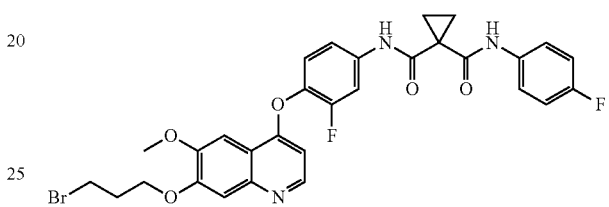

505 mg (1 mmol, 1.0 eq) N-(3-fluoro-4-((7-hydroxyl-6-methoxyquinolin-4-yl)oxy)phenyl)-N-(4-fluorophenyl)cyclopropane-1,1-dimethylformamide (see Preparation Example 1 for the synthesis method) and 732 mg (3 mmol, 3.0 eq) of 1,3-dibromopropane were dissolved in 10 mL N,N-dimethylformamide. Add 414 mg (3.0 mmol, 3.0 eq) potassium carbonate powder at room temperature. After the addition, the reaction system was stirred overnight at room temperature. After the reaction was complete monitored by TLC, the reaction system was poured into 150 mL water, and then extracted with 200 mL ethyl acetate. The organic phase was washed sequentially with water and saturated brine twice. The organic phase was dried over anhydrous sodium sulfate and evaporated to dryness. The residue was purified by silica gel column chromatography to give the product (600 mg, yield=95%).

Step C: S-(3-((4-(2-fluoro-4-(1-((4-fluorophenyl)aminoformyl)cyclopropane-1-carboxamido)phenoxy)-6-methoxyquinolin-7-yl)oxy)propyl)-(S)-2-((tert-butoxycarbonyl)amino)-3-methylthiobutyrate

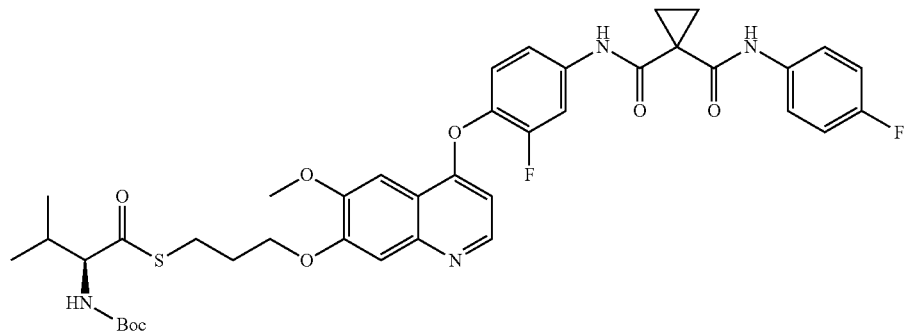 [SMILES: COc1cc2c(Oc3ccc(NC(=O)C4(C(=O)Nc5ccc(F)cc5)CC4)cc3F)ccnc2cc1OCCCSC(=O)[C@@H](NC(=O)OC(C)(C)C)C(C)C]

500 mg (0.80 mmol, 1.0 eq) N-(4-((7-(3-bromopropoxy)-6-methoxyquinolin-4-yl)oxy)-3-fluorophenyl)-N-(4-fluorophenyl)cyclopropane-1,1-diformamide and 332 mg (2.4 mmol, 3.0 eq) potassium carbonate powder were dissolved in 20 mL acetone. Add 560 mg (2.4 mmol, 3.0 eq) (S)-2-(N-tert-butoxycarbonyl)-3-methylthiobutyric acid at room temperature. The reaction system was reacted at room temperature for 4 hours. After the reaction was complete monitored by TLC, the solvent was evaporated to dryness. 150 mL water was added to the residue, which was then extracted with 250 mL ethyl acetate. After extraction, the organic phase was washed successively with water and saturated brine twice, and then the organic phase was dried over anhydrous sodium sulfate, evaporated to dryness. The residue was purified by silica gel column chromatography to afford the product (401 mg, yield=63%).

$^1$H NMR (400 MHz, CDCl$_3$) δ 10.08 (s, 1H), 8.62 (s, 1H), 7.81 (d, J=12.0 Hz, 1H), 7.60 (s, 2H), 7.54-7.47 (m, 2H), 7.34 (s, 1H), 7.30 (s, 1H), 7.25 (t, J=8.6 Hz, 1H), 7.08 (t, J=8.6 Hz, 2H), 6.50 (s, 1H), 5.12 (s, 1H), 4.30-4.01 (m, 3H), 4.07 (s, 3H), 3.13 (s, 2H), 2.30-2.00 (m, 3H), 1.82 (s, 2H), 1.68 (s, 2H), 1.50 (s, 9H), 1.02 (d, J=6.7 Hz, 3H), 0.90 (d, J=6.7 Hz, 3H).

Step D: S-(3-((4-(2-fluoro-4-(1-((4-fluorophenyl)aminoformyl)cyclopropane-1-carboxamido)phenoxy)-6-methoxyquinolin-7-yl)oxy)propyl)-(S)-2-amino-3-methylthiobutyrate hydrochloride

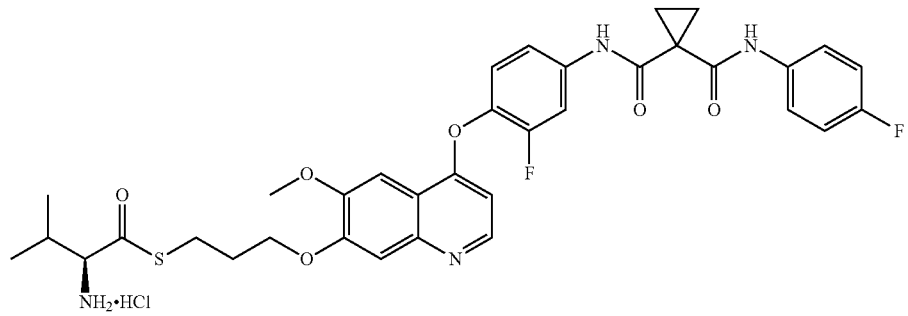

40 mg (0.14 mmol, 1.0 eq) S-(3-((4-(2-fluoro-4-(1-((4-fluorophenyl)aminoformyl)cyclopropane-1-carboxamido)phenoxy)-6-methoxyquinolin-7-yl)oxy)propyl)-(S)-2-((tert-butoxycarbonyl)amino)-3-methylthiobutyrate was dissolved in 10 mL ethyl acetate. Pass hydrochloric acid gas into the system and react for 30 minutes at room temperature. After the reaction was completed monitored by TLC, the reaction solution was concentrated and evaporated to dryness. The residue was slurried with 15 mL of ether with stirring. After vacuum filtration, the solid was rinsed with ether, and then vacuum dried to afford the product (35 mg, yield=95%).

$^1$H NMR (400 MHz, d-DMSO) δ 10.54 (s, 1H), 10.01 (s, 1H), 8.81 (s, 1H), 8.53 (s, 2H), 8.00 (d, J=14.1 Hz, 1H), 7.76 (s, 1H), 7.73 (s, 1H), 7.70-7.62 (m, 3H), 7.61 (s, 1H), 7.56 (d, J=9.1 Hz, 1H), 7.17 (t, J=8.9 Hz, 2H), 6.90 (s, 1H), 4.25 (t, J=8.0 Hz, 2H), 4.19 (s, 1H), 4.06 (s, 3H), 3.27-3.16 (m, 2H), 2.25-2.10 (m, 3H), 1.51 (d, J=10.3 Hz, 4H), 1.00 (dd, J=11.5, 7.0 Hz, 6H).

LC-MS: m/z=679 [M+H]$^+$.

Example 2 S-(3-((4-(2-Fluoro-4-(1-((4-fluorophenyl)aminoformyl)cyclopropane-1-carboxamido)phenoxy)-6-methoxyquinolin-7-yl)oxy)butyl)-(S)-2-amino-3-methylthiobutyrate hydrochloride

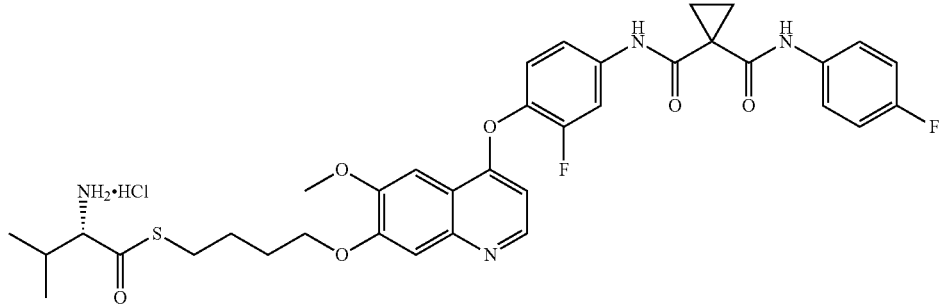

Refer to the process described in Example 1, replacing 1,3-dibromopropane with 1,4-dibromobutane to prepare the target compound (37 mg, 94%).

$^1$H NMR (400 MHz, d-DMSO) δ 10.55 (s, 1H), 10.03 (s, 1H), 8.82 (d, J=6.1 Hz, 1H), 8.54 (s, 2H), 8.01 (d, J=13.2 Hz, 1H), 7.75 (d, J=11.5 Hz, 2H), 7.72-7.60 (m, 4H), 7.57 (d, J=8.8 Hz, 1H), 7.18 (t, J=8.9 Hz, 2H), 6.92 (s, 1H), 4.29 (s, 2H), 4.17 (s, 1H), 4.06 (s, 3H), 3.14 (m, 2H), 2.25 (s, 1H), 2.04-1.90 (m, 2H), 1.83-1.60 (m, 2H), 1.52 (d, J=9.6 Hz, 4H), 1.01 (dd, J=10.1, 7.0 Hz, 6H).

LC-MS: m/z=693 [M+H]$^+$.

Example 3 S-(3-((4-(2-fluoro-4-(1-((4-fluorophenyl)aminoformyl)cyclopropane-1-carboxamido)phenoxy)-6-methoxyquinolin-7-yl)oxy)pentyl)-(S)-2-amino-3-methylthiobutyrate hydrochloride

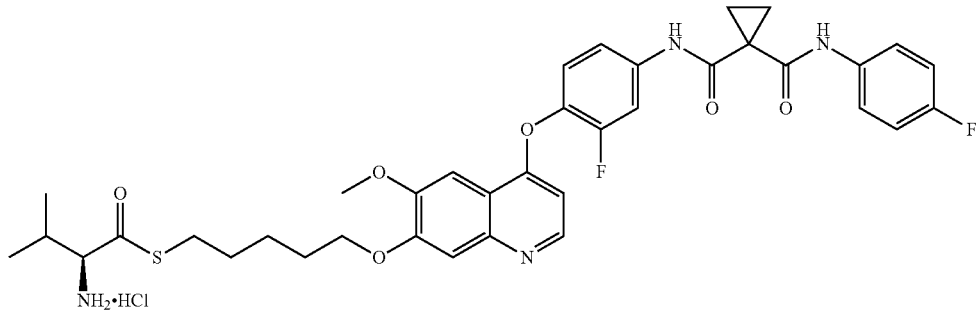

With reference to the process described in Example 1, replacing 1,3-dibromopropane with 1,5-dibromopentane to prepare the target compound (38 mg, 96%).

$^1$H NMR (400 MHz, d-DMSO) δ 10.56 (s, 1H), 10.04 (s, 1H), 8.82 (d, J=6.3 Hz, 1H), 8.56 (s, 2H), 8.01 (d, J=13.1 Hz, 1H), 7.77 (s, 2H), 7.71-7.61 (m, 3H), 7.58 (d, J=9.0 Hz, 1H), 7.18 (t, J=8.9 Hz, 2H), 6.92 (s, 1H), 4.25 (t, J=10.0 Hz, 2H), 4.15 (s, 1H), 4.07 (s, 3H), 3.08-2.95 (m, 2H), 2.26-2.19 (m, 1H), 1.92-1.80 (m, 2H), 1.75-1.58 (m, 2H), 1.6-1.46 (m, 6H), 1.07-0.93 (dd, J=10.1, 7.0 Hz, 6H).

LC-MS: m/z=707 [M+H]$^+$.

Example 4 S-(3-((4-(2-fluoro-4-(1-((4-fluorophenyl)aminoformyl)cyclopropane-1-carboxamido)phenoxy)-6-methoxyquinolin-7-yl)oxy)hexyl)-(S)-2-amino-3-methylthiobutyrate hydrochloride

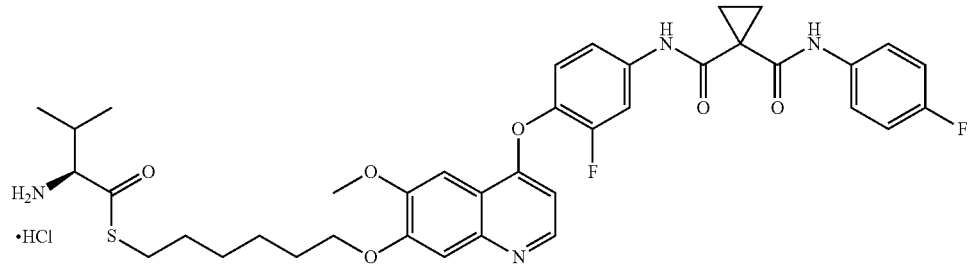 [SMILES: Cl ; COc1cc2c(Oc3ccc(NC(=O)C4(C(=O)Nc5ccc(F)cc5)CC4)cc3F)ccnc2cc1OCCCCCCSC(=O)[C@@H](N)C(C)C]

With reference to the process described in Example 1, replacing 1,3-dibromopropane with 1,6-dibromohexane to prepare the target compound (20 mg, 85%).

$^1$H NMR (400 MHz, d-DMSO) δ 10.53 (s, 1H), 10.01 (s, 1H), 8.80 (s, 1H), 8.48 (s, 2H), 8.00 (d, J=13.8 Hz, 1H), 7.75 (s, 2H), 7.66 (dd, J=24.3, 10.3 Hz, 4H), 7.56 (d, J=8.6 Hz, 1H), 7.18 (t, J=8.8 Hz, 2H), 6.89 (s, 1H), 4.24 (t, J=13.8 Hz, 2H), 4.16 (s, 1H), 4.05 (s, 3H), 3.10-2.95 (m, 2H), 2.28-2.08 (m, 1H), 1.88-1.77 (m, 2H), 1.64-1.52 (m, 2H), 1.51-1.40 (m, 8H), 1.00 (dd, J=11.4, 6.8 Hz, 6H).

LC-MS: m/z=721 [M+H]$^+$.

Example 5 4-(2-fluoro-4-(1-((4-fluorophenyl)aminoformyl)cyclopropane-1-carboxamido)phenoxy)-6-methoxyquinoline-7-lipoic acid ester

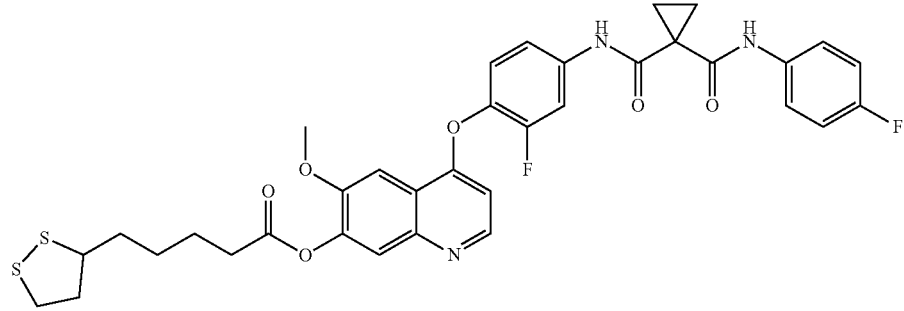 [SMILES: COc1cc2c(Oc3ccc(NC(=O)C4(C(=O)Nc5ccc(F)cc5)CC4)cc3F)ccnc2cc1OC(=O)CCCCC1CCSS1]

250 mg (0.50 mmol, 1.0 eq) N-(3-fluoro-4-((7-hydroxyl-6-methoxyquinolin-4-yl)oxy)phenyl)-N-(4-fluorophenyl)cyclopropane-1,1-diformamide, 153 mg (0.75 mmol, 1.5 eq) lipoic acid and 151 mg (1.50 mmol, 3.0 eq) triethylamine were dissolved in 10 mL dichloromethane. Add 144 mg (0.75 mmol, 1.5 eq) 1-(3-dimethylaminopropyl)-3-ethylcarbodiimide hydrochloride and 101 mg (0.75 mmol, 1.5 eq) 1-hydroxyl benzotriazole. After adding, stir and react at room temperature overnight. After the completion of the reaction monitored by TLC, the reaction system was poured into 100 mL water, extracted with 150 mL ethyl acetate. The organic phase was washed twice with water and saturated brine in turn, and then was dried over anhydrous sodium sulfate, evaporated to dryness. The residue was purified by silica gel column chromatography to afford the product (180 mg, yield=52%).

LC-MS: m/z=694 [M+H]$^+$.

Example 6 S-(3-((4-(2-fluoro-4-(1-((4-fluorophenyl)aminoformyl)cyclopropane-1-carboxamido)phenoxy)-6-methoxyquinolin-7-yl)oxy)propyl) (S)-2-amino-3-methylthiobutyrate hydrochloride

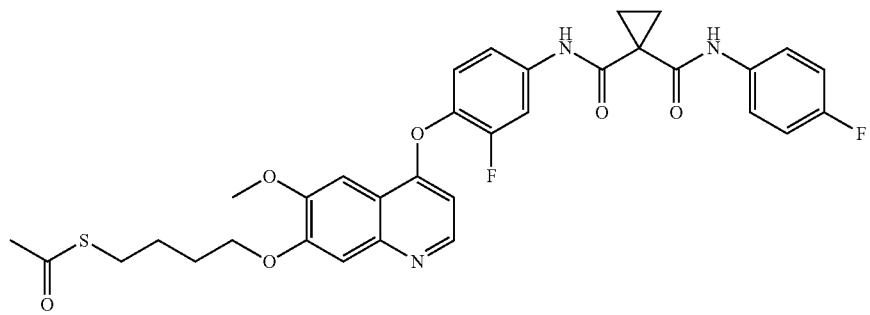 [SMILES: COc1cc2c(Oc3ccc(NC(=O)C4(C(=O)Nc5ccc(F)cc5)CC4)cc3F)ccnc2cc1OCCCCSC(C)=O]

Step A: S-(4-bromobutyl)-acetylthioester

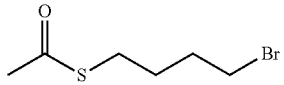

1 g (8.77 mmol, 1.0 eq) potassium thioacetate and 5.66 g (26.3 mmol, 3.0 eq) 1,4-dibromobutane were added to 15 mL acetone. After the addition, the reaction was stirred at room temperature for 3 hours. After the reaction was complete monitored by TLC, filter the reaction solution. White solid was rinsed with dichloromethane, and the organic filtrate was distilled under reduced pressure. The obtained residue was purified by silica gel column chromatography to provide the product (1.25 g, yield=68%).

$^1$H NMR (400 MHz, CDCl$_3$) δ 3.44 (t, J=6.6 Hz, 2H), 2.93 (t, J=7.2 Hz, 2H), 2.36 (s, 3H), 2.02-1.90 (m, 2H), 1.78 (m, 2H).

Step B: S-(4-((4-(2-Fluoro-4-(1-((4-fluorophenyl)aminoformyl)cyclopropane-1-carboxamido)phenoxy)-6-methoxyquinolin-7-yl)oxy)butyl)-acetylthioester

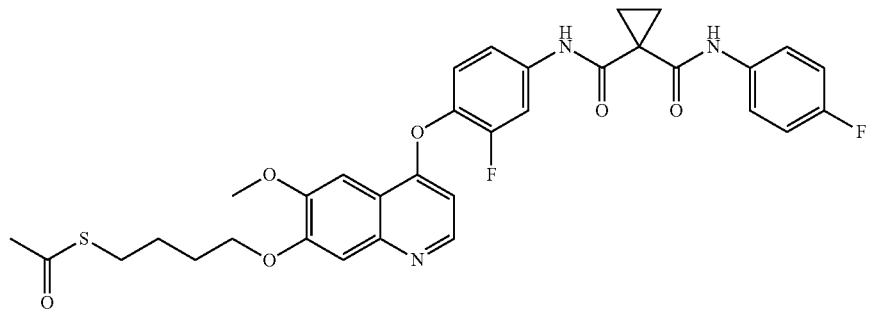 [SMILES: COc1cc2c(Oc3ccc(NC(=O)C4(C(=O)Nc5ccc(F)cc5)CC4)cc3F)ccnc2cc1OCCCCSC(C)=O]

505 mg (1 mmol, 1.0 eq) N-(3-fluoro-4-((7-hydroxyl-6-methoxyquinolin-4-yl)oxy)phenyl)-N-(4-fluorophenyl)cyclopropane-1,1-dimethylformamide and 422 mg (2 mmol, 2.0 eq) S-(4-bromobutyl)-acetylthioester were dissolved in 10 mL N,N-dimethylformamide and added 414 mg (3.0 mmol, 3.0 eq) potassium carbonate powder at room temperature. After the addition, the reaction was stirred overnight at room temperature. The reaction was completed by TLC monitoring, and then the reaction system was poured into 150 mL water. Extract the solution with 200 mL ethyl acetate, and the organic phase was then washed with water and saturated brine twice. The organic phase was dried over anhydrous sodium sulfate and evaporated to dryness, and the residue was purified by silica gel column chromatography to afford the product (497 mg, yield=78%).

LC-MS: m/z=636 [M+H]$^+$.

Example 7 N-(3-fluoro-4-((7-(4-mercaptobutoxy)-6-methoxyquinolin-4-yl)oxy)phenyl)-N-(4-fluorophenyl) cyclopropane-1,1-diformamide

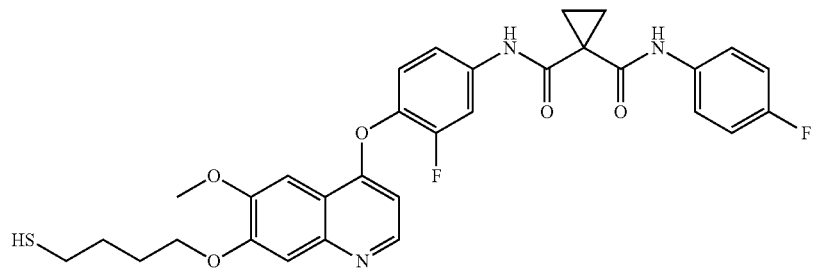 [SMILES: COc1cc2c(Oc3ccc(NC(=O)C4(C(=O)Nc5ccc(F)cc5)CC4)cc3F)ccnc2cc1OCCCCS]

200 mg (0.80 mmol, 1.0 eq) S-(4-((4-(2-fluoro-4-(1-((4-fluorophenyl)aminoformyl)cyclopropane-1-carboxamido)phenoxy)-6-methoxyquinolin-7-yl)oxy)butyl)-acetylthioester was dissolved in 10 mL methanol, and then 560 mg (2.4 mmol, 10.0 eq) sodium borohydride was added under ice bath. Keep the reaction in an ice bath for 10 minutes, then warm to room temperature and react for 2 hours. The reaction was complete by TLC monitoring, then the solvent was evaporated to dryness. 100 mL of citric acid aqueous solution (10%) was added to the residue, and extracted with 120 mL ethyl acetate. The organic phase was successively washed with water and saturated brine twice, then the organic phase was dried over anhydrous sodium sulfate, evaporated to dryness. The residue was purified by silica gel column chromatography to afford the product (55 mg, yield=29%).

LC-MS: m/z=594 [M+H]$^+$.

Example 8 S-(5-((4-(2-fluoro-4-(1-((4-fluorophenyl)aminoformyl)cyclopropane-1-carboxamido)phenoxy)-6-methoxyquinolin-7-yl)oxy)pentyl)-acetylthioester

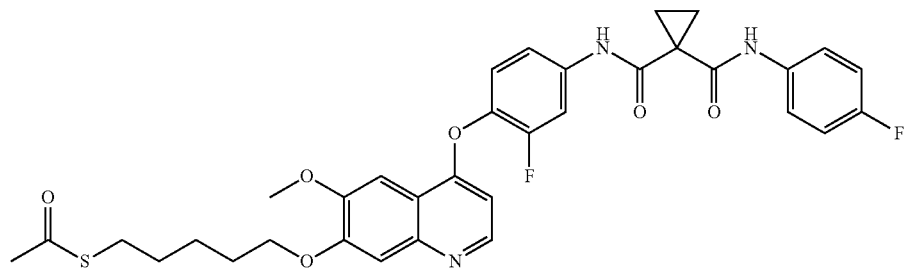 [SMILES: COc1cc2c(Oc3ccc(NC(=O)C4(C(=O)Nc5ccc(F)cc5)CC4)cc3F)ccnc2cc1OCCCCCSC(C)=O]

With reference to the process described in Example 6, replacing 1,4-dibromobutane with 1,5-dibromopentane to prepare the target compound (380 mg, 86%).

LC-MS: m/z=650 [M+H]$^+$.

$^1$H NMR (400 MHz, CDCl$_3$) δ 9.86 (s, 1H), 9.47 (s, 1H), 8.50 (d, J=4.1 Hz, 1H), 7.86 (d, J=11.8 Hz, 1H), 7.68-7.52 (m, 3H), 7.48-7.36 (m, 2H), 7.34-7.17 (m, 1H), 7.07 (s, 2H), 6.43 (s, 1H), 4.20 (s, 2H), 4.06 (s, 3H), 3.05 (s, 2H), 2.94 (s, 3H), 2.37 (s, 4H), 1.98 (s, 2H), 1.67 (m, 4H).

Example 9 N-(3-fluoro-4-((7-(5-mercaptopentyloxy)-6-methoxyquinolin-4-yl)oxy)phenyl)-N-(4-fluorophenyl) cyclopropane-1,1-diformamide

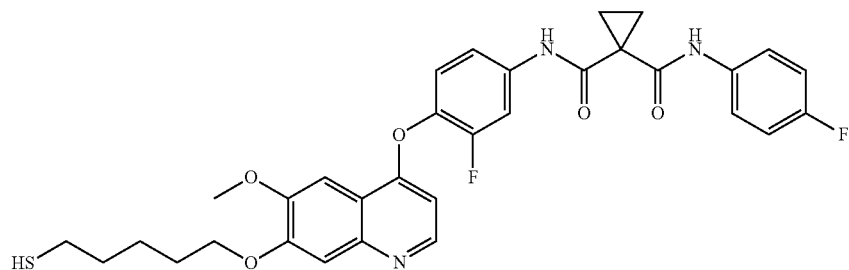 [SMILES: COc1cc2c(Oc3ccc(NC(=O)C4(C(=O)Nc5ccc(F)cc5)CC4)cc3F)ccnc2cc1OCCCCCS]

The target compound (28 mg, 26%) was prepared according to the process described in Example 7.

LC-MS: m/z=608 [M+H]$^+$.

$^1$H NMR (400 MHz, CDCl$_3$) δ 9.73 (s, 1H), 9.29 (s, 1H), 8.51 (d, J=5.2 Hz, 1H), 7.84 (d, J=11.8 Hz, 1H), 7.65-7.54 (m, 3H), 7.44 (s, 1H), 7.37 (d, J=8.8 Hz, 1H), 7.26 (t, J=8.6 Hz, 1H), 7.08 (t, J=8.6 Hz, 2H), 6.42 (d, J=5.1 Hz, 1H), 4.23 (d, J=6.1 Hz, 2H), 4.07 (s, 3H), 2.62 (dd, J=14.5, 7.3 Hz, 2H), 2.47-2.38 (m, 2H), 2.02-1.97 (m, 2H), 1.76 (dd, J=14.1, 6.9 Hz, 2H), 1.71-1.62 (s, 4H).

Example 10 S-(6-((4-(2-fluoro-4-(1-((4-fluorophenyl)aminoformyl)cyclopropane-1-carboxamido)phenoxy)-6-methoxyquinolin-7-yl)oxy)hexyl)-acetylthioester

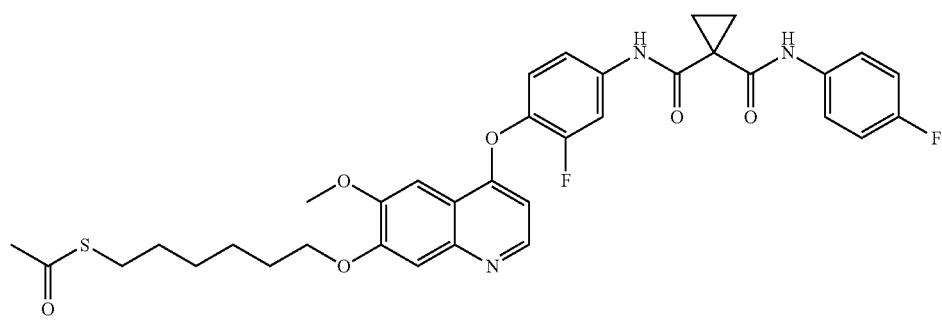 [SMILES: COc1cc2c(Oc3ccc(NC(=O)C4(C(=O)Nc5ccc(F)cc5)CC4)cc3F)ccnc2cc1OCCCCCCSC(C)=O]

With reference to the process described in Example 6, replacing 1,4-dibromobutane with 1,6-dibromohexane to prepare the target compound (320 mg, 81%).

LC-MS: m/z=664 [M+H]$^+$.

Example 11 N-(3-fluoro-4-((7-(6-mercaptohexyloxy)-6-methoxyquinolin-4-yl)oxy)phenyl)-N-(4-fluorophenyl) cyclopropane-1,1-diformamide

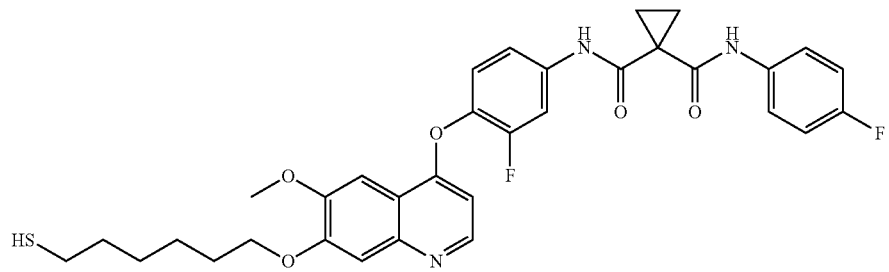

The target compound (20 mg, 35%) was prepared according to the process described in Example 7.
LC-MS: m/z=622 [M+H]$^+$.

Example 12 S-(7-((4-(2-fluoro-4-(1-((4-fluorophenyl)aminoformyl)cyclopropane-1-carboxamido)phenoxy)-6-methoxyquinolin-7-yl)oxy)heptyl)-acetylthioester

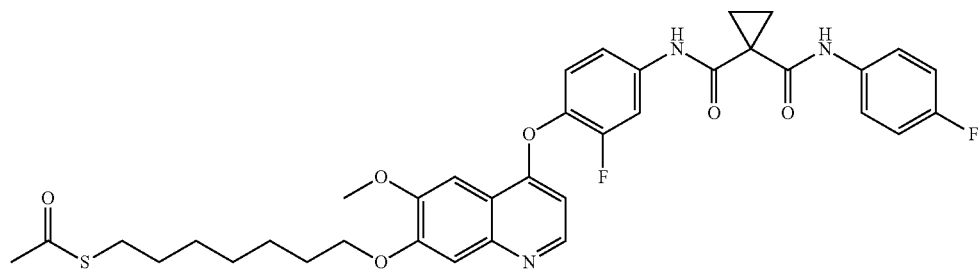 [SMILES: COc1cc2c(Oc3ccc(NC(=O)C4(C(=O)Nc5ccc(F)cc5)CC4)cc3F)ccnc2cc1OCCCCCCCSC(C)=O]

With reference to the process described in Example 6, replacing 1,4-dibromobutane with 1,7-dibromoheptane to prepare the target compound (280 mg, 85%).
LC-MS: m/z=678 [M+H]$^+$.

Example 13 N-(3-fluoro-4-((7-(7-mercaptoheptyloxy)-6-methoxyquinolin-4-yl)oxy)phenyl)-N-(4-fluorophenyl) cyclopropane-1,1-diformamide

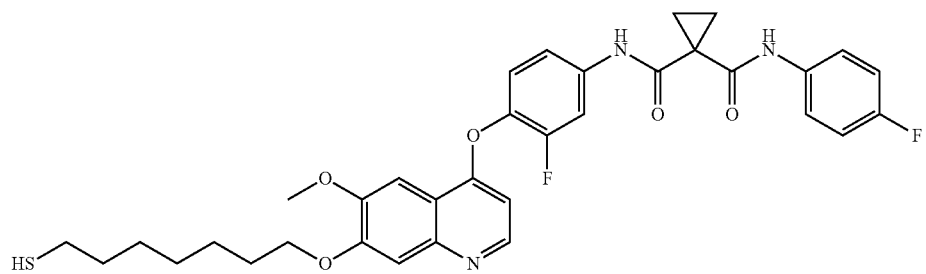 [SMILES: COc1cc2c(Oc3ccc(NC(=O)C4(C(=O)Nc5ccc(F)cc5)CC4)cc3F)ccnc2cc1OCCCCCCCS]

The target compound (50 mg, 31%) was prepared according to the steps described in Example 7.

1H NMR (400 MHz, CDCl$_3$) δ 10.20 (s, 1H), 8.63 (s, 1H), 8.48 (d, J=4.8 Hz, 1H), 7.80 (s, 1H), 7.78 (d, J=10.1 Hz, 1H), 7.58 (s, 1H), 7.51-7.41 (m, 3H), 7.32 (s, 1H), 7.22 (t, J=8.5 Hz, 1H), 7.05 (t, J=8.6 Hz, 2H), 6.42 (d, J=5.0 Hz, 1H), 4.17 (d, J=6.3 Hz, 2H), 4.05 (s, 3H), 2.54 (d, J=7.4 Hz, 2H), 1.99-1.89 (m, 2H), 1.83-1.75 (m, 2H), 1.70-1.56 (m, 4H), 1.52 (s, 2H), 1.42 (s, 4H).

Example 14 S-(8-((4-(2-fluoro-4-(1-((4-fluorophenyl)aminoformyl)cyclopropane-1-carboxamido)phenoxy)-6-methoxyquinolin-7-yl)oxy)octyl)-acetylthioester

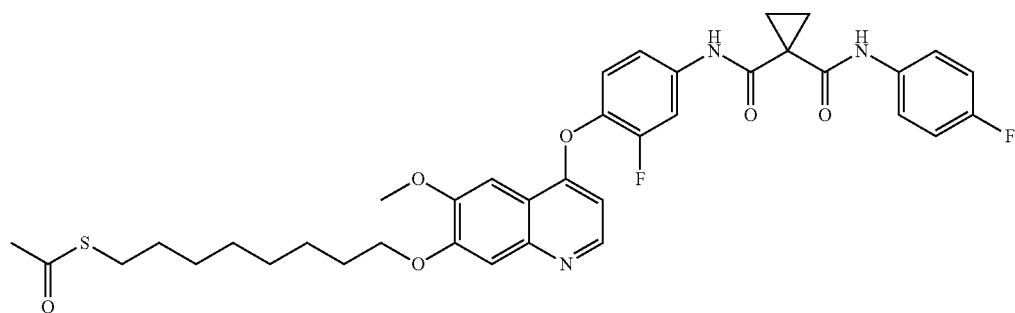 [SMILES: COc1cc2c(Oc3ccc(NC(=O)C4(C(=O)Nc5ccc(F)cc5)CC4)cc3F)ccnc2cc1OCCCCCCCCSC(C)=O]

Refer to the process described in Example 6, replacing 1,4-dibromobutane with 1,8-dibromooctane to prepare the target compound (300 mg, 83%).

LC-MS: m/z=692 [M+H]$^+$.

Example 15 N-(3-Fluoro-4-((7-(8-mercaptooctyloxy)-6-methoxyquinolin-4-yl)oxy)phenyl)-N-(4-fluorophenyl) cyclopropane-1,1-diformamide

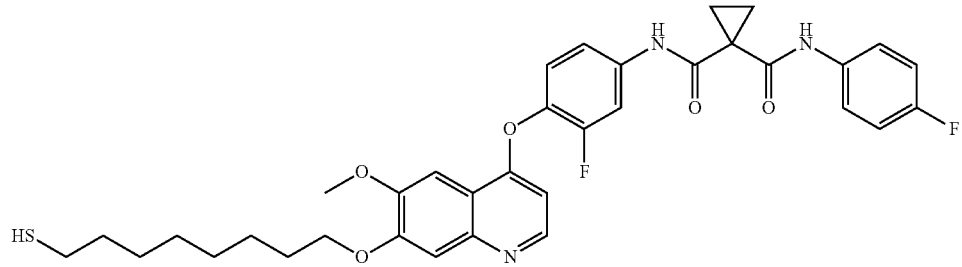 [SMILES: COc1cc2c(Oc3ccc(NC(=O)C4(C(=O)Nc5ccc(F)cc5)CC4)cc3F)ccnc2cc1OCCCCCCCCS]

The target compound (22 mg, 35%) was prepared according to the process described in Example 7.

$^1$H-NMR (400 MHz, CDCl$_3$) δ 10.09 (s, 1H), 8.51 (d, J=4.7 Hz, 1H), 8.33 (s, 1H), 7.81 (dd, J=12.4, 1.9 Hz, 1H), 7.60 (s, 1H), 7.49 (dd, J=9.0, 4.8 Hz, 2H), 7.44 (s, 1H), 7.34-7.23 (m, 2H), 7.10 (t, J=8.6 Hz, 2H), 6.43 (d, J=5.1 Hz, 1H), 4.27-4.16 (m, 2H), 4.08 (s, 3H), 2.57 (dd, J=14.7, 7.5 Hz, 2H), 2.01-1.95 (m, 2H), 1.85 (dd, J=7.6, 4.8 Hz, 2H), 1.71-1.24 (m, 12H).

LC-MS: m/z=650 [M+H]$^+$.-

Example 16 S-(9-((4-(2-fluoro-4-(1-((4-fluorophenyl)aminoformyl)cyclopropane-1-carboxamido)phenoxy)-6-methoxyquinolin-7-yl)oxy)nonyl)-acetylthioester

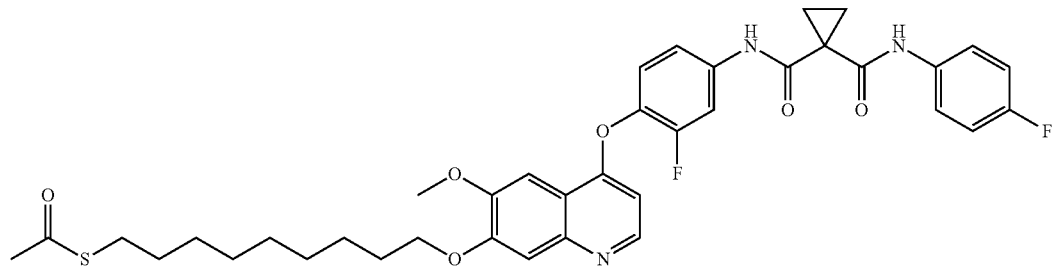 [SMILES: COc1cc2c(Oc3ccc(NC(=O)C4(C(=O)Nc5ccc(F)cc5)CC4)cc3F)ccnc2cc1OCCCCCCCCCSC(C)=O]

Refer to the process described in Example 6, 1,4-dibromobutane was replaced with 1,9-dibromononane to prepare the target compound (320 mg, 810%).

$^1$H-NMR (400 MHz, CDCl$_3$) δ 10.01 (s, 1H), 8.47 (d, J=5.3 Hz, 1H), 8.29 (s, 1H), 7.76 (dd, J=12.0, 2.3 Hz, 1H), 7.56 (s, 1H), 7.45 (dd, J=9.0, 4.7 Hz, 2H), 7.39 (s, 1H), 7.30-7.18 (m, 2H), 7.06 (t, J=8.6 Hz, 2H), 6.38 (d, J=5.2 Hz, 1H), 4.18 (t, J=6.9 Hz, 2H), 4.04 (s, 3H), 2.90-2.83 (m, 2H), 2.32 (s, 3H), 1.98-1.89 (m, 2H), 1.80 (dd, J=7.7, 4.9 Hz, 2H), 1.62 (dd, J=7.7, 4.8 Hz, 2H), 1.58-1.27 (m, 12H).

LC-MS: m/z=706[M+H]$^+$.

Example 17 N-(3-Fluoro-4-((7-(9-mercaptononyloxy)-6-methoxyquinolin-4-yl)oxy)phenyl)-N-(4-fluorophenyl)cyclopropane-1,1-diformamide

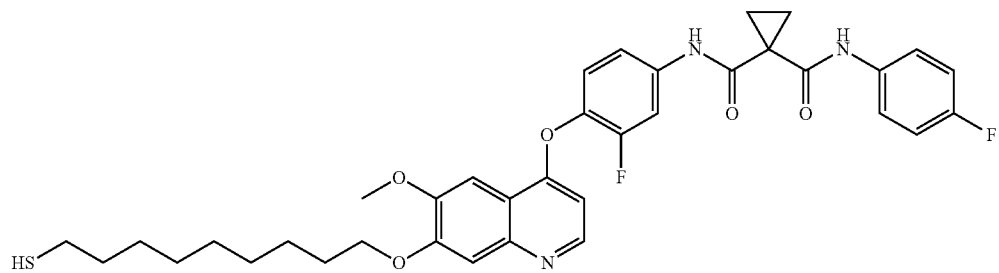 [SMILES: COc1cc2c(Oc3ccc(NC(=O)C4(C(=O)Nc5ccc(F)cc5)CC4)cc3F)ccnc2cc1OCCCCCCCCCS]

The target compound (38 mg, 32%) was prepared according to the process described in Example 7.

$^1$H NMR (400 MHz, CDCl$_3$) δ 10.08 (s, 1H), 8.51 (d, J=5.2 Hz, 1H), 8.41 (s, 1H), 7.80 (d, J=11.8 Hz, 1H), 7.60 (s, 1H), 7.54-7.40 (m, 3H), 7.34-7.23 (m, 2H), 7.10 (t, J=8.6 Hz, 2H), 6.43 (d, J=5.1 Hz, 1H), 4.23 (t, J=6.8 Hz, 2H), 4.08 (s, 3H), 2.56 (dd, J=14.8, 7.5 Hz, 2H), 2.02-1.94 (m, 2H), 1.89-1.80 (m, 2H), 1.73-1.23 (m, 14H).

LC-MS: m/z=664 [M+H]$^+$.-

Example 18 S-(10-((4-(2-fluoro-4-(1-((4-fluorophenyl)aminoformyl)cyclopropane-1-carboxamido)phenoxy)-6-methoxyquinolin-7-yl)oxy)decyl)-acetylthioester

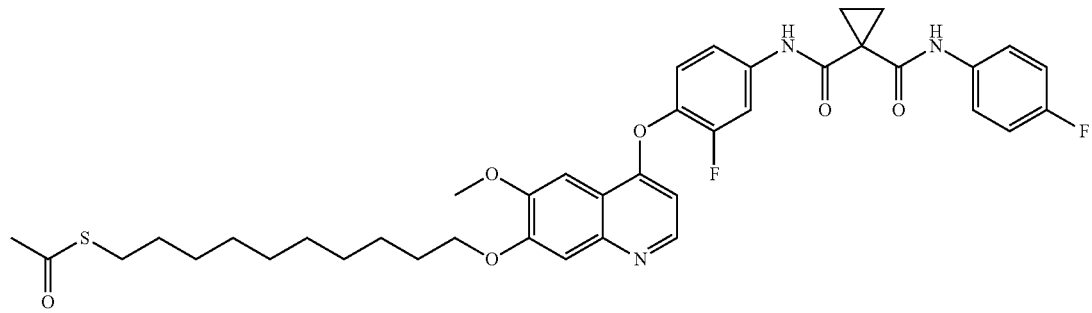 [SMILES: COc1cc2c(Oc3ccc(NC(=O)C4(C(=O)Nc5ccc(F)cc5)CC4)cc3F)ccnc2cc1OCCCCCCCCCCSC(C)=O]

Refer to the process described in Example 6, replacing 1,4-dibromobutane with 1,10-dibromodecane to prepare the target compound (265 mg, 76%).
LC-MS: m/z=720 [M+H]$^+$.

Example 19 N-(3-fluoro-4-((7-(10-mercaptodecyloxy)-6-methoxyquinolin-4-yl)oxy)phenyl)-N-(4-fluorophenyl) cyclopropane-1,1-diformamide

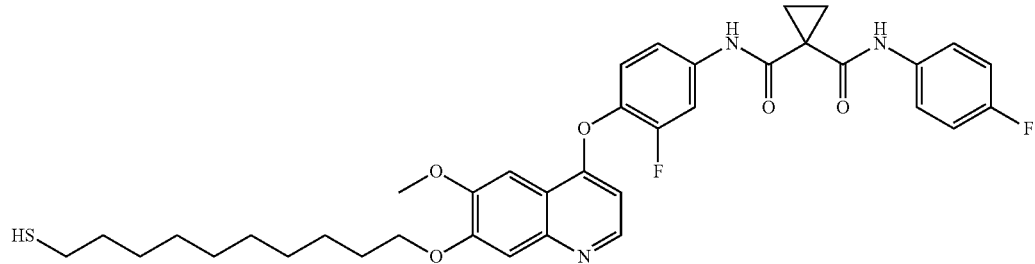 [SMILES: COc1cc2c(Oc3ccc(NC(=O)C4(C(=O)Nc5ccc(F)cc5)CC4)cc3F)ccnc2cc1OCCCCCCCCCCS]

The target compound (42 mg, 29%) was prepared according to the process described in Example 7.
$^1$H-NMR (400 MHz, CDCl$_3$) δ 10.08 (s, 1H), 8.48 (d, J=5.5 Hz, 1H), 8.37 (s, 1H), 7.78 (d, J=13.3 Hz, 1H), 7.57 (s, 1H), 7.51-7.37 (m, 3H), 7.35-7.17 (m, 2H), 7.07 (t, J=8.3 Hz, 2H), 6.46-6.33 (m, 1H), 4.18 (t, J=6.7 Hz, 2H), 4.05 (s, 3H), 2.53 (dd, J=14.7, 7.7 Hz, 2H), 2.01-1.91 (m, 2H), 1.85-1.77 (m, 2H), 1.67-1.20 (m, 16H).
LC-MS: m/z=678 [M+H]$^+$.

Example 20 (E)-S-(6-((4-(2-fluoro-4-(1-((4-fluorophenyl)carbamoyl)cyclopropane-1-formamido)phenoxy)-6-methoxyquinolin-7-yl)oxy)hexyl-3-en-1-yl) acetylthioester

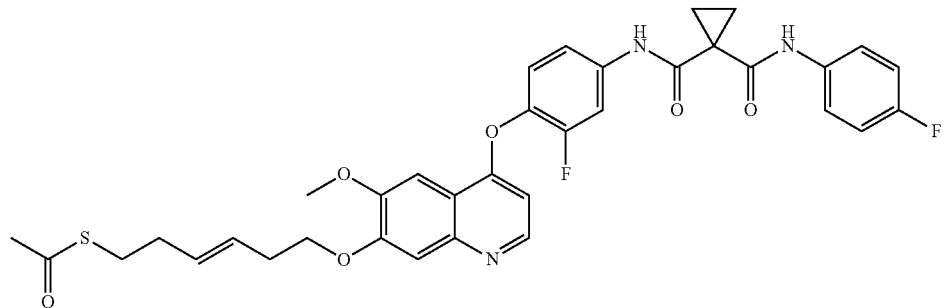 [SMILES: COc1cc2c(Oc3ccc(NC(=O)C4(C(=O)Nc5ccc(F)cc5)CC4)cc3F)ccnc2cc1OCC/C=C/CCSC(C)=O]

Step A: (E)-1,6-dibromo-3-hexene

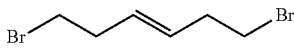

5.0 g (7.4 mmol, 1.0 eq) 4-bromo-1-butene and 311 mg (0.37 mmol, 0.05 eq) 1,3-bis(2,4,6-trimethylphenyl)-2-(imidazolidinylidene) (dichlorobenzylidene) (tricyclohexylphosphine) ruthenium (Grubbs second-generation catalyst) were added to 5 mL toluene, ventilate with nitrogen three times, stirred at 90° C. for 3 hours, and then ventilate with nitrogen three times again. Stir at 90° C. overnight. The reaction was complete by TLC monitoring, then solvent was distilled off under reduced pressure. The residue was purified by silica gel column chromatography to afford the product (2.70 g, yield=61%).

$^1$H NMR (400 MHz, CDCl$_3$) δ 5.65-5.56 (m, 2H), 3.50-3.42 (m, 4H), 2.67-2.60 (m, 4H).

Step B: (E)-6-bromo-3-hexene acetylthio ester

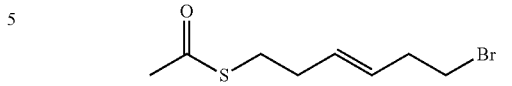

0.35 g (3.07 mmol, 1.0 eq) potassium thioacetate and 1.95 g (26.3 mmol, 3.0 eq) (E)-1,6-dibromo-3-hexene were added to 15 mL acetone. Then, the reaction system was stirred at room temperature for 3 hours. After the completion of the reaction monitored by TLC, filtered, and rinsed the white solid with dichloromethane. The organic filtrate was distilled under reduced pressure, and the residue was purified by silica gel column chromatography to afford the product (0.47 g, yield=65%).

Step C: (E)-S-(6-((4-(2-fluoro-4-(1-((4-fluorophenyl)aminoformyl)cyclopropane-1-carbamoyl)phenoxy)-6-methoxyquinolin-7-yl)oxy)hexyl-3-en-1-yl) acetylthio ester

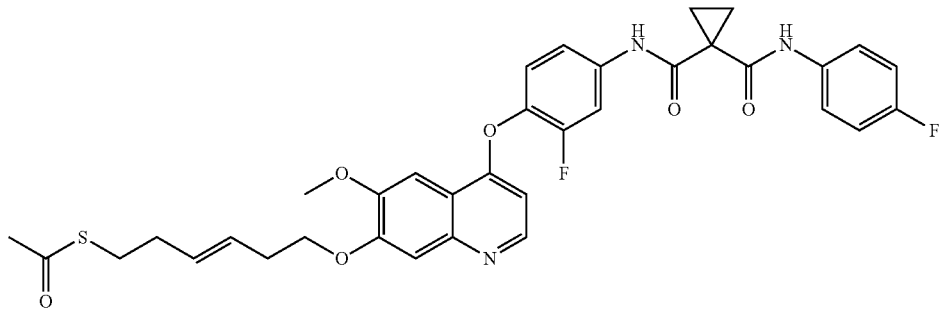 [SMILES: COc1cc2c(Oc3ccc(NC(=O)C4(C(=O)Nc5ccc(F)cc5)CC4)cc3F)ccnc2cc1OCC/C=C/CCSC(C)=O]

250 mg (0.5 mmol, 1.0 eq) N-(3-fluoro-4-((7-hydroxyl-6-methoxyquinolin-4-yl)oxy)phenyl)-N-(4-fluorophenyl) cyclopropane-1,1-dimethylformamide and 237 mg (1 mmol, 2.0 eq) (E)-6-bromo-3-hexene acetylthioester were dissolved in 10 mL N,N-dimethylformamide, to which 207 mg (1.5 mmol, 3.0 eq) potassium carbonate powder was added at room temperature. The reaction system was stirred at room temperature overnight. After completion of the reaction monitored by TLC, the reaction system was poured into 100 mL water, then extracted with 200 mL ethyl acetate. The organic phase was sequentially washed with water and saturated brine twice, and then was dried over anhydrous sodium sulfate, evaporated to dryness, and the residue was purified by silica gel column chromatography to afford the product (140 mg, yield=42%).

$^1$H NMR (400 MHz, CDCl$_3$) δ 10.18 (s, 1H), 8.60 (s, 1H), 8.50 (d, J=5.2 Hz, 1H), 7.80 (d, J=12.1 Hz, 1H), 7.60 (s, 1H), 7.49 (dd, J=8.6, 4.7 Hz, 2H), 7.43 (s, 1H), 7.32 (s, 1H), 7.24 (t, J=8.5 Hz, 1H), 7.08 (t, J=8.5 Hz, 2H), 6.43 (d, J=5.0 Hz, 1H), 5.63 (m, 2H), 4.21 (t, J=6.8 Hz, 2H), 4.07 (s, 3H), 2.95 (t, J=7.4 Hz, 2H), 2.70-2.63 (m, 2H), 2.40-2.28 (m, 5H), 1.82 (m, 2H), 1.67 (m, 2H).

Example 21 (E)-N-(3-fluoro-4-((7-((6-mercapto-hexyl-3-en-1-yl)oxy)-6-methoxyquinolin-4-yl)oxy)phenyl)-N-(4-fluorophenyl)cyclopropane-1,1-diformamide

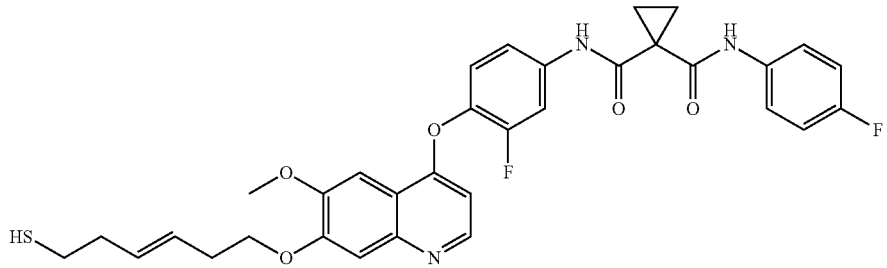 [SMILES: COc1cc2c(Oc3ccc(NC(=O)C4(C(=O)Nc5ccc(F)cc5)CC4)cc3F)ccnc2cc1OCC/C=C/CCS]

Hydrolysis was performed with reference to the process described in Example 7, the target compound (150 mg, 36%) was prepared from Example 20.

$^1$H NMR (400 MHz, CDCl$_3$) δ 10.11 (s, 1H), 8.52 (d, J=5.3 Hz, 2H), 8.42 (s, 1H), 7.81 (d, J=12.3 Hz, 1H), 7.60 (s, 1H), 7.49 (dd, J=8.9, 4.8 Hz, 3H), 7.31 (s, 1H), 7.29-7.21 (m, 1H), 7.10 (t, J=5.5 Hz, 2H), 6.44 (d, J=4.9 Hz, 1H), 5.76-5.53 (m, 2H), 4.28-4.18 (m, 2H), 4.07 (s, 3H), 2.83-2.55 (m, 4H), 2.50-2.38 (m, 2H), 1.87-1.80 (m, 2H), 1.75-1.66 (m, 2H).

Example 22 (E)-S-(7-((4-(2-fluoro-4-(1-((4-fluorophenyl)aminoformyl)cyclopropane-1-carbamoyl)phenoxy)-6-methoxyquinolin-7-yl)oxy)heptyl-4-en-1-yl)acetylthio ester

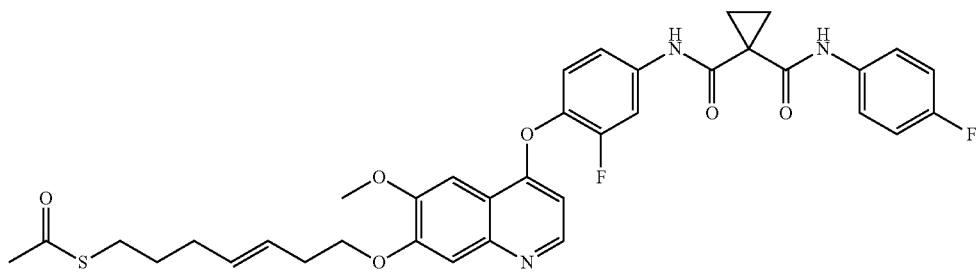 [SMILES: COc1cc2c(Oc3ccc(NC(=O)C4(C(=O)Nc5ccc(F)cc5)CC4)cc3F)ccnc2cc1OCC/C=C/CCCSC(C)=O]

Step A: 1-pentenyl acetylthioester

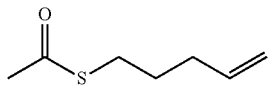

Add 2.0 g (17.5 mmol, 1.0 eq) potassium thioacetate and 3.10 g (21.0 mmol, 1.2 eq) 5-bromo-1-pentene to 15 mL acetone, then stir it at room temperature for 3 hours. After the reaction was completed by TLC monitoring, filtering, and rinsing the white solid with dichloromethane. Then, the organic filtrate was distilled under reduced pressure, and the residue was purified by silica gel column chromatography to afford the product (1.54 g, yield=61%).

Step B: N-(4-((7-(1-butenyloxy)-6-methoxyquinolin-4-yl)oxy)-3-fluorophenyl)-N-(4-fluorophenyl)cyclopropane-1,1-diformamide

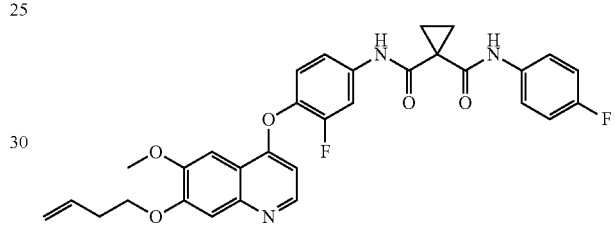

400 mg (0.79 mmol, 1.0 eq) N-(3-fluoro-4-((7-hydroxyl-6-methoxyquinolin-4-yl)oxy)phenyl)-N-(4-fluorophenyl)cyclopropane-1,1-dimethylformamide and 213 mg (1.58 mmol, 2.0 eq) 4-bromo-1-butene were dissolved in 10 mL N,N-dimethylformamide. 327 mg (2.37 mmol, 3.0 eq) potassium carbonate powder was added at room temperature. After the addition, the reaction was stirred overnight at room temperature. The reaction system was poured into 100 mL water after the completion of reaction monitored by TLC, extracted with 100 mL ethyl acetate. The organic phase was then washed with water and saturated brine twice, dried over anhydrous sodium sulfate and evaporated to dryness. The residue was purified by silica gel column chromatography to afford the product (260 mg, yield=59%).

$^1$H NMR (400 MHz, CDCl$_3$) δ 10.21 (s, 1H), 8.66 (s, 1H), 8.50 (d, J=4.0 Hz, 1H), 8.05 (s, 1H), 7.81 (dd, J=4.0, 4.0 Hz, 1H), 7.60 (s, 1H), 7.52-7.49 (m, 2H), 7.44 (s, 1H), 7.34-7.28 (m, 2H), 7.25 (t, J=8.0 Hz, 1H), 7.09 (t, J=8.0 Hz, 2H), 6.42

(d, J=4.0 Hz, 1H), 6.02-5.95 (m, 1H), 5.25 (d, J=12.0 Hz, 1H), 5.18 (d, J=12.0 Hz, 1H), 4.28 (t, J=4.0 Hz, 2H), 4.08 (s, 3H), 2.75 (q, J=12.0 Hz, 2H), 1.88-1.76 (m, 2H), 1.71-1.64 (m, 2H).

Step C: (E)-S-(7-((4-(2-fluoro-4-(1-((4-fluorophenyl)aminoformyl)cyclopropane-1-carbamoyl)phenoxy)-6-methoxyquinolin-7-yl)oxy)heptyl-4-en-1-yl) acetylthio ester

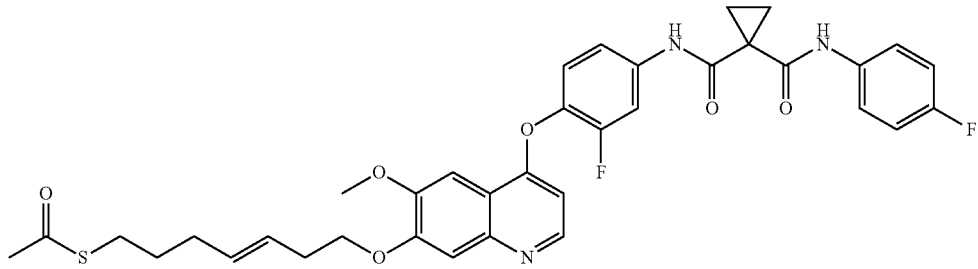 [SMILES: COc1cc2c(Oc3ccc(NC(=O)C4(C(=O)Nc5ccc(F)cc5)CC4)cc3F)ccnc2cc1OCC/C=C/CCCSC(C)=O]

100 mg (0.18 mmol, 1.0 eq) N-(4-((7-(1-butenoxy)-6-methoxyquinolin-4-yl)oxy)-3-fluorophenyl)-N-(4-fluorophenyl)cyclopropane-1,1-diformamide, 150 mg (1.8 mmol, 10.0 eq) 1-pentenyl acetylthioester and 15 mg (0.018 mmol, 0.1 eq) 1,3-bis(2,4,6-trimethylphenyl)-2-(imidazolidinylidene)(dichlorobenzylidene)(tricyclohexylphosphine)ruthenium (Grubbs second-generation catalyst) were added to 5 mL toluene. Nitrogen ventilation was performed three times, and the reaction system was stirred at 90° C. for 4 hours, followed by nitrogen ventilation for three times again and stirred at 90° C. overnight. After the completion of the reaction monitored by TLC, the solvent was distilled off under reduced pressure. The residue was purified by silica gel column chromatography to afford the product (20 mg, yield=17%).

$^1$H NMR (400 MHz, CDCl$_3$) δ 10.25 (s, 1H), 8.72 (s, 1H), 8.50 (d, J=4.0 Hz, 1H), 7.79 (d, J=8.0, 1H), 7.81 (t, J=4.0 Hz, 1H), 7.61 (s, 1H), 7.52-7.49 (m, 2H), 7.36-7.27 (m, 1H), 7.25 (t, J=8.0 Hz, 1H), 7.08 (t, J=8.0 Hz, 2H), 6.45 (d, J=4.0 Hz, 1H), 5.59-5.56 (m, 1H), 5.25 (m, 1H), 4.25 (t, J=8.0 Hz, 2H), 3.96 (s, 3H), 2.59 (m, 2H), 2.56-2.48 (m, 5H), 1.58-1.52 (m, 2H), 1.50 (s, 6H).

Example 23 (E)-N-(3-fluoro-4-((7-((7-mercaptoheptyl-3-en-1-yl)oxy)-6-methoxyquinolin-4-yl)oxy)phenyl)-N-(4-fluorophenyl)cyclopropane-1,1-diformamide

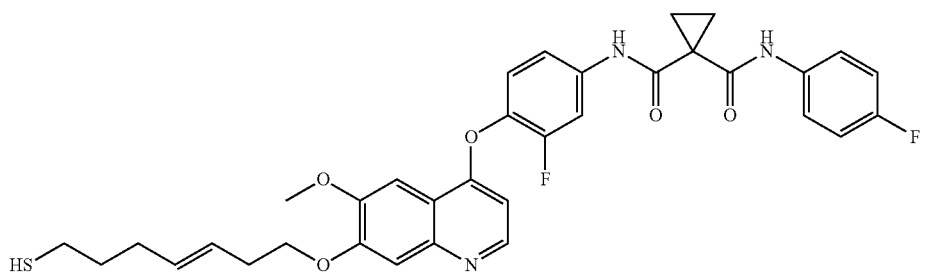 [SMILES: COc1cc2c(Oc3ccc(NC(=O)C4(C(=O)Nc5ccc(F)cc5)CC4)cc3F)ccnc2cc1OCC/C=C/CCCS]

Hydrolysis was performed with reference to the process described in Example 7, the target compound (15 mg, 53%) was prepared from Example 22.
LC-MS: m/z=634 [M+H]⁺.

Example 24 (E)-S-(7-((4-(2-fluoro-4-(1-((4-fluorophenyl)aminoformyl)cyclopropane-1-carbamoyl)phenoxy)-6-methoxyquinolin-7-yl)oxy)heptyl-5-en-1-yl)acetylthio ester

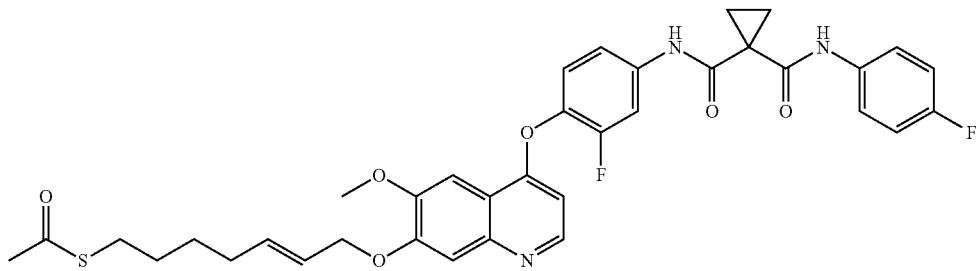 [SMILES: COc1cc2c(Oc3ccc(NC(=O)C4(C(=O)Nc5ccc(F)cc5)CC4)cc3F)ccnc2cc1OC/C=C/CCCCSC(C)=O]

Step A: 1-hexenyl acetyl thioester

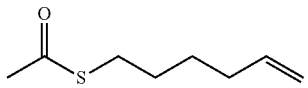

1 g (0.88 mmol, 1.0 eq) potassium thioacetate and 1.71 g (11.1 mmol, 1.2 eq) 6-bromo-1-hexene were added to 15 mL acetone. The reaction was stirred at room temperature for 3 hours. After completion of the reaction monitored by TLC, filter, and rinse the white solid with dichloromethane. The organic filtrate was distilled under reduced pressure, and the residue was purified by silica gel column chromatography to afford the product (0.81 g, yield=63%).

Step B: (E)-S-(7-bromoheptyl-5-en-1-yl)acetylthio ester

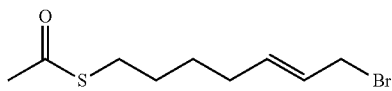

100 mg (0.63 mmol, 1.0 eq) 1-hexenyl acetylthioester, 230 mg (1.89 mmol, 3.0 eq) 3-bromopropene and 40 mg (0.063 mmol, 0.1 eq), 1,3-bis(2,4,6-trimethylphenyl)-2-(imidazolidinylidene)(dichlorobenzylidene)(tricyclohexylphosphine)ruthenium (Grubbs second-generation catalyst) were added to 2 mL of dichloromethane, and ventilate with nitrogen for three times. The reaction was stirred for 3 hours under reflux. After the completion of the reaction monitored by TLC, the solvent was distilled off under reduced pressure, and the residue was purified by silica gel column chromatography to afford the product (60 mg, yield=38%).

Step C: (E)-S-(7-((4-(2-fluoro-4-(1-((4-fluorophenyl)carbamoyl)cyclopropane-1-carbamoyl)phenoxy)-6-methoxyquinolin-7-yl)oxy)heptyl-5-en-1-yl) acetylthio ester

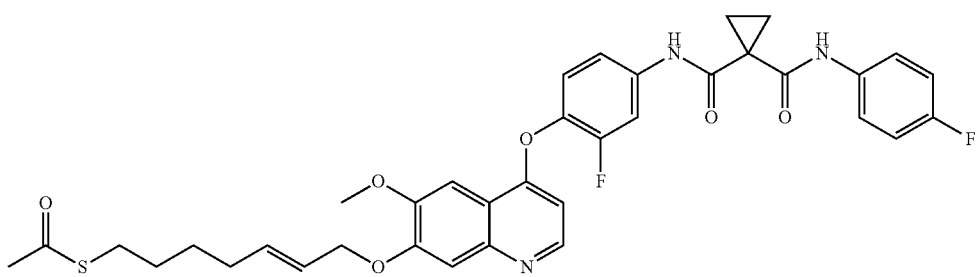 [SMILES: COc1cc2c(Oc3ccc(NC(=O)C4(C(=O)Nc5ccc(F)cc5)CC4)cc3F)ccnc2cc1OC/C=C/CCCCSC(C)=O]

50 mg (0.1 mmol, 1.0 eq) N-(3-fluoro-4-((7-hydroxyl-6-methoxyquinolin-4-yl)oxy)phenyl)-N-(4-fluorophenyl)cyclopropane-1,1-diformamide and 50 mg (0.20 mmol, 2.0 eq) (E)-S-(7-bromoheptyl-5-en-1-yl) acetylthioester were dissolved in 1 mL N,N-dimethylformamide. Then, 35 mg (0.25 mmol, 2.5 eq) potassium carbonate powder was added at room temperature. The reaction system was stirred overnight at room temperature. After the completion of the reaction monitored by TLC, the reaction system was poured into 100 mL water, and then extracted with 50 mL ethyl acetate. The organic phase was washed twice with water and saturated brine in turn, and was then dried over anhydrous sodium sulfate, evaporated to dryness. The residue was purified by silica gel column chromatography to afford the product (25 mg, yield=38%).

¹H NMR (400 MHz, CDCl₃) δ 10.08 (s, 1H), 8.51 (d, J=5.2 Hz, 1H), 8.44 (s, 1H), 7.81 (d, J=11.6 Hz, 1H), 7.61 (s, 1H), 7.55-7.42 (m, 3H), 7.32 (m, 1H), 7.28-7.24 (m, 1H), 7.12-7.08 (m, 2H), 6.44 (d, J=5.0 Hz, 1H), 5.99-5.84 (m, 2H), 4.75 (d, J=5.8 Hz, 2H), 4.09 (s, 3H), 2.91 (t, J=7.1 Hz, 2H), 2.36 (s, 3H), 2.16 (d, J=7.1 Hz, 2H), 1.67-1.61 (m, 2H), 1.55-1.52 (m, 2H), 1.30 (m, 4H).

LC-MS: m/z=676 [M+H]⁺.

Example 25 (E)-N-(3-fluoro-4-((7-((7-mercaptohep-tyl-2-en-1-yl)oxy)-6-methoxyquinolin-4-yl)oxy)phenyl)-N-(4-fluorophenyl)cyclopropane-1,1-difor-mamide

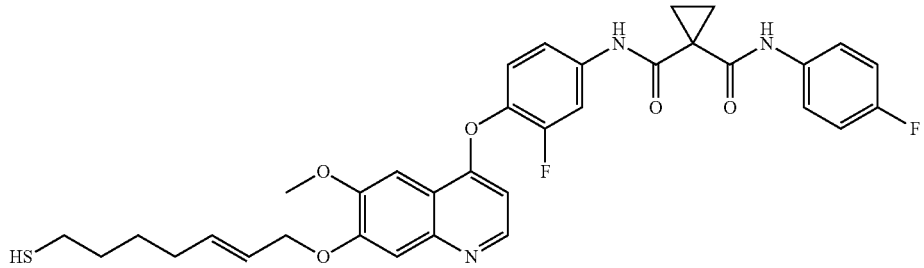 [SMILES: COc1cc2c(Oc3ccc(NC(=O)C4(C(=O)Nc5ccc(F)cc5)CC4)cc3F)ccnc2cc1OC/C=C/CCCCS]

Hydrolysis was performed with reference to the process described in Example 7, the target compound (39 mg, yield=48%) was prepared from Example 24.

¹H NMR (400 MHz, CDCl₃) δ 10.13 (s, 1H), 8.59-8.42 (m, 2H), 7.81 (d, J=11.8 Hz, 1H), 7.61 (s, 1H), 7.51-7.47 (m, 3H), 7.32 (s, 1H), 7.25-7.23 (m, 1H), 7.11-7.07 (m, 2H), 6.44 (d, J=5.2 Hz, 1H), 5.98-5.83 (m, 2H), 4.75 (d, J=5.8 Hz, 2H), 4.08 (s, 3H), 2.89 (brs, 1H), 2.57-2.52 (m, 2H), 2.16-2.15 (m, 2H), 1.66 (m, 2H), 1.62-1.44 (m, 2H), 1.29 (m, 4H).

LC-MS: m/z=634 [M+H]⁺.

Example 26 (E)-S-(6-((4-(2-fluoro-4-(1-((4-fluoro-phenyl)aminoformyl)cyclopropane-1-carbamoyl)phenoxy)-6-methoxyquinolin-7-yl)oxy)hexyl-4-en-1-yl)acetylthio ester

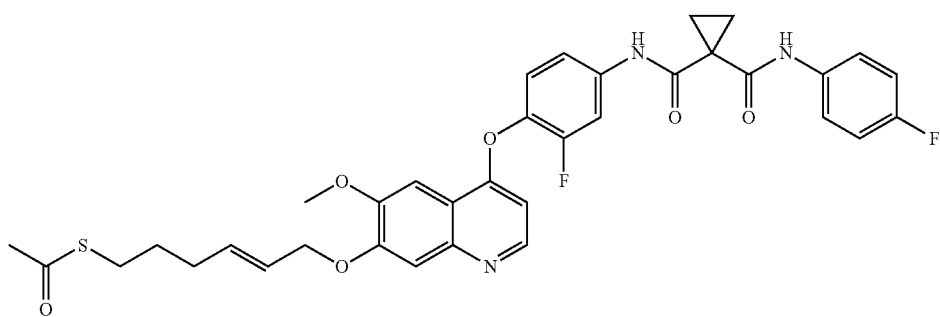 [SMILES: COc1cc2c(Oc3ccc(NC(=O)C4(C(=O)Nc5ccc(F)cc5)CC4)cc3F)ccnc2cc1OC/C=C/CCCSC(C)=O]

With reference to the process described in Example 24, 6-bromo-1-hexene was replaced with 5-bromo-1-pentene to prepare the target compound (180 mg, yield=71%).

¹H NMR (400 MHz, CDCl₃) δ 10.08 (s, 1H), 8.51 (d, J=5.2 Hz, 1H), 8.40 (s, 1H), 7.83-7.79 (m, 1H), 7.62 (s, 1H), 7.54-7.41 (m, 3H), 7.31-7.22 (m, 2H), 7.13-7.08 (m, 2H), 6.44 (d, J=4.4 Hz, 1H), 4.75 (d, J=5.2 Hz, 2H), 4.09 (s, 3H), 2.92 (t, J=7.2 Hz, 2H), 2.37 (s, 3H), 2.24-2.2 (m, 2H), 1.85-1.83 (m, 2H), 1.76 (s, 4H).

LC-MS: m/z=662 [M+H]⁺.

Example 27 (E)-N-(3-fluoro-4-((7-((6-mercapto-hexyl-2-en-1-yl)oxy)-6-methoxyquinolin-4-yl)oxy)phenyl)-N-(4-fluorophenyl)cyclopropane-1,1-dimethylamid

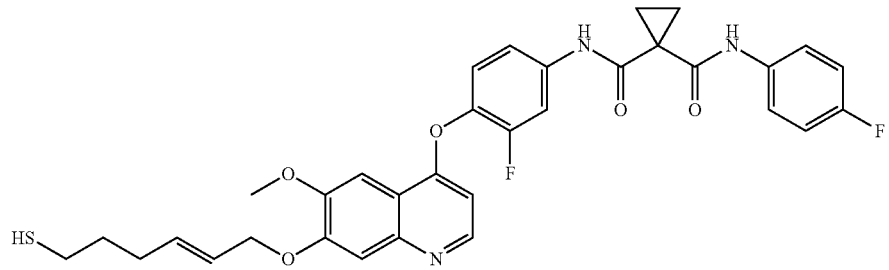 [SMILES: COc1cc2c(Oc3ccc(NC(=O)C4(C(=O)Nc5ccc(F)cc5)CC4)cc3F)ccnc2cc1OC/C=C/CCCS]

Hydrolysis was performed with reference to the process described in Example 7, the target compound (42 mg, yield=37%) was prepared from Example 26.

$^1$H NMR (400 MHz, CDCl$_3$) δ 10.08 (s, 1H), 8.50 (s, 1H), 8.43 (s, 1H), 7.80 (d, J=11.2 Hz, 1H), 7.61 (s, 1H), 7.48-7.46 (m, 3H), 7.26 (d, J=8.2 Hz, 2H), 7.09 (m, 2H), 6.44 (s, 1H), 5.92-5.89 (m, 2H), 4.75 (s, 2H), 4.08 (s, 3H), 2.58-2.56 (m, 2H), 2.27-2.25 (m, 2H), 2.07 (s, 1H), 1.90-1.72 (m, 2H), 1.34 (s, 4H).

LC-MS: m/z=620 [M+H]$^+$.

Example 28 (E)-S-(5-((4-(2-fluoro-4-(1-((4-fluorophenyl)aminoformyl)cyclopropane-1-carbamoyl)phenoxy)-6-methoxyquinolin-7-yl)oxy)pentyl-3-en-1-yl)acetylthio ester

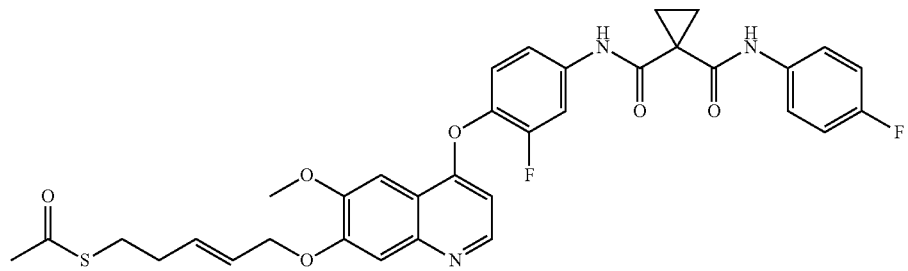 [SMILES: COc1cc2c(Oc3ccc(NC(=O)C4(C(=O)Nc5ccc(F)cc5)CC4)cc3F)ccnc2cc1OC/C=C/CCSC(C)=O]

With reference to the process described in Example 24, 6-bromo-1-hexene was replaced with 4-bromo-1-butene to prepare the target compound (190 mg, yield=75%).

LC-MS: m/z=648 [M+H]$^+$.

$^1$H-NMR (400 MHz, CDCl$_3$) δ 10.06 (s, 1H), 8.47 (s, 1H), 8.23 (s, 1H), 7.78 (d, J=11.0 Hz, 1H), 7.58 (s, 1H), 7.50-7.39 (m, 3H), 7.33-7.17 (m, 2H), 7.07 (t, J=8.5 Hz, 2H), 6.42 (d, J=4.6 Hz, 1H), 5.97-5.82 (m, 2H), 4.78-4.67 (m, 2H), 4.05 (s, 3H), 2.96 (t, J=7.2 Hz, 2H), 2.44-2.27 (m, 5H), 1.86-1.75 (m, 2H), 1.68-1.56 (m, 2H).

Example 29 (E)-N-(3-fluoro-4-((7-((5-mercaptoheptyl-2-en-1-yl)oxy)-6-methoxyquinolin-4-yl)oxy)phenyl)-N-(4-fluorophenyl)cyclopropane-1,1-diformamide

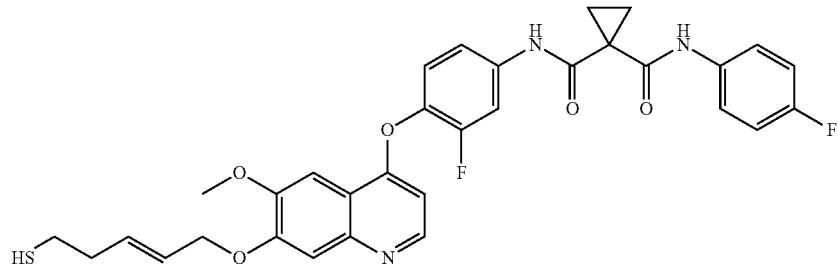 [SMILES: COc1cc2c(Oc3ccc(NC(=O)C4(C(=O)Nc5ccc(F)cc5)CC4)cc3F)ccnc2cc1OC/C=C/CCS]

Hydrolysis was performed with reference to the process described in Example 7, the target compound (52 mg, yield=48%) was prepared from Example 28.

LC-MS: m/z=606 [M+H]$^+$.

$^1$H-NMR (400 MHz, CDCl$_3$) δ 10.07 (s, 1H), 8.50 (d, J=5.1 Hz, 1H), 8.23 (s, 1H), 7.80 (d, J=12.1 Hz, 1H), 7.60 (s, 1H), 7.51-7.43 (m, 3H), 7.35-7.19 (m, 2H), 7.09 (t, J=8.1 Hz, 2H), 6.44 (d, J=5.8 Hz, 1H), 6.00-5.87 (m, 2H), 4.80-4.74 (m, 2H), 4.08 (s, 3H), 2.65 (dd, J=14.5, 7.6 Hz, 2H), 2.52-2.41 (m, 2H), 1.98-1.55 (m, 4H).

Example 30 S-(7-((4-(2-fluoro-4-(1-((4-fluorophenyl)aminoformyl)cyclopropane-1-carboxamido)phenoxy)-6-methoxyquinolin-7-yl)oxy)heptyl)-2-methylthiopropionate

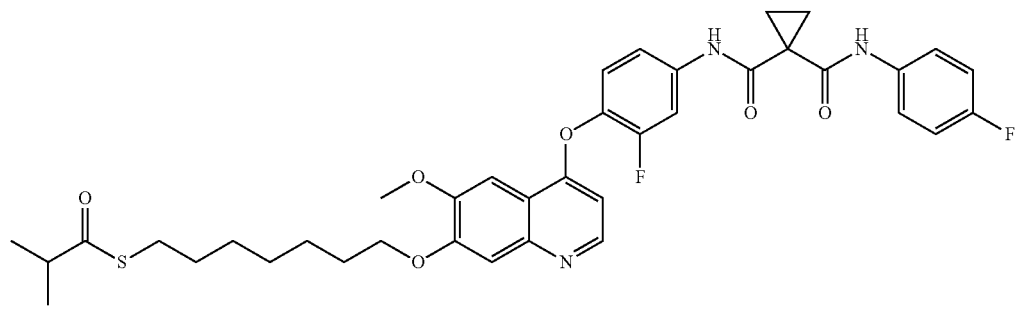 [SMILES: COc1cc2c(Oc3ccc(NC(=O)C4(C(=O)Nc5ccc(F)cc5)CC4)cc3F)ccnc2cc1OCCCCCCCSC(=O)C(C)C]

N-(3-fluoro-4-((7-(7-mercaptoheptyloxy)-6-methoxyquinolin-4-yl)oxy)phenyl)-N-(4-fluorophenyl)cyclopropane-1,1-diformamide (100 mg, 0.157 mmol, from Example 13) and triethylamine (50 mg, 0.494 mmol) were dissolved in DCM (15 ml). Add isobutyryl chloride (100 mg, 0.943 mmol) on ice bath and keep the reaction at low temperature for 3 hours. After the reaction was complete, the system was washed twice with saturated NaHCO$_3$ aqueous solution and once with saturated NaCl aqueous solution. The organic phase was dried, concentrated, and purified by column to afford the target compound (32 mg, 29%).

$^1$H NMR (400 MHz, CDCl$_3$) δ 10.07 (s, 1H), 8.59-8.35 (m, 2H), 7.79 (dd, J=12.0, 2.2 Hz, 1H), 7.60 (s, 1H), 7.53-7.45 (m, 2H), 7.43 (s, 1H), 7.27-7.23 (m, 2H), 7.11-7.07 (m, 2H), 6.43 (d, J=5.2 Hz, 1H), 4.21 (t, J=6.8 Hz, 2H), 4.07 (s, 3H), 2.90 (t, J=7.2 Hz, 2H), 1.99-1.94 (m, 2H), 1.65 (m, 5H), 1.50-1.41 (m, 6H), 1.30 (s, 4H), 1.23 (d, J=6.8 Hz, 6H).

LC-MS: m/z=706 [M+H]$^+$.

Example 31 S-(7-((4-(2-fluoro-4-(1-((4-fluorophenyl)aminoformyl)cyclopropane-1-carboxamido)phenoxy)-6-methoxyquinolin-7-yl)oxy)heptyl)-2,2-dimethylthiopropionate

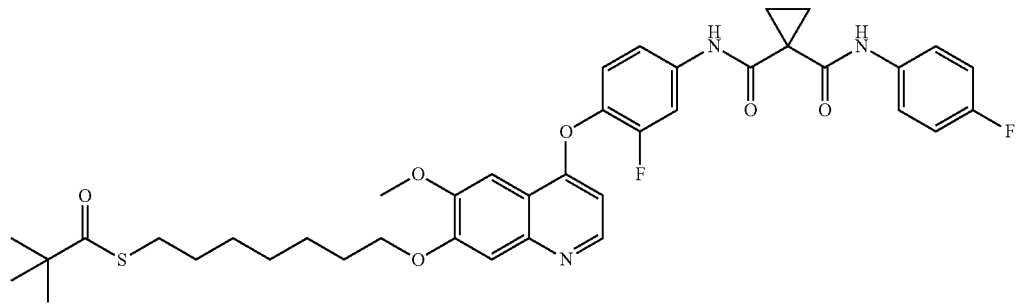 [SMILES: COc1cc2c(Oc3ccc(NC(=O)C4(C(=O)Nc5ccc(F)cc5)CC4)cc3F)ccnc2cc1OCCCCCCCSC(=O)C(C)(C)C]

The target compound (88 mg, 85%) was prepared according to the process described in Example 30.

$^1$H NMR (400 MHz, CDCl$_3$) δ 10.03 (s, 1H), 8.51 (d, J=5.2 Hz, 1H), 8.35 (s, 1H), 7.85-7.74 (m, 1H), 7.60 (s, 1H), 7.54-7.40 (m, 3H), 7.29-7.19 (m, 2H), 7.10 (t, J=8.6 Hz, 2H), 6.43 (d, J=4.8 Hz, 1H), 4.22 (t, J=6.6 Hz, 2H), 4.08 (s, 3H), 2.88 (t, J=7.2 Hz, 2H), 2.03-1.93 (m, 2H), 1.85-1.83 (m, 2H), 1.68-1.55 (m, 6H), 1.45 (s, 4H), 1.27 (s, 9H).

LC-MS: m/z=720 [M+H]$^+$.

Example 32 S-(7-((4-(2-fluoro-4-(1-((4-fluorophenyl)aminoformyl)cyclopropane-1-carboxamido)phenoxy)-6-methoxyquinolin-7-yl)oxy)heptyl)thiobenzoate

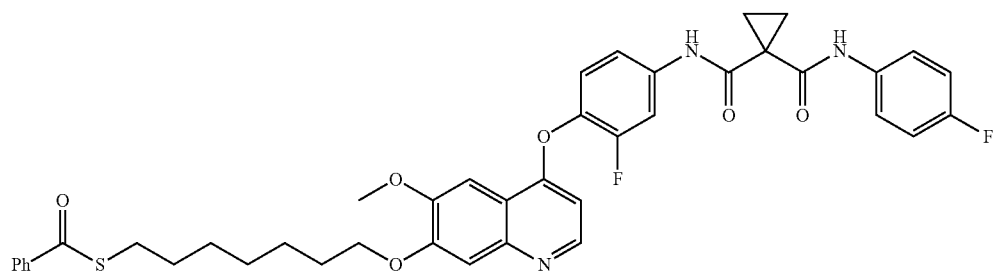 [SMILES: COc1cc2c(Oc3ccc(NC(=O)C4(C(=O)Nc5ccc(F)cc5)CC4)cc3F)ccnc2cc1OCCCCCCCSC(=O)c1ccccc1]

The target compound (62 mg, 59%) was prepared according to the process described in Example 30.

$^1$H NMR (400 MHz, CDCl$_3$) δ 10.07 (s, 1H), 8.53 (d, J=5.3 Hz, 1H), 8.46 (s, 1H), 8.03-8.01 (m, 2H), 7.81 (dd, J=12.0, 2.2 Hz, 1H), 7.61-7.59 (m, 2H), 7.52-7.47 (m, 5H), 7.28-7.24 (m, 2H), 7.13-7.08 (m, 2H), 6.45 (d, J=5.0 Hz, 1H), 4.24 (t, J=6.8 Hz, 2H), 4.08 (s, 3H), 3.13 (t, J=7.2 Hz, 2H), 2.02-1.96 (m, 2H), 1.86-1.82 (m, 2H), 1.79-1.74 (m, 2H), 1.69-1.66 (m, 2H), 1.63-1.44 (m, 2H), 1.31 (s, 4H).

LC-MS: m/z=740 [M+H]$^+$.-

Example 33 S-(7-((4-(2-fluoro-4-(1-((4-fluorophenyl)aminoformyl)cyclopropane-1-carboxamido)phenoxy)-6-methoxyquinolin-7-yl)oxy)heptyl)(S)-2-amino-3-methylthiobutyrate hydrochloride

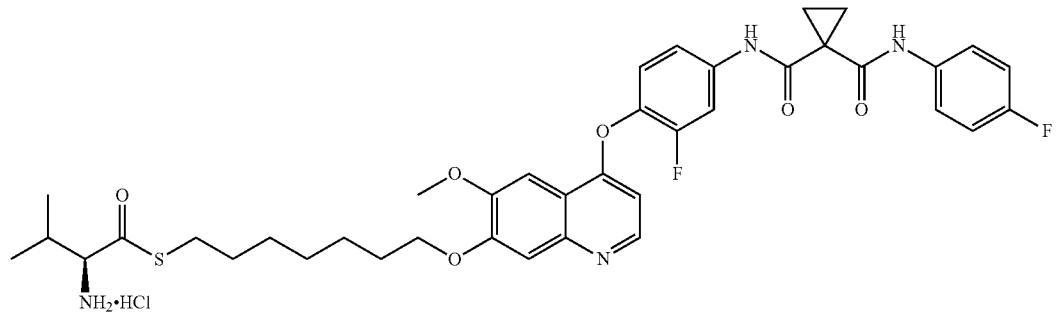

Step A: S-(7-((4-(2-fluoro-4-(1-((4-fluorophenyl)aminoformyl)cyclopropane-1-carboxamido)phenoxy)-6-methoxyquinolin-7-yl)oxy)heptyl)(S)-2-((tert-butoxycarbonyl)amino)-3-methylthiobutyrate

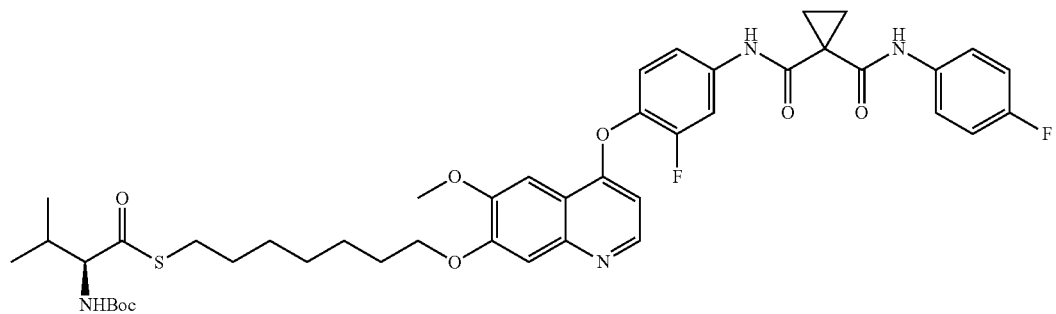 [SMILES: COc1cc2c(Oc3ccc(NC(=O)C4(C(=O)Nc5ccc(F)cc5)CC4)cc3F)ccnc2cc1OCCCCCCCSC(=O)[C@@H](NC(=O)OC(C)(C)C)C(C)C]

Boc-L-valine (85 mg, 0.376 mmol) was dissolved in DCM (15 ml), followed by 4-dimethylaminopyridine (20 mg, 0.376 mmol) and 1-(3-dimethylaminopropyl)-3-ethylcarbodiimide hydrochloride (123 mg, 0.628 mmol) were added in ice bath, and keep the reaction at low temperature for 10 min. Then, add N-(3-fluoro-4-((7-(7-mercaptoheptyloxy)-6-methoxyquinolin-4-yl)oxy)phenyl)-N-(4-fluorophenyl)cyclopropane-1,1-diformamide (100 mg, 0.157 mmol, from Example 13) to the reaction system, and keep reaction overnight at room temperature. After the reaction was complete, the system was washed twice with saturated NaHCO$_3$ aqueous solution and once with saturated NaCl aqueous solution, the organic phase was dried, concentrated, and purified by column to afford the target compound (110 mg, 85%).

$^1$H NMR (400 MHz, CDCl$_3$) δ 10.06 (s, 1H), 8.52 (d, J=4.0 Hz, 1H), 8.39 (s, 1H), 7.81 (s, 1H), 7.61 (d, J=10.1 Hz, 1H), 7.51-7.41 (m, 2H), 7.45 (s, 1H), 7.38-7.26 (m, 2H), 7.11 (t, J=8.6 Hz, 2H), 6.43 (d, J=4.0 Hz, 1H), 4.30-4.26 (m, 1H), 4.23 (t, J=4.0 Hz, 2H), 4.08 (s, 3H), 2.93 (t, J=4.0 Hz, 2H), 2.35-2.25 (m, 1H), 2.20-1.93 (m, 2H), 1.88-1.83 (m, 2H), 1.81-1.74 (m, 2H), 1.70-1.60 (m, 4H), 1.59-1.40 (m, 13H), 1.04 (d, J=4.0 Hz, 3H), 0.91 (d, J=4.0 Hz, 3H).

Step B: S-(7-((4-(2-fluoro-4-(1-((4-fluorophenyl)aminoformyl)cyclopropane-1-carboxamido)phenoxy)-6-methoxyquinolin-7-yl)oxy)heptyl)-(S)-2-amino-3-methylthiobutyrate hydrochloride

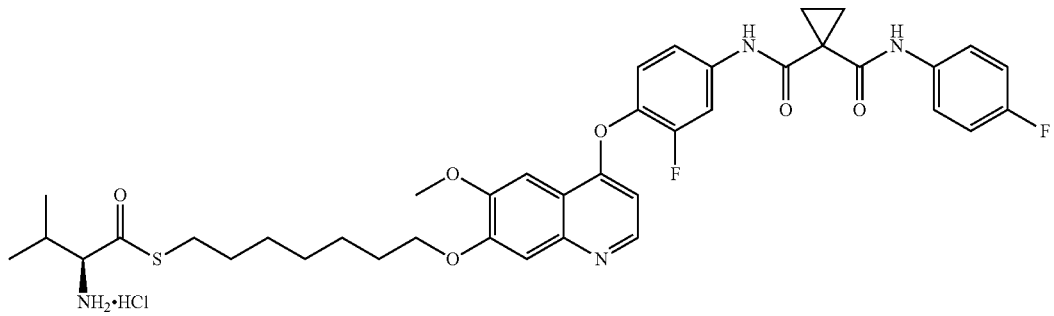

The target compound (65 mg, 87%) was prepared with reference to step D described in Example 1.

$^1$H NMR (400 MHz, DMSO-d6) δ 10.57 (s, 1H), 10.04 (s, 1H), 8.82 (d, J=6.4 Hz, 1H), 8.63 (brs, 1H), 8.03 (d, J=6.4 Hz, 2H), 7.81-7.55 (m, 6H), 7.18 (m, 2H), 6.90 (d, J=6.4 Hz, 1H), 4.24 (t, J=13.8 Hz, 2H), 4.16 (s, 1H), 4.05 (s, 3H), 3.10-2.95 (m, 2H), 2.28-2.08 (m, 1H), 1.88-1.77 (m, 2H), 1.64-1.52 (m, 2H), 1.51-1.40 (m, 10H), 1.00 (dd, J=11.4, 6.8 Hz, 6H).

Example 34 S-(7-((4-(2-fluoro-4-(1-((4-fluorophenyl)aminoformyl)cyclopropane-1-carboxamido)phenoxy)-6-methoxyquinolin-7-yl)oxy)heptyl)-(R)-2-amino-3-(1-methyl-1H-indol-3-yl)thiopropionate hydrochloride

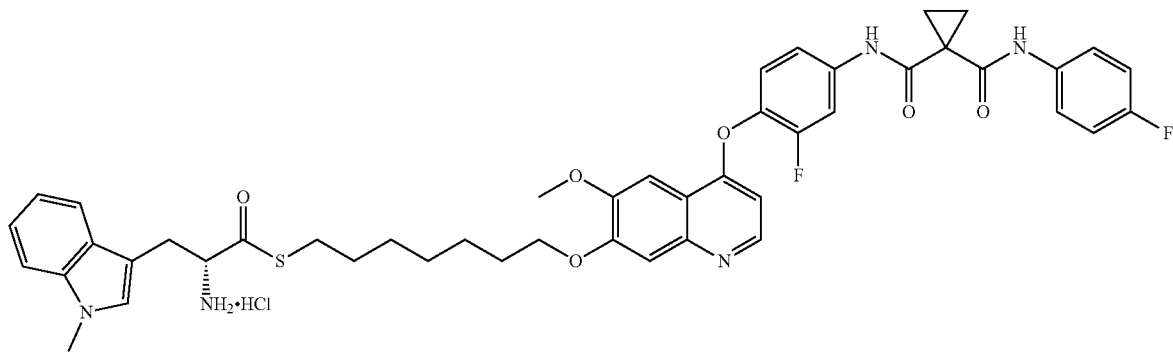

The target compound (51 mg, 59%) was prepared according to the process described in Example 33.

$^1$H NMR (400 MHz, DMSO-d6) δ 10.56 (s, 1H), 10.04 (s, 1H), 8.82 (d, J=6.4 Hz, 1H), 8.63 (brs, 3H), 8.07-7.95 (m, 1H), 7.78-7.76 (m, 2H), 7.71-7.53 (m, 5H), 7.43 (d, J=8.2 Hz, 1H), 7.25 (s, 1H), 7.26-7.16 (m, 3H), 7.07 (t, J=7.0 Hz, 1H), 6.92 (d, J=6.4 Hz, 1H), 4.42 (m, 1H), 4.25 (t, J=6.4 Hz, 2H), 4.06 (s, 3H), 3.77 (s, 3H), 2.92-2.86 (m, 2H), 2.53 (t, J=4.0 Hz, 2H), 1.89-1.87 (m, 2H), 1.58-1.22 (m, 12H).

Example 35 O-ethyl-S-(7-((4-(2-fluoro-4-(1-((4-fluorophenyl)aminoformyl)cyclopropane-1-carboxamido)phenoxy)-6-methoxyquinolin-7-yl)oxy)heptyl)methyl thiocarbonate

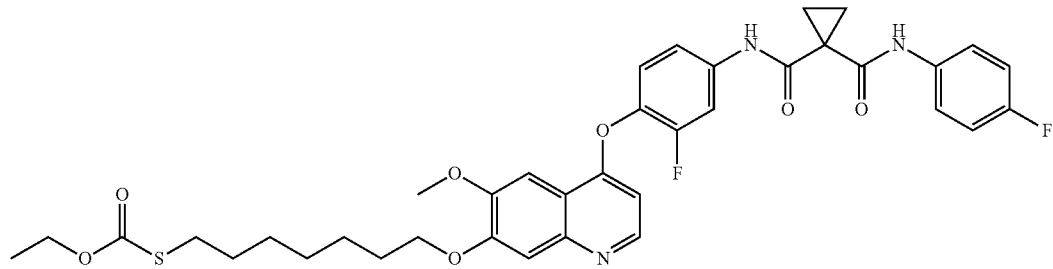 [SMILES: CCOC(=O)SCCCCCCCOc1cc2nccc(Oc3ccc(NC(=O)C4(C(=O)Nc5ccc(F)cc5)CC4)cc3F)c2cc1OC]

Follow the steps described in Example 30, replacing isobutyryl chloride with ethyl chloroformate to prepare the target compound (50 mg, 31%).
LC-MS: m/z=708 [M+H]$^+$.

Example 36 N-ethyl-S-(7-((4-(2-fluoro-4-(1-((4-fluorophenyl)aminoformyl)cyclopropane-1-carboxamido)phenoxy)-6-methoxyquinolin-7-yl)oxy)heptyl)thiocarbamate

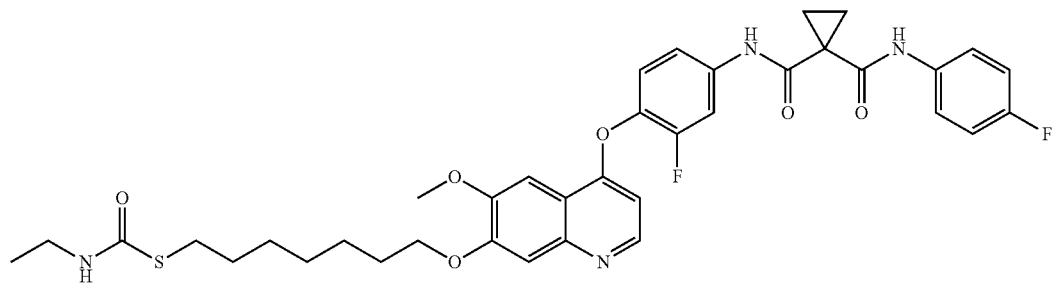 [SMILES: CCNC(=O)SCCCCCCCOc1cc2nccc(Oc3ccc(NC(=O)C4(C(=O)Nc5ccc(F)cc5)CC4)cc3F)c2cc1OC]

Follow the process described in Example 30 to replace isobutyryl chloride with ethyl isocyanate to prepare the target compound (48 mg, 32%).
LC-MS: m/z=707[M+H]$^+$.

Example 37 S-(7-((4-(4-(1-((4-fluorophenyl)carbamoyl)cyclopropane-1-carboxamido)phenoxy)-6-methoxyquinolin-7-yl)oxy)heptyl)thioacetate

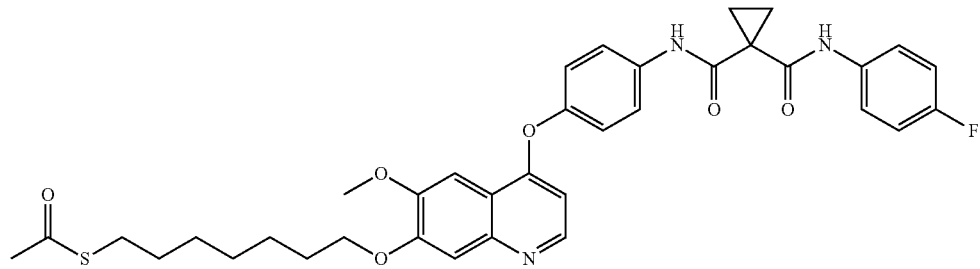 [SMILES: COc1cc2c(Oc3ccc(NC(=O)C4(C(=O)Nc5ccc(F)cc5)CC4)cc3)ccnc2cc1OCCCCCCCSC(C)=O]

Step A: S-(6-bromoheptyl)-acetylthioester

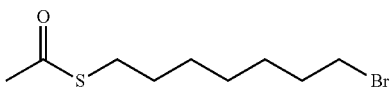

The target compound (1.58 g, yield=72%) was prepared with reference to step A described in Example 6.

Step B: S-(7-((4-(4-(1-((4-fluorophenyl)carbamoyl)cyclopropane-1-carboxamido)phenoxy)-6-methoxyquinolin-7-yl)oxy)heptyl)thioacetate

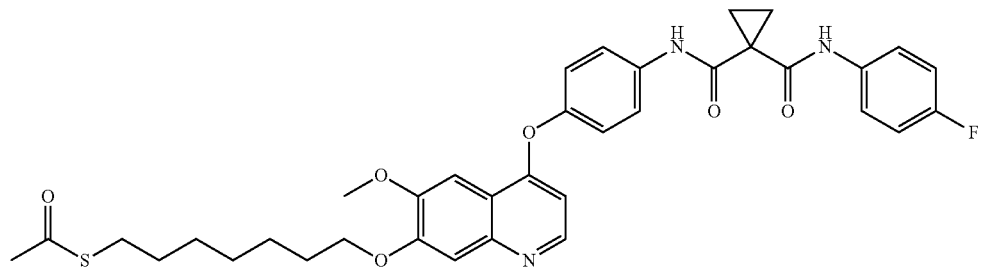 [SMILES: COc1cc2c(Oc3ccc(NC(=O)C4(C(=O)Nc5ccc(F)cc5)CC4)cc3)ccnc2cc1OCCCCCCCSC(C)=O]

487 mg (1 mmol, 1.0 eq) N-(4-fluorophenyl)-N-(4-((7-hydroxy-6-methoxyquinolin-4-yl)oxy)phenyl)cyclopropane-1,1-diformamide (see Preparation Example 2 for the synthesis method) and 506 mg (2 mmol, 2.0 eq) S-(7-bromoheptyl)-acetylthioester were dissolved in 10 mL N,N-dimethylformamide. 414 mg (3.0 mmol, 3.0 eq) potassium carbonate powder was added at room temperature. The reaction system was stirred overnight at room temperature. After the completion of the reaction monitored by TLC, the reaction system was poured into 150 mL water, and extracted with 200 mL ethyl acetate. The organic phase was washed twice sequentially with water and saturated brine, and was then dried over anhydrous sodium sulfate, evaporated to dryness. The residue was purified by silica gel column chromatography to afford the product (485 mg, yield=74%).

$^1$H NMR (400 MHz, CDCl$_3$) δ 9.48 (s, 1H), 8.86 (s, 1H), 8.54 (s, 1H), 7.67 (d, J=8.4 Hz, 2H), 7.55-7.50 (m, 4H), 7.20 (d, J=8.8 Hz, 2H), 7.08-7.06 (m, 2H), 6.51 (d, J=5.4 Hz, 1H), 4.20 (s, 2H), 4.06 (s, 3H), 2.92 (t, J=7.2 Hz, 2H), 2.36 (s, 3H), 1.99-1.97 (m, 2H), 1.78-1.76 (m, 2H), 1.70-1.61 (m, 2H), 1.55-1.52 (m, 4H), 1.30 (m, 4H).

LC-MS: m/z=660[M+H]$^+$.

Example 38 S-(7-((4-(4-(1-((4-fluorophenyl)carbamoyl)cyclopropane-1-carboxamido)phenoxy)-6-methoxyquinolin-7-yl)oxy)hexyl)thioacetate

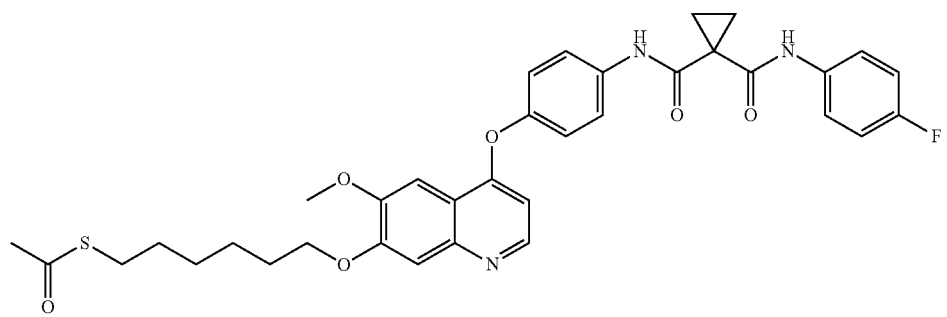 [SMILES: COc1cc2c(Oc3ccc(NC(=O)C4(C(=O)Nc5ccc(F)cc5)CC4)cc3)ccnc2cc1OCCCCCCSC(C)=O]

The target compound (88 mg, 69%) was prepared according to the process described in Example 37.

$^1$H NMR (400 MHz, CDCl$_3$) δ 9.46 (s, 1H), 8.86 (s, 1H), 8.54 (s, 1H), 7.66 (d, J=8.4 Hz, 2H), 7.57-7.52 (m, 4H), 7.20 (d, J=8.8 Hz, 2H), 7.09-7.01 (m, 2H), 6.50 (d, J=5.4 Hz, 1H), 4.20 (s, 2H), 4.06 (s, 3H), 2.93 (t, J=7.2 Hz, 2H), 2.36 (s, 3H), 1.98-1.96 (m, 2H), 1.78-1.76 (m, 2H), 1.74-1.62 (m, 2H), 1.54-1.52 (m, 2H), 1.31 (m, 4H).

LC-MS: m/z=646[M+H]$^+$.

Example 39 S-(7-((4-(2-fluoro-4-(1-((4-fluorophenyl)carbamoyl)cyclopropane-1-carboxamido)phenoxy)-6-methoxyquinolin-7-yl)oxy)heptyl)-(S)-2-amino-3-(1H-indol-3-yl)thiopropionate hydrochloride

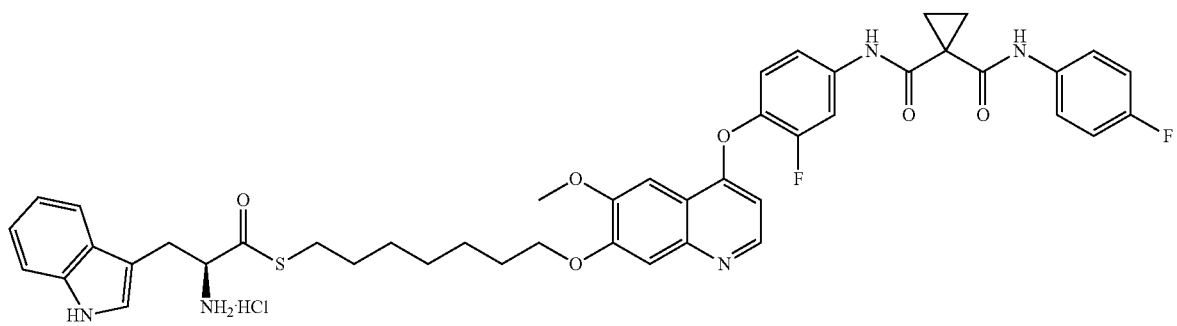

The target compound (81 mg, 63%) was prepared according to the process described in Example 33.

LC-MS: m/z=856[M+H]$^+$.

Example 40 S-(4-((2-((2-((4-(2-fluoro-4-(1-((4-fluorophenyl)carbamoyl)cyclopropane-1-carboxamido)phenoxy)-6-methoxyquinolin-7-yl)oxy)ethyl)amino)butyl)thioacetate

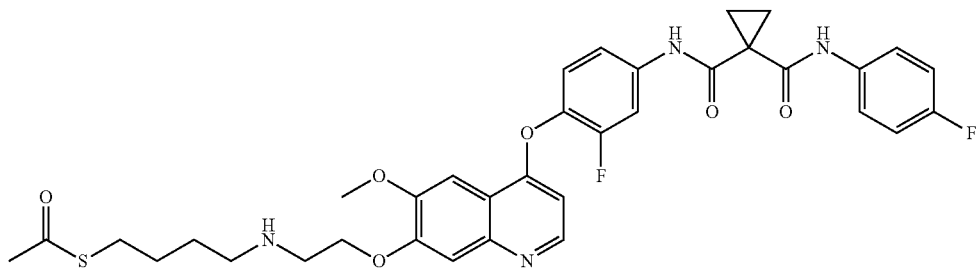

Step A: S-(4,4-dimethoxybutyl)acetylthioester

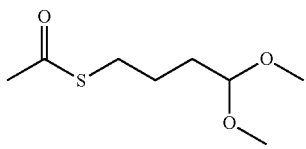

4-bromo-1,1-dimethoxybutane (1.97 g, 10 mmol) was dissolved in acetone (15 ml), potassium thioacetate (1.14 mg, 10 mmol) was added at room temperature and the reaction was kept at room temperature for 2 h. After the reaction was complete, filter the reaction solution. The filter cake was washed with DCM, and the organic phase was dried, concentrated, and purified by column to afford the target compound (1.72 g, 89%).

Step B: S-(4-carbonylbutyl) acetyl thioester

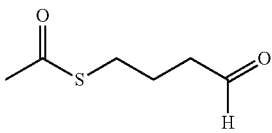

S-(4,4-dimethoxybutyl) acetyl thioester (500 mg, 2.6 mmol) was dissolved in THF (5 ml), 6N hydrochloric acid solution (1.5 ml) was added under ice bath and kept at room temperature to react for 45 min. After the reaction was complete, the reaction system was washed twice with saturated NaHCO₃ aqueous solution, once with saturated NaCl aqueous solution. The organic phase was dried, and concentrated to afford the target compound (320 mg, 85%) for directly use in the next step.

Step C: N-(4-((7-(2-aminoethoxy)-6-methoxyquinolin-4-yl)oxy)-3-fluorophenyl)-N-(4-fluorophenyl) cyclopropane-1,1-diformamide

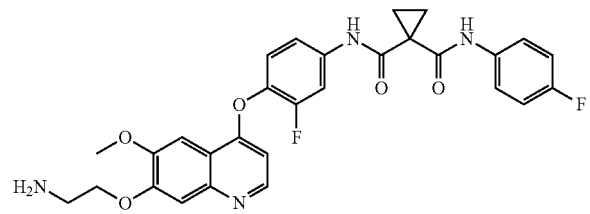 [SMILES: COc1cc2c(Oc3ccc(NC(=O)C4(C(=O)Nc5ccc(F)cc5)CC4)cc3F)ccnc2cc1OCCN]

505 mg (1 mmol, 1.0 eq) N-(3-fluoro-4-((7-hydroxyl-6-methoxyquinolin-4-yl)oxy)phenyl)-N-(4-fluorophenyl) cyclopropane-1,1-dimethylformamide and 174 mg (1.5 mmol, 1.5 eq) 2-chloroethylamine hydrochloride were dissolved in 10 mL N,N-dimethylformamide, and then 414 mg (3.0 mmol, 3.0 eq) potassium carbonate powder was added at room temperature. The reaction system was stirred at room temperature overnight. TLC monitored the reaction completed, and then the reaction system was then poured into 150 mL water and extracted with 200 mL ethyl acetate. The organic phase was washed with water and saturated brine twice, and then dried over sodium sulfate and evaporated to dryness. The residue was purified by silica gel column chromatography to afford the product (320 mg, yield=58%).

LC-MS: m/z=549 [M+H]⁺.

Step D: S-(4-((2-((4-(2-fluoro-4-(1-((4-fluorophenyl)carbamoyl)cyclopropane-1-carboxamido)phenoxy)-6-methoxyquinolin-7-yl)oxy)ethyl)amino)butyl)thioacetate

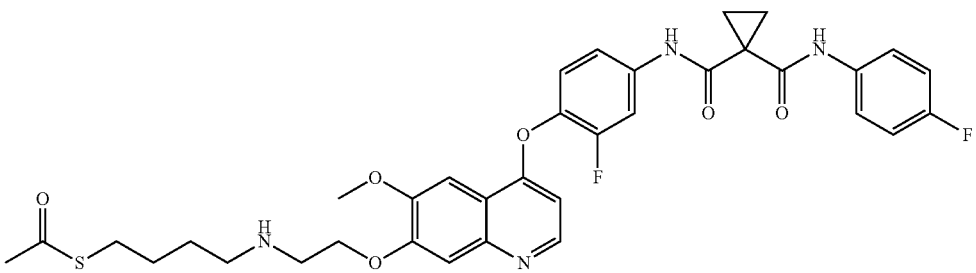 [SMILES: COc1cc2c(Oc3ccc(NC(=O)C4(C(=O)Nc5ccc(F)cc5)CC4)cc3F)ccnc2cc1OCCNCCCCSC(C)=O]

S-(4-carbonylbutyl) acetylthioester (292 mg, 2.0 mmol) was dissolved in THF (3 ml), and N-(4-((7-(2-aminoethoxy)-6-(methoxyquinolin-4-yl)oxy)-3-fluorophenyl)-N-(4-fluorophenyl)cyclopropane-1,1-diformamide (548 mg, 1.0 mmol) was added along with one drop acetic acid, which was then kept at room temperature for 1.5 hours. After the reaction was completed, the system was added with sodium triacetylborohydride (870 mg, 4.1 mmol) and kept at room temperature for 5 hours, followed by washed twice with saturated aqueous NaHCO₃ solution, washed once with saturated aqueous NaCl solution. After that, the organic phase was dried, concentrated and purified by column to afford the target compound (351 mg, 52%).

LC-MS: m/z=679[M+H]⁺.

Example 41 N-(3-fluoro-4-((6-methoxy-7-(3-((2-homocysteine lactone-3-yl)amino)propoxy)quinolin-4-yl)oxy)phenyl)-N-(4-fluorophenyl)cyclopropane-1,1-diformamide

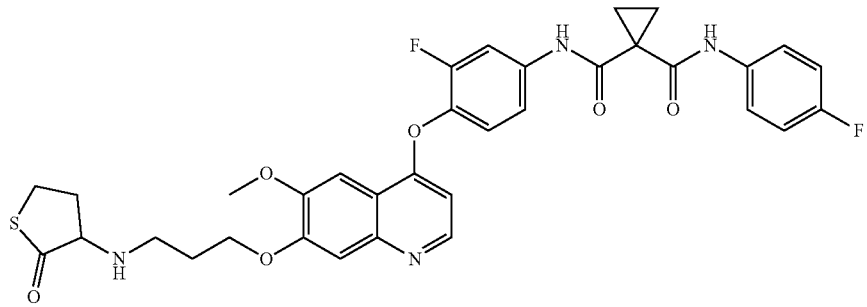 [SMILES: COc1cc2c(Oc3ccc(NC(=O)C4(C(=O)Nc5ccc(F)cc5)CC4)cc3F)ccnc2cc1OCCCNC1CCSC1=O]

Step A: N-(4-((7-(3,3-dimethoxypropoxy)-6-methoxyquinolin-4-yl)oxy)-3-fluorophenyl)-N-(4-fluorophenyl)cyclopropane-1,1-diformamide

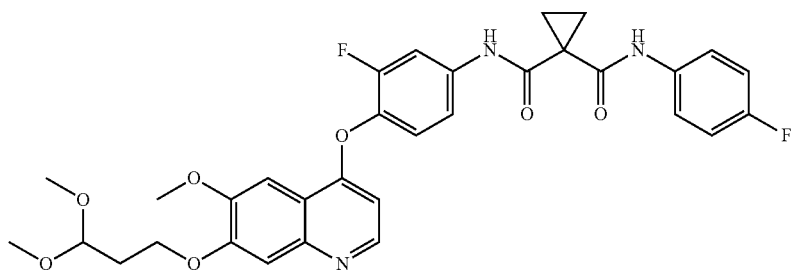 [SMILES: COc1cc2c(Oc3ccc(NC(=O)C4(C(=O)Nc5ccc(F)cc5)CC4)cc3F)ccnc2cc1OCCC(OC)OC]

Referring to step C described in Example 20, (E)-6-bromo-3-hexenyl acetylthio ester was replaced with 3-bromo-1,1-dimethoxypropane to prepare the target compound (120 mg, 78%).

LC-MS: m/z=608[M+H]$^+$.

Step B: N-(3-fluoro-4-((6-methoxy-7-(3-aldehyde propoxy)quinolin-4-yl)oxy)phenyl)-N-(4-fluorophenyl) cyclopropane-1,1-diformamide

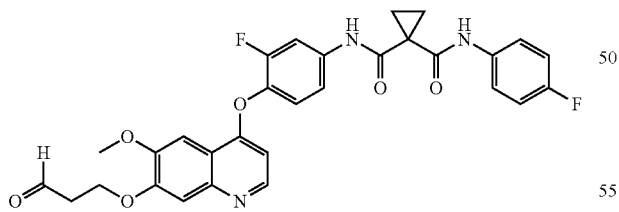

N-(4-((7-(3,3-dimethoxypropoxy)-6-methoxyquinolin-4-yl)oxy)-3-fluorophenyl)-N-(4-fluorophenyl)cyclopropane-1,1-diformamide (100 mg, 0.164 mmol) was dissolved in THF (5 ml), 2N hydrochloric acid (1 ml) was added under ice bath and reacted at room temperature for 1 hour. After the reaction was complete, the system was washed twice with saturated NaHCO$_3$ aqueous solution, once with saturated NaCl aqueous solution. The organic phase was then dried and concentrated to afford the target compound (80 mg, 87%).

LC-MS: m/z=562[M+H]$^+$.

Step C: N-(3-fluoro-4-((6-methoxy-7-(3-((2-homo-cysteine lactone-3-yl)amino)propoxy)quinolin-4-yl)oxy)phenyl)-N-(4-fluorophenyl)cyclopropane-1,1-diformamide

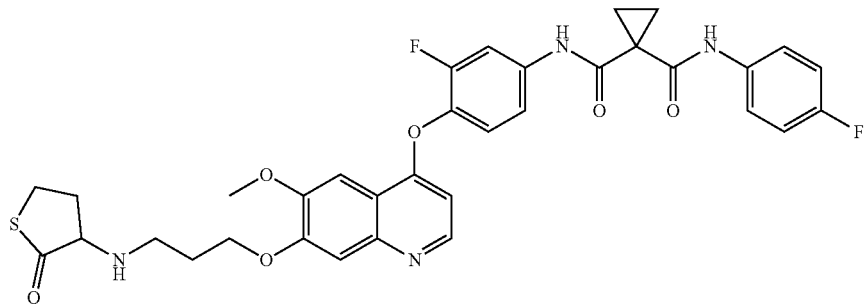 [SMILES: COc1cc2c(Oc3ccc(NC(=O)C4(C(=O)Nc5ccc(F)cc5)CC4)cc3F)ccnc2cc1OCCCNC1CCSC1=O]

N-(3-fluoro-4-((6-methoxy-7-(3-aldehyde propoxy)quinolin-4-yl)oxy)phenyl)-N-(4-fluorophenyl) cyclopropane-1,1-diformamide (100 mg, 0.164 mmol) was dissolved in THF (3 ml), homocysteine thiolactone (25 mg, 0.164 mmol) was added at room temperature, and a drop of acetic acid was added to keep it at room temperature reacted for 1 hour. After the reaction was complete, add sodium triacetylborohydride (174 mg, 0.82 mmol) to the system, keep at room temperature to react for 3 hours. Wash the reaction system twice with saturated NaHCO$_3$ aqueous solution, and once with saturated aqueous NaCl solution. The organic phase was then dried, concentrated, and purified by column to get the target compound (46 mg, 39%).

LC-MS: m/z=663[M+H]$^+$.

Example 42 (3-((4-(2-fluoro-4-(1-((4-fluorophenyl)carbamoyl)cyclopropane-1-carboxamido)phenoxy)-6-methoxyquinolin-7-yl)oxy)propyl)homocysteine

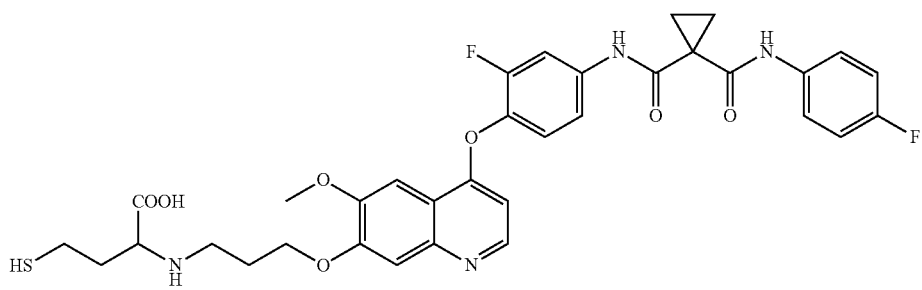 [SMILES: COc1cc2c(Oc3ccc(NC(=O)C4(C(=O)Nc5ccc(F)cc5)CC4)cc3F)ccnc2cc1OCCCNC(CCS)C(=O)O]

N-(3-fluoro-4-((6-methoxy-7-(3-((2-homocysteine lactone-3-yl)amino)propoxy)quinolin-4-yl)oxy)phenyl)-N-(4-fluorophenyl)cyclopropane-1,1-diformamide (20 mg, 0.03 mmol) was dissolved in THF (1 ml), and 1N sodium hydroxide solution (0.1 ml) was added under ice bath. The solution was kept at room temperature and reacted for 10 min. After the reaction was complete, the pH of the reaction system was adjusted to neutral with 1N hydrochloric acid aqueous solution. Then the system was extracted with DCM, and the organic phase was dried, concentrated to afford the target compound (12 mg, 60%).

LC-MS: m/z=681[M+H]$^+$.

Example 43 N-(3-fluoro-4-((6-methoxy-7-(3-((2-homocysteine lactone-3-yl)amino)propoxy)quinolin-4-yl)oxy)phenyl)-N-(4-fluorophenyl)cyclopropane-1,1-diformamide

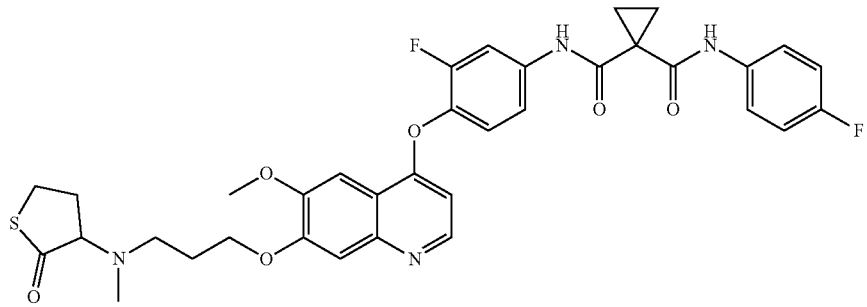 [SMILES: COc1cc2c(Oc3ccc(NC(=O)C4(C(=O)Nc5ccc(F)cc5)CC4)cc3F)ccnc2cc1OCCCN(C)C1CCSC1=O]

N-(3-fluoro-4-((6-methoxy-7-(3-((2-homocysteine lactone-3-yl)amino)propoxy)quinolin-4-yl)oxy)phenyl)-N-(4-fluorophenyl)cyclopropane-1,1-diformamide (20 mg, 0.03 mmol) was dissolved in THF (1 ml), and formaldehyde aqueous solution (0.1 ml) was added at room temperature), and add a drop of acetic acid to keep the reaction at room temperature for 1 hour. After the reaction was complete, add sodium triacetylborohydride (32 mg, 0.15 mmol) to the system and keep it at room temperature for 1.5 hours. Then, wash the system twice with saturated $NaHCO_3$ aqueous solution, and once with saturated brine solution. The organic phase was dried, concentrated, and purified by a thin-layer preparation plate to afford the target compound (6 mg, 29%).

LC-MS: m/z=677[M+H]$^+$.

Example 44 N-(3-fluoro-4-((6-methoxy-7-(3-((2-homocysteine lactone-3-yl)amino)propoxy)quinolin-4-yl)oxy)phenyl)-N-(4-fluorophenyl)cyclopropane-1,1-diformamide

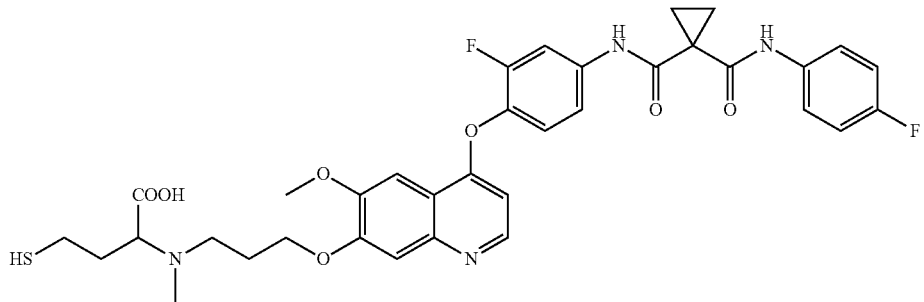 [SMILES: COc1cc2c(Oc3ccc(NC(=O)C4(C(=O)Nc5ccc(F)cc5)CC4)cc3F)ccnc2cc1OCCCN(C)C(CCS)C(=O)O]

Hydrolysis was performed with reference to the step described in Example 42, and the target compound (5 mg, 71%) was prepared from Example 43.

LC-MS: m/z=695[M+H]$^+$.-

Example 45 N-(4-fluorophenyl)-N-(4-((7-((7-mercaptoheptyl)oxy)-6-methoxyquinolin-4-yl)oxy)phenyl) cyclopropane-1,1-diformamide

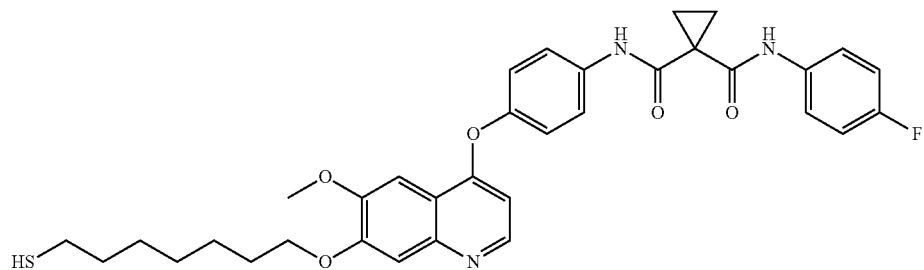 [SMILES: COc1cc2c(Oc3ccc(NC(=O)C4(C(=O)Nc5ccc(F)cc5)CC4)cc3)ccnc2cc1OCCCCCCCS]

S-(7-((4-(4-(1-((4-fluorophenyl)carbamoyl)cyclopropane-1-carboxamido)phenoxy)-6-methoxyquinolin-7-yl)oxy)heptyl)thioacetate (50 mg, 0.03 mmol) was dissolved in THF (2.5 ml), and 1N sodium hydroxide aqueous solution (0.1 ml) was added at room temperature. The reaction was maintained at room temperature for 0.5 hours. The pH of the reaction solution was adjusted to neutral with 1N hydrochloric acid solution, and was then washed twice with the saturated brine. The organic phase was dried, concentrated, and purified on a thin-layer preparation plate to afford the target compound (32 mg, 68%).

LC-MS: m/z=618[M+H]$^+$.

Example 46 N-(4-fluorophenyl)-N-(4-((7-((6-mercaptohexyl)oxy)-6-methoxyquinolin-4-yl)oxy)phenyl)cyclopropane-1,1-diformamide

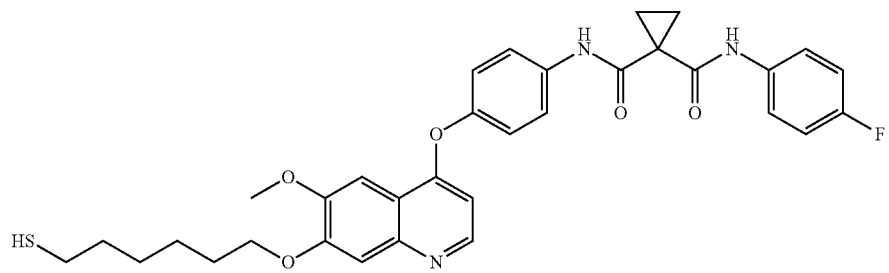 [SMILES: COc1cc2c(Oc3ccc(NC(=O)C4(C(=O)Nc5ccc(F)cc5)CC4)cc3)ccnc2cc1OCCCCCCS]

Hydrolysis was performed with reference to the step described in Example 45, and the target compound (5 mg, 71%) was prepared from Example 38.

LC-MS: m/z=604[M+H]$^+$.

Example 47 S-(7-((4-(2-fluoro-4-(1-((4-fluorophe-nyl)carbamoyl)cyclopropane-1-carboxamido)phe-noxy)-6-methoxyquinolin-7-yl)oxy)heptyl) 2-amino acetylthioester hydrochloride

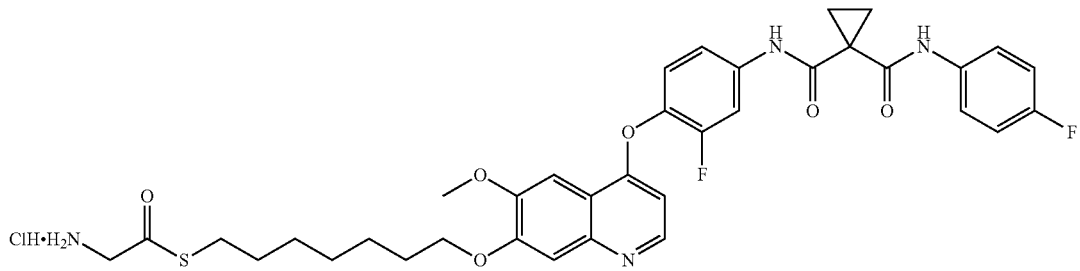

With reference to the amino acid condensation and de-Boc steps described in Example 33, the target compound (18 mg, 71%) was prepared from Example 13.
LC-MS: m/z=730[M+H]$^+$.

Example 48 S-(7-((4-(2-fluoro-4-(1-((4-fluorophe-nyl)carbamoyl)cyclopropane-1-carboxamido)phe-noxy)-6-methoxyquinolin-7-yl)oxy)heptyl)-(S)-ser-ine thioester hydrochloride

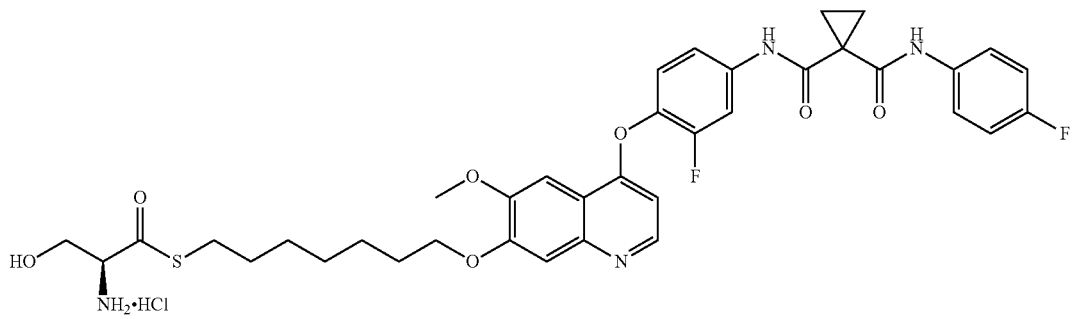

With reference to the amino acid condensation and de-Boc steps described in Example 33, the target compound (18 mg, 71%) was prepared from Example 13.
LC-MS: m/z=760[M+H]$^+$.

Example 49 N-(3-fluoro-4-((7-(2-((4-mercaptobutyl)amino)ethoxy)-6-methoxyquinolin-4-yl)oxy)phe-nyl)-N-(4-fluorophenyl)cyclopropane-1,1-diforma-mide

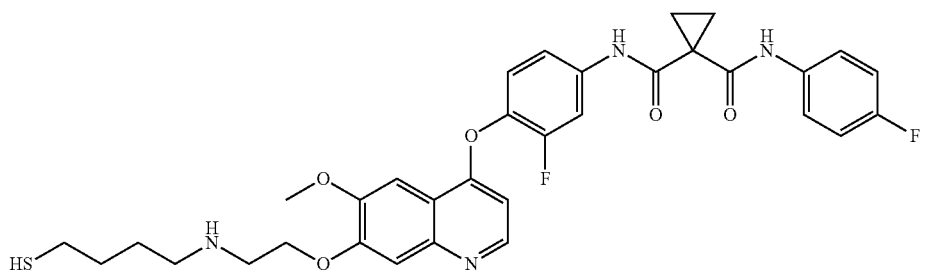 [SMILES: COc1cc2c(Oc3ccc(NC(=O)C4(C(=O)Nc5ccc(F)cc5)CC4)cc3F)ccnc2cc1OCCNCCCCS]

With reference to the process described in Example 45 to perform hydrolysis, the target compound (49 mg, 64%) was prepared using Example 40 as a raw material.

LC-MS: m/z=637[M+H]$^+$.

Example 50 S-(3-((3-((4-(2-fluoro-4-(1-((4-fluorophenyl)carbamoyl)cyclopropane-1-carboxamido)phenoxy)-6-methoxyquinolin-7-yl)oxy)propyl)amino)propyl)thioacetate

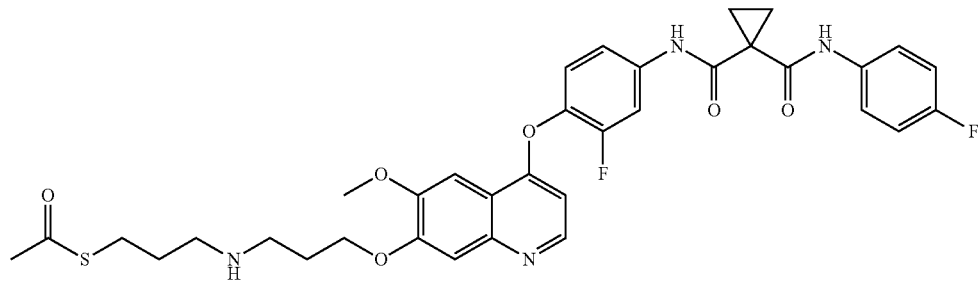 [SMILES: COc1cc2c(Oc3ccc(NC(=O)C4(C(=O)Nc5ccc(F)cc5)CC4)cc3F)ccnc2cc1OCCCNCCCSC(C)=O]

The target compound (46 mg, 58%) was prepared according to the process described in Example 40.

LC-MS: m/z=679[M+H]$^+$.

$^1$H NMR (400 MHz, CDCl$_3$) δ 10.23 (s, 1H), 8.58 (s, 1H), 8.52 (d, J=5.0 Hz, 1H), 7.82 (d, J=12.5 Hz, 1H), 7.64 (s, 1H), 7.49 (m, 2H), 7.45 (s, 1H), 7.37-7.22 (m, 2H), 7.19-7.15 (m, 2H), 6.85 (brs, 1H), 6.46 (d, J=5.0 Hz, 1H), 4.34 (q, J=4.0 Hz, 2H), 4.09 (s, 3H), 3.59 (q, J=4.0 Hz, 2H), 2.35 (s, 3H), 2.30 (s, 2H), 2.16 (m, 2H), 2.08 (s, 4H), 1.84 (m, 2H), 1.68 (m, 2H).

Example 51 N-(3-fluoro-4-((7-(3-((3-mercaptopropyl)amino)propoxy)-6-methoxyquinolin-4-yl)oxy)phenyl)-N-(4-fluorophenyl)cyclopropane-1,1-diformamide

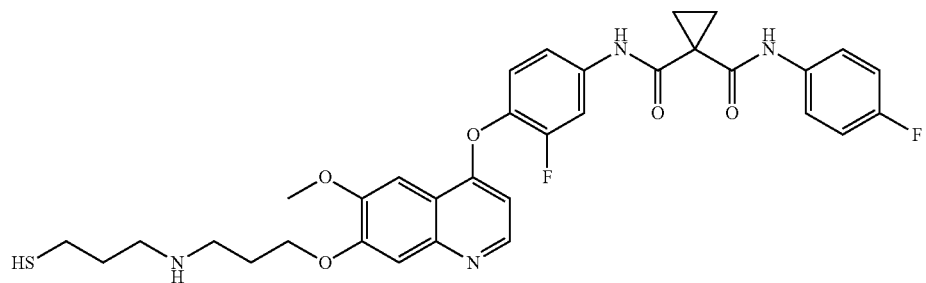 [SMILES: COc1cc2c(Oc3ccc(NC(=O)C4(C(=O)Nc5ccc(F)cc5)CC4)cc3F)ccnc2cc1OCCCNCCCS]

Follow the process described in Example 45 to perform hydrolysis, the target compound (57 mg, 54%) was prepared from Example 50.

LC-MS: m/z=637[M+H]$^+$.

$^1$H NMR (400 MHz, CDCl$_3$) δ 10.31 (s, 1H), 8.63 (d, J=15.4 Hz, 2H), 7.90 (d, J=10.9 Hz, 1H), 7.72 (s, 1H), 7.65-7.56 (m, 3H), 7.47-7.29 (m, 3H), 7.23-7.11 (m, 2H), 6.92 (s, 1H), 6.55 (s, 1H), 4.42 (s, 2H), 4.18 (s, 3H), 3.67 (s, 2H), 2.27-2.20 (m, 8H), 1.92 (s, 2H), 1.77 (s, 2H).

Example 52 S-(3-((3-((4-(2-fluoro-4-(1-((4-fluoro-phenyl)carbamoyl)cyclopropane-1-carboxamido)phenoxy)-6-methoxyquinolin-7-yl)oxy)propyl)(methyl)amino)propyl)thioacetate

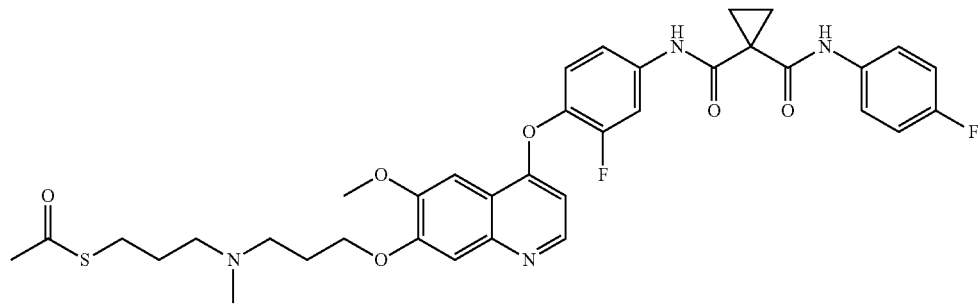 [SMILES: COc1cc2c(Oc3ccc(NC(=O)C4(C(=O)Nc5ccc(F)cc5)CC4)cc3F)ccnc2cc1OCCCN(C)CCCSC(C)=O]

(50 mg, 0.074 mmol) S-(3-((3-((4-(2-fluoro-4-(1-((4-fluorophenyl)carbamoyl)cyclopropane-1-carboxamido)phenyloxy)-6-methoxyquinolin-7-yl)oxy)propyl)amino)propyl)thioacetate (prepared as the process in example 50) was dissolved in THF (1.5 ml). At room temperature, add formaldehyde aqueous solution (0.1 ml), Pd/C (47 mg, 0.22 mmol), and then $H_2$ ventilation three times. Keep the reaction at room temperature for 3.0 hours, and then performed vacuum filtration. The organic phase was concentrated, and then purified through thin-layer preparation plate to afford the target compound (12 mg, 24%).

LC-MS: m/z=693[M+H]$^+$.

Example 53 N-(3-fluoro-4-((7-(3-((3-mercaptopropyl)(methyl)amino)propoxy)-6-methoxyquinolin-4-yl)oxy)phenyl)-N-(4-fluorophenyl)cyclopropane-1,1-diformamide

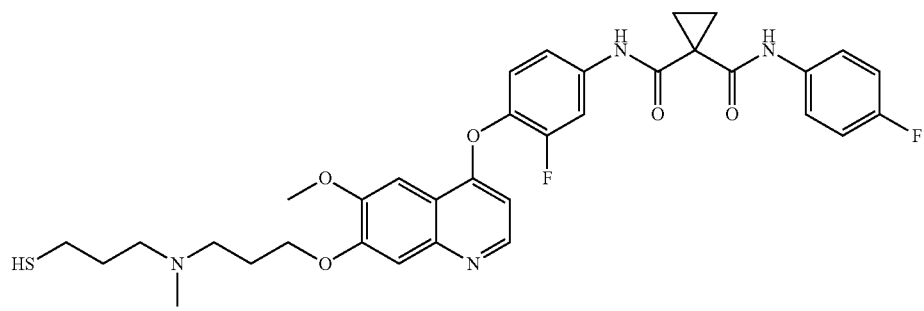 [SMILES: COc1cc2c(Oc3ccc(NC(=O)C4(C(=O)Nc5ccc(F)cc5)CC4)cc3F)ccnc2cc1OCCCN(C)CCCS]

Hydrolysis was performed as the process described in Example 45 to prepare the target compound (7 mg, 48%).

LC-MS: m/z=651[M+H]$^+$.

Example 54 N-(3-fluoro-4-((7-(3-((5-thio-1,3,4-trithiazol-2-yl)sulfanyl)propoxy)-6-methoxyquinolin-4-yl)oxy)phenyl)-N-(4-fluorophenyl)cyclopropane-1,1-diformamide

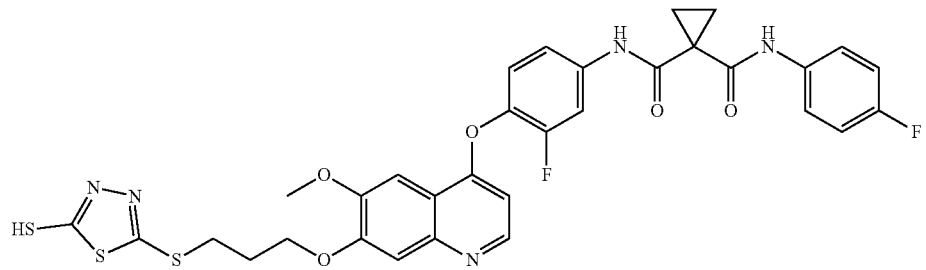 [SMILES: COc1cc2c(Oc3ccc(NC(=O)C4(C(=O)Nc5ccc(F)cc5)CC4)cc3F)ccnc2cc1OCCCSc1nnc(S)s1]

120 mg (0.8 mmol, 5.0 eq) 1,3,4-trithiazole-2,5-dithiophenol was dissolve in 10 mL N,N-dimethylformamide, and 64 mg (1.6 mmol, 10.0 eq) NaH was added at room temperature. Stir for the reaction for 10 min. Then add 100 mg (1 mmol, 1.0 eq) N-(4-((7-(3-bromopropoxy)-6-methoxyquinolin-4-yl)oxy)-3-fluorophenyl)-N-(4-fluorophenyl)cyclopropane-1,1-diformamide (the synthesis method was as step B of Example 1). The reaction system was allowed to react overnight at room temperature. After the completion of the reaction monitored by TLC, the reaction system was poured into 150 mL of water and then was extracted with 200 mL ethyl acetate. Wash the organic phase with water and saturated brine twice in turn. The organic phase was then dried over anhydrous sodium sulfate and evaporated to dryness. The residue was purified by silica gel column chromatography to afford the product (14 mg, yield Rate=13%).

LC-MS: m/z=696[M+H]$^+$.

$^1$H NMR (400 MHz, CDCl$_3$) δ 9.99 (s, 1H), 8.82 (s, 1H), 8.42 (s, 1H), 7.82-7.73 (m, 2H), 7.55 (s, 1H), 7.53 (m, 2H), 7.37 (d, J=7.7 Hz, 1H), 7.18 (q, J=8.0 Hz, 1H), 7.06 (t, J=8.0 Hz, 2H), 6.20 (s, 1H), 4.57 (s, 2H), 4.30 (brs, 1H), 4.15 (s, 3H), 3.41 (s, 2H), 2.48 (s, 2H), 1.83 (s, 2H), 1.72 (s, 2H).

Example 55 S-(2-(3-(2-((4-(2-fluoro-4-(1-((4-fluorophenyl)carbamoyl)cyclopropane-1-carboxamido)phenyloxy)-6-methoxyquinolin-7-yl)(oxy)ethyl)ureido)ethyl)ethanethiolat

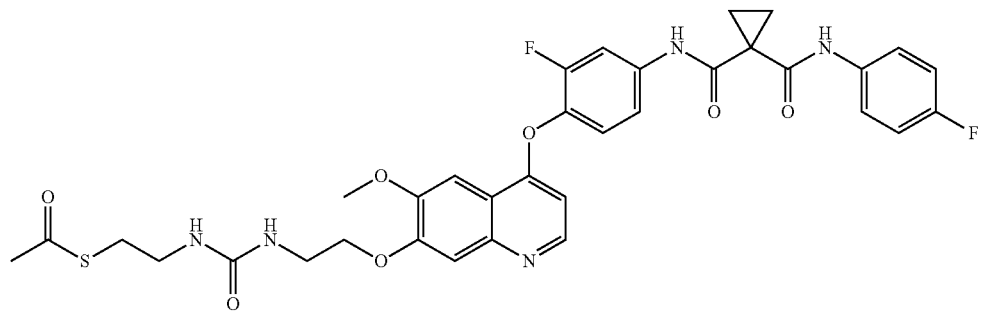 [SMILES: COc1cc2c(Oc3ccc(NC(=O)C4(C(=O)Nc5ccc(F)cc5)CC4)cc3F)ccnc2cc1OCCNC(=O)NCCSC(C)=O]

Step A: N-(4-((7-(2-(3-(2-chloroethyl)ureido)ethoxy)-6-methoxyquinolin-4-yl)oxy)-3-fluorophenyl)-N-(4-fluorophenyl)cyclopropane-1,1-diformamide

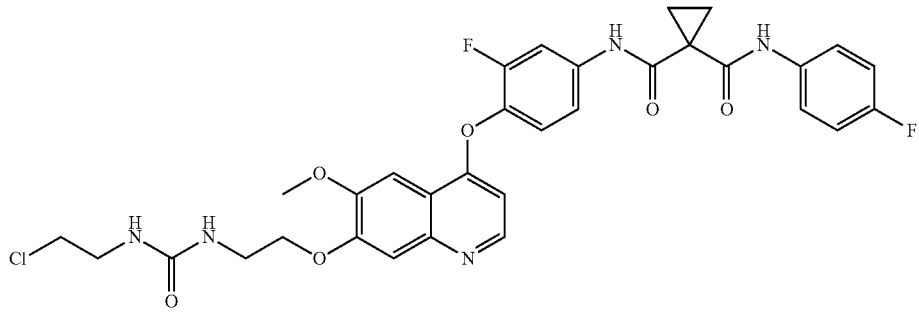 [SMILES: COc1cc2c(Oc3ccc(NC(=O)C4(C(=O)Nc5ccc(F)cc5)CC4)cc3F)ccnc2cc1OCCNC(=O)NCCCl]

At 0° C., add triethylamine and triphosgene (54 mg, 0.183 mmol) to 2-chloroethylamine hydrochloride (64 mg, 0.547 mmol) in DCM, keep the reaction at this temperature for 1 h, and add the reaction mixture dropwise to N-(4-((7-(2-aminoethoxy)-6-methoxyquinolin-4-yl)oxy)-3-fluorophenyl)-N-(4-fluorophenyl)cyclopropane-1,1-diformamide in DCM, react at room temperature for 1 hour, quench the reaction by adding water, extract 3 times with DCM, wash the combined organic phase once with saturated brine, and dry with anhydrous sodium sulfate, concentrate by distillation under reduced pressure. The residue was purified by silica gel column chromatography to afford the product (65 mg).

Step B: S-(2-(3-(2-((4-(2-fluoro-4-(1-((4-fluorophenyl)carbamoyl)cyclopropane-1-carboxamido)phenyloxy)-6-methoxyquinolin-7-yl)(oxy)ethyl)ureido)ethyl)thioacetate

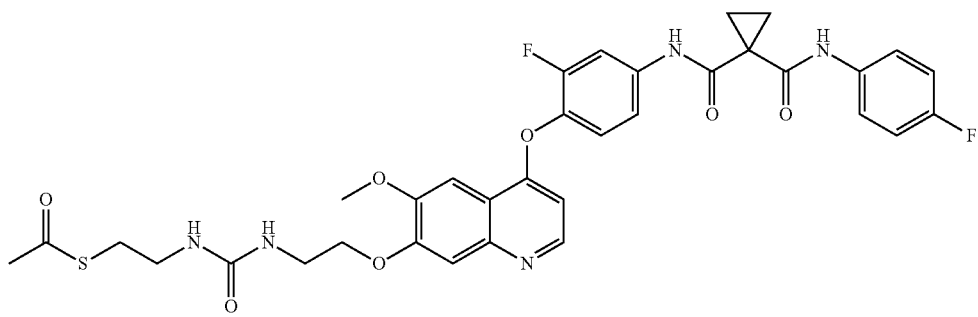 [SMILES: COc1cc2c(Oc3ccc(NC(=O)C4(C(=O)Nc5ccc(F)cc5)CC4)cc3F)ccnc2cc1OCCNC(=O)NCCSC(C)=O]

To N-(4-((7-(2-(3-(2-chloroethyl)ureido)ethoxy)-6-methoxyquinolin-4-yl)oxy)-3-fluorophenyl)-N-(4-fluorophenyl)cyclopropane-1,1-diformamide (60 mg, 0.092 mmol) in acetone was added potassium thioacetate (21 mg, 0.183 mmol), heated to 40° C., and reacted for 3 hours. Cool to room temperature, concentrate by distillation under reduced pressure, and purify by silica gel column chromatography to afford the product (17 mg).

$^1$H NMR (400 MHz, CDCl$_3$) δ 10.13 (s, 1H), 9.94 (s, 1H), 9.50 (s, 1H), 8.50 (s, 1H), 7.91-7.77 (m, 1H), 7.70-7.37 (m, 5H), 7.24-7.22 (m, 2H), 7.07 (s, 2H), 6.42 (s, 1H), 4.28 (s, 2H), 4.03 (s, 3H), 3.82-3.47 (m, 4H), 3.06 (m, 2H), 2.43 (s, 3H), 1.30 (s, 4H). LC-MS: m/z=694 [M+H]$^+$.

Example 56 N-(3-fluoro-4-((7-(2-(3-(2-mercapto-ethyl)ureido)ethoxy)-6-methoxyquinolin-4-yl)oxy)phenyl)-N-(4-fluorophenyl)cyclopropane-1,1-diformamide

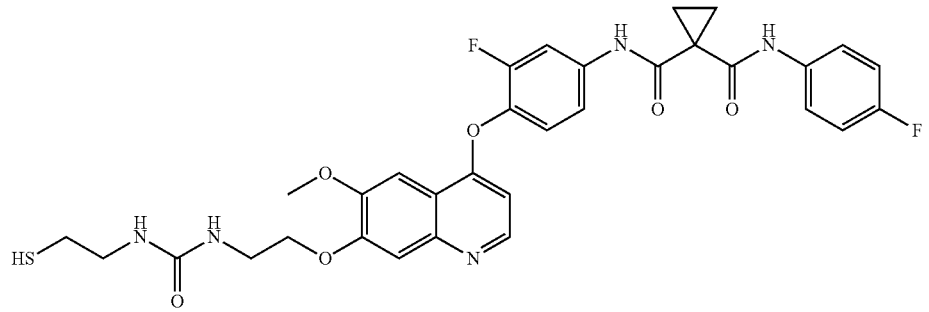 [SMILES: COc1cc2c(Oc3ccc(NC(=O)C4(C(=O)Nc5ccc(F)cc5)CC4)cc3F)ccnc2cc1OCCNC(=O)NCCS]

Hydrolyze as the process described in Example 45 to prepare the target compound (8 mg, 54%).
LC-MS: m/z=652[M+H]$^+$.

Example 57 S-(2-((5-((4-(2-fluoro-4-(1-((4-fluorophenyl)carbamoyl)cyclopropane-1-carboxamido)phenoxy)-6-methoxyquinolin-7-yl)oxy)pentyl)amino)-2-oxo-ethyl)thioacetate

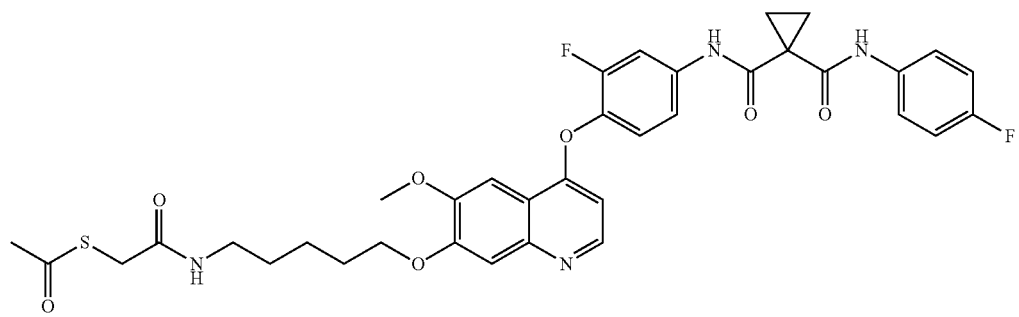 [SMILES: COc1cc2c(Oc3ccc(NC(=O)C4(C(=O)Nc5ccc(F)cc5)CC4)cc3F)ccnc2cc1OCCCCCNC(=O)CSC(C)=O]

Step A: tert-butyl (5-((4-(2-fluoro-4-(1-((4-fluorophenyl)carbamoyl)cyclopropane-1-carboxamido)phenoxy)-6-methoxyquinolin-7-yl)oxy)pentyl)aminocarboxylate

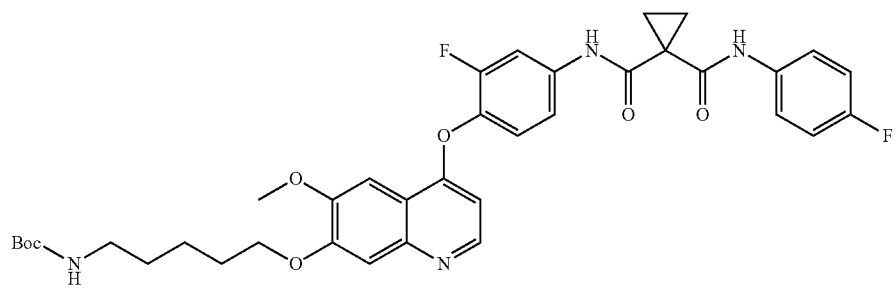 [SMILES: COc1cc2c(Oc3ccc(NC(=O)C4(C(=O)Nc5ccc(F)cc5)CC4)cc3F)ccnc2cc1OCCCCCNC(=O)OC(C)(C)C]

At 0° C., to N-(3-fluoro-4-((7-hydroxy-6-methoxyquino-lin-4-yl)oxy)phenyl)-N-(4-fluorophenyl)cyclopropane-1,1-diformamide (505 mg, 1.0 mmol), tert-butyl (5-hydroxypentyl) carbamate (406 mg, 2.0 mmol) and triphenylphosphine (786 mg, 3.0 mmol) in DCM slowly dropwise added diisoester azodicarboxylate (606 mg, 3.0 mmol). Keep reacted at room temperature for 5 h. Add water to quench the reaction, extract 3 times with DCM, wash the combined organic phase once with saturated brine, and dry with anhydrous sodium sulfate. The organic phase was concentrated by distillation under reduced pressure, and purified by silica gel column chromatography to afford the product (380 mg, 55%).

Step B: N-(4-((7-((5-aminopentyl)oxy)-6-methoxy-quinolin-4-yl)oxy)-3-fluorophenyl)-N-(4-fluorophenyl)cyclopropane-1,1-diformamide

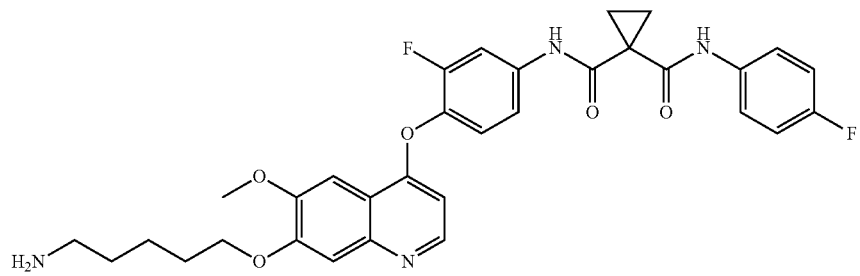 [SMILES: COc1cc2c(Oc3ccc(NC(=O)C4(C(=O)Nc5ccc(F)cc5)CC4)cc3F)ccnc2cc1OCCCCCN]

To tert-butyl (5-((4-(2-fluoro-4-(1-((4-fluorophenyl)carbamoyl)cyclopropane-1-carboxamido)phenoxy)-6-methoxyquinolin-7-yl)oxy)pentyl)carbamate (200 mg, 0.29 mmol) in DCM added trifluoroacetic acid (0.5 ml), and reacted at room temperature for 3 h, then quenched with saturated sodium bicarbonate aqueous solution. The reaction solution was extracted 3 times with DCM, and the combined organic phase was washed once with saturated brine, dried over anhydrous sodium sulfate, and concentrated by distillation under reduced pressure to afford the crude product (130 mg, 76%) directly used in the next reaction.

Step C: S-(2-((5-((4-(2-Fluoro-4-(1-((4-fluorophenyl)carbamoyl)cyclopropane-1-carboxamido)phenoxy)-6-methoxyquinolin-7-yl)oxy)pentyl)amino)-2-oxo-ethyl)thioacetate

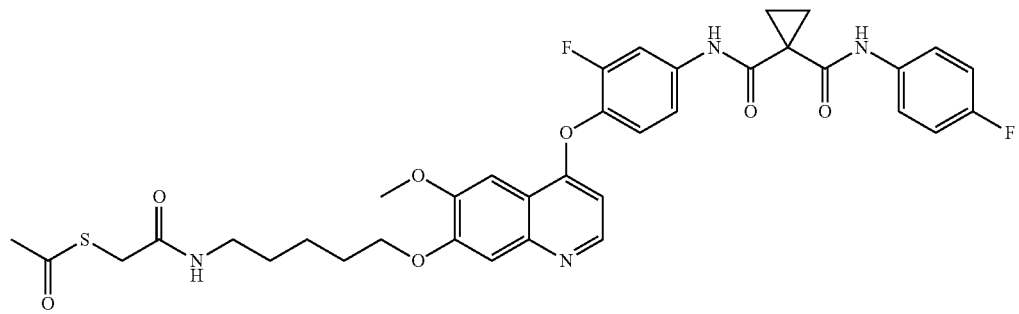 [SMILES: COc1cc2c(Oc3ccc(NC(=O)C4(C(=O)Nc5ccc(F)cc5)CC4)cc3F)ccnc2cc1OCCCCCNC(=O)CSC(C)=O]

At 0° C., to N-(4-((7-((5-aminopentyl)oxy)-6-methoxyquinolin-4-yl)oxy)-3-fluorophenyl)-N-(4-fluorophenyl)cyclopropane-1,1-diformamide (100 mg, 0.17 mmol) and 2-(thioacetate)acetic acid (34 mg, 0.25 mmol) in DMF/DCM mixed solution added DIEA (84 uL, 0.507 mmol) and HATU (130 mg, 0.25 mmol), and then warmed to room temperature and reacted for 2 hours, quenched the reaction with water, extracted 3 times with DCM, and washed the combined organic phase with saturated brine once, dried with anhydrous sodium sulfate, and concentrated by distillation under reduced pressure, purified by silica gel column chromatography to afford the product (60 mg, 50%).

$^1$H NMR (400 MHz, CDCl$_3$) δ 10.06 (s, 1H), 8.52 (s, 1H), 8.34 (s, 1H), 7.81 (d, J=12.4 Hz, 1H), 7.61 (s, 1H), 7.50-7.46 (m, 3H), 7.26-7.24 (m, 2H), 7.12-7.08 (m, 2H), 6.45 (s, 1H), 6.33 (s, 1H), 4.23 (s, 2H), 4.08 (s, 3H), 3.57 (s, 2H), 3.33-3.31 (m, 2H), 2.43 (s, 3H), 1.86-1.84 (m, 2H), 1.79-1.76 (m, 4H), 1.67 (s, 4H). LC-MS: m/z=707 [M+H]$^+$.

Example 58 N-(3-fluoro-4-((7-((5-(2-mercaptoacetylamino)pentyl)oxy)-6-methoxyquinolin-4-yl)oxy)phenyl)-N-(4-fluorophenyl)cyclopropane-1,1-diformamide

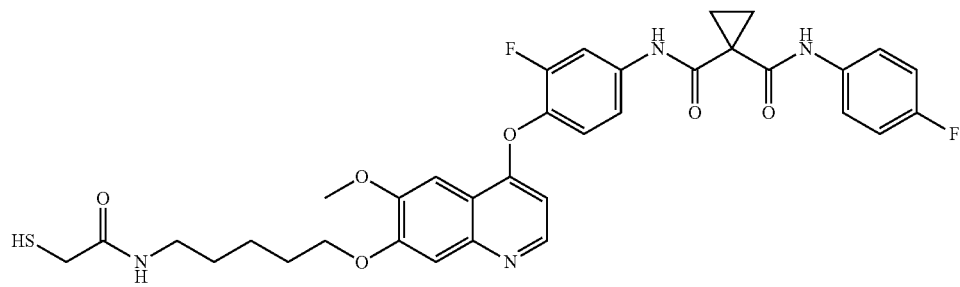 [SMILES: COc1cc2c(Oc3ccc(NC(=O)C4(C(=O)Nc5ccc(F)cc5)CC4)cc3F)ccnc2cc1OCCCCCNC(=O)CS]

Hydrolyze as the process described in Example 45 to prepare the target compound (12 mg, 67%) from example 57.

LC-MS: m/z=665[M+H]$^+$.

Example 59 S-(2-((5-((4-(2-Fluoro-4-(1-((4-fluorophenyl)carbamoyl)cyclopropane-1-carboxamido)phenoxy)-6-methoxyquinolin-7-yl)oxy)pentyl)amino)-2-oxo-ethyl)thioacetate

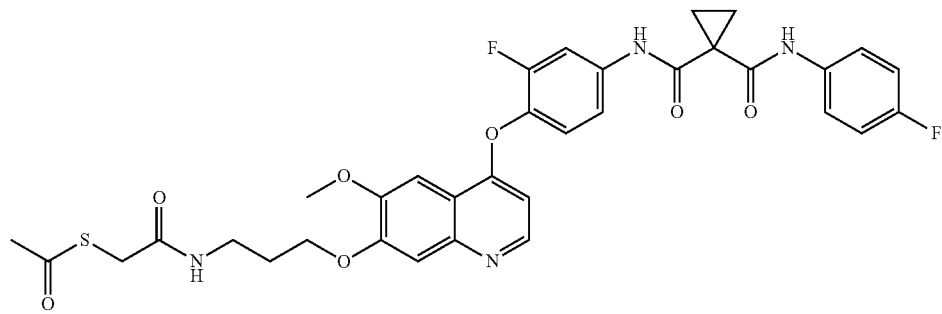 [SMILES: COc1cc2c(Oc3ccc(NC(=O)C4(C(=O)Nc5ccc(F)cc5)CC4)cc3F)ccnc2cc1OCCCNC(=O)CSC(C)=O]

prepare the target compound (86 mg, 58%) as the process described in example 57.

LC-MS: m/z=679[M+H]$^+$.

Example 60 N-(3-fluoro-4-((7-((5-(2-mercap-
toacetylamino)pentyl)oxy)-6-methoxyquinolin-4-yl)
oxy)phenyl)-N-(4-fluorophenyl)cyclopropane-1,1-
diformamide

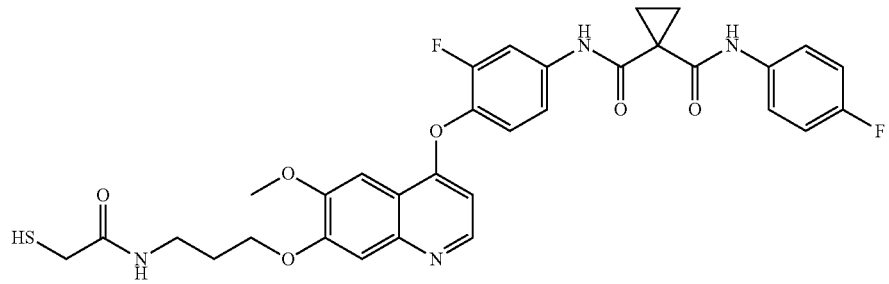 [SMILES: COc1cc2c(Oc3ccc(NC(=O)C4(C(=O)Nc5ccc(F)cc5)CC4)cc3F)ccnc2cc1OCCCNC(=O)CS]

Hydrolyze as the process described in Example 45 to prepare the target compound (35 mg, 39%) from example 59.
LC-MS: m/z=637[M+H]⁺.

Example 61 S-(2-((5-((4-(2-fluoro-4-(1-((4-fluoro-
phenyl)carbamoyl)cyclopropane-1-carboxamido)
phenoxy)-6-methoxyquinolin-7-yl)oxy)pentyl)
amino)-2-oxo-ethyl)thioacetate

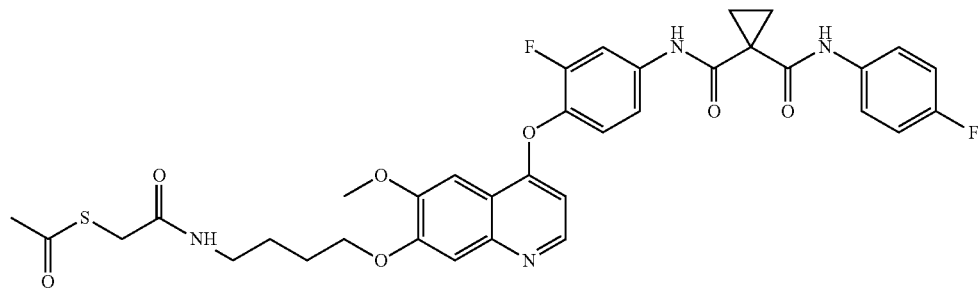 [SMILES: COc1cc2c(Oc3ccc(NC(=O)C4(C(=O)Nc5ccc(F)cc5)CC4)cc3F)ccnc2cc1OCCCCNC(=O)CSC(C)=O]

Prepare the target compound (49 mg, 56%) as the process described in example 57.
LC-MS: m/z=693[M+H]⁺.

Example 62 N-(3-fluoro-4-((7-((5-(2-mercap-
toacetylamino)pentyl)oxy)-6-methoxyquinolin-4-yl)
oxy)phenyl)-N-(4-fluorophenyl)cyclopropane-1,1-
diformamide

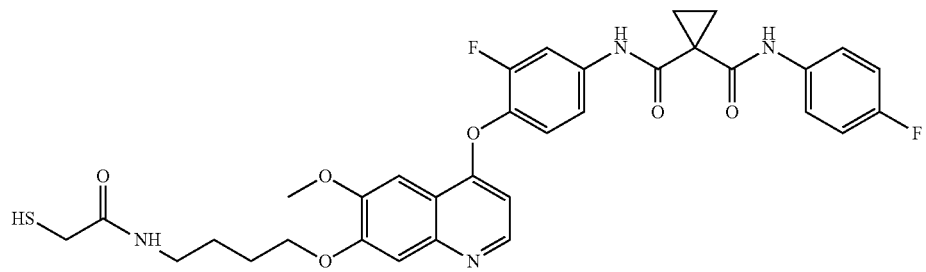 [SMILES: COc1cc2c(Oc3ccc(NC(=O)C4(C(=O)Nc5ccc(F)cc5)CC4)cc3F)ccnc2cc1OCCCCNC(=O)CS]

Hydrolyze as the process described in Example 45 to prepare the target compound (60 mg, 71%) from example 61.
LC-MS: m/z=651[M+H]⁺.

Example 63 S-(2-((5-((4-(2-fluoro-4-(1-((4-fluorophenyl)carbamoyl)cyclopropane-1-carboxamido)phenoxy)-6-methoxyquinolin-7-yl)oxy)pentyl)amino)-2-oxo-ethyl)thioacetate

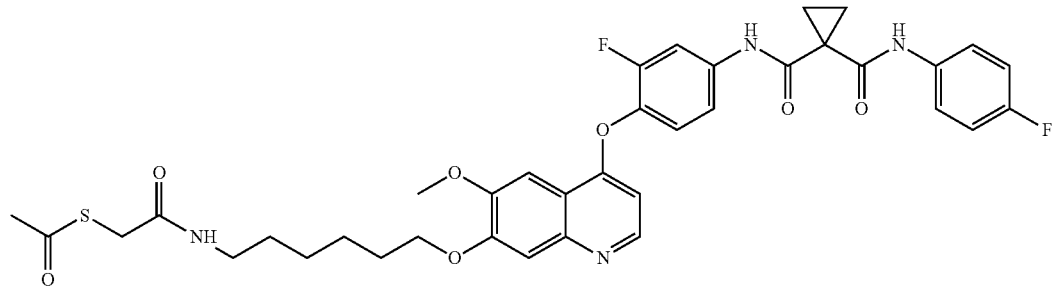 [SMILES: COc1cc2c(Oc3ccc(NC(=O)C4(C(=O)Nc5ccc(F)cc5)CC4)cc3F)ccnc2cc1OCCCCCCNC(=O)CSC(C)=O]

Prepare the target compound (120 mg, 64%) as the process described in example 57.

LC-MS: m/z=721[M+H]$^+$.

Example 64 N-(3-fluoro-4-((7-((5-(2-mercaptoacetylamino)pentyl)oxy)-6-methoxyquinolin-4-yl)oxy)phenyl)-N-(4-fluorophenyl)cyclopropane-1,1-diformamide

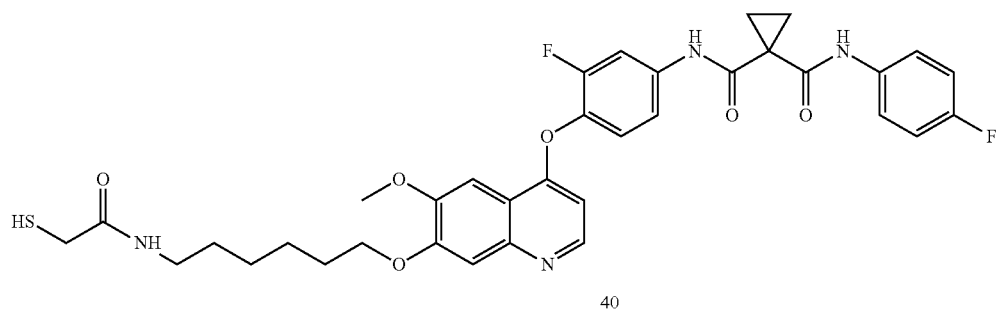

Hydrolyze as the process described in Example 45 to prepare the target compound (52 mg, 72%) from example 63.

LC-MS: m/z=679[M+H]$^+$.

Example 65 S-(2-((5-((4-(4-(1-((4-fluorophenyl)carbamoyl)cyclopropane-1-carboxamido)phenoxy)-6-(methoxyquinolin-7-yl)oxy)pentyl)amino)-2-oxo-ethyl)thioacetate

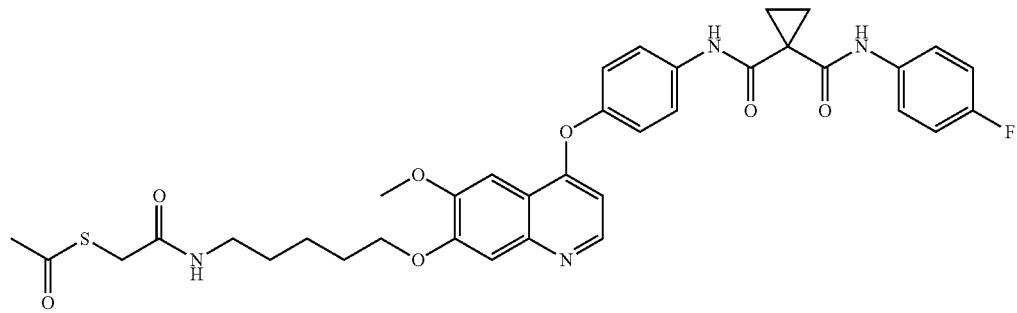 [SMILES: COc1cc2c(Oc3ccc(NC(=O)C4(C(=O)Nc5ccc(F)cc5)CC4)cc3)ccnc2cc1OCCCCCNC(=O)CSC(C)=O]

Prepare the target compound (92 mg, 52%) as the process described in example 57.

LC-MS: m/z=689 [M+H]$^+$.

Example 66 N-(4-fluorophenyl)-N-(4-((7-((5-(2-mercaptoacetamido)pentyl)oxy)-6-methoxyquinolin-4-yl)oxy)phenyl)cyclopropane-1,1-diformamide

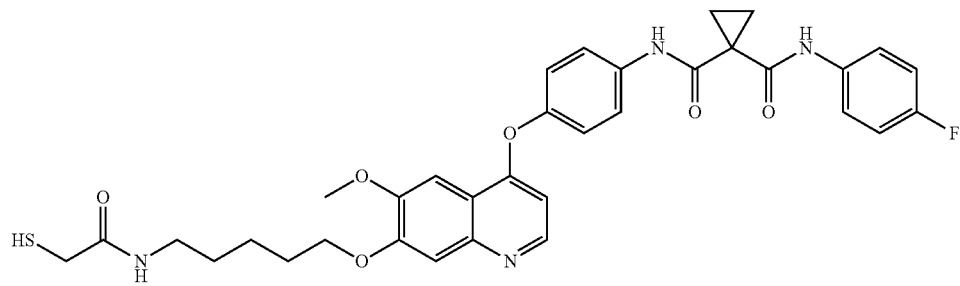 [SMILES: COc1cc2c(Oc3ccc(NC(=O)C4(C(=O)Nc5ccc(F)cc5)CC4)cc3)ccnc2cc1OCCCCCNC(=O)CS]

Hydrolyze as the process described in Example 45 to prepare the target compound (32 mg, 46%) from example 65.

LC-MS: m/z=647[M+H]$^+$.

Example 67 S-(2-((5-((4-(4-(1-(cyclopropylcarbamoyl)cyclopropane-1-carboxamido)-2-fluorophenoxy)-6-methoxyquinolin-7-yl)oxy)pentyl)amino)-2-oxo-ethyl)thioacetate

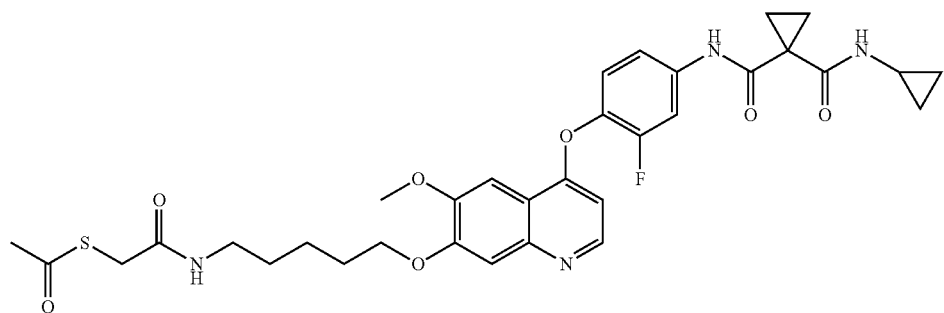 [SMILES: COc1cc2c(Oc3ccc(NC(=O)C4(C(=O)NC5CC5)CC4)cc3F)ccnc2cc1OCCCCCNC(=O)CSC(C)=O]

Prepare the target compound (150 mg, 79%) as the process described in example 57.

$^1$H NMR (400 MHz, CDCl$_3$) δ 11.35 (s, 1H), 8.50 (q, J=4.0 Hz, 1H), 7.84 (dd, J=4.0, 8.0 Hz, 1H), 7.62 (s, 1H), 7.42 (s, 1H), 7.36-7.30 (m, 2H), 7.24 (q, J=8.0 Hz, 1H), 6.03-5.92 (m, 1H), 4.24 (q, J=4.0 Hz, 2H), 4.08 (s, 3H), 3.43-3.25 (m, 2H), 3.02 (s, 2H), 2.80-2.70 (m, 1H), 2.19-1.92 (m, 5H), 1.84-1.75 (m, 2H), 1.71-1.56 (m, 4H), 1.38-1.25 (m, 2H), 0.89 (dd, J=4.0, 8.0 Hz, 2H), 0.58 (dd, J=4.0, 8.0 Hz, 2H).

LC-MS: m/z=653 [M+H]$^+$.

Example 68 N-cyclopropyl-N-(3-fluoro-4-((7-((5-(2-mercaptoacetamido)pentyl)oxy)-6-methoxyquinolin-4-yl)oxy)phenyl)cyclopropane-1,1-diformamide

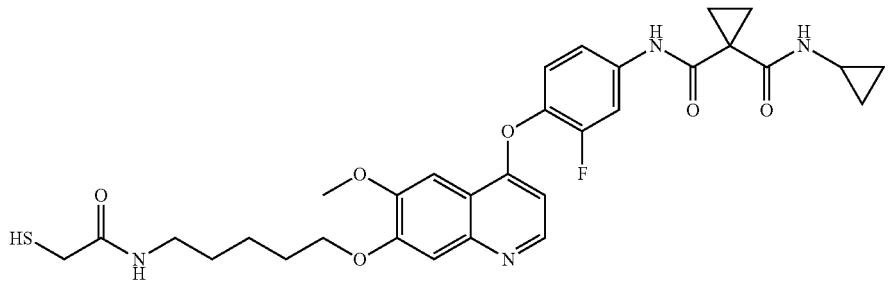 [SMILES: COc1cc2c(Oc3ccc(NC(=O)C4(C(=O)NC5CC5)CC4)cc3F)ccnc2cc1OCCCCCNC(=O)CS]

Hydrolyze as the process described in Example 45 to prepare the target compound (22 mg, 38%) from example 67.

LC-MS: m/z=611[M+H]$^+$.

Example 69 S-(2-((5-((6-carbamoyl-4-(3-chloro-4-(3-cyclopropylurea)phenoxy)quinolin-7-yl)oxy)pentyl)amino)-2-oxo-ethyl)thioacetate

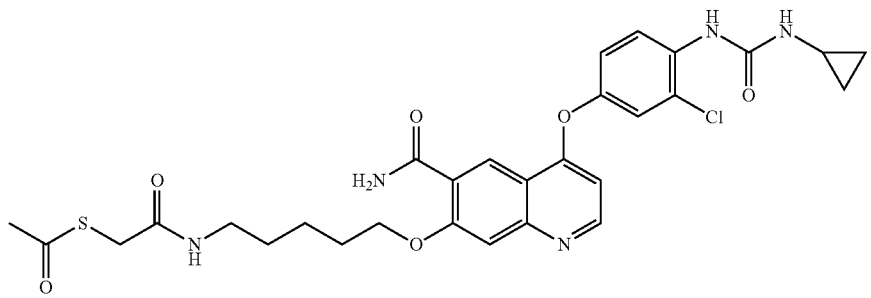 [SMILES: CC(=O)SCC(=O)NCCCCCOc1cc2nccc(Oc3ccc(NC(=O)NC4CC4)c(Cl)c3)c2cc1C(N)=O]

Step A: 5-bromopentylamine hydrobromide salt

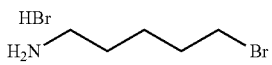

Slowly add 5-aminopentanol (20 g, 194 mmol) to 40% hydrogen bromide aqueous solution (200 ml) at room temperature, and react at 100° C. for 4 h. Distill under reduced pressure to remove the solvent, and the water in residue was taken with methanol (150 ml). The solvent was distilled off under reduced pressure again. The final residue was slurried with DCM, and the solid was collected by vacuum filtration and rinsed with DCM, and dried naturally to give the product (35 g, 75%).

Step B: S-(2-((5-bromopentyl)amino)-2-oxo-ethyl)thioacetate

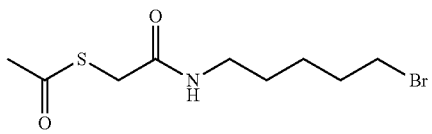

Under ice bath, add DMF (1 mL) and oxalyl chloride (2.5 mL, 30 mmol) to 2-(acetylthio)acetic acid (2.68 g, 20 mmol) in DCM, warm to room temperature and react for 2 hours. Remove the solvent by distillation under reduced pressure. The residue was diluted with 100 mL DCM and the solvent was distilled off under reduced pressure again. The residue was directly used in the next step reaction (3.0 g).

To the residue in DCM (50 mL) was added 5-bromopentylamine hydrobromide (2.47 g, 10 mmol), and DIEA (9 mL, 50 mmol) was slowly added dropwise to the reaction system under ice bath. The temperature was raised to room temperature, and reacted for 1 hour. The reaction was quenched by adding water, and the reaction solution was washed with 30% citric acid aqueous solution (100 mL×2). The organic phase was washed once with saturated brine, dried with anhydrous sodium sulfate, concentrated by distillation under reduced pressure, and purified by silica gel column chromatography to afford the product (1.31 g, 46%).

$^1$H NMR (400 MHz, CDCl$_3$) δ 6.30 (brs, 1H), 3.55 (s, 2H), 3.44 (q, J=4.0 Hz, 2H), 3.33-3.23 (m, 2H), 2.45 (s, 3H), 1.93-1.86 (m, 2H), 1.57-1.46 (m, 4H).

Step C: 4-(3-chloro-4-(3-cyclopropylurea)phenoxy)-7-hydroxyquinoline-6-carboxamide

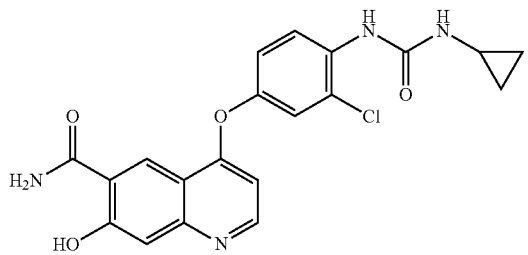 [SMILES: NC(=O)c1cc2c(Oc3ccc(NC(=O)NC4CC4)c(Cl)c3)ccnc2cc1O]

Under ice bath, to 4-[3-chloro-4-(cyclopropylamino carbonyl)aminophenoxy]-7-methoxy-6-quinolinecarboxamide (1.39 g, 3.37 mmol) in DCM (30 mL) was added BBr3 (5 mL, 52 mmol). after the addition, the reaction was kept under ice bath for 5 hours. The solvent was distilled off under reduced pressure, and the reaction solution was washed with saturated sodium bicarbonate aqueous solution (100 mL×2), and the organic phase was washed with saturated brine once. Dry with sodium sulfate, concentrate under reduced pressure, and purify by silica gel column chromatography to afford the product (0.89 g, 66%).

Step D: S-(2-((5-((6-carbamoyl-4-(3-chloro-4-(3-cyclopropylurea)phenoxy)quinolin-7-yl)oxy)pentyl)amino)-2-oxo-ethyl)thioacetate

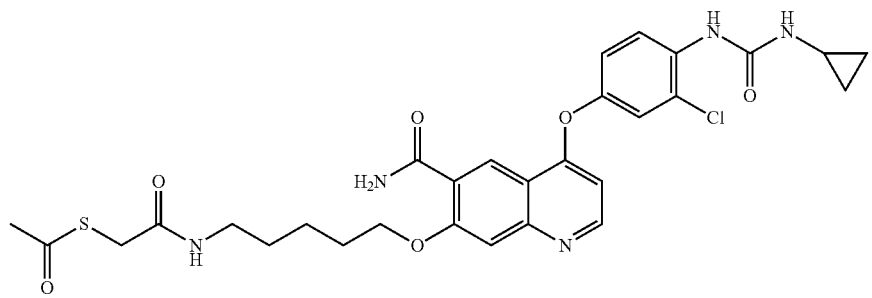 [SMILES: CC(=O)SCC(=O)NCCCCCOc1cc2nccc(Oc3ccc(NC(=O)NC4CC4)c(Cl)c3)c2cc1C(N)=O]

At room temperature, to 4-(3-chloro-4-(3-cyclopropylurea)phenoxy)-7-hydroxyquinoline-6-carboxamide (300 mg, 0.73 mmol) in DMF, were added potassium carbonate (201 mg, 1.46 mmol) and S-(2-((5-bromopentyl)amino)-2-oxo-ethyl)thioacetate (206 mg, 0.73 mmol). React at room temperature for 3 h, add water, and extract 3 times with DCM. The combined organic phase was washed once with saturated brine, dried over anhydrous sodium sulfate, and concentrated by distillation under reduced pressure to afford a crude product. The residue was purified by silica gel column chromatography to afford the product (130 mg, 29%).

$^1$H NMR (400 MHz, CDCl$_3$) δ 9.25 (s, 1H), 8.66 (s, 1H), 8.42 (d, J=8.0 Hz, 1H), 7.92 (s, 1H), 7.83 (s, 1H), 7.53 (s, 1H), 7.21 (s, 1H), 7.11 (d, J=8.0 Hz, 1H), 6.55-6.48 (m, 3H), 5.84 (brs, 1H), 4.31 (s, 2H), 3.58 (s, 2H), 3.33 (s, 2H), 2.69 (s, 1H), 2.43 (s, 3H), 2.01 (s, 2H), 1.69-1.53 (m, 4H), 0.95-0.82 (m, 2H), 0.79-0.71 (m, 2H). LC-MS: m/z=636 [M+Na]$^+$.

Example 70 4-(3-chloro-4-(3-cyclopropylurea)phenoxy)-7-((5-(2-mercaptoacetamido)pentyl)oxy)quinoline-6-formamide

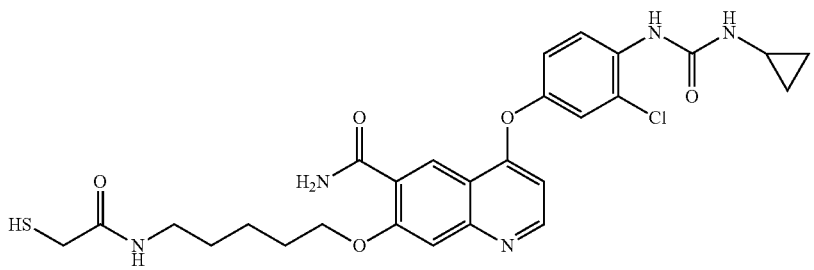 [SMILES: NC(=O)c1cc2c(Oc3ccc(NC(=O)NC4CC4)c(Cl)c3)ccnc2cc1OCCCCCNC(=O)CS]

Hydrolyze as the process described in Example 45 to prepare the target compound (22 mg, 38%) from example 69.

LC-MS: m/z=572 [M+H]$^+$.

Example 71 S-(2-((5-(((6-carbamoyl-4-(2-fluoro-4-(1-((4-fluorophenyl)carbamoyl)cyclopropane-1-methylamido)phenoxy)quinolin-7-yl)oxy)pentyl)amino)-2-oxo-ethyl)thioacetate

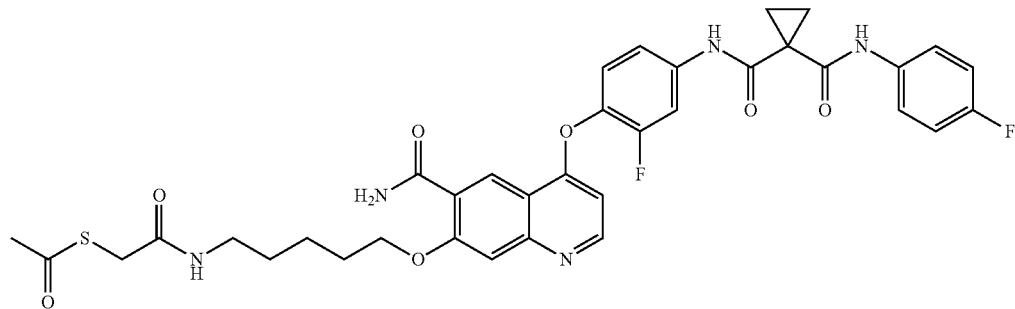 [SMILES: CC(=O)SCC(=O)NCCCCCOc1cc2nccc(Oc3ccc(NC(=O)C4(C(=O)Nc5ccc(F)cc5)CC4)cc3F)c2cc1C(N)=O]

Prepare the target compound (100 mg, 21%) as the process described in example 69.

$^1$H NMR (400 MHz, CDCl$_3$) δ 10.11 (s, 1H), 9.46 (s, 1H), 9.23 (s, 1H), 8.64 (d, J=4.0 Hz, 1H), 7.98 (s, 1H), 7.87 (d, J=8.0 Hz, 1H), 7.53-7.49 (m, 3H), 7.18 (q, J=8.0 Hz, 1H), 7.03 (q, J=8.0 Hz, 1H), 6.53-6.42 (m, 2H), 6.39 (d, J=4.0 Hz, 1H), 4.30 (q, J=4.0 Hz, 2H), 3.58 (s, 2H), 3.33 (t, J=4.0 Hz, 2H), 2.44 (s, 3H), 2.08-1.95 (m, 2H), 1.74 (s, 4H), 1.68-1.55 (m, 4H).

LC-MS: m/z=720 [M+H]$^+$.

Example 72 N-(4-((6-carbamoyl-7-((5-(2-mercaptoacetamido)pentyl)oxy)quinolin-4-yl)oxy)-3-fluorophenyl)-N-(4-fluorophenyl)cyclopropane-1,1-diformamide

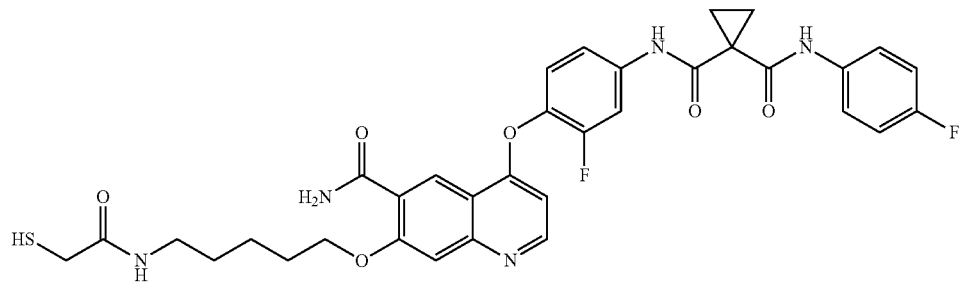 [SMILES: NC(=O)c1cc2c(Oc3ccc(NC(=O)C4(C(=O)Nc5ccc(F)cc5)CC4)cc3F)ccnc2cc1OCCCCCNC(=O)CS]

Hydrolyze as the process described in Example 45 to prepare the target compound (18 mg, 43%) from example 71.

LC-MS: m/z=678 [M+H]$^+$.-

Example 73 S-(2-((5-((6-carbamoyl-4-(4-(1-(cyclo-propanylcarbamoyl)cyclopropane-1-carboxamido)-2-fluorophenoxy)quinolin-7-yl)oxy)pentyl)amino)-2-oxo-ethyl)thioacetate

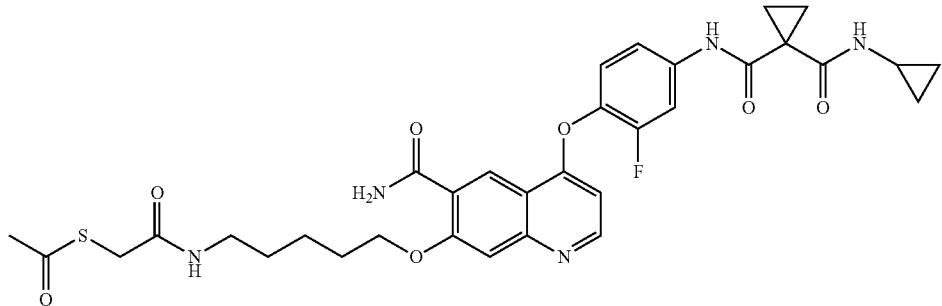 [SMILES: CC(=O)SCC(=O)NCCCCCOc1cc2nccc(Oc3ccc(NC(=O)C4(C(=O)NC5CC5)CC4)cc3F)c2cc1C(N)=O]

Prepare the target compound (100 mg, 29%) as the process described in example 69.

$^1$H NMR (400 MHz, CDCl$_3$) δ11.23 (s, 1H), 9.32 (s, 1H), 8.68 (d, J=8.0 Hz, 1H), 7.88-7.80 (m, 2H), 7.54 (s, 1H), 7.34 (t, J=8.0 Hz, 1H), 7.23 (t, J=8.0 Hz, 1H), 6.44 (d, J=4.0 Hz, 1H), 6.33 (brs, 1H), 6.09 (s, 1H), 5.95 (s, 1H), 4.33 (t, J=4.0 Hz, 2H), 3.57 (s, 2H), 3.34 (q, J=4.0 Hz, 2H), 2.76 (s, 1H), 2.45 (s, 3H), 2.09-2.00 (m, 2H), 1.85-1.78 (m, 2H), 1.68-1.61 (m, 6H), 0.89-0.84 (m, 2H), 0.59-0.54 (m, 2H).

LC-MS: m/z=666 [M+H]$^+$.

Example 74 N-(4-((6-carbamoyl-7-((5-(2-mercap-toacetamido)pentyl)oxy)quinolin-4-yl)oxy)-3-fluoro-phenyl)-N-cyclopropyl-cyclopropane-1,1-diforma-mide

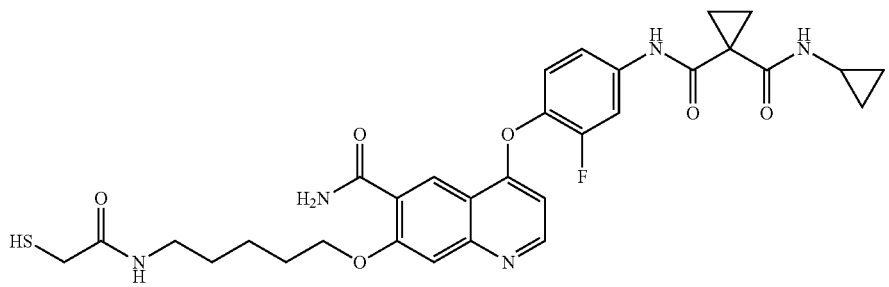 [SMILES: NC(=O)c1cc2c(Oc3ccc(NC(=O)C4(C(=O)NC5CC5)CC4)cc3F)ccnc2cc1OCCCCCNC(=O)CS]

Hydrolyze as the process described in Example 45 to prepare the target compound (14 mg, 28%) from example 73.

LC-MS: m/z=624 [M+H]$^+$.

Example 75 S-(2-((5-((4-(2-fluoro-4-(1-((4-fluoro-phenyl)carbamoyl)cyclopropane-1-carboxamido)phenoxy)-6-methoxyquinolin-7-yl)sulfanyl)pentyl)amino)-2-oxo-ethyl thioacetate

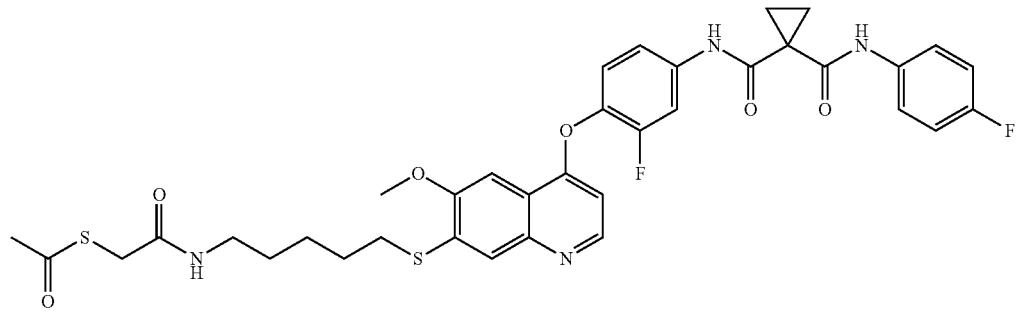 [SMILES: COc1cc2c(Oc3ccc(NC(=O)C4(C(=O)Nc5ccc(F)cc5)CC4)cc3F)ccnc2cc1SCCCCCNC(=O)CSC(C)=O]

Step A: tert-butyl (5-bromopentyl) carbamate

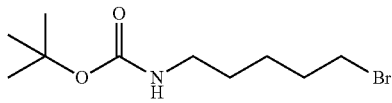

At room temperature, to the dichloromethane solution (30 ml) of 5-bromopentylamine hydrogen bromide (2.07 g, 8.38 mmol) was added di-tert-butyl dicarbonate (2.35 g, 10.89 mmol), then slowly add triethylamine (1.69 g, 16.76 mmol) dropwise under ice bath. The reaction solution was reacted at room temperature for 4 h, and then washed with 20% citric acid aqueous solution. The organic phase was dried, concentrated, and purified by column chromatography to afford the product (1.93 g, 87%).

Step B: S-(5-((tert-butoxycarbonyl)amino)pentyl) thioacetate

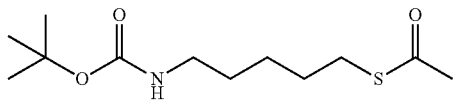 [SMILES: CC(=O)SCCCCCNC(=O)OC(C)(C)C]

At room temperature, potassium thioacetate (0.43 g, 3.76 mmol) was added to tert-butyl (5-bromopentyl) carbamate (1.0 g, 3.76 mmol) in DCM, and the reaction was carried out at room temperature for 2 hours. Filter and rinse the filter cake with DCM. The filtrate was collected and concentrated by distillation under reduced pressure, and the residue was purified by silica gel column chromatography to afford the product (0.66 g, 66%).
LC-MS: m/z=262 [M+H]$^+$.

Step C: tert-butyl (5-mercapto pentyl) carbamate

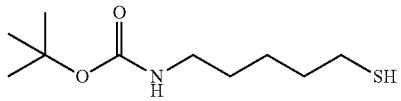

Under ice bath, add 1N sodium hydroxide aqueous solution (3.80 mL, 3.80 mmol) to S-(5-((tert-butoxycarbonyl)amino)pentyl)thioacetate (0.66 g, 2.53 mmol) in methanol (30 mL), and then keep the reaction in ice bath for 10 minutes. Raise to room temperature and react for 1 hour, add DCM and water for extraction. The organic phase was washed once with saturated brine, dried over anhydrous sodium sulfate, concentrated by distillation under reduced pressure, and the residue was directly used in the next reaction (0.49 g, 89%).
LC-MS: m/z=220 [M+H]$^+$.

Step D: 4-(2-fluoro-4-(1-((4-fluorophenyl)carbamoyl)cyclopropane-1-carboxamido)phenoxy)-6-methoxyquinolin-7-trifluoromethanesulfonate

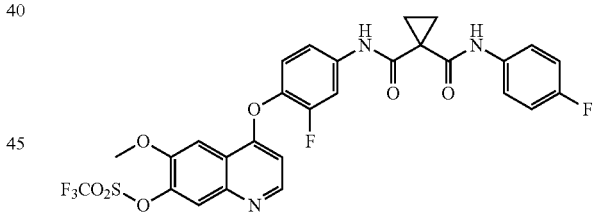

At 0° C., to N-(3-fluoro-4-((7-hydroxy-6-methoxyquinolin-4-yl)oxy)phenyl)-N-(4-fluorophenyl)cyclopropane-1,1-diformamide (505 mg, 1.0 mmol) and potassium carbonate (414 mg, 3.0 mmol) in DMF, trifluoromethanesulfonic anhydride (423 mg, 1.5 mmol) was added, and reacted for 5 h at room temperature. Add water to quench the reaction, extract 3 times with DCM, and the combined organic phase was washed 3 times with saturated brine, dried over anhydrous sodium sulfate, concentrated by distillation under reduced pressure, and purified by silica gel column chromatography to afford the product (380 mg, 60%).
LC-MS: m/z=638 [M+H]$^+$.

Step E: tert-butyl (5-((4-(2-fluoro-4-(1-((4-fluoro-phenyl)carbamoyl)cyclopropane-1-carboxamido)phenoxy)-6-methoxyquinolin-7-yl)sulfanyl) pentyl) carbamate

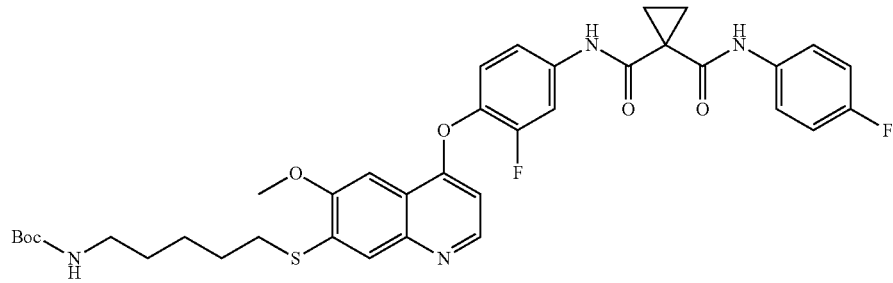 [SMILES: COc1cc2c(Oc3ccc(NC(=O)C4(C(=O)Nc5ccc(F)cc5)CC4)cc3F)ccnc2cc1SCCCCCNC(=O)OC(C)(C)C]

To 4-(2-fluoro-4-(1-((4-fluorophenyl)carbamoyl)cyclopropane-1-carboxamido)phenoxy)-6-methoxyquinoline-7-trifluoromethanesulfonate (505 mg, 1.0 mmol) in dioxane, tert-butyl (5-mercapto pentyl) carbamate (414 mg, 3.0 mmol) and DIEA (423 mg, 1.5 mmol) were added, and nitrogen was ventilated for three times; then $Pd_2(dba)_3$ (414 mg, 3.0 mmol) and ant-Phos(414 mg, 3.0 mmol) were added; nitrogen was ventilated again for three times; raise to 120° C. and react overnight. Add water to quench the reaction and extract with DCM for 3 times. The combined organic phase was washed once with saturated brine, dried over anhydrous sodium sulfate, concentrated by distillation under reduced pressure, and purified by silica gel column chromatography to afford the product (380 mg, 60%).

LC-MS: m/z=707 [M+H]$^+$.

Step F: S-(2-((5-((4-(2-fluoro-4-(1-((4-fluorophenyl)carbamoyl)cyclopropane-1-carboxamido)phenoxy)-6-methoxyquinolin-7-yl)sulfanyl)pentyl)amino)-2-oxo-ethyl)thioacetate

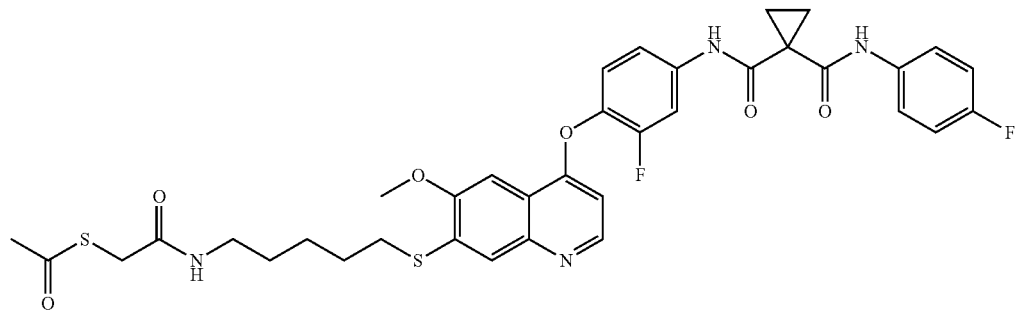 [SMILES: COc1cc2c(Oc3ccc(NC(=O)C4(C(=O)Nc5ccc(F)cc5)CC4)cc3F)ccnc2cc1SCCCCCNC(=O)CSC(C)=O]

The target compound (35 mg, 24%) was prepared with reference to the steps B and C described in Example 57.

$^1$H NMR (400 MHz, CDCl3) δ10.05 (s, 1H), 8.54 (d, J=8.0 Hz, 1H), 8.23 (s, 1H), 7.84-7.78 (m, 2H), 7.57 (s, 1H), 7.53-7.46 (m, 2H), 7.27 (t, J=12 Hz, 1H), 7.15-7.04 (t, J=8.0 Hz, 2H), 6.46 (d, J=8.0 Hz, 1H), 6.32 (brs, 1H), 4.10 (s, 3H), 3.57 (s, 2H), 3.29 (q, J=8.0 Hz, 2H), 3.10 (t, J=8.0 Hz, 2H), 2.46 (s, 3H), 1.90-1.81 (m, 4H), 1.68-1.57 (m, 6H).

LC-MS: m/z=723 [M+H]$^+$.

Example 76 N-(3-fluoro-4-((7-((5-(2-mercaptoacet-amido)pentyl)sulfanyl)-6-methoxyquinolin-4-yl)oxy)phenyl)-N-(4-fluorophenyl)cyclopropane-1,1-diformamide

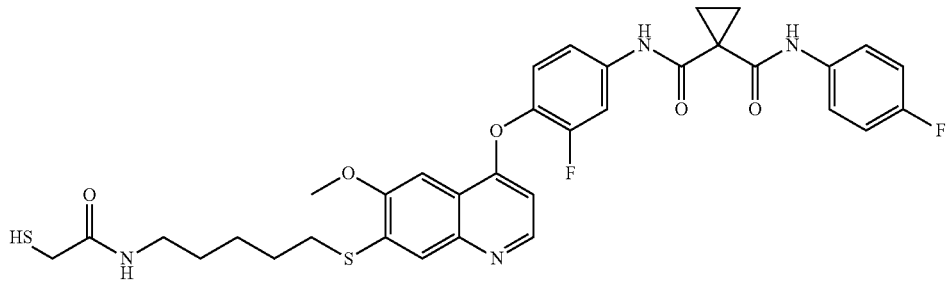 [SMILES: COc1cc2c(Oc3ccc(NC(=O)C4(C(=O)Nc5ccc(F)cc5)CC4)cc3F)ccnc2cc1SCCCCCNC(=O)CS]

Hydrolyze as the process described in Example 45 to prepare the target compound (40 mg, 30%) from example 75.

LC-MS: m/z=681 [M+H]$^+$.

Example 77 N-(3-fluoro-4-((7-((5-(2-sulfanylacet-amido)pentyl)-6-methoxyquinolin-4-yl)oxy)phenyl)-N-(4-fluorophenyl)cyclopropane-1,1-diformamide

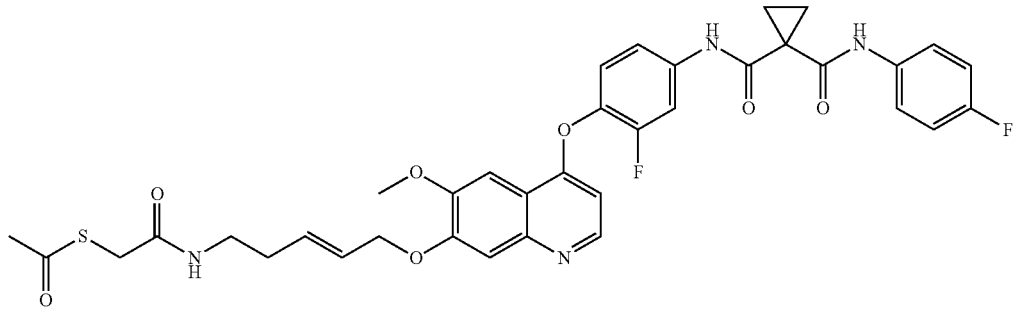 [SMILES: COc1cc2c(Oc3ccc(NC(=O)C4(C(=O)Nc5ccc(F)cc5)CC4)cc3F)ccnc2cc1OC/C=C/CCNC(=O)CSC(C)=O]

The target compound (32 mg, 43%) was prepared with reference to the process described in Example 24.

LC-MS: m/z=705 [M+H]$^+$.

Example 78 S-(7-((6-carbamoyl-4-(3-chloro-4-(3-cyclopropylurea)phenoxy)quinolin-7-yl)oxy)heptyl)thioacetate

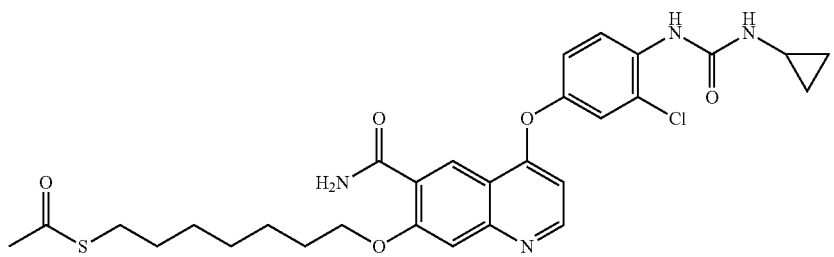 [SMILES: CC(=O)SCCCCCCCOc1cc2nccc(Oc3ccc(NC(=O)NC4CC4)c(Cl)c3)c2cc1C(N)=O]

With reference to the process described in Example 69, S-(2-((5-bromopentyl)amino)-2-oxo-ethyl)thioacetate was replaced with S-(7-bromoheptyl)-acetylthioester to prepare the target compound (41 mg, 46%).

LC-MS: m/z=585 [M+H]$^+$.

Example 79 4-(3-chloro-4-(3-cyclopropylurea)phenoxy)-7-((7-mercaptoheptyl)oxy)quinoline-6-carbamoyl

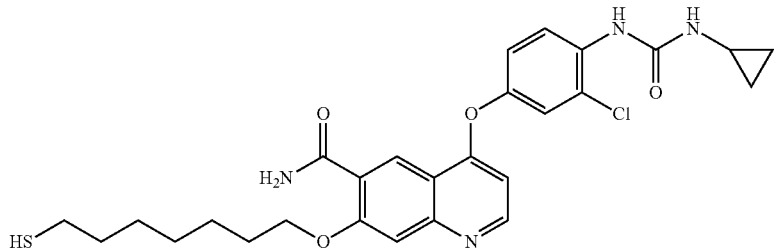 [SMILES: NC(=O)c1cc2c(Oc3ccc(NC(=O)NC4CC4)c(Cl)c3)ccnc2cc1OCCCCCCCS]

Hydrolyze as the process described in Example 45 to prepare the target compound (22 mg, 38%) from example 78.

LC-MS: m/z=543 [M+H]$^+$.

Example 80 S-(2-((5-((4-(2-fluoro-4-(1-((4-fluorophenyl)carbamoyl)cyclopropane-1-carboxamido)phenoxy)-6-methoxyquinolin-7-yl)oxy)pentyl)amino)-2-oxo-ethyl)2-aminothioacetate hydrochloride

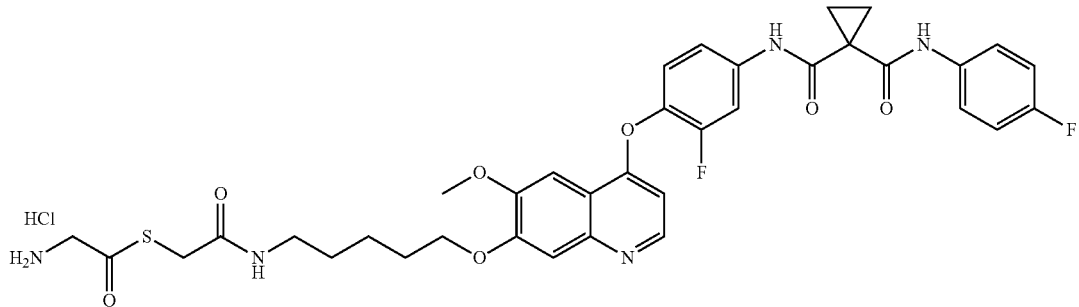 [SMILES: Cl ; COc1cc2c(Oc3ccc(NC(=O)C4(C(=O)Nc5ccc(F)cc5)CC4)cc3F)ccnc2cc1OCCCCCNC(=O)CSC(=O)CN]

With reference to the amino acid condensation and de-Boc steps described in Example 33, Example 58 was used to prepare the target compound (42 mg, 62%).

LC-MS: m/z=722 [M+H]$^+$.

Example 81 S-(2-((5-((4-(2-fluoro-4-(1-((4-fluorophenyl)carbamoyl)cyclopropane-1-carboxamido)phenoxy)-6-methoxyquinolin-7-yl)oxy)pentyl)amino)-2-oxo-ethyl)-(S)-2-amino-3-methylthiobutyrate hydrochloride

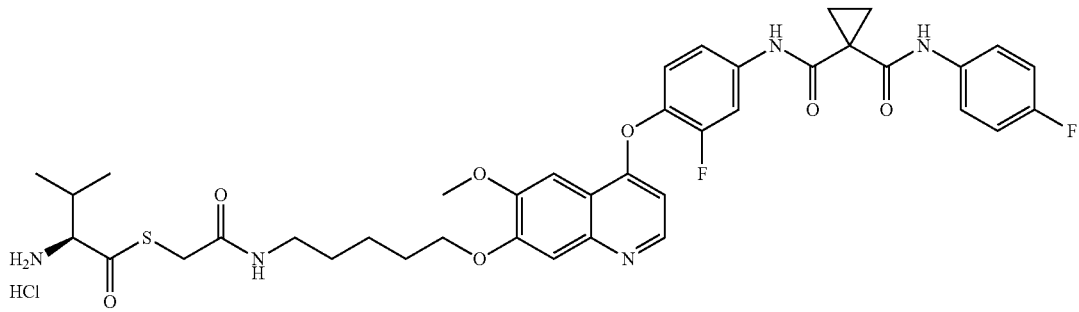 [SMILES: Cl ; COc1cc2c(Oc3ccc(NC(=O)C4(C(=O)Nc5ccc(F)cc5)CC4)cc3F)ccnc2cc1OCCCCCNC(=O)CSC(=O)[C@@H](N)C(C)C]

With reference to the amino acid condensation and de-Boc steps described in Example 33, Example 58 was used to prepare the target compound (58 mg, 58%).

LC-MS: m/z=764 [M+H]$^+$.

Example 82 S-(2-((5-((4-(2-fluoro-4-(1-((4-fluoro-phenyl)carbamoyl)cyclopropane-1-carboxamido)phenoxy)-6-methoxyquinolin-7-yl)oxy)pentyl)amino)-2-oxo-ethyl)-(R)-2-amino-3-(1-methyl-1H-indol-3-yl)thiopropionate hydrochloride

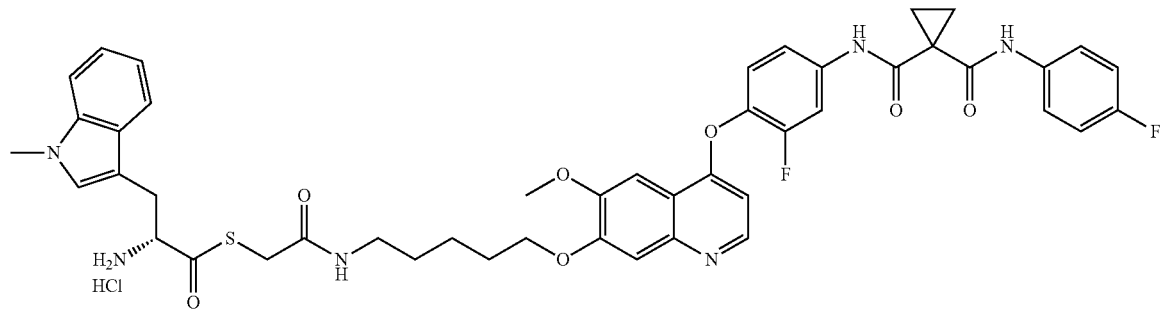 [SMILES: COc1cc2c(Oc3ccc(NC(=O)C4(C(=O)Nc5ccc(F)cc5)CC4)cc3F)ccnc2cc1OCCCCCNC(=O)CSC(=O)[C@H](N)Cc1cn(C)c2ccccc12 ; Cl]

With reference to the amino acid condensation and de-Boc steps described in Example 33, Example 58 was used to prepare the target compound (80 mg, 69%).

LC-MS: m/z=901 [M+H]$^+$.

Example 83 S-(2-((5-((6-carbamoyl-4-(3-chloro-4-(3-cyclopropylurea)phenoxy)quinolin-7-yl)oxy)pentyl)amino)-2-oxo-ethyl)-2-aminothioacetate hydrochloride

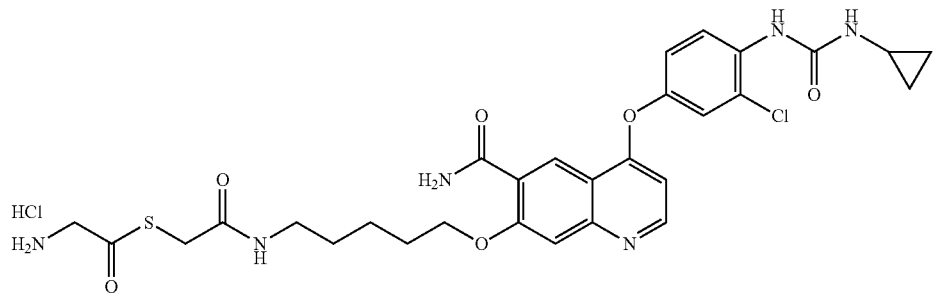 [SMILES: Cl ; NCC(=O)SCC(=O)NCCCCCOc1cc2nccc(Oc3ccc(NC(=O)NC4CC4)c(Cl)c3)c2cc1C(N)=O]

With reference to the amino acid condensation and de-Boc steps described in Example 33, Example 70 was used to prepare the target compound (59 mg, 67%).

LC-MS: m/z=629 [M+H]$^+$.

Example 84 S-(2-((5-(((6-carbamoyl-4-(3-chloro-4-(3-cyclopropylurea)phenoxy)quinolin-7-yl)oxy)pentyl)amino)-2-oxo-ethyl)-(S)-2-amino-3-methylthiobutyrate hydrochloride

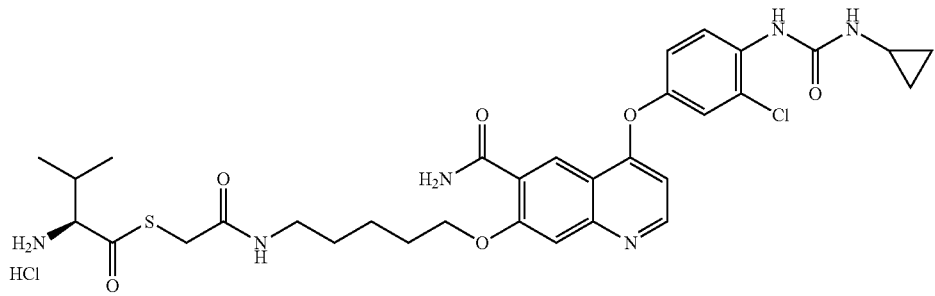 [SMILES: Cl ; CC(C)[C@H](N)C(=O)SCC(=O)NCCCCCOc1cc2nccc(Oc3ccc(NC(=O)NC4CC4)c(Cl)c3)c2cc1C(N)=O]

With reference to the amino acid condensation and de-Boc steps described in Example 33, Example 70 was used to prepare the target compound (49 mg, 36%).
LC-MS: m/z=671 [M+H]$^+$.

Example 85 S-(2-((5-(((6-carbamoyl-4-(3-chloro-4-(3-cyclopropylurea)phenoxy)quinolin-7-yl)oxy)pentyl)amino)-2-oxo-ethyl)-(R)-2-amino-3-(1-methyl-1H-indol-3-yl)thiopropionate hydrochloride

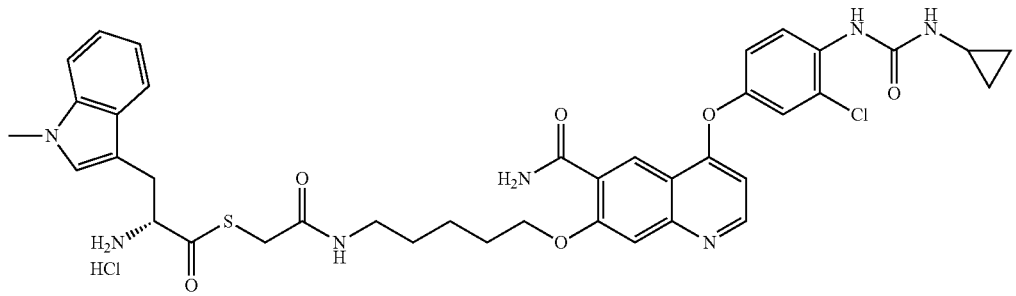 [SMILES: Cn1cc(C[C@@H](N)C(=O)SCC(=O)NCCCCCOc2cc3nccc(Oc4ccc(NC(=O)NC5CC5)c(Cl)c4)c3cc2C(N)=O)c2ccccc21 ; Cl]

With reference to the amino acid condensation and de-Boc steps described in Example 33, Example 70 was used to prepare the target compound (63 mg, 51%).
LC-MS: m/z=772 [M+H]$^+$.

Example 86 S-(7-((6-carbamoyl-4-(3-chloro-4-(3-cyclopropylurea)phenoxy)quinolin-7-yl)oxy)hexyl) thioacetate

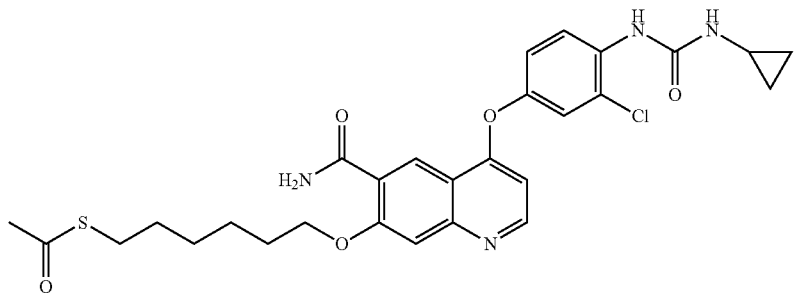 [SMILES: CC(=O)SCCCCCCOc1cc2nccc(Oc3ccc(NC(=O)NC4CC4)c(Cl)c3)c2cc1C(N)=O]

Referring to the steps described in Example 69, S-(2-((5-bromopentyl)amino)-2-oxo-ethyl)thioacetate was replaced with S-(7-bromohexyl)-acetyl thioester to prepare the target compound (52 mg, 49%).

¹H NMR (400 MHz, CDCl₃) δ9.31 (s, 1H), 8.70 (d, J=4.0 Hz, 1H), 8.45 (d, J=8.0 Hz, 1H), 7.95 (s, 1H), 7.80 (s, 1H), 7.65 (s, 1H), 7.25 (d, J=4.0 Hz, 1H), 7.13 (dd, J=8.0, 4.0 Hz, 1H), 6.53 (d, J=8.0 Hz, 1H), 6.25 (s, 1H), 5.47 (brs, 1H), 4.34 (t, J=8.0 Hz, 2H), 2.94 (t, J=4.0 Hz, 2H), 2.74-2.67 (m, 1H), 2.37 (s, 3H), 2.03-1.95 (m, 2H), 1.72-1.48 (m, 6H), 0.97-0.92 (m, 2H), 0.83-0.76 (m, 2H).

LC-MS: m/z=571 [M+H]⁺.

Example 87 4-(3-Chloro-4-(3-cyclopropylurea)phenoxy)-7-((7-mercaptohexyl)oxy)quinoline-6-carbamoyl

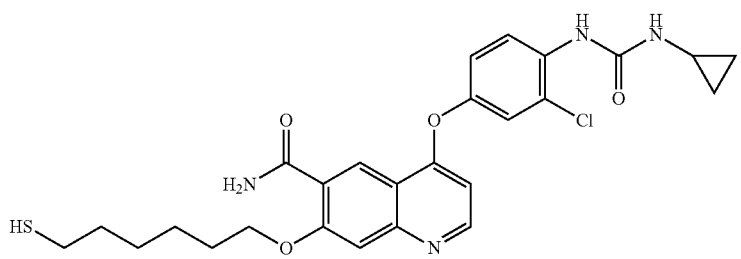 [SMILES: NC(=O)c1cc2c(Oc3ccc(NC(=O)NC4CC4)c(Cl)c3)ccnc2cc1OCCCCCCS]

With reference to the hydrolysis step described in Example 45, the target compound (45 mg, 40%) was prepared from Example 86.

LC-MS: m/z=529 [M+H]⁺.

Example 88 S-(2-((5-((4-(2-fluoro-4-(1-((4-fluorophenyl)carbamoyl)cyclopropane-1-carboxamido)phenoxy)-6-methoxyquinolin-7-yl)oxo)phenyl)amino)-2-oxo-ethyl)2-methylthiopropionate

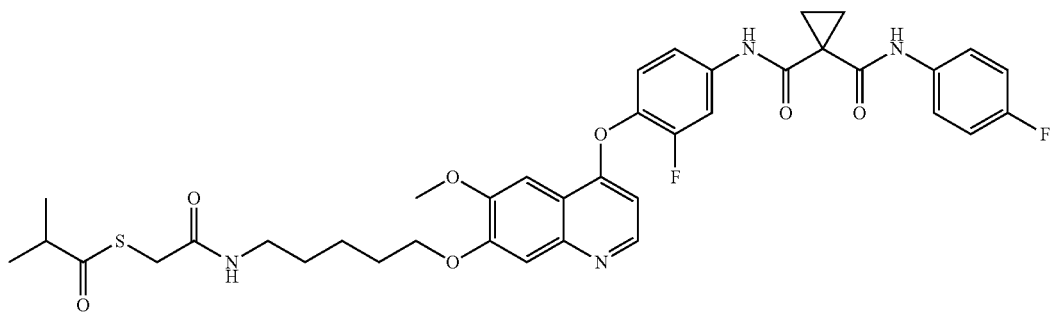 [SMILES: COc1cc2c(Oc3ccc(NC(=O)C4(C(=O)Nc5ccc(F)cc5)CC4)cc3F)ccnc2cc1OCCCCCNC(=O)CSC(=O)C(C)C]

With reference to the amino acid condensation and de-Boc steps described in Example 33, Example 58 was used to prepare the target compound (80 mg, 69%).

¹H NMR (400 MHz, CDCl₃) δ 10.05 (brs, 1H), 8.71 (brs, 1H), 7.83 (dd, J=4.0, 8.0 Hz, 1H), 7.60 (s, 1H), 7.58-7.47 (m, 3H), 7.44 (brs, 1H), 7.22 (t, J=8.0 Hz, 1H), 7.08 (t, J=8.0 Hz, 2H), 6.53-6.40 (m, 2H), 4.14-3.95 (m, 5H), 3.58 (s, 2H), 3.53 (s, 1H), 3.29 (q, J=8.0 Hz, 2H), 2.84 (dt, 1H), 2.00-1.90 (m, 2H), 1.87-1.80 (m, 2H), 1.77-1.68 (m, 2H), 1.66-1.57 (m, 2H), 1.57-1.45 (m, 2H), 1.26 (s, 3H), 1.25 (s, 3H).

LC-MS: m/z=735 [M+H]⁺.

Example 89 S-(2-((5-((4-(2-fluoro-4-(1-((4-fluoro-phenyl)carbamoyl)cyclopropane-1-carboxamido)phenoxy)-6-methoxyquinolin-7-yl)oxo)phenyl)amino)-2-oxo-ethyl)2,2-dimethylthiopropionate

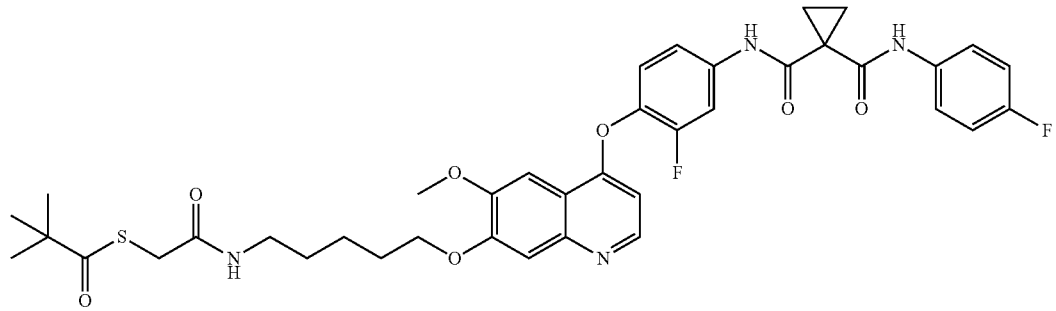 [SMILES: COc1cc2c(Oc3ccc(NC(=O)C4(C(=O)Nc5ccc(F)cc5)CC4)cc3F)ccnc2cc1OCCCCCNC(=O)CSC(=O)C(C)(C)C]

Under ice bath, to N-(3-fluoro-4-((7-((5-(2-mercaptoacetylamino)pentyl)oxy)-6-methoxyquinolin-4-yl)oxy)phenyl)-N-(4-fluorophenyl)cyclopropane-1,1-diformamide (300 mg, 0.45 mmol, prepared in Example 58) and triethylamine (136 mg, 1.35 mmol) in DCM were added pivaloyl chloride (82 mg, 0.68 mmol). React at room temperature for 2 h, add water, and extract 3 times with DCM. The combined organic phases were washed once with saturated brine, dried over anhydrous sodium sulfate, and concentrated under reduced pressure to afford a crude product which was then passed through a silica gel column chromatographic for purification to give the product (220 mg, 65%).

$^1$H NMR (400 MHz, CDCl$_3$) δ 10.20 (brs, 1H), 8.54 (brs, 1H), 7.85 (dd, J=4.0, 8.0 Hz, 1H), 7.68-7.57 (m, 2H), 7.55-7.35 (m, 3H), 7.27 (t, J=8.0 Hz, 1H), 7.09 (t, J=8.0 Hz, 2H), 6.53 (d, J=8.0 Hz, 1H), 6.44 (brs, 1H), 4.25-4.01 (m, 5H), 3.56 (s, 2H), 3.29 (q, J=8.0 Hz, 2H), 2.02-1.90 (m, 2H), 1.88-1.82 (m, 2H), 1.75-1.45 (m, 6H), 1.31 (s, 9H).

LC-MS: m/z=749 [M+H]$^+$.

Example 90 S-(2-((5-((4-(2-fluoro-4-(1-((4-fluoro-phenyl)carbamoyl)cyclopropane-1-carboxamido)phenoxy)-6-methoxyquinolin-7-yl)oxo)phenyl)amino)-2-oxo-ethyl)thiocaprylate

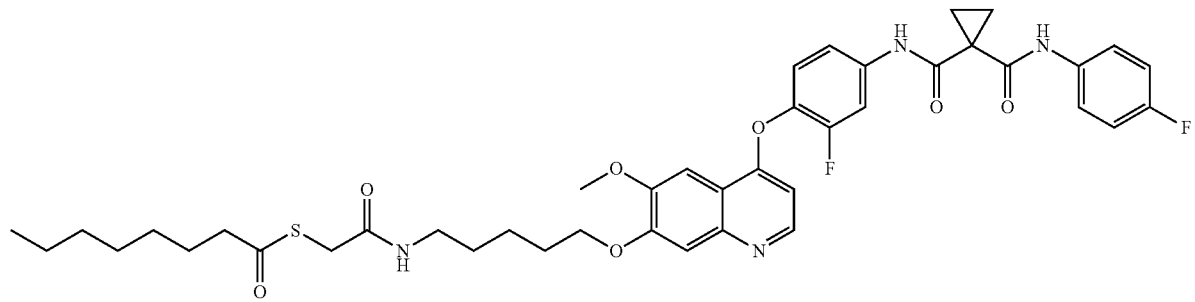 [SMILES: CCCCCCCC(=O)SCC(=O)NCCCCCOc1cc2nccc(Oc3ccc(NC(=O)C4(C(=O)Nc5ccc(F)cc5)CC4)cc3F)c2cc1OC]

With reference to the amino acid condensation step described in Example 33, the target compound (64 mg, 73%) was prepared from Example 58.

$^1$H NMR (400 MHz, CDCl$_3$) δ 10.20 (s, 1H), 8.77 (s, 1H), 8.50 (s, 1H), 7.82 (d, J=8.0 Hz, 1H), 7.61 (s, 1H), 7.55-7.41 (m, 3H), 7.34 (d, J=8.0 Hz, 1H), 7.25 (t, J=8.0 Hz, 1H), 7.07 (t, J=8.0 Hz, 2H), 6.52-6.40 (m, 2H), 4.22 (t, J=8.0 Hz, 2H), 4.07 (s, 3H), 3.57 (s, 2H), 3.31 (q, J=8.0 Hz, 2H), 2.63 (t, J=8.0 Hz, 2H), 2.05-1.90 (m, 2H), 1.86-1.77 (m, 2H), 1.75-1.55 (m, 6H), 1.45-1.20 (m, 10H), 0.89 (t, J=8.0 Hz, 3H).

LC-MS: m/z=791 [M+H]$^+$.

Example 91 S-(2-((5-((4-(2-fluoro-4-(1-((4-fluoro-phenyl)carbamoyl)cyclopropane-1-carboxamido)phenoxy)-6-methoxyquinolin-7-yl)oxy)pentyl)amino)-2-oxo-ethyl)2-aminothioacetate benzenesulfonate

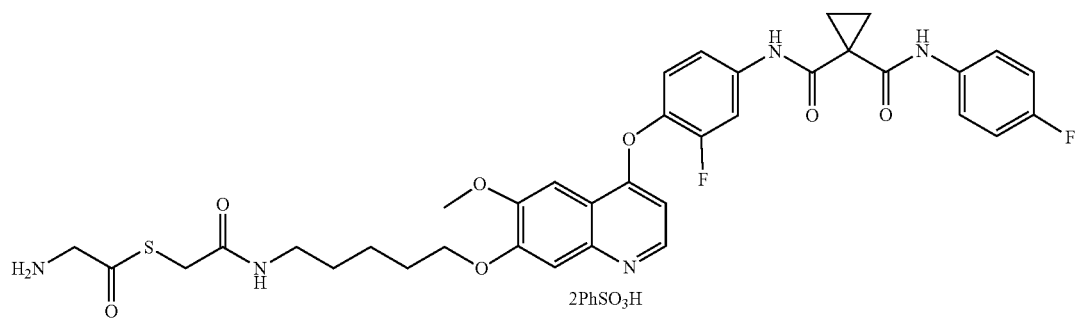 [SMILES: COc1cc2c(Oc3ccc(NC(=O)C4(C(=O)Nc5ccc(F)cc5)CC4)cc3F)ccnc2cc1OCCCCCNC(=O)CSC(=O)CN]

With reference to the amino acid condensation and de-Boc steps described in Example 33 (hydrochloric acid gas was replaced with benzenesulfonic acid), the target compound (42 mg, 62%) was prepared from Example 58.

LC-MS: m/z=722 [M+H]$^+$.

Example 92 S-(2-((5-((4-(2-fluoro-4-(1-((4-fluoro-phenyl)carbamoyl)cyclopropane-1-carboxamido)phenoxy)-6-methoxyquinolin-7-yl)oxy)pentyl)amino)-2-oxo-ethyl)-(S)-2-amino-3-methylthiobutyrate benzenesulfonate

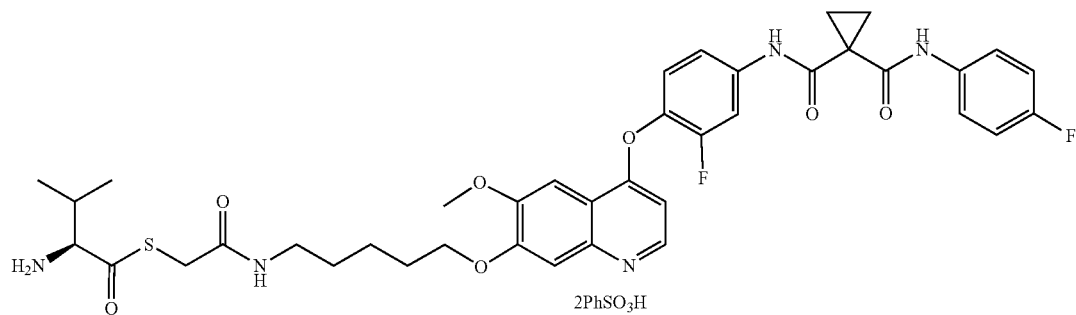 [SMILES: COc1cc2c(Oc3ccc(NC(=O)C4(C(=O)Nc5ccc(F)cc5)CC4)cc3F)ccnc2cc1OCCCCCNC(=O)CSC(=O)[C@@H](N)C(C)C]

With reference to the amino acid condensation and de-Boc steps described in Example 33 (hydrochloric acid gas was replaced with benzenesulfonic acid), the target compound (58 mg, 53%) was prepared from Example 58.

LC-MS: m/z=764 [M+H]$^+$.

Example 93 S-(2-((5-((4-(2-fluoro-4-(1-((4-fluoro-phenyl)carbamoyl)cyclopropane-1-carboxamido)phenoxy)-6-methoxyquinolin-7-yl)oxy)pentyl)amino)-2-oxo-ethyl)-(R)-2-amino-3-(1-methyl-1H-indol-3-yl)thiopropionate benzenesulfonate

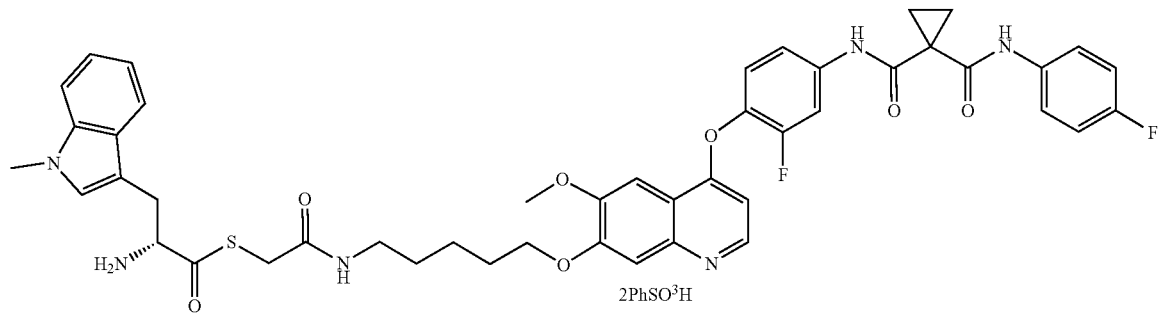 [SMILES: COc1cc2c(Oc3ccc(NC(=O)C4(C(=O)Nc5ccc(F)cc5)CC4)cc3F)ccnc2cc1OCCCCCNC(=O)CSC(=O)[C@H](N)Cc1cn(C)c2ccccc12]

With reference to the amino acid condensation and de-Boc steps described in Example 33 (hydrochloric acid gas was replaced with benzenesulfonic acid), the target compound (80 mg, 69%) was prepared from Example 58.

LC-MS: m/z=865 [M+H]$^+$.

Example 94 S-(2-((5-((4-(2-Fluoro-4-(1-((4-fluoro-phenyl)carbamoyl)cyclopropane-1-carboxamido)phenoxy)-6-methoxyquinolin-7-yl)oxy)pentyl)amino)-2-oxo-ethyl)-(R)-2-acetylamino-3-(1-methyl-1H-indol-3-yl)thiopropionate

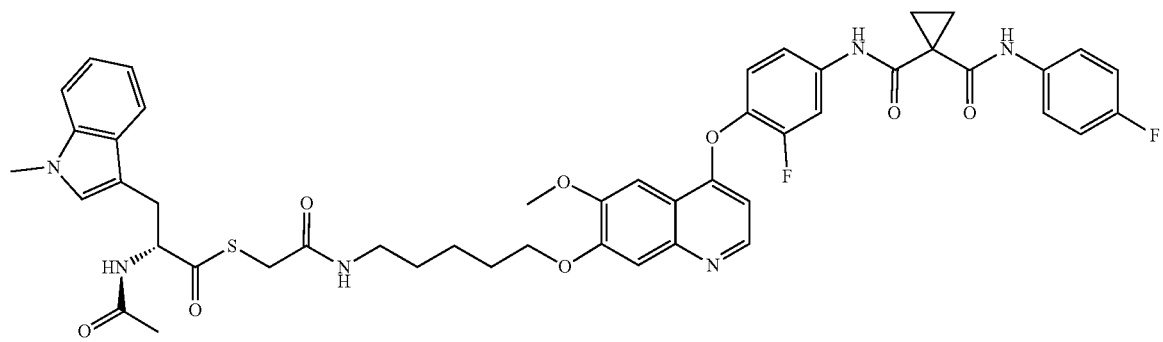

Step A: N-acetyl-1-methyl-D-tryptophan

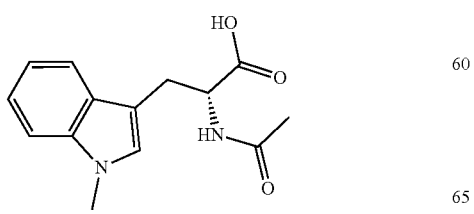

5.0 g (22.9 mmol, 1.0 eq) 1-methyl-D-tryptophan was dissolved in 50 mL THF, and 10 mL of sodium bicarbonate aqueous solution (80.3 mmol, 3.5 eq) was added at room temperature, and then, acetic anhydride 2.48 g (22.9 mmol, 1.0 eq) was added dropwise. After the addition, the reaction was stirred vigorously for 3 hours, and the reaction was monitored by TLC. After completion of the reaction, the reaction solution was concentrated to remove the solvent, and the residue was adjusted to pH 5 with citric acid aqueous solution, and a white solid was precipitated. The solid was collected by filtration, washed with water, and dried to give the target product (5.10 g, yield=86%).

LC-MS: m/z=261[M+H]$^+$.

Step B: S-(2-((5-((4-(2-fluoro-4-(1-((4-fluorophenyl)carbamoyl)cyclopropane-1-carboxamido)phenoxy)-6-methoxyquinolin-7-yl)oxy)pentyl)amino)-2-oxo-ethyl)-(R)-2-acetylamino-3-(1-methyl-1H-indol-3-yl)thiopropionate

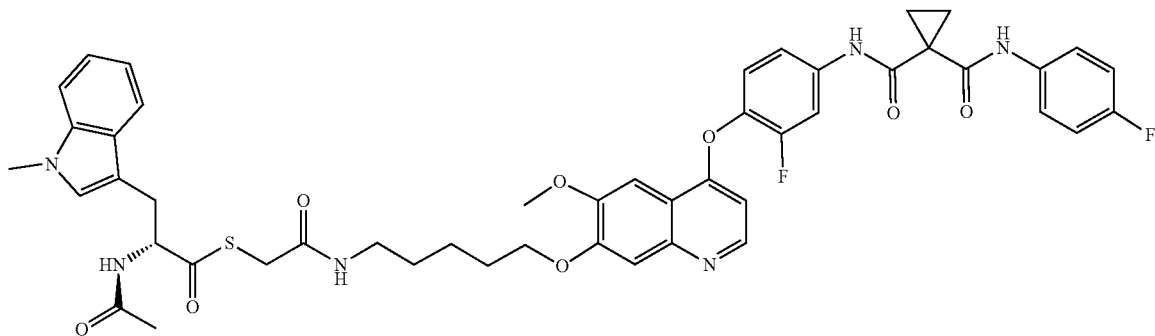

With reference to the amino acid condensation step described in Example 33, the target compound (78 mg, 63%) was prepared from Example 58.

LC-MS: m/z=907 [M+H]$^+$.

$^1$H NMR (400 MHz, CDCl$_3$) δ 8.47 (d, J=4.0 Hz, 1H), 7.88 (dd, J=4.0, 8.0 Hz, 1H), 7.64-7.55 (m, 3H), 7.53-7.45 (m, 2H), 7.41-7.32 (m, 2H), 7.28 (d, J=8.0 Hz, 1H), 7.16-7.05 (m, 3H), 7.03-6.95 (m, 2H), 6.57 (d, J=4.0 Hz, 1H), 4.20 (t, J=8.0 Hz, 2H), 4.02 (s, 3H), 3.73 (s, 3H), 3.37-3.33 (m, 7H), 1.95 (s, 3H), 1.69 (s, 4H), 1.67-1.56 (m, 6H).

Example 95 S-(2-((5-((4-(2-fluoro-4-(1-((4-fluorophenyl)carbamoyl)cyclopropane-1-carboxamido)phenoxy)-6-methoxyquinolin-7-yl)oxy)pentyl)amino)-2-oxo-ethyl)-2-acetylaminothioacetate

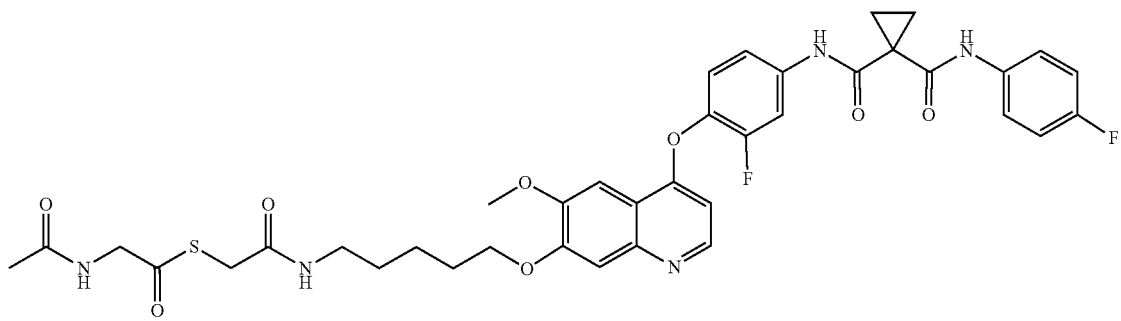 [SMILES: COc1cc2c(Oc3ccc(NC(=O)C4(C(=O)Nc5ccc(F)cc5)CC4)cc3F)ccnc2cc1OCCCCCNC(=O)CSC(=O)CNC(C)=O]

Referring to the steps described in Example 92, N-acetyl-1-methyl-D-tryptophan was replaced with acetylglycine, and the target compound (105 mg, 78%) was prepared from Example 58.

LC-MS: m/z=764 [M+H]$^+$.

Example 96 N-(3-fluoro-4-(((6-methoxy-7-((5-(2-(methyldisulfanyl)acetylamino)pentyl)oxy)quinolin-4-yl)oxy)phenyl)-N-(4-fluorophenyl)cyclopropyl-1,1-diformamide

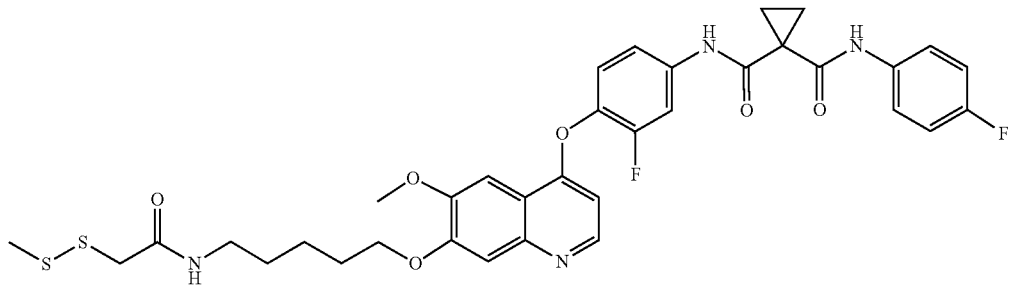 [SMILES: COc1cc2c(Oc3ccc(NC(=O)C4(C(=O)Nc5ccc(F)cc5)CC4)cc3F)ccnc2cc1OCCCCCNC(=O)CSSC]

300 mg (0.45 mmol, 1.0 eq) N-(3-fluoro-4-((7-((5-(2-mercaptoacetylamino)pentyl)oxy)-6-methoxyquinolin-4-yl)oxy)phenyl)-N-(4-fluorophenyl)cyclopropane-1,1-diformamide and 68 mg (0.54 mmol, 1.2 eq) methyl methylthiosulfonate were dissolved in 5 mL ethanol. The reaction was carried out at room temperature for 3 hours and monitored by TLC. After completion, the reaction solution was concentrated to remove the solvent, and the residue was purified by column to afford the product (180 mg, yield=56%).

LC-MS: m/z=711 [M+H]$^+$.

$^1$H NMR (400 MHz, CDCl$_3$) δ 10.09 (s, 1H), 8.77 (s, 1H), 8.47 (d, J=4.0 Hz, 1H), 7.80 (dd, J=4.0, 8.0 Hz, 1H), 7.61 (s, 1H), 7.55-7.47 (m, 2H), 7.41 (s, 1H), 7.33 (s, 1H), 7.25 (t, J=8.0 Hz, 1H), 7.09 (t, J=8.0 Hz, 2H), 6.58 (s, 1H), 6.42 (d, J=8.0 Hz, 1H), 4.22 (t, J=8.0 Hz, 2H), 4.07 (s, 3H), 3.46 (s, 2H), 3.40 (q, J=4.0 Hz, 2H), 2.49 (s, 3H), 2.05-1.95 (m, 2H), 1.86-1.79 (m, 2H), 1.75-1.55 (m, 6H).

Example 97 N-(3-fluoro-4-(((6-methoxy-7-((5-(2-(pyridine-2-disulfanyl)acetamido)pentyl)oxo)quinoline-4-yl)oxo)phenyl)-N-(4-fluorophenyl)cyclopropane-1,1-diformamide

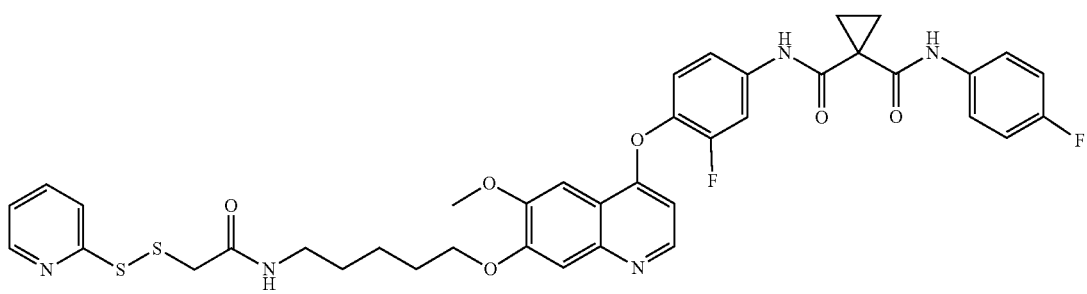 [SMILES: COc1cc2c(Oc3ccc(NC(=O)C4(C(=O)Nc5ccc(F)cc5)CC4)cc3F)ccnc2cc1OCCCCCNC(=O)CSSc1ccccn1]

Under nitrogen protection, acetic acid (23 mg, 0.38 mmol) was added to a solution of 2,2'-dithiodipyridine (165 mg, 0.76 mmol) in ethanol (3 mL), and N-(4-((7-((5-aminopentyl)oxy)-6-methoxyquinolin-4-yl)oxy)-3-fluorophenyl)-N-(4-fluorophenyl)cyclopropane-1,1-diformamide (250 mg, 0.38 mmol; synthesized by referring to the steps described in Example 58) in ethanol (1 mL) was added dropwise at room temperature. React at room temperature for 5 h. Then, add saturated sodium bicarbonate aqueous solution, extract 3 times with DCM, combine the organic phases which was then washed with saturated brine once, dry with anhydrous sodium sulfate, concentrate by distillation under reduced pressure, and purify by silica gel column chromatography to afford the product (32 mg, 11%).

LC-MS: m/z=774 [M+H]⁺.

Example 98 N,N'-(((((((2,2'-disulfanyldiylbis(acetyl))bis(ureadiyl))bis(pentyl-5,1-diyl)) Bis(oxy))bis(6-methoxyquinoline-7,4-diyl))bis(oxy))bis(3-fluoro-4,1-phenyl))bis(N-(4-fluorophenyl)cyclopropane-1,1-diformamide)

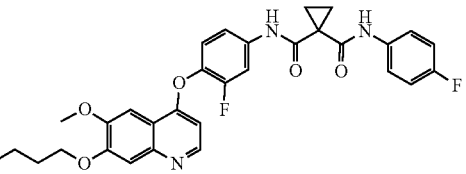
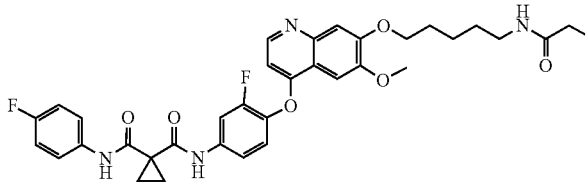

Step A: 2,2'-thiodiacetyl chloride

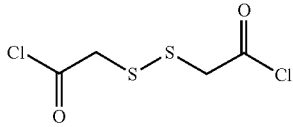

77 mg (0.42 mmol, 1.0 eq) 2,2-dithiodiacetic acid was dissolved in 10 mL dichloromethane, and 150 mg (1.27 mmol, 3.0 eq) thionyl chloride was added at room temperature, and then 1 drop of N, N-dimethylformamide was added. Stir at room temperature for 30 minutes. TLC monitored the completion of the reaction, and the reaction system was concentrated to dryness which was directly used in the next step reaction (93 mg, yield=100%).

Step B: N,N'-(((((((2,2'-Disulfanyldiylbis(acetyl))bis(ureadiyl))bis(pentyl-5,1-diyl)) bis(oxy))bis(6-methoxyquinoline-7,4-diyl))bis(oxy))bis(3-fluoro-4,1-phenyl))bis(N-(4-fluorophenyl) cyclopropane-1,1-diformamide)

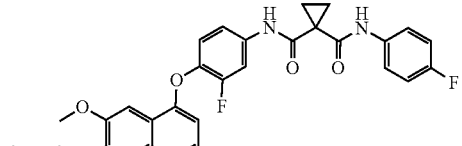
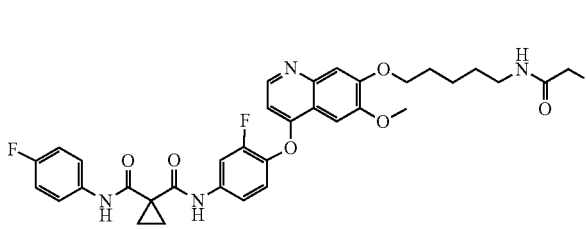

At 0° C., to N-(4-((7-((5-aminopentyl)oxy)-6-methoxyquinolin-4-yl)oxy)-3-fluorophenyl)-N-(4-fluorophenyl)cyclopropane-1,1-diformamide (100 mg, 0.17 mmol) (synthesized according to step B described in Example 57) in DCM was sequentially added Et$_3$N (70 uL, 0.51 mmol), 2,2'-thiodiacetyl chloride (77 mg, 1.0 mmol). The reaction solution was warmed to room temperature and reacted for 30 minutes, and then water was added to quench the reaction. The aqueous phase was extracted once with DCM, and the combined organic phase was washed with saturated brine once, dried over anhydrous sodium sulfate, concentrated by distillation under reduced pressure, and purified by silica gel column chromatography to afford the product (32 mg, 18%).

LC-MS: m/z=1327[M+H]$^+$.

Effect Evaluation

1. Inhibitory Activity of the Compounds on HDAC6

HDAC6 fluorescence analysis method was used to detect the inhibitory effect of the compounds on the activity of HDAC6. The specific operation is as follows:

Prepare a 10 mM stock solution of a compound with DMSO. Take 10 μl of stock solution and dilute with 90 μl DMSO to become a 1 mM working solution. The compound was three-fold serially diluted to total of 11 concentrations including a DMSO negative control. Add 3 μl of each concentration to 197 μl reaction buffer (20 mM Hepes pH 8.0, 137 mM NaCl, 2.7 mM KCl, 1 mM MgCl2, 0.05% BSA, 0.5 mM TCEP), mix well and add 10 μl to a 384-well plate. In the final reaction system, the concentrations of the compound were 10 μM to 0.51 nM. Duplicate, and add 10 μl 3XHDAC solution (BPS, Cat. 50006, 0.3 nM) to each well, followed by incubating at 23° C. for 20 minutes. Then, add 3× substrate solution (Anaspec, Cat. 61855, 15 μM), centrifuge to mix, and incubate at 23° C. for 90 minutes. Add 30 μl trypsin/SAHA mixture (20 mM Hepes pH 8.0, 100 mM NaCl, 10 mM SAHA, 0.01 mg/ml trypsin), incubate at 23° C. for 60 minutes to terminate the reaction. Finally, read fluorescence data by Envision (390 nm excitation, 460 nm emission). A high value at 430 nm indicates high kinase activity, while low value at 430 nm indicates that the kinase activity was inhibited. Finally, analyze the data by XLfit5 software and calculate the IC$_{50}$ value of the compound. Vorinostat (SAHA) was a positive reference compound. The results are shown in Table 1.1.

TABLE 1

Inhibitory effects of the compounds on kinase HDAC6

| Examples | IC$_{50}$(nM) |
|---|---|
| 10 | 65.97 |
| 11 | 39.35 |
| 12 | 67.84 |
| 13 | 18 |
| 25 | 34.82 |
| 28 | 96.46 |
| 29 | 42.43 |
| Cabozantinib | >10000 |
| 57 | 48.34 |
| 58 | 15.36 |
| 61 | 29.92 |
| 62 | 16.31 |
| 63 | 97.80 |
| 64 | 28.77 |
| 69 | 8.94 |
| 71 | 27 |

2. Inhibitory Activities of the Compounds on VEGFR2

Detect compounds on VEGFR2 (KDR) by mobility shift assay. The initial test concentration of a compound was 1000 nM, 3 times dilution, 10 concentrations, and detection in duplicate. Nintedanib (Selleckchem, Cat. S1010) was used as the positive control compound. The operation method was briefly described as follows: kinase VEGFR2 (Carna, Cat. 08-191) at the final concentration of 0.5 nM and the test compound were mixed in the Optiplate-384F well plate and incubated for 10 minutes at room temperature. Then, ATP at a final concentration of 95 μM and 3 μM Kinase substrate 22 (Gill Biochemical (glbiochem), Cat. 112393) were added. After mixing, react at room temperature for 30 minutes. Add stop detection solution to terminate the reaction and read the conversion rate with Caliper EZ ReaderII.

Data Analysis:

$$\% \text{ Inhibition} = \frac{\text{Conversion \%\_max} - \text{Conversion \%\_sample}}{\text{Conversion \%\_max} - \text{Conversion \%\_min}} \times 100$$

Wherein, Conversion %_sample refers to the conversion rate reading of the sample; Conversion %_min: the average value of the negative control wells, which represents the conversion rate readings of the wells without enzyme activity; Conversion %_max: the average value of the positive control wells, represents the conversion rate readings of the wells without compound inhibition.

Fitting the dose-response curve: Take the log of the concentration as the X-axis, and the percentage of inhibition rate as the Y-axis. The dose response curve was fitted by the analysis software GraphPad Prism 5 with log(inhibitor) vs. response—Variable slope to obtain the inhibitory activity (IC$_{50}$) of each compound. The results are shown in Table 2.

TABLE 2

Inhibitory effects of the compounds on kinase VEGFR2

| Examples | IC$_{50}$(nM) |
|---|---|
| 6 | 79 |
| 7 | 57 |
| 25 | 79 |
| 27 | 33 |
| 50 | 6.6 |
| 51 | 7.7 |
| 52 | 3.2 |
| 53 | 4.7 |
| 54 | 54 |
| 55 | 30 |
| 57 | 20 |
| 58 | 25 |
| 61 | 12 |
| 62 | 17 |
| 63 | 36 |
| 64 | 51 |
| 65 | 13 |
| 67 | 30 |
| 69 | 0.96 |
| 71 | 4.6 |
| 73 | 45 |
| 86 | 2.6 |

3. Pharmacokinetic Experiment

The female SD rats were divided into groups, 3 rats in each group, and the example compounds 10, 12, 24, 57, 61, 89, 90, 93, 94, 96 (10 mg/kg) were administered by intragastric administration. Fasting overnight before administration, and the fasting time was from 10 hours before administration to 4 hours after administration. Blood was collected at 0.25, 0.5, 1, 2, 4, 8 and 24 hours after administration.

Small animal anesthesia machine was used for isoflurane anesthesia. After that, 0.3 mL of whole blood was collected from the fundus venous plexus and placed in a heparin anticoagulation tube. The sample was centrifuged at 4° C., 4000 rpm, for 5 minutes, and the plasma was transferred to a centrifuge tube, and stored at −80° C. until analysis. The plasma sample was extracted by protein precipitation method, and the extract was processed and analyzed by LC/MS/MS. The results of the pharmacokinetic experiment are shown in Table 3.

TABLE 3

Pharmacokinetic parameters of rats after intragastric administration of 10 mg/kg compounds of the examples

| | Examples | | | | | | | | | |
|---|---|---|---|---|---|---|---|---|---|---|
| | 10 | 12 | 24 | 57 | 61 | 89 | 90 | 93 | 94 | 96 |
| $T_{1/2}$ (hr) | 1.24 | 3.00 | 6.69 | 6.42 | 1.84 | 5.94 | 4.25 | 5.49 | 6.14 | 6.92 |
| $T_{max}$ (hr) | 0.833 | 1.00 | 1.33 | 0.33 | 0.50 | 0.833 | 0.333 | 0.667 | 0.50 | 0.417 |
| $C_{max}$ (ng/mL) | 377 | 946 | 430 | 1590 | 121 | 1005 | 852 | 429 | 289 | 724 |
| $AUC_{0\text{-}inf}$ (hr*ng/mL) | 468 | 1873 | 1066 | 2792 | 175 | 1647 | 689 | 790 | 499 | 1043 |

In order to illustrate the present application, although the preferred embodiments have been disclosed, those skilled in the art would understand that various modifications, additions, and replacements may be made without departing from the concept and scope of the present disclosure as defined by the claims.

The invention claimed is:

1. A compound represented by formula (I) or (II), or a pharmaceutically acceptable salt, or stereoisomer thereof,

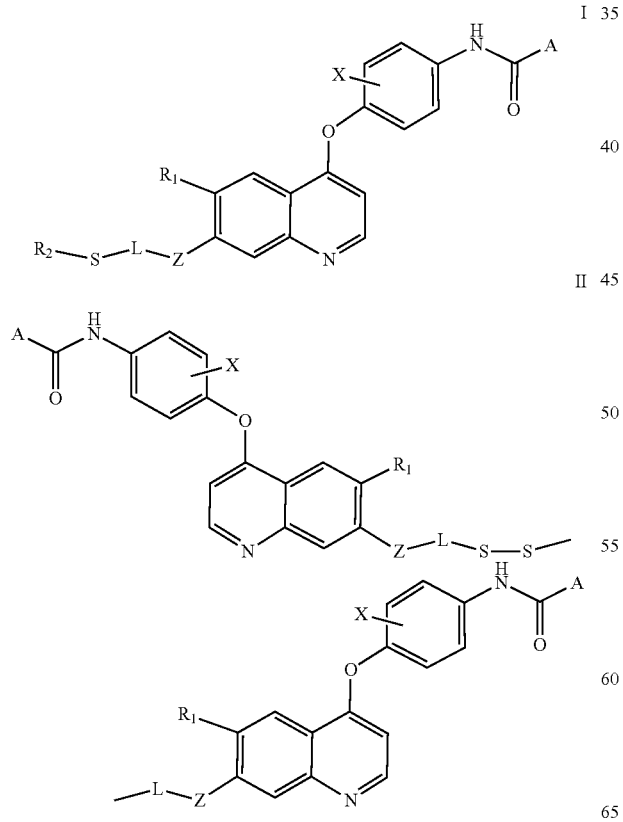

wherein,

A represents

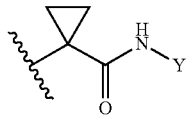

or —NR$_3$R$_4$;

X represents hydrogen, halogen or substituted or unsubstituted C$_{1-8}$ alkyl;

Y represents a substituted or unsubstituted C$_{3-8}$ cycloalkyl, C$_{3-8}$ heterocyclyl containing one or more heteroatoms selected from the group consisting of O, S and N, C$_{6-20}$ aryl or C$_{2-20}$ heteroaryl containing one or more heteroatoms selected from the group consisting of O, S and N;

Z represents —O— or —S—;

L represents linear —(CH$_2$)$_n$—, n represents an integer from 3 to 10, wherein optionally one or more —CH$_2$— are replaced with one or more of —NR$_5$—, —(CO)—, —(CS)—, and —CR$_5$R$_6$—, and/or optionally one or more of —CH$_2$CH$_2$— are replaced with —CH=CH—;

R$_1$ represents C$_{1-6}$ alkoxy, C$_{1-6}$ alkylsulfanyl or —(CO)NR$_7$R$_8$;

R$_2$ represents substituted or unsubstituted hydrogen, C$_{1-8}$ alkyl, C$_{1-8}$ alkoxy, C$_{1-8}$ alkylsulfanyl, C$_{1-8}$ haloalkyl, C$_{3-8}$ cycloalkyl, C$_{3-8}$ heterocyclyl containing one or more heteroatoms selected from the group consisting of N, O and S, C$_{6-20}$ aryl, C$_{2-20}$ heteroaryl containing one or more heteroatoms selected from the group consisting of N, O and S, —(CO)R$_9$, —(CS)R$_9$, or R$_2$ is connected with one of —CH$_2$— in L group so that R$_2$, S and —CH$_2$— together form C$_{3-8}$ heterocyclic group optionally containing additional one or more N, O and S, or C$_{2-20}$ heteroaryl optionally containing additional one or more N, O and S;

R$_3$ and R$_4$ independently represent substituted or unsubstituted hydrogen, C$_{1-8}$ alkyl, C$_{1-8}$ alkoxyl, C$_{1-8}$ alkylsulfanyl, C$_{1-8}$ haloalkyl, C$_{3-8}$ cycloalkyl, C$_{3-8}$ heterocyclyl containing one or more heteroatoms selected from the group consisting of O, S and N, C$_{6-20}$ aryl or C$_{2-20}$ heteroaryl containing one or more heteroatoms selected from the group consisting of O, S and N;

R$_5$ and R$_6$ independently represent substituted or unsubstituted hydrogen, C$_{1-8}$ alkyl, C$_{1-8}$ alkoxyl, C$_{1-8}$ alkylsulfanyl, C$_{1-8}$ haloalkyl, hydroxyl, mercapto, carboxyl, amino or cyano;

R$_7$ and R$_8$ independently represent substituted or unsubstituted hydrogen or C$_{1-8}$ alkyl;

R$_9$ represents substituted or unsubstituted C$_{1~8}$ alkyl, C$_{1~8}$ alkoxyl, C$_{1~8}$ alkylsulfanyl, C$_{1~8}$ haloalkyl, C$_{1~6}$ alkylsulfonyl, C$_{1~6}$ alkylamino, C$_{3~8}$ cycloalkyl, C$_{3~8}$ heterocyclyl containing at least one N atom, C$_{6~20}$ aryl, C$_{2~20}$ heteroaryl containing at least one N atom, C$_{1~6}$ alkylene C$_{3~8}$ cycloalkyl, C$_{1~6}$ alkylene C$_{3~8}$ heterocyclyl containing at least one N atom, C$_{1~6}$ alkylene C$_{6~20}$ aryl, C$_{1~6}$ alkylene C$_{2~20}$ heteroaryl containing at least one N atom, hydroxyl, mercapto, nitro, amino, cyano, or R$_9$ is connected with anyone of —CH$_2$— in the L group, so that —(CO) R$_9$ or —(CS)R$_9$ together with S and —CH$_2$— forms C$_{3~8}$ heterocyclyl optionally containing additional one or more N, O and S, or C$_{2~20}$ heteroaryl optionally containing additional one or more N, O and S;

The substituents of the above groups, if any, are selected from halogen, C$_{1~8}$ alkyl, C$_{2~8}$ alkenyl, C$_{2~8}$ alkynyl, C$_{1~8}$ haloalkyl, C$_{1~8}$ alkoxyl, C$_{1~8}$ alkylsulfanyl, C$_{3~8}$ cycloalkyl, C$_{3~8}$ heterocyclyl, C$_{6~20}$ aryl, C$_{2~20}$ heteroaryl, C$_{1~6}$ alkoxycarbonyl, C$_{1~6}$ alkanoyl, C$_{1~6}$ alkylamino, C$_{1~6}$ alkylsufonyl, amino, hydroxyl, mercapto, carboxyl, nitro, carboxamido, or cyano.

2. The compound according to claim 1, wherein the formula (I) or (II) is represented by (I-1), (I-2), (II-1) or (I-2):

wherein, X represents hydrogen, F or Cl; or a pharmaceutically acceptable salt, or stereoisomer thereof.

3. The compound according to claim 1, wherein A represents the following group:

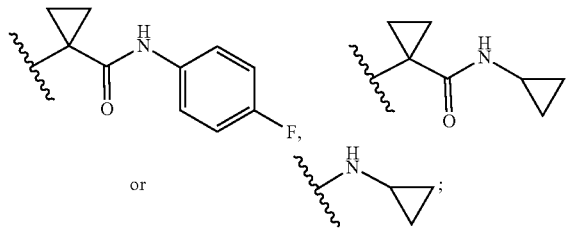

or a pharmaceutically acceptable salt, or stereoisomer thereof.

4. The compound according to claim 1, wherein L represents one of the following groups: —CH$_2$—CO—NH—(CH$_2$)$_p$—*, p represents an integer from 3 to 6, and one or more of —CH$_2$CH$_2$— are optionally replaced with —CH═CH—, and "*" means the end connected to the group "Z"; or linear-(CH$_2$)$_o$—, "o" represents an integer from 5 to 7, and one or more of —CH$_2$CH$_2$— are optionally

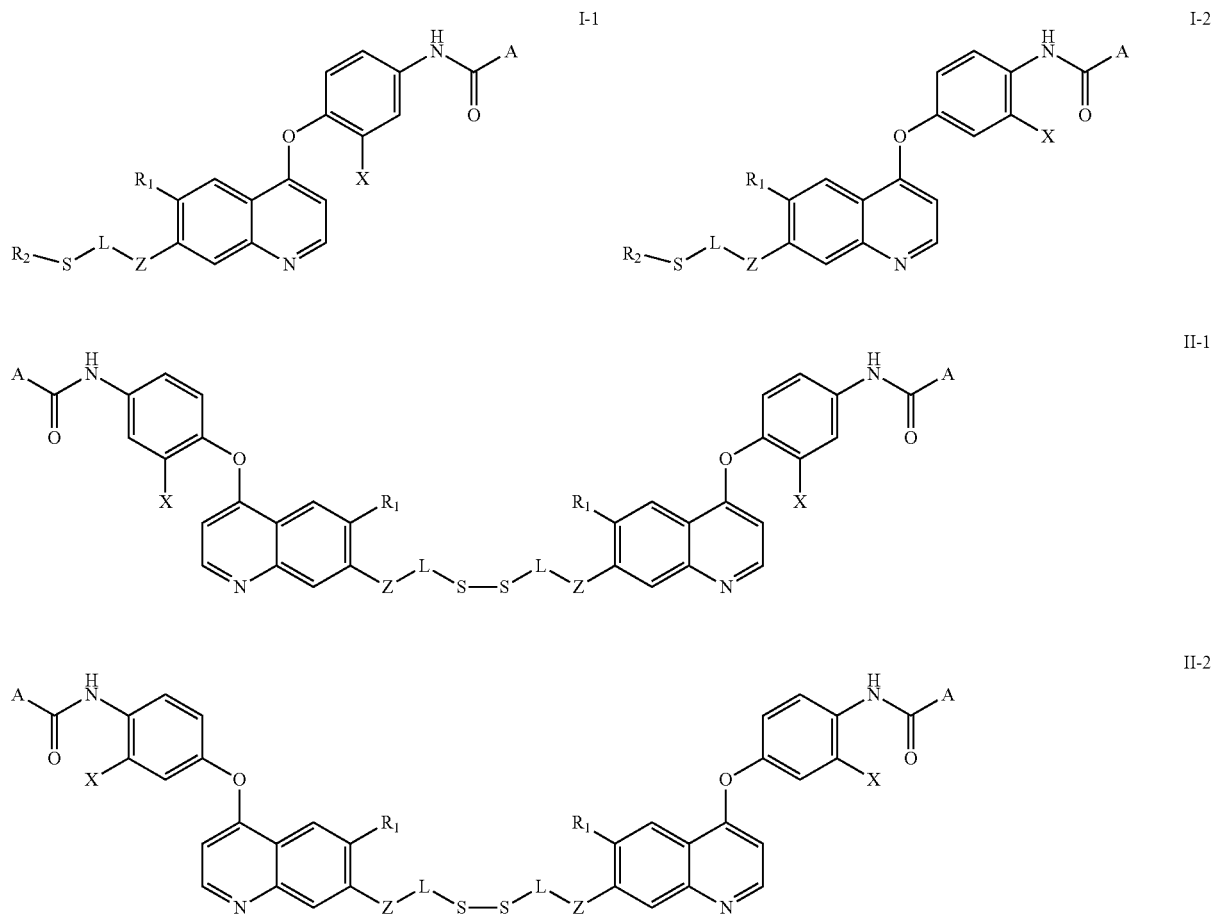

replaced with —CH=CH—; or a pharmaceutically acceptable salt, or stereoisomer thereof.

5. The compound according to claim 1, wherein L represents one of the following groups:

*—CH$_2$CH=CH(CH$_2$)$_q$—, *—(CH$_2$)$_2$CH=CH(CH$_2$)$_q$— or *—(CH$_2$)$_3$CH=CH(CH$_2$)$_q$—, q represents an integer from 1 to 4, where the "*" represents the end connected to the Z group; or a pharmaceutically acceptable salt, or stereoisomer thereof.

6. The compound according to claim 1, wherein R$_1$ is selected from C$_{1\sim4}$ alkoxyl or —(CO)NH$_2$; or a pharmaceutically acceptable salt, or stereoisomer thereof.

7. The compound according to claim 1, wherein R$_2$ is selected from substituted or unsubstituted hydrogen, C$_{1\sim4}$ alkyl, or —(CO)R$_9$;

where R$_9$ is selected from substituted or unsubstituted C$_{1\sim4}$ alkyl, C$_{1\sim4}$ alkoxyl, C$_{1\sim4}$ haloalkyl, C$_{3\sim6}$ cycloalkyl, C$_{3\sim6}$ heterocyclyl containing at least one N atom, C$_{6\sim12}$ aryl, C$_{3\sim12}$ heteroaryl containing at least one N atom, C$_{1\sim4}$ alkylene C$_{3\sim6}$ cycloalkyl, C$_{1\sim4}$ alkylene C$_{3\sim6}$ heterocyclyl containing at least one N atom, C$_{1\sim4}$ alkylene C$_{6\sim12}$ aryl, C$_{1\sim4}$ alkylene C$_{3\sim12}$ heteroaryl containing at least one N atom, hydroxyl, mercapto, nitro, amino or cyano; and the optional substituent is selected from F, Cl, Br, methyl, ethyl, n-propyl, isopropyl, —NH$_2$, hydroxyl, carboxyl, mercapto or cyano; or a pharmaceutically acceptable salt, or stereoisomer thereof.

8. The compound according to claim 1, which is selected from the group consisting of the following compounds:

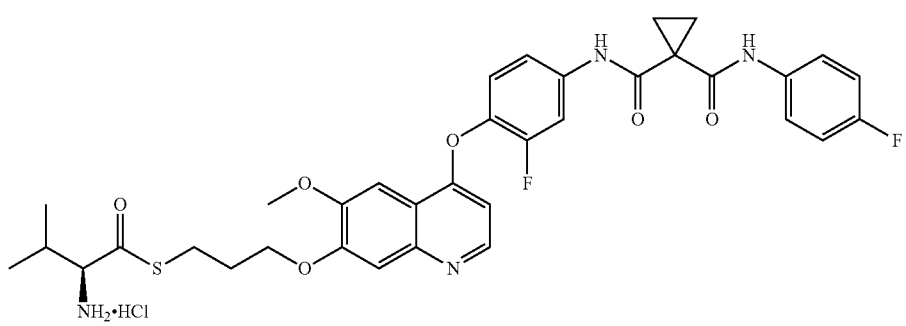

1

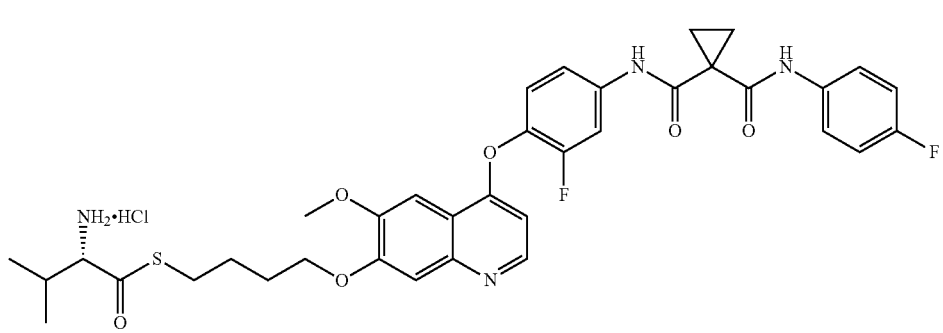

2

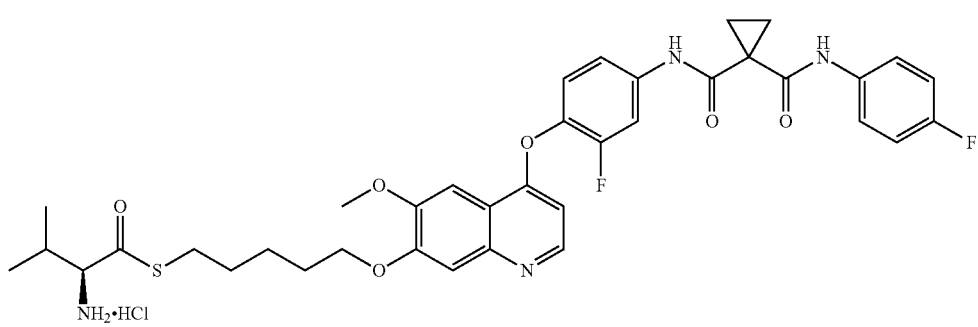

3

4
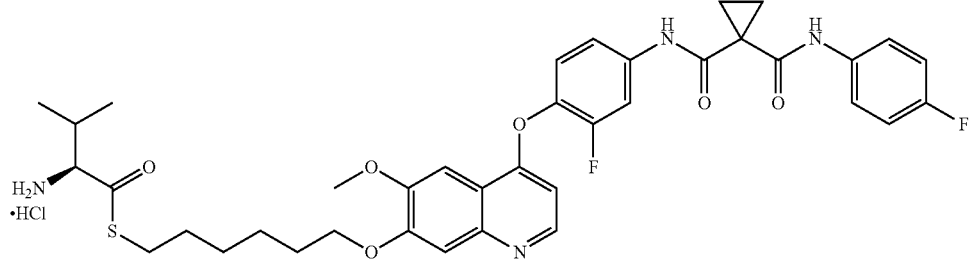
5
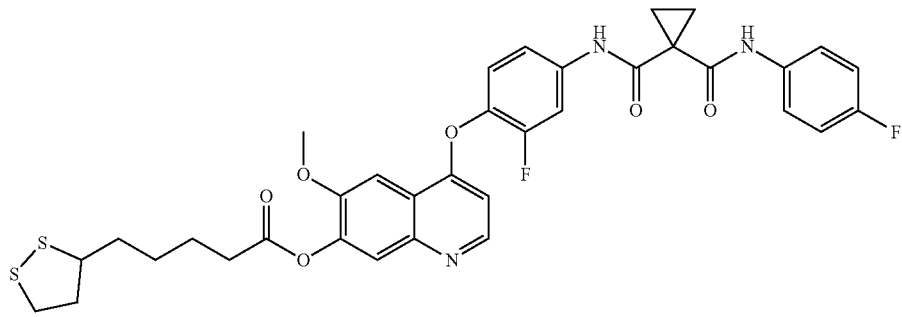
6
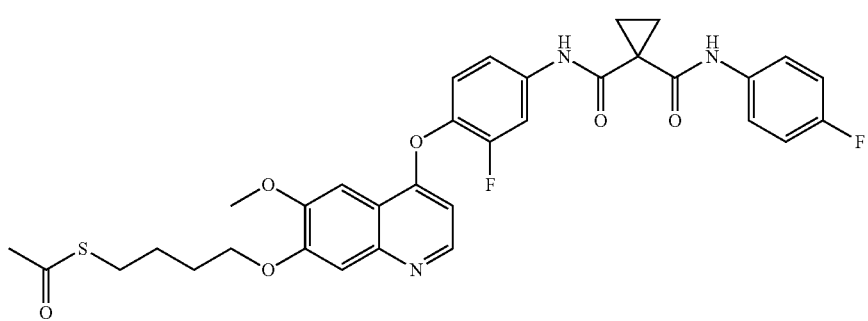
7
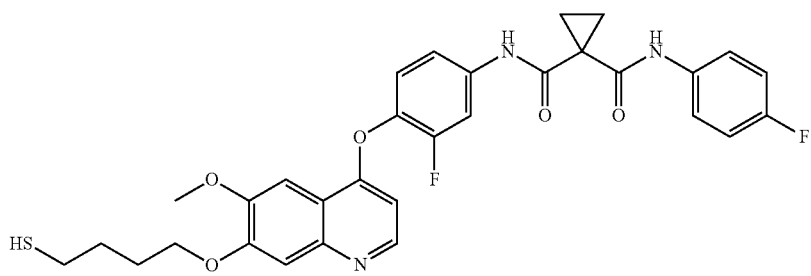
8
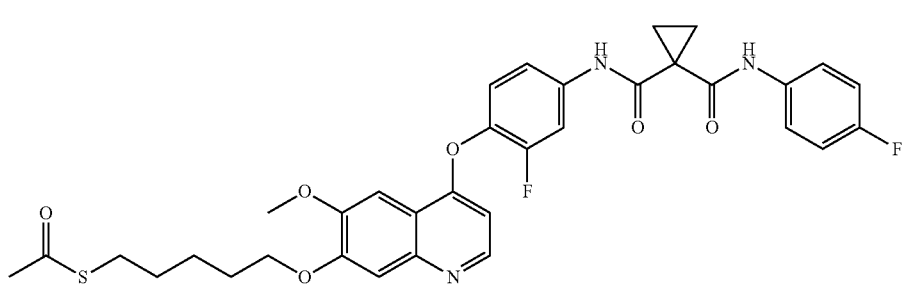

-continued
9
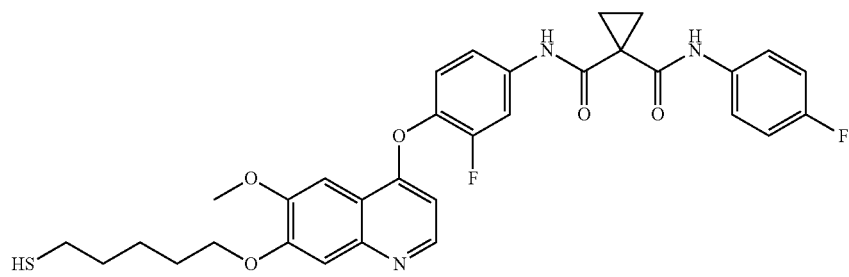
10
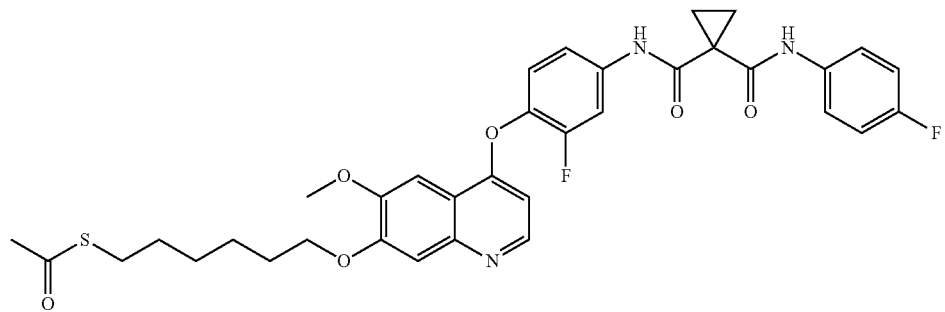
11
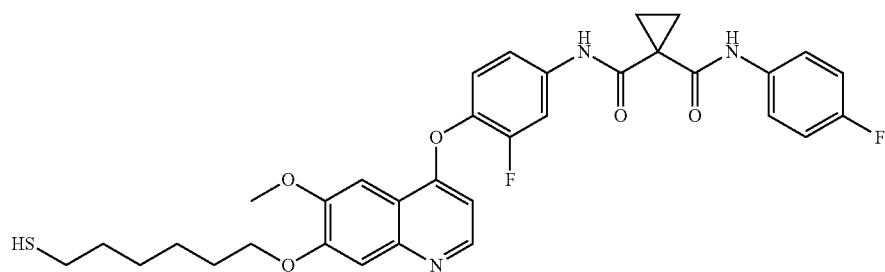
12
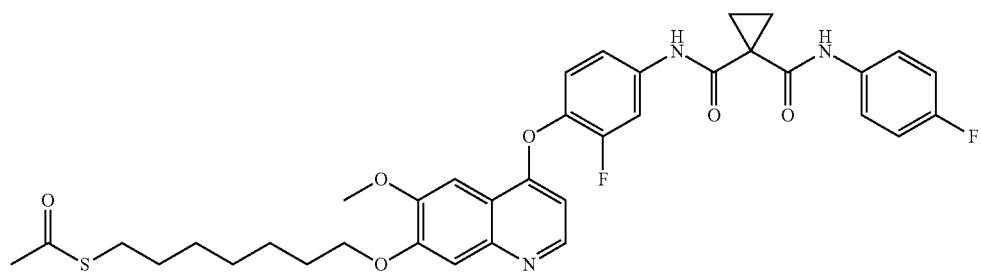
13
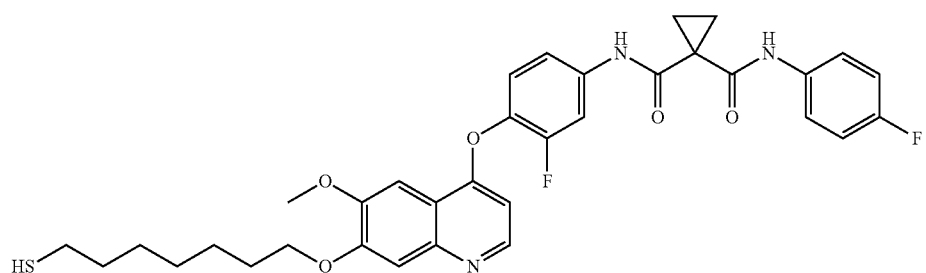

14
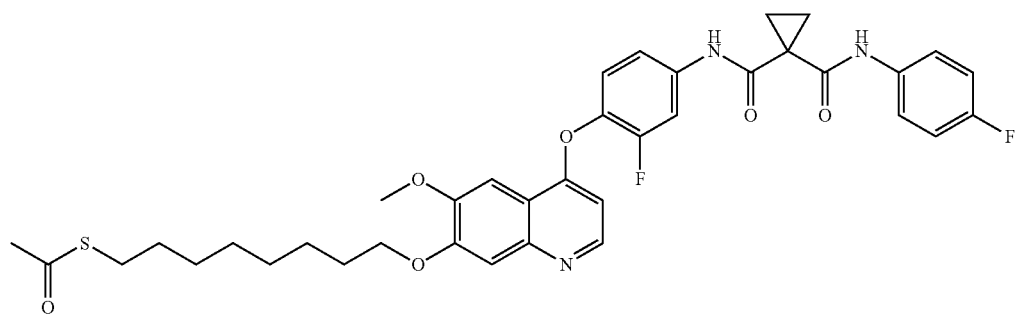
15
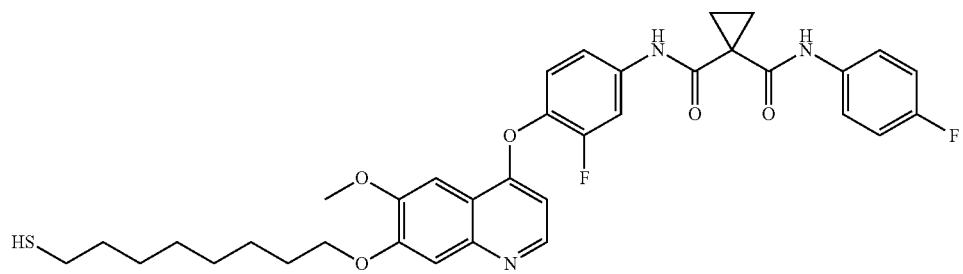
16
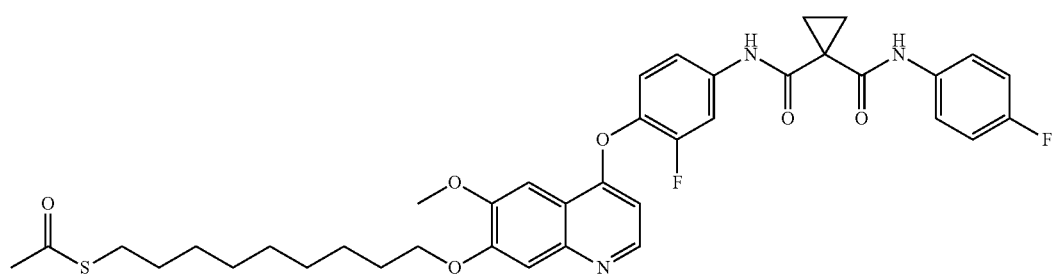
17
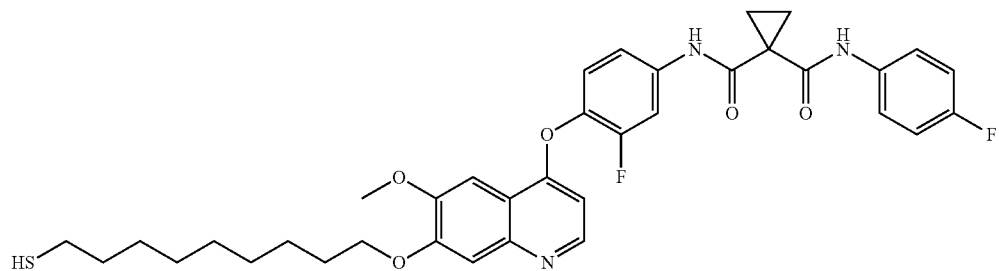
18
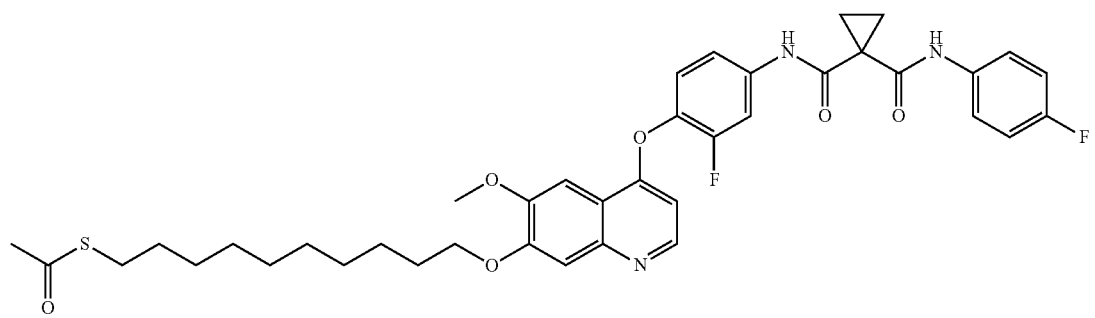

-continued
19
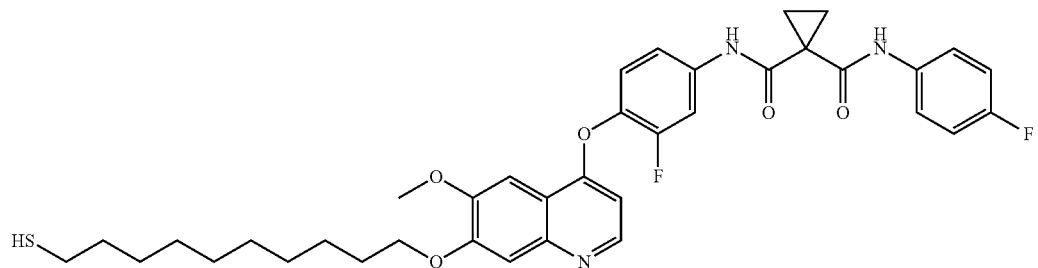
20
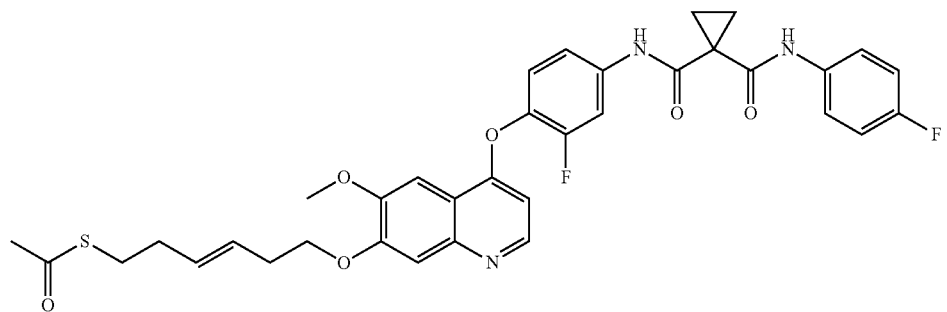
21
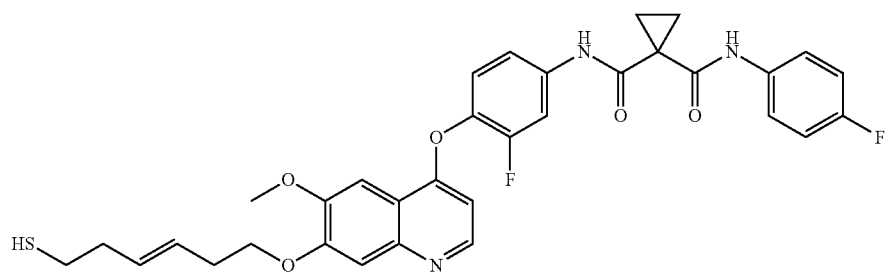
22
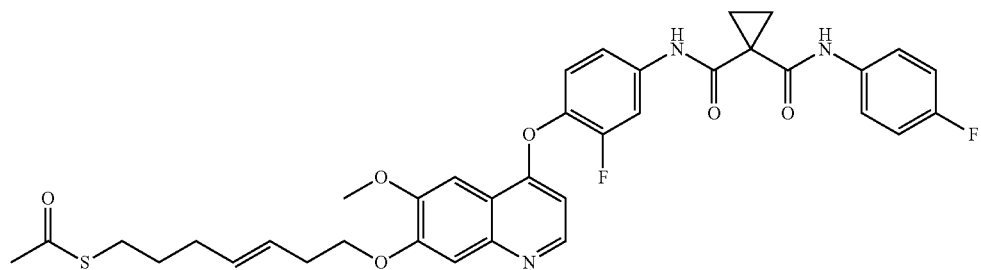
23
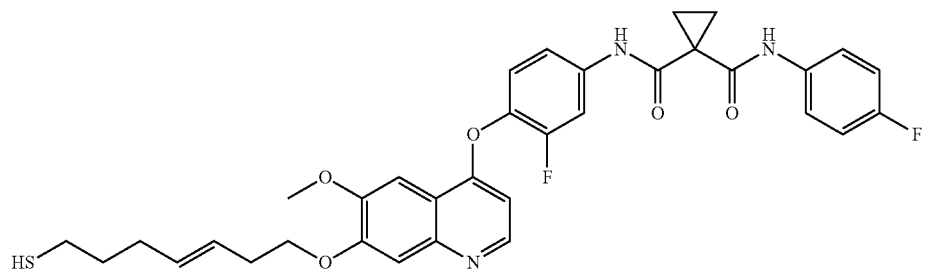

-continued
24
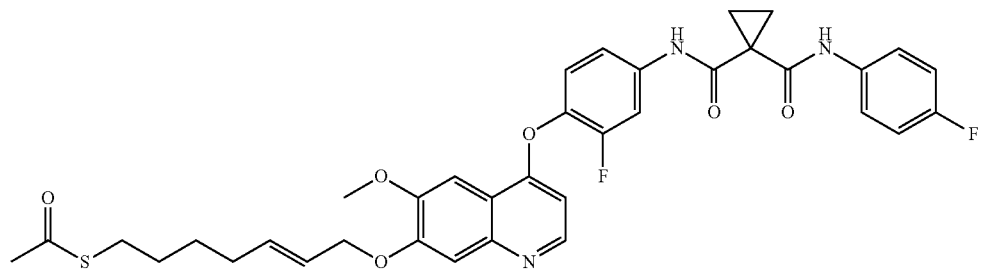
25
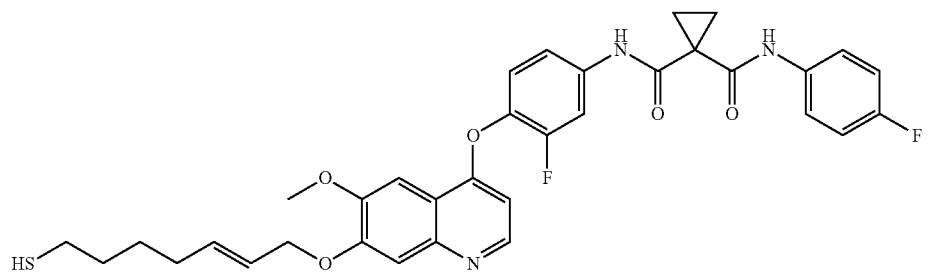
26
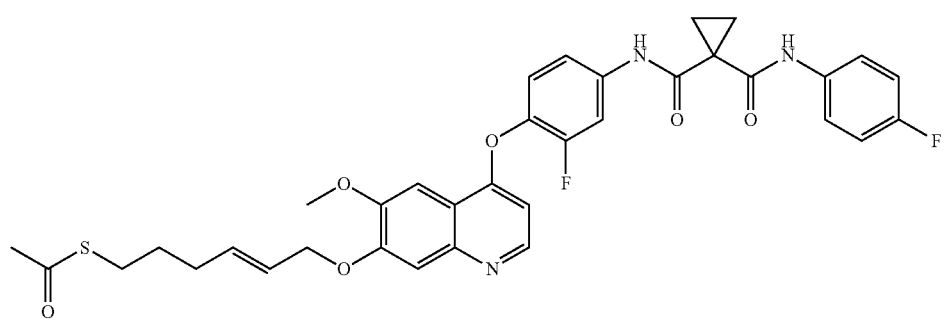
27
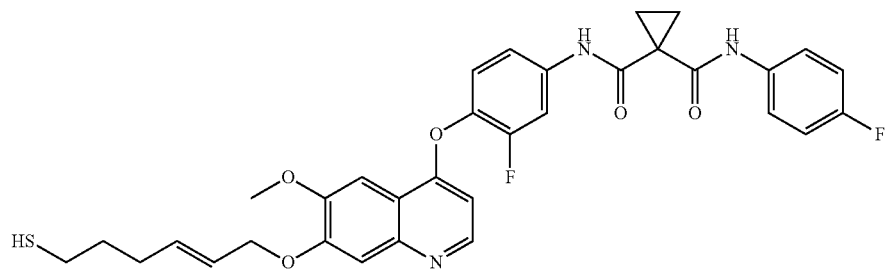
28
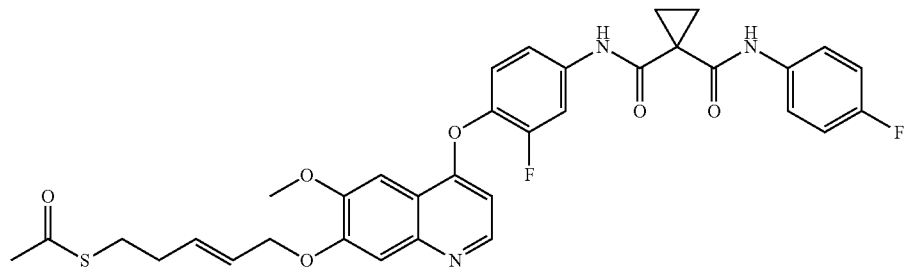

-continued
29
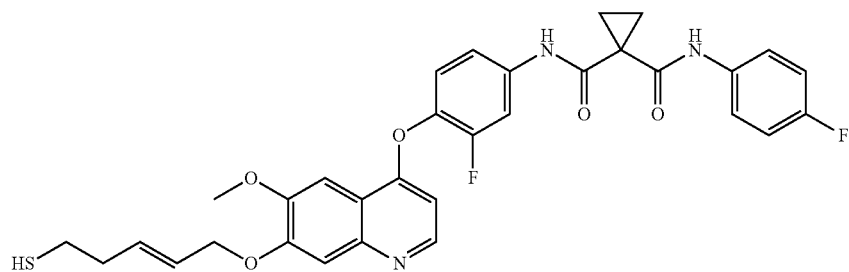
30
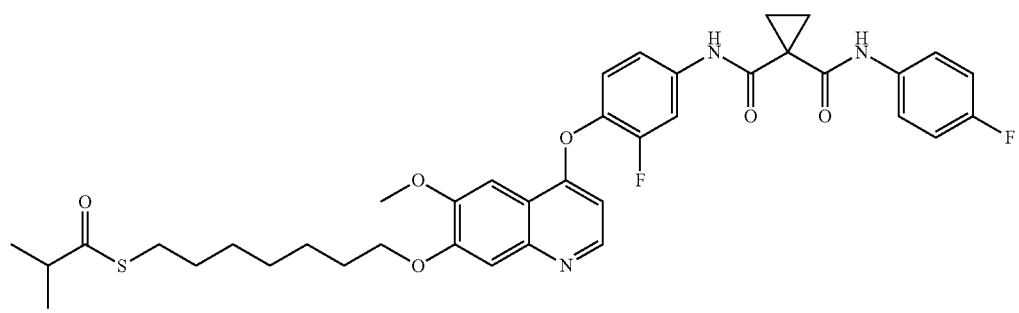
31
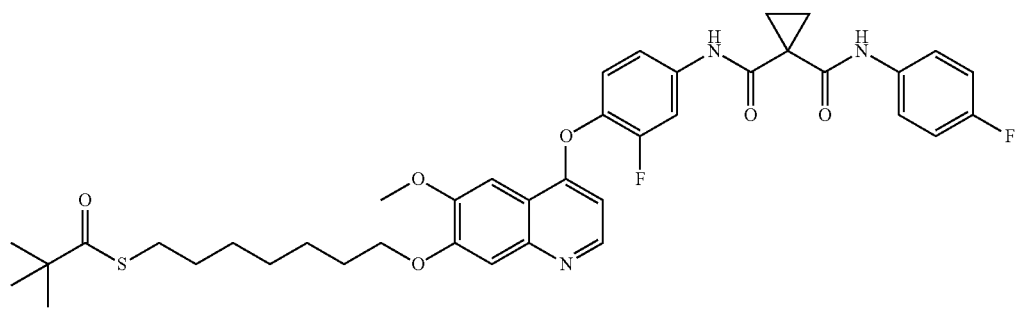
32
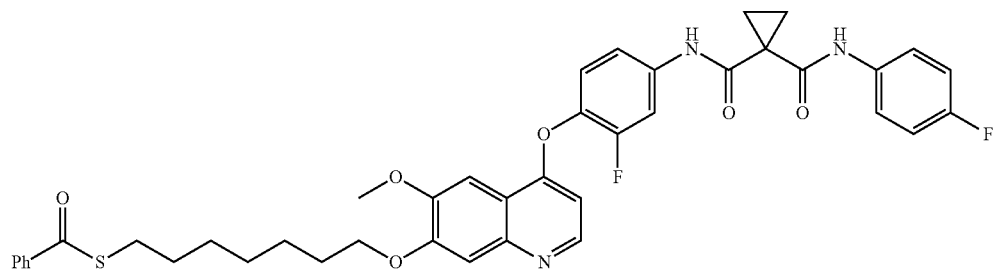
33
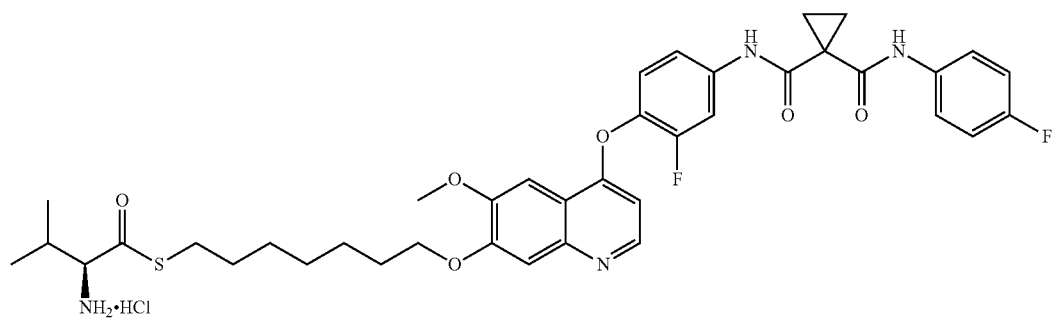

34
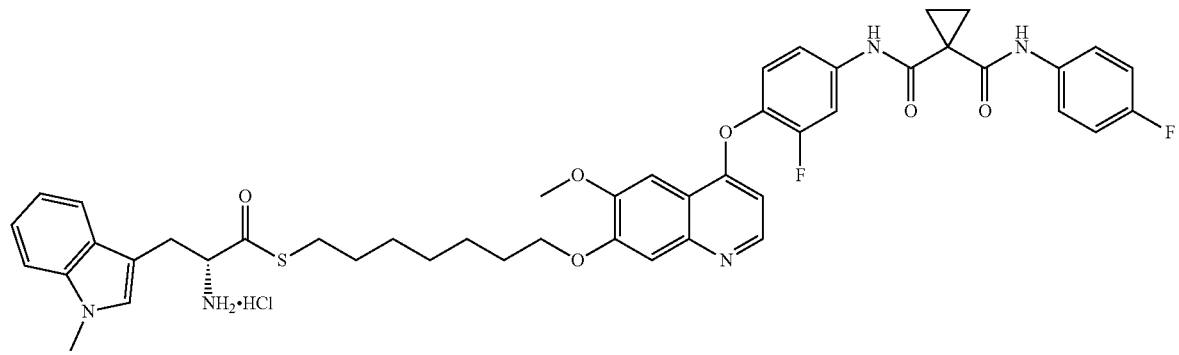
35
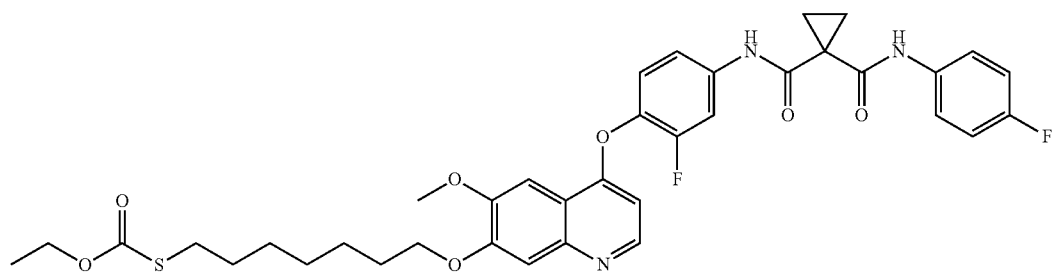
36
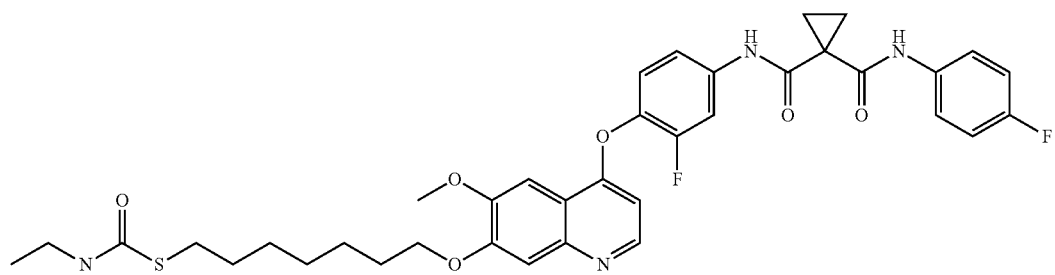
37
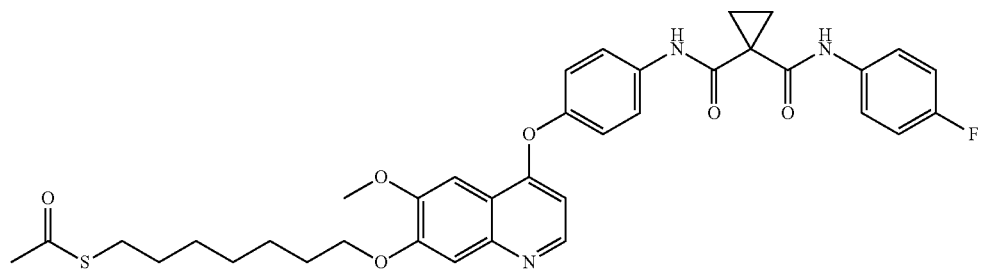
38
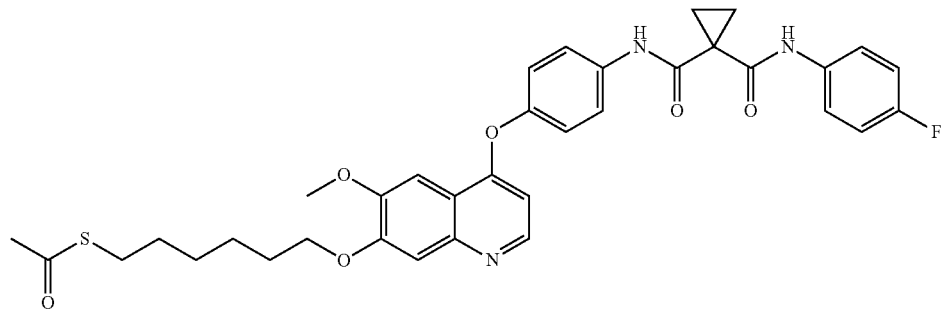

39
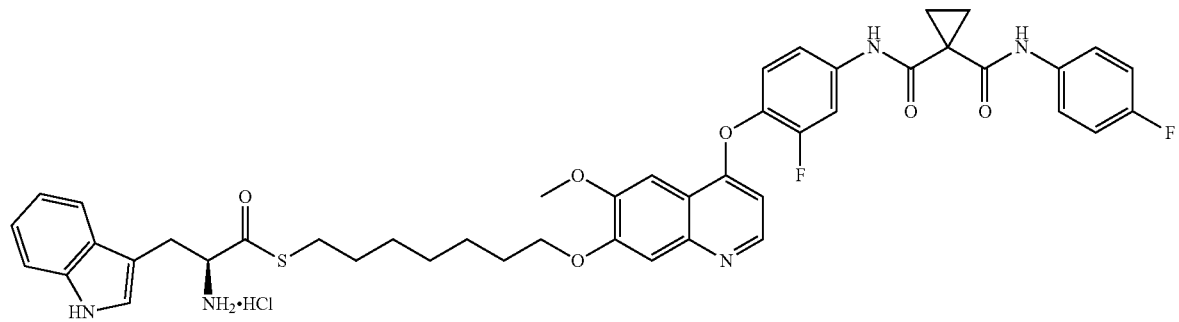
40
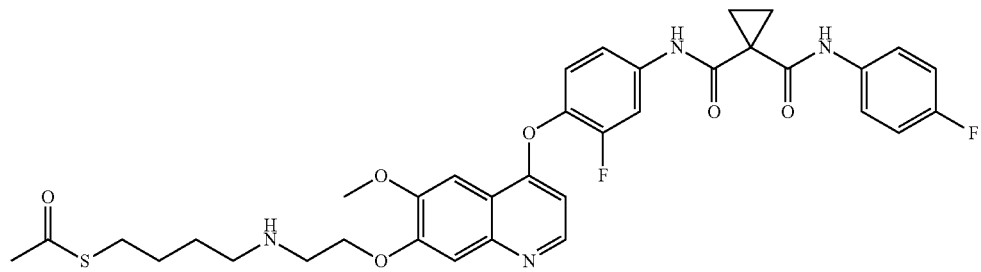
41
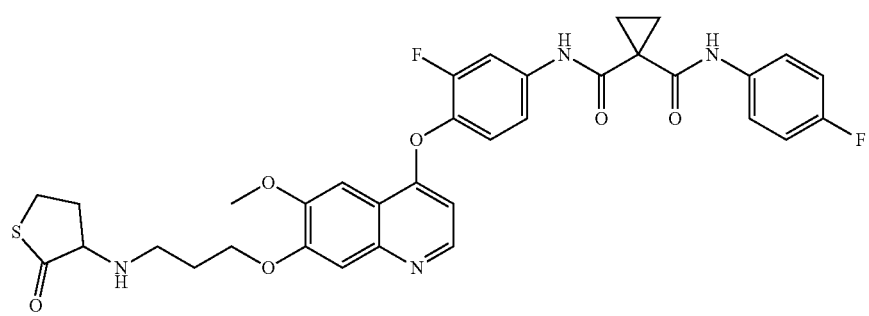
42
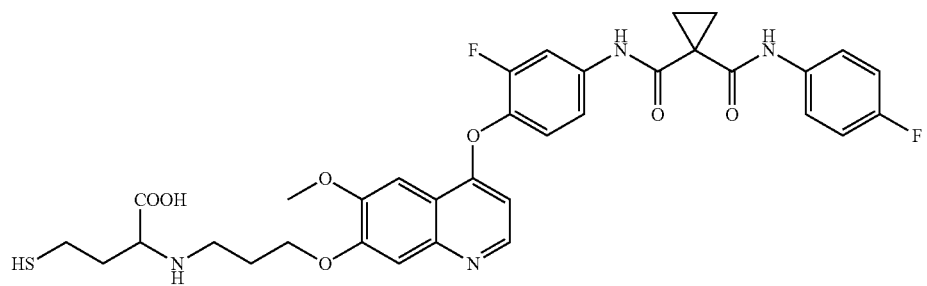
43
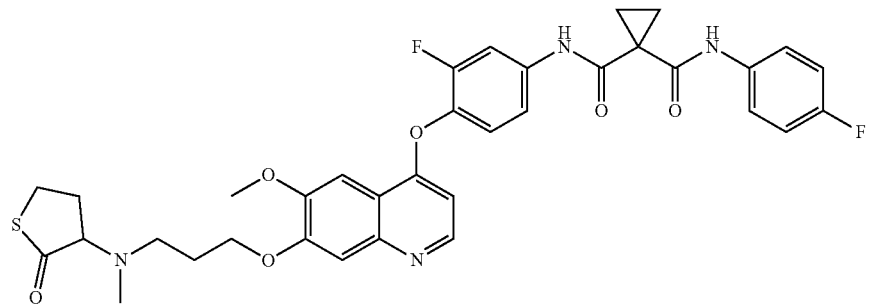

44
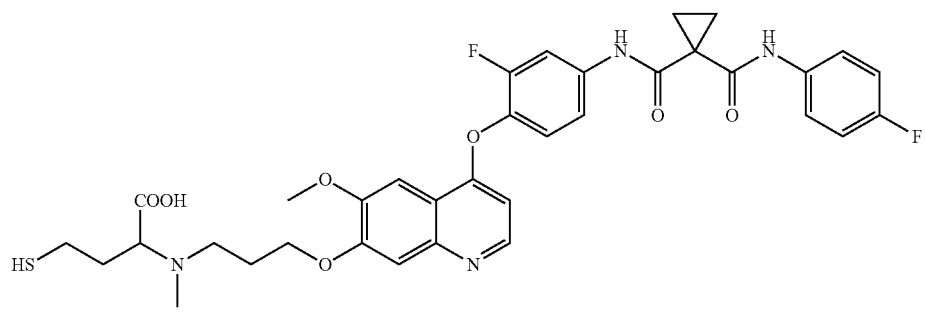
45
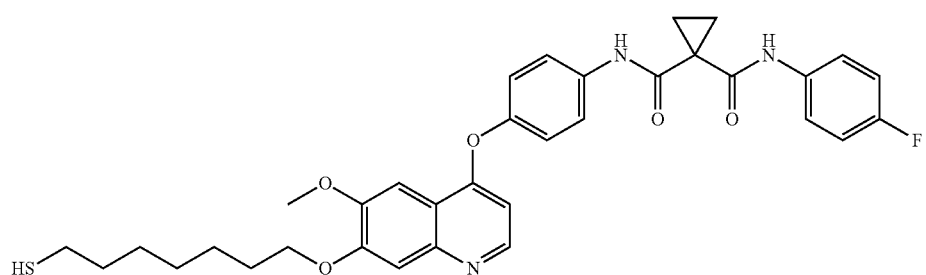
46
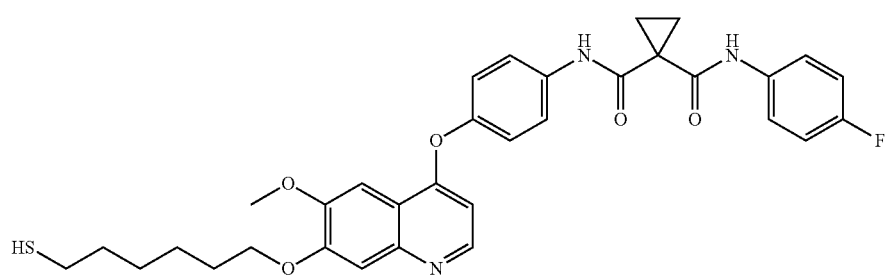
47
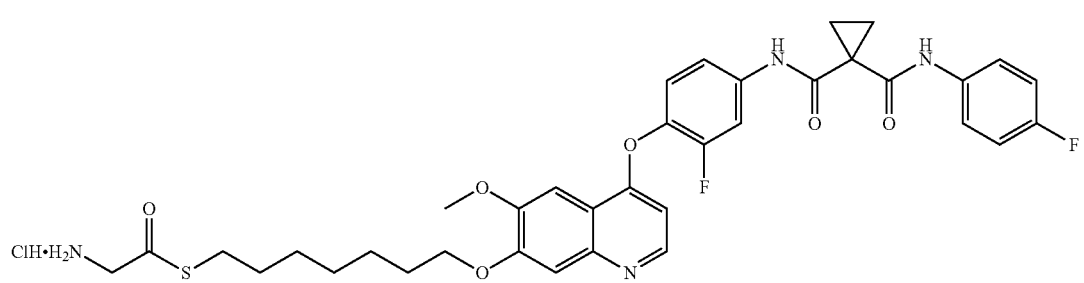
48
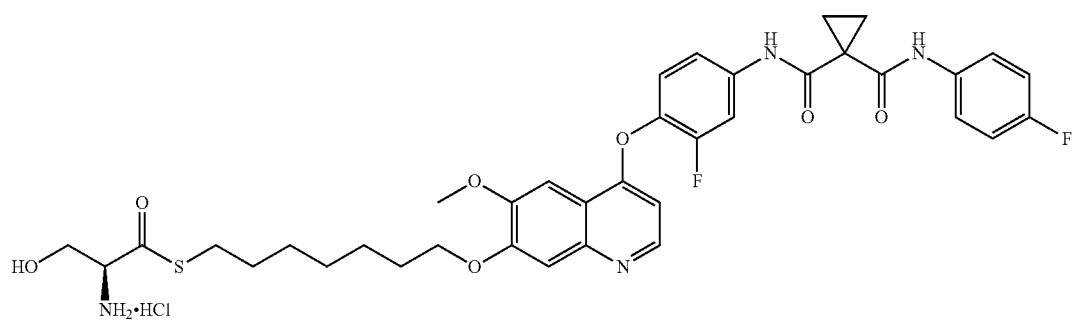

49
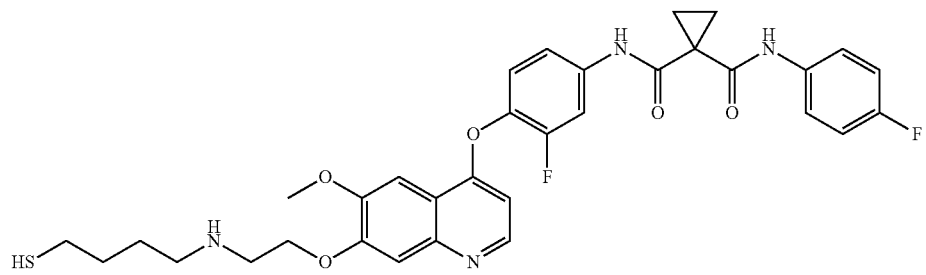
50
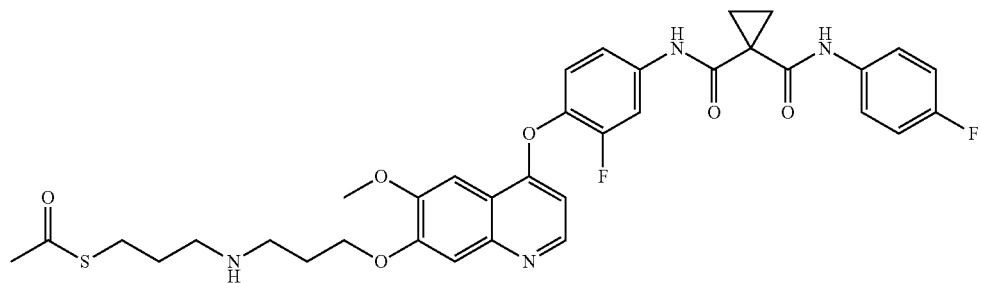
51
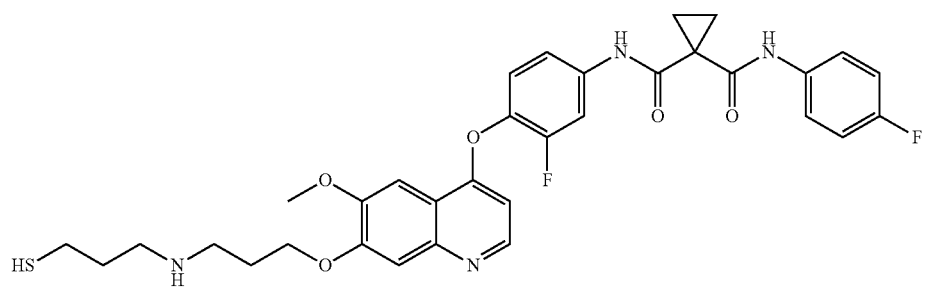
52
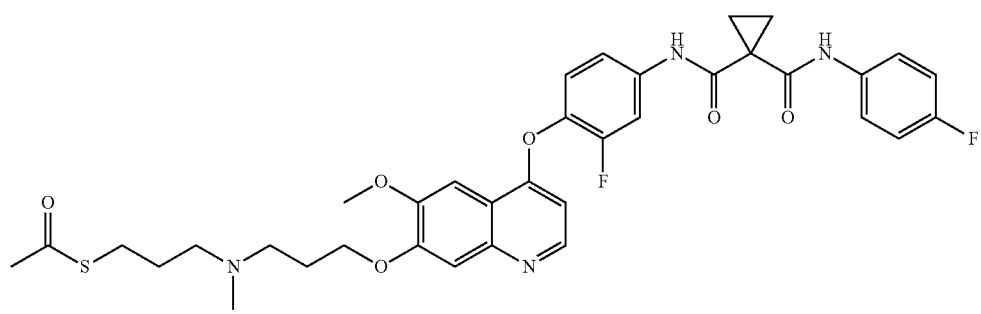
53
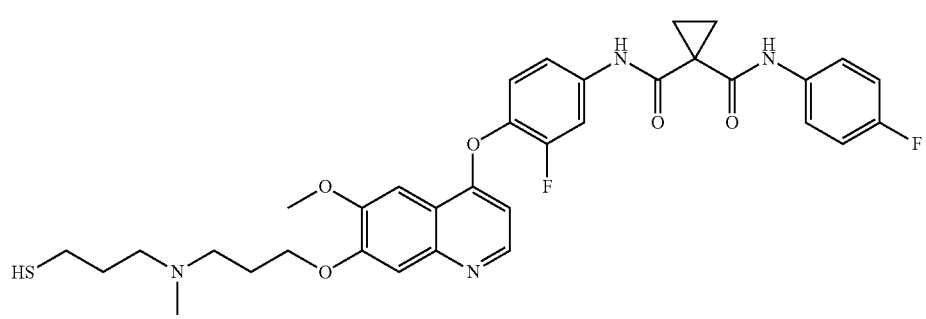

54
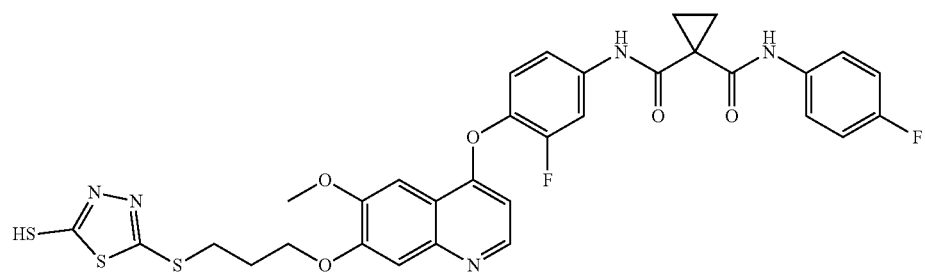
55
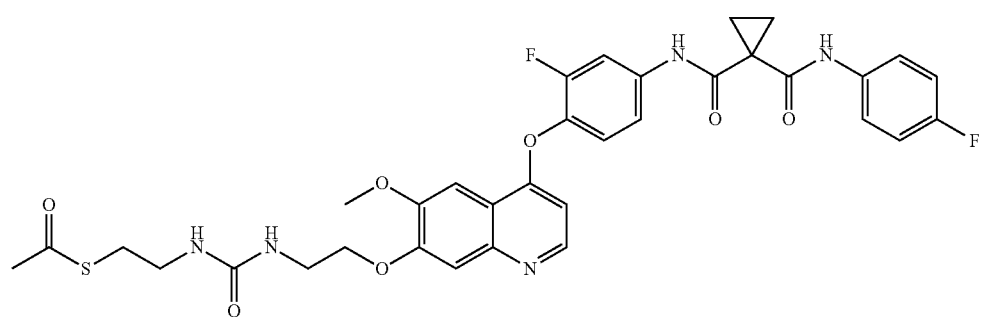
56
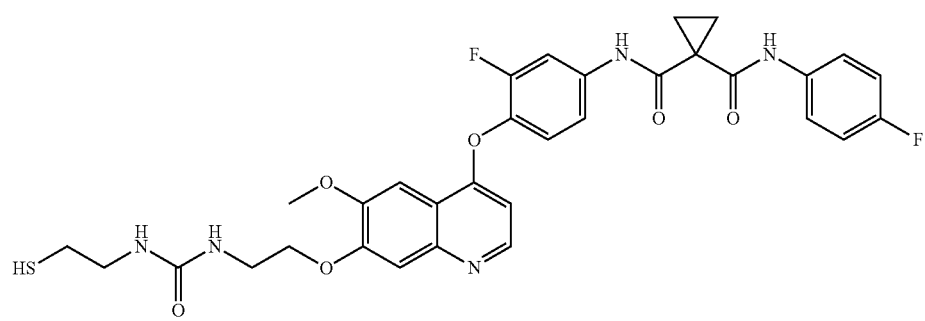
57
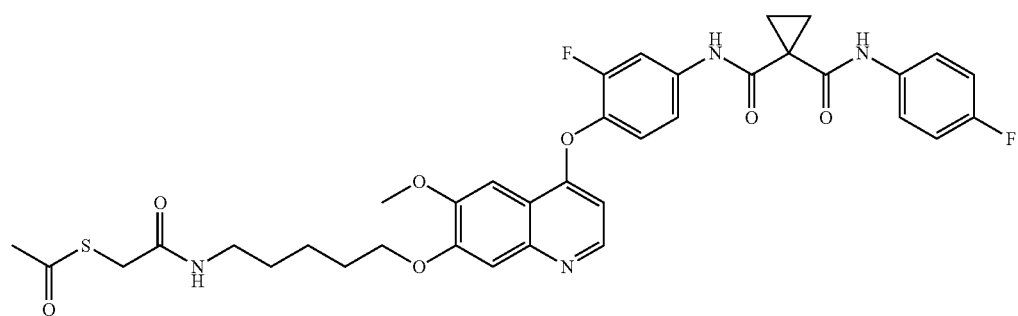
58
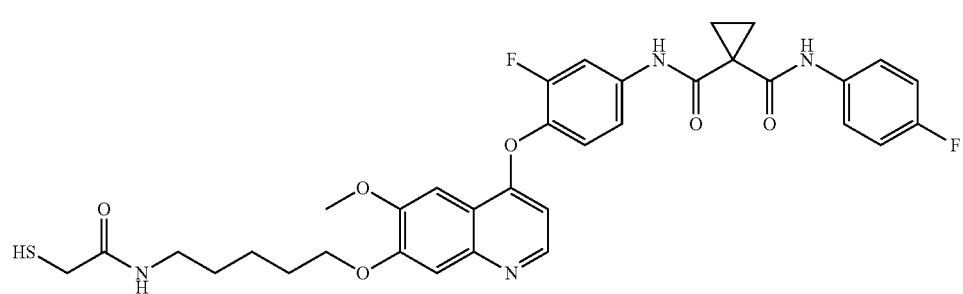

59
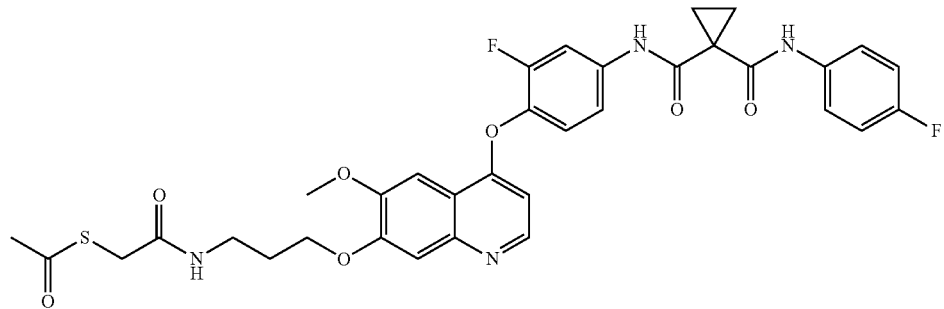
60
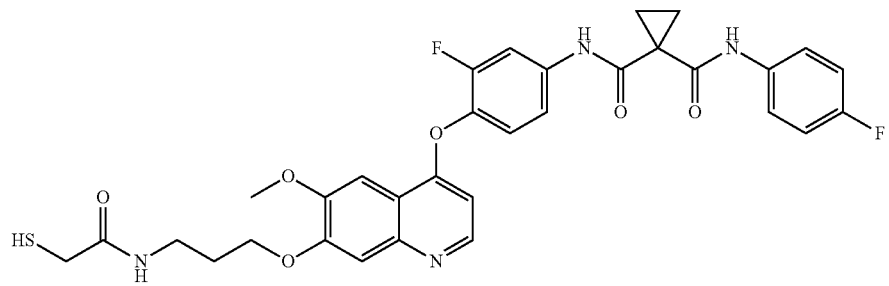
61
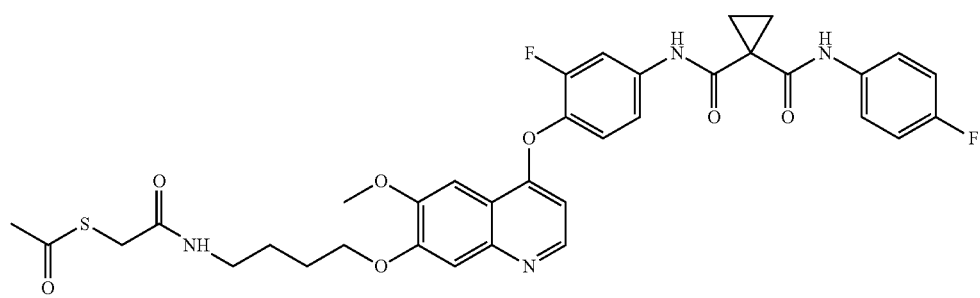
62
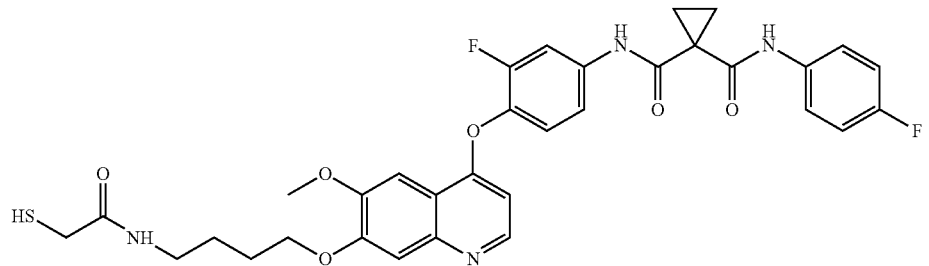
63
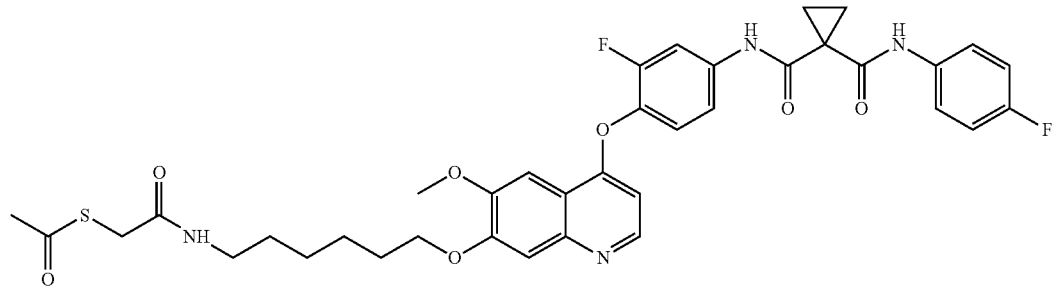

64
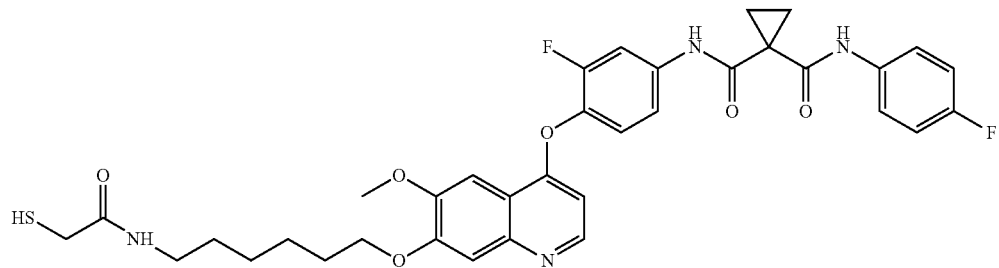
65
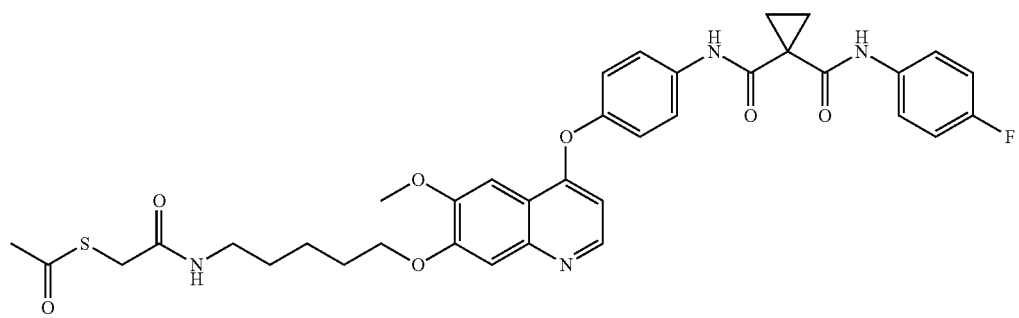
66
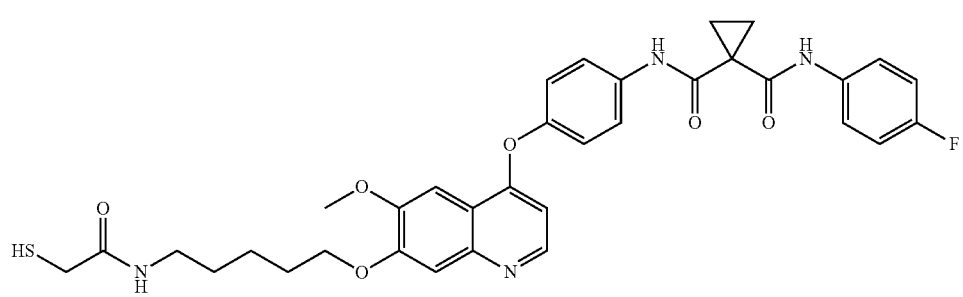
67
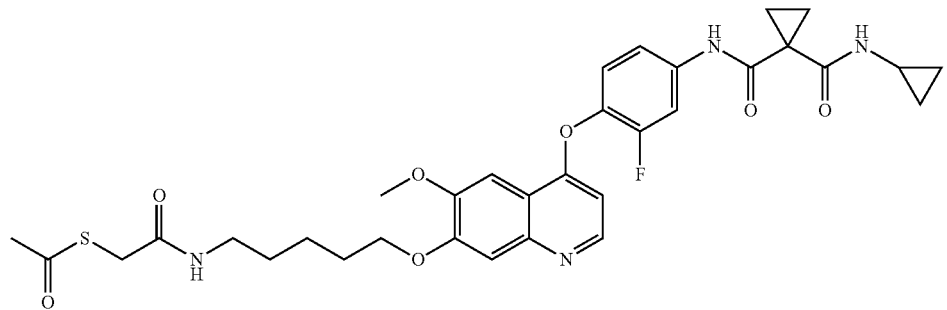
68
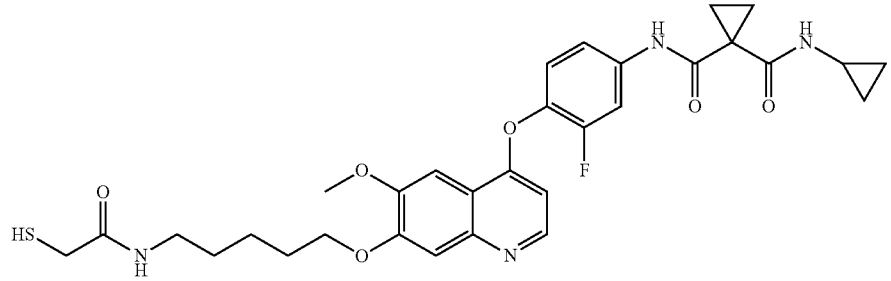

69
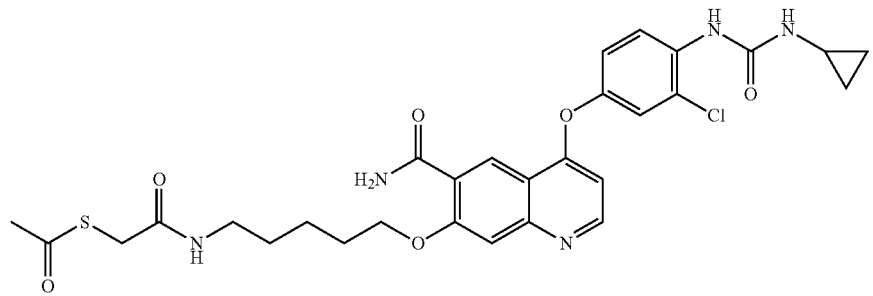
70
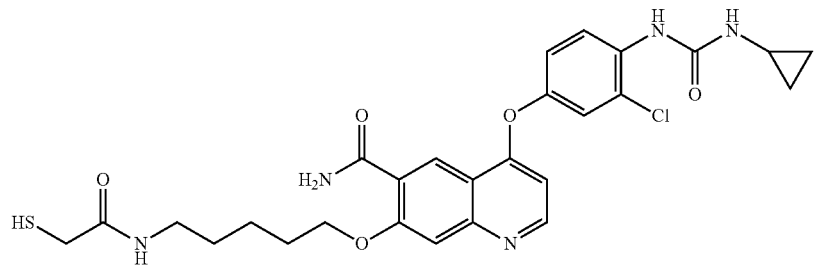
71
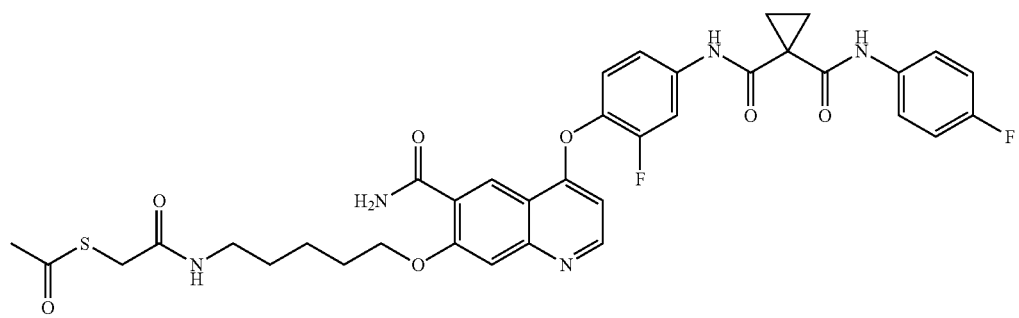
72
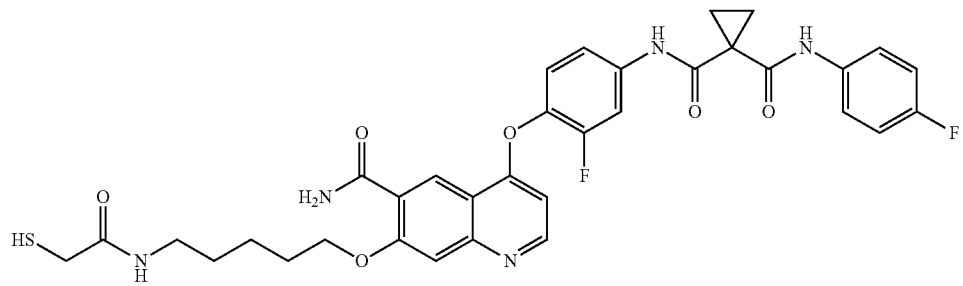
73
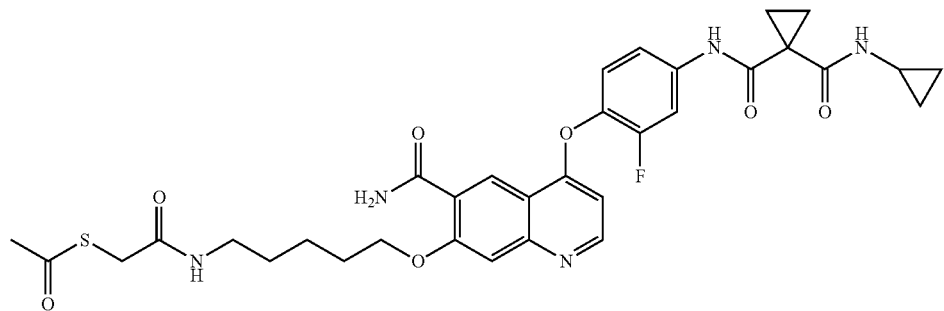

74
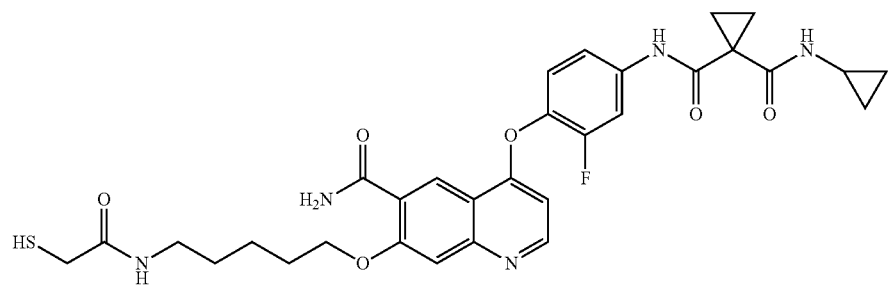
75
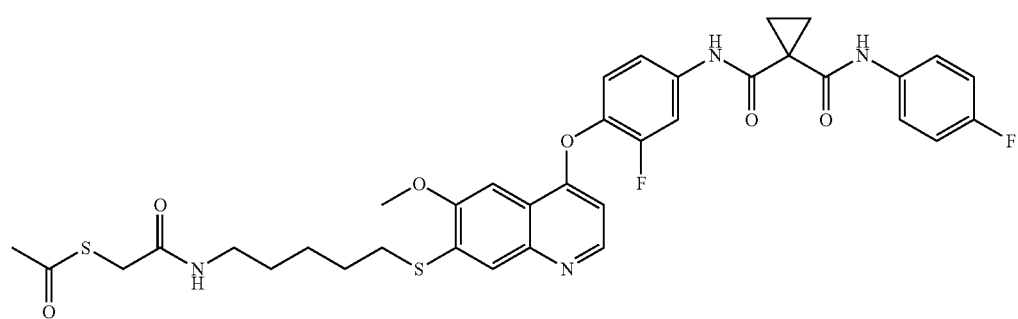
76
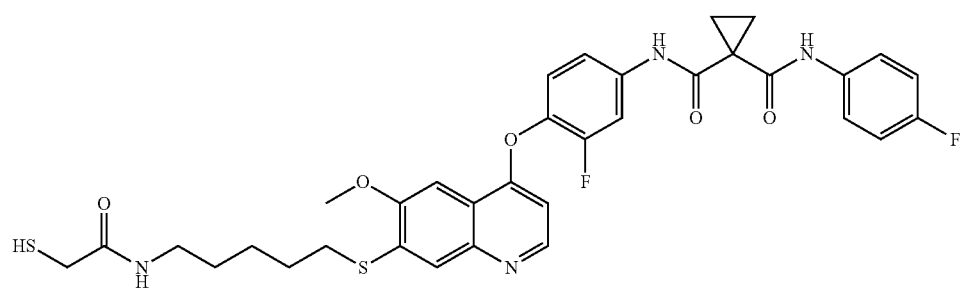
77
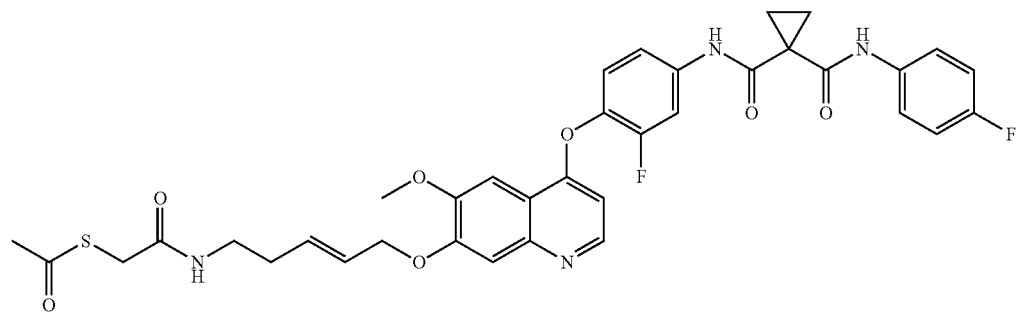
78
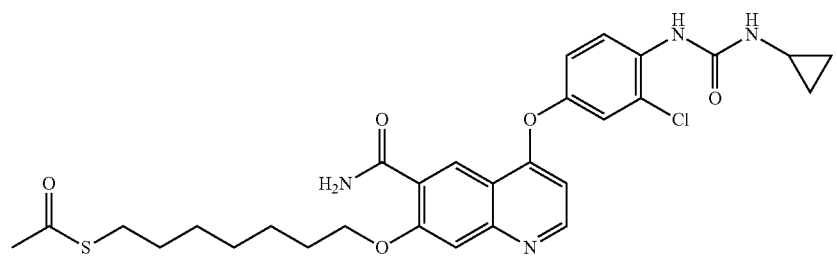

-continued
| | |
|---|---|
| 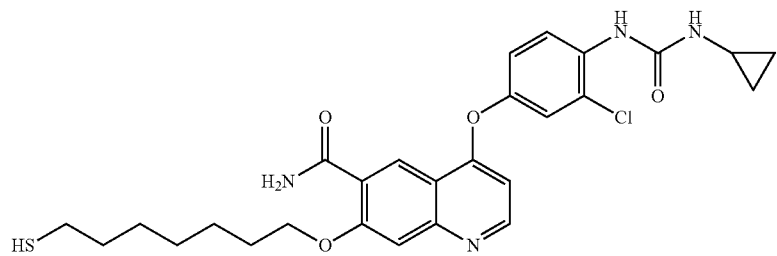 | 79 |
| 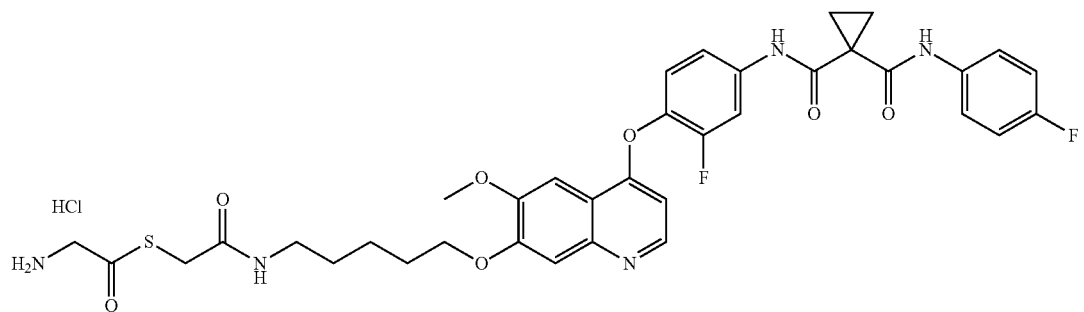 | 80 |
| 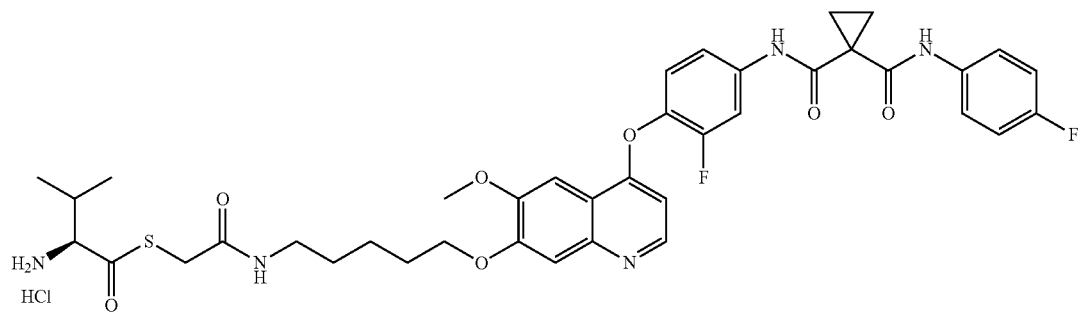 | 81 |
| 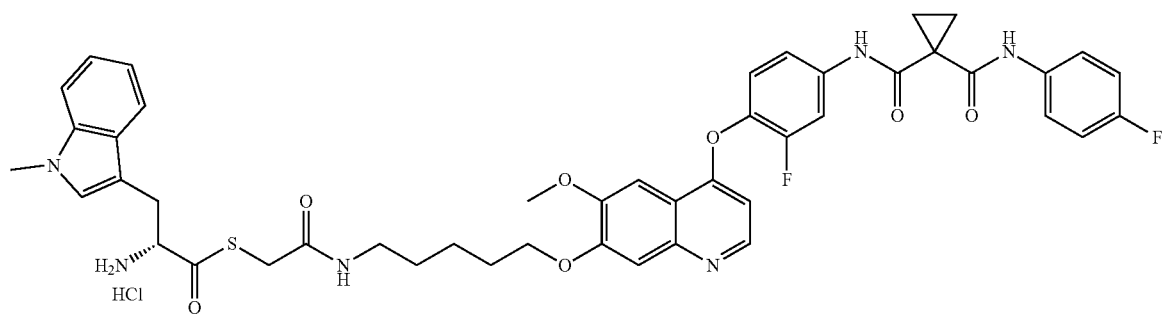 | 82 |
| 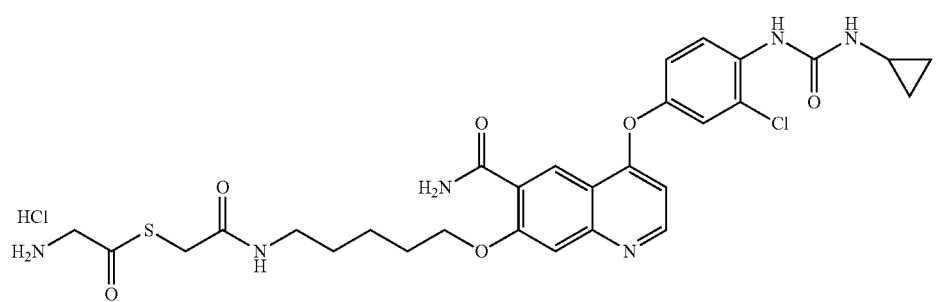 | 83 |

-continued
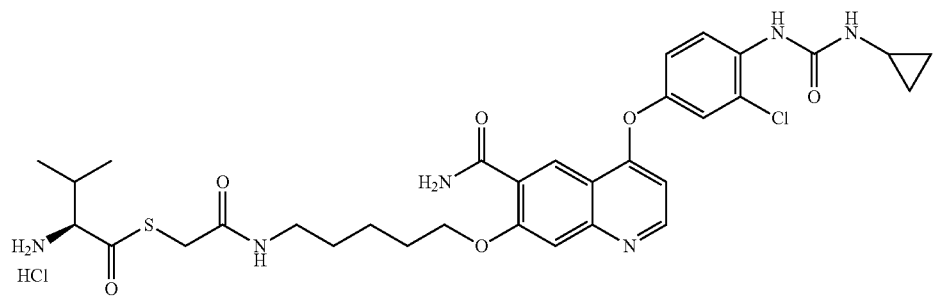
84
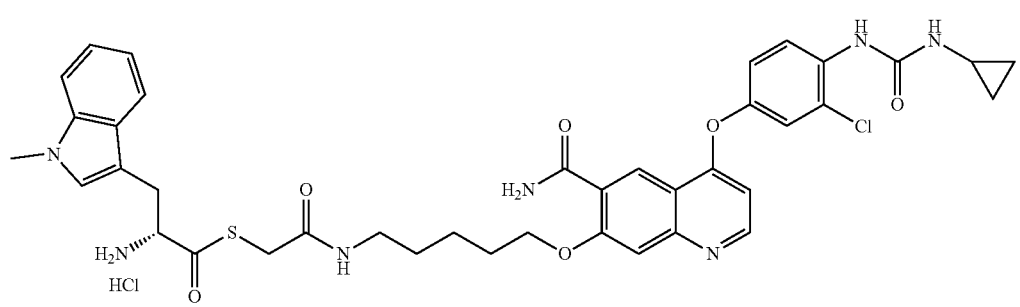
85
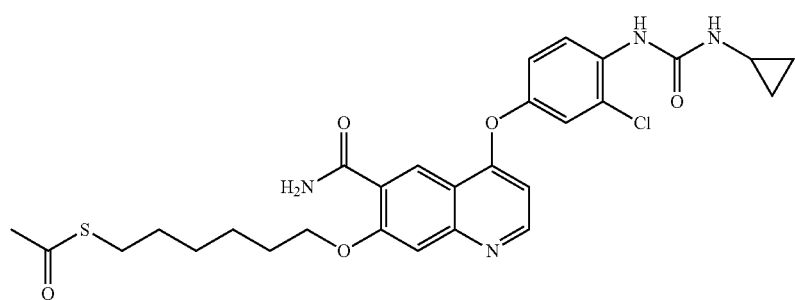
86
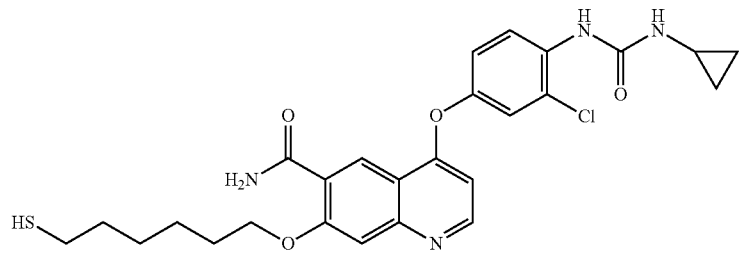
87
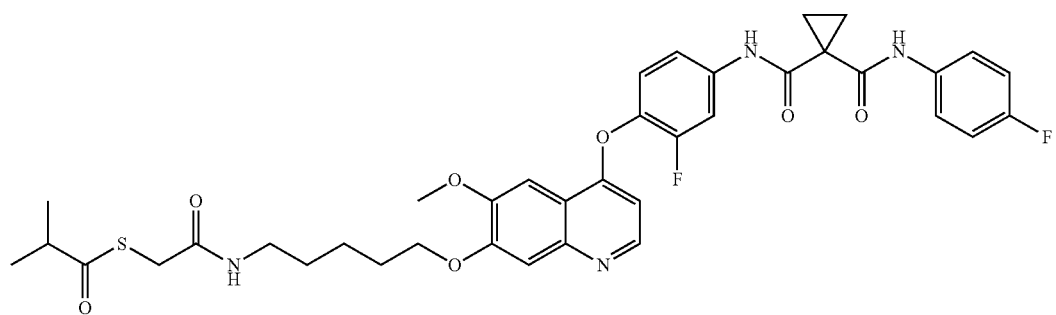
88

-continued
89
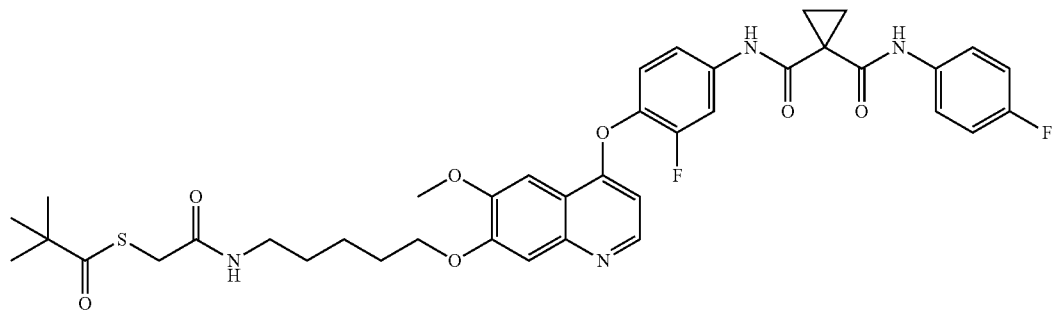
90
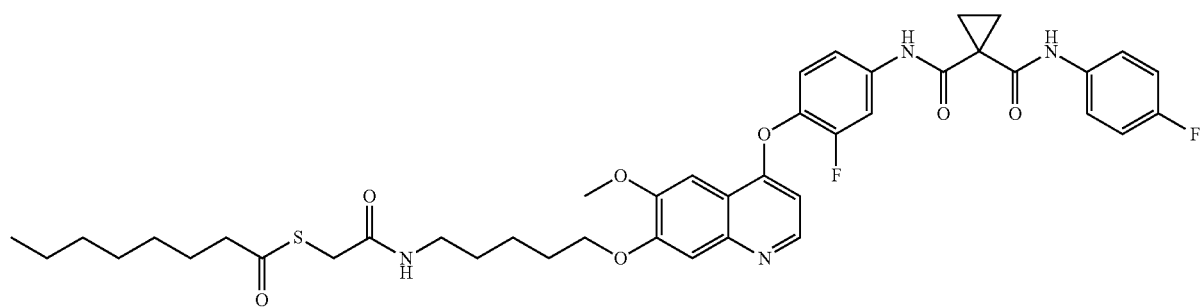
91
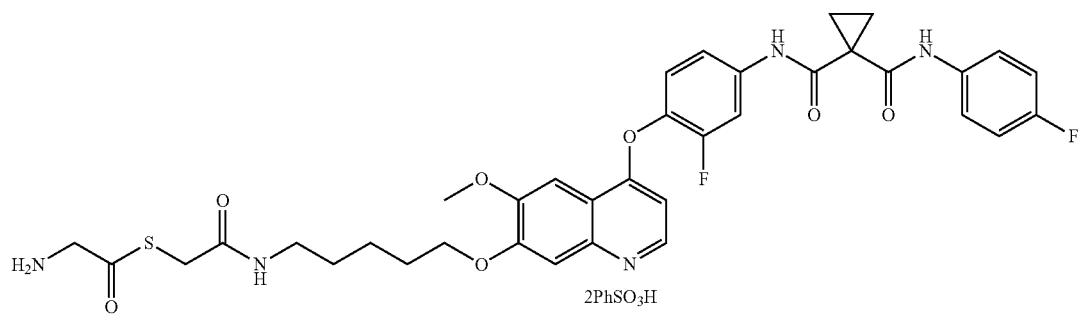
92
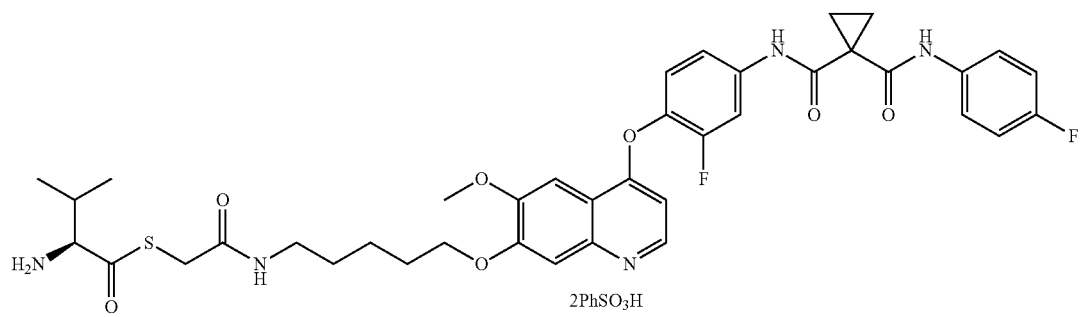
93
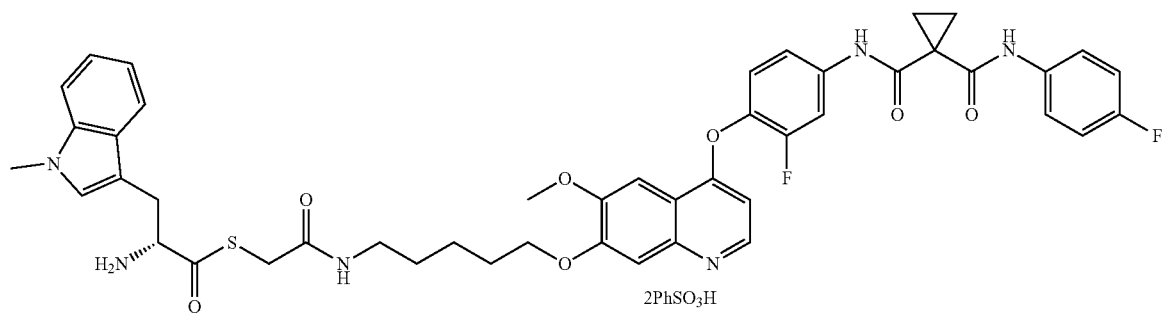

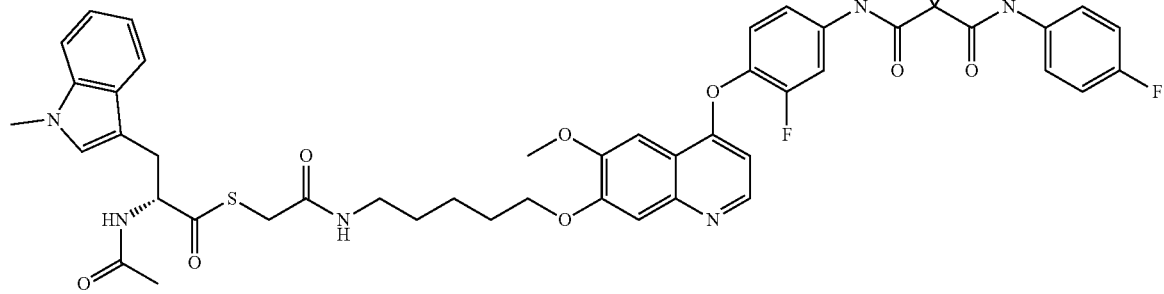
94
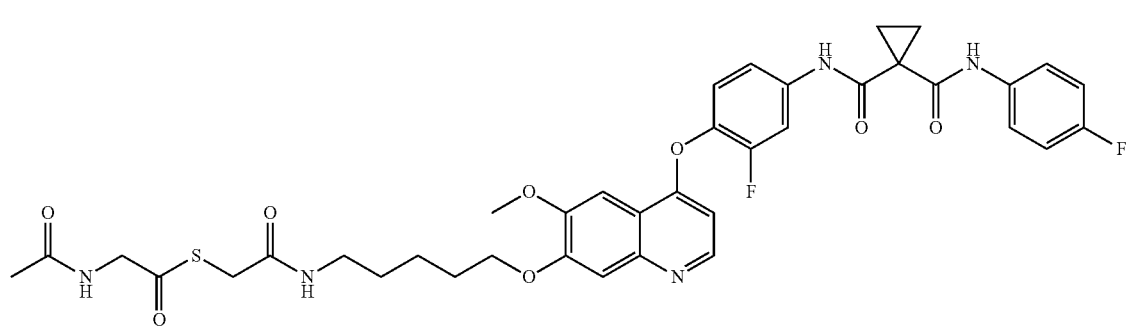
95
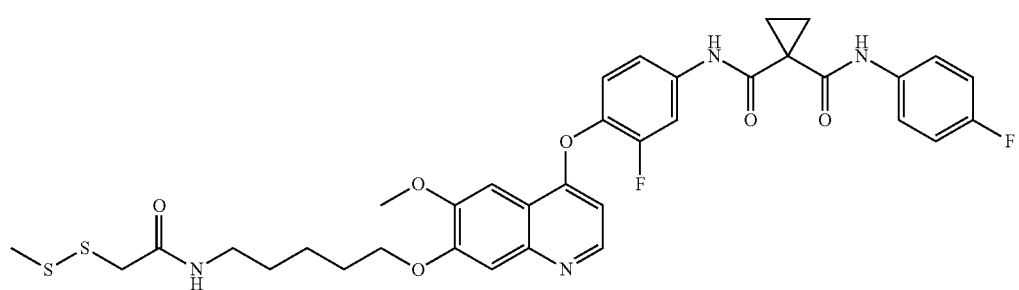
96
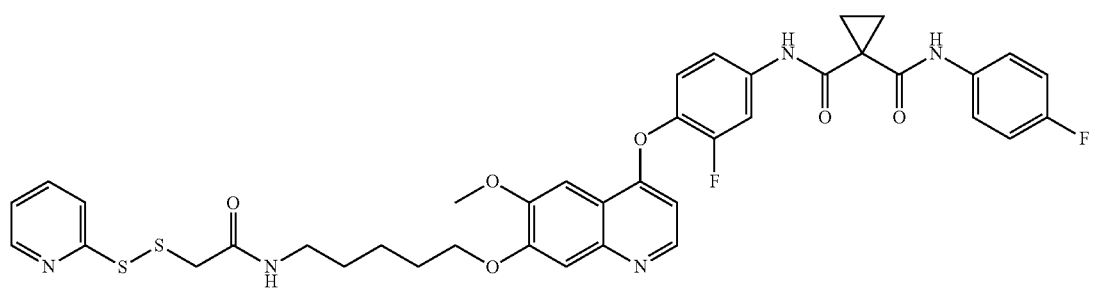
97

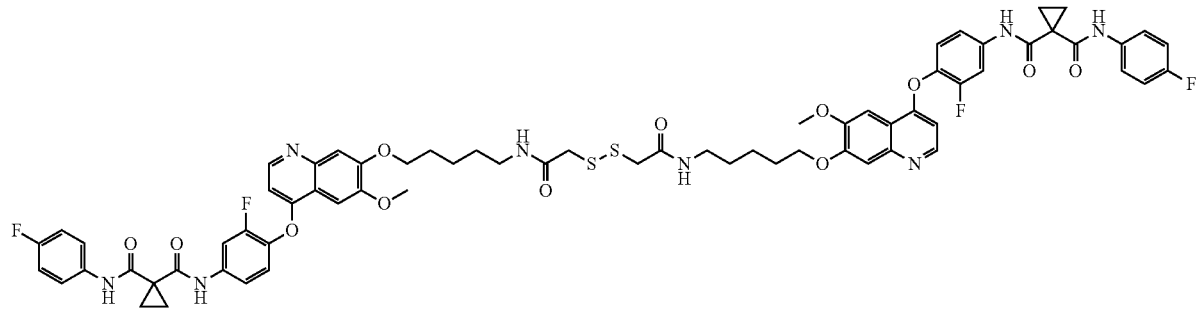 [SMILES: COc1cc2c(Oc3ccc(NC(=O)C4(C(=O)Nc5ccc(F)cc5)CC4)cc3F)ccnc2cc1OCCCCCNC(=O)CSSCC(=O)NCCCCCOc1cc2nccc(Oc3ccc(NC(=O)C4(C(=O)Nc5ccc(F)cc5)CC4)cc3F)c2cc1OC]

or a pharmaceutically acceptable salt, or stereoisomer thereof.

9. A pharmaceutical composition comprising an effective amount of the compound or a pharmaceutically acceptable salt or stereoisomer thereof of claim 1, and a pharmaceutically acceptable carrier.

10. The compound according to claim 7, wherein $R_9$ is selected from substituted or unsubstituted methyl, ethyl, n-propyl, isopropyl, n-butyl, isobutyl, sec-butyl, tert-butyl, methoxy, ethoxy, methylthio, —$(CH_2)_m$—$C_{3~6}$ heterocyclyl containing at least one N atom, —$(CH_2)_m$—$C_{3~12}$ heteroaryl containing at least one N atom, phenyl, naphthyl or biphenyl, and m is an integer of 1 to 3; or a pharmaceutically acceptable salt or stereoisomer thereof.

\* \* \* \* \*